US007504225B2

(12) United States Patent
Ring et al.

(10) Patent No.: US 7,504,225 B2
(45) Date of Patent: Mar. 17, 2009

(54) REAGENTS AND METHODS FOR USE IN CANCER DIAGNOSIS, CLASSIFICATION AND THERAPY

(75) Inventors: Brian Z. Ring, Foster City, CA (US); Douglas T. Ross, Burlingame, CA (US); Robert S. Seitz, Hampton Cove, AL (US); Tyler O. Kirby, Palm Harbor, FL (US); Warner Huh, Birmingham, AL (US)

(73) Assignees: Applied Genomics, Inc., Sunnyvale, CA (US); The UAB Research Foundation, Birmingham, AL (US)

( * ) Notice: Subject to any disclaimer, the term of this patent is extended or adjusted under 35 U.S.C. 154(b) by 0 days.

(21) Appl. No.: 11/432,604

(22) Filed: May 11, 2006

(65) Prior Publication Data

US 2007/0065888 A1 Mar. 22, 2007

Related U.S. Application Data

(60) Provisional application No. 60/680,924, filed on May 12, 2005.

(51) Int. Cl.
*G01N 33/53* (2006.01)
(52) U.S. Cl. ...................................... 435/7.1
(58) Field of Classification Search ................... 435/7.1
See application file for complete search history.

(56) References Cited

U.S. PATENT DOCUMENTS

| | | | |
|---|---|---|---|
| 4,579,827 A | 4/1986 | Sakamoto et al. |
| 4,666,845 A | 5/1987 | Mattes et al. |
| 5,790,761 A | 8/1998 | Heseltine et al. |
| 5,840,507 A | 11/1998 | Fruehauf |
| 5,843,684 A | 12/1998 | Levine et al. |
| 5,882,864 A | 3/1999 | An et al. |
| 5,983,211 A | 11/1999 | Heseltine et al. |
| 6,063,586 A | 5/2000 | Grandis |
| 6,087,090 A | 7/2000 | Mascarenhas |
| 6,294,349 B1 | 9/2001 | Streckfus et al. |
| 6,303,324 B1 | 10/2001 | Fruehauf |
| 6,607,894 B1 | 8/2003 | Lopata et al. |
| 6,631,330 B1 | 10/2003 | Poynard |
| 6,670,141 B2 | 12/2003 | Streckfus et al. |
| 6,763,307 B2 | 7/2004 | Berg et al. |
| 6,794,501 B2 | 9/2004 | Chen et al. |
| 2003/0198972 A1 | 10/2003 | Erlander et al. |
| 2005/0112622 A1 | 5/2005 | Ring et al. |

FOREIGN PATENT DOCUMENTS

| | | |
|---|---|---|
| WO | WO 91/16632 | 10/1991 |
| WO | WO 98/22139 | 5/1998 |
| WO | WO 99/44063 | 9/1999 |
| WO | WO 01/51924 | 7/2001 |
| WO | WO-02/064798 | 8/2002 |
| WO | WO-03/015613 | 2/2003 |
| WO | WO 03/087761 | 10/2003 |
| WO | WO-2005/008213 | 1/2005 |

OTHER PUBLICATIONS

Tockman et al (Cancer Res., 1992, 52:2711s-2718s).*
CRF error report.*
Aas, et al., "Specific P53 Mutations are Associated with de novo Resistance to Doxorubicin in Breast Cancer Patients", *Nature Medicine*, 2(7): 811-814, 1996.
Alizadeh, et al., "Distinct Types of Diffuse Large B-Cell Lymphoma Identified by Gene Expression Profiling", *Nature*, 403: 503-511, 2000.
Alon, et al., "Broad Patterns of Gene Expression Revealed by Clustering Analysis of Tumor and Normal Colon Tissues Probed by Oligonucleotide Arrays", *Proc. Natl. Acad. Sci. USA*, 96: 6745-6750, 1999.
Andersen, et al., "Prognostic Significance of TP53 Alterations in Breast Carcinoma", *Br. J. Cancer*, 68: 540-548, 1993.
Baxa, et al., "Human Adipocyte Lipid-Binding Protein: Purification of the Protein and Cloning of its Complementary DNA", *Biochemistry*, 28: 8683-8690, 1989.
Beer, et al., "Gene-Expression Profiles Predict Survival of Patients with Lung Adenocarcinoma", *Nature Medicine*, 8(8): 816-824, 2002.
Berns, et al., "Prevalence of Amplification of the Oncogenes c-myc: HER2/neu, and Int-2 in One Thousand Human Breast Tumours: Correlation with Steroid Receptors", *Eur. J. Cancer*, 28(2/3): 697-700, 1992.
Bhargava, et al., "Bcl-2 Immunoreactivity in Breast Carcinoma Correlates with Hormone Receptor Positivity", *American Journal of Pathology*, 145(3): 535-540, 1994.
Bhattacharjee, et al., "Classification of Human Lung Carcinomas by mRNA Expression Profiling Reveals Distinct Adenocarcinoma Subclasses", *Proc. Nat. Acad. Sci. USA*, 98: 13790-13795, 2001.
"Breast", AJCC Cancer Staging Manual, Lippincott, 5th Ed., pp. 171-180, 1997.
Cahill, et al., "Mutations of Mitotic Checkpoint Genes in Human Cancers", *Nature*, 392: 300-303, 1998.
Cho, et al., "A Genome-Wide Transcriptional Analysis of the Mitotic Cell Cycle", *Molecular Cell*, 2: 65-73, 1998.
Chu, et al., "The Transcriptional Program of Sporulation in Budding Yeast", *Science*, 282: 699-705, 1998.
Crnogorac-Jurcevic, et al., "Expression Profiling of Microdissected Pancreatic Adenocarcinomas", *Oncogene*, 21: 4587-4594, 2002.
Dairkee, et al., "Expression of Basal and Luminal Epithelium-Specific Keratins in Normal, Benign, and Malignant Breast Tissue", *Journal of the National Cancer Institute*, 80(9): 691-695, 1988.
DeRisi, et al., "Exploring the Metabolic and Genetic Control of Gene Expression on a Genomic Scale", *Science*, 278: 680-686, 1997.

(Continued)

*Primary Examiner*—Sean E Aeder
(74) *Attorney, Agent, or Firm*—Brenda Herschbach Jarrell; Charles E. Lyon; D. Phil Choate

(57) ABSTRACT

Methods and reagents for classifying tumors and for identifying new tumor classes and subclasses. Methods for correlating tumor class or subclass with therapeutic regimen or outcome, for identifying appropriate (new or known) therapies for particular classes or subclasses, and for predicting outcomes based on class or subclass. New therapeutic agents and methods for the treatment of cancer.

9 Claims, 20 Drawing Sheets

OTHER PUBLICATIONS

Dhanasekaran, et al., "Delineation of Prognosis Biomarkers in Prostate Cancer", *Nature*, 412: 822-826, 2001.

Di Leo, et al., "Predictive Molecular Markers in the Adjuvant Therapy of Breast Cancer: State of the Art in the Year 2002", *Int. J. Clin. Oncol.* 7: 245-253, 2002.

Eisen, et al., "Cluster Analysis and Display of Genome-Wide Expression Patterns", *Proc. Natl. Acad. Sci. USA*, 95: 14863-14868, 1998.

Eisen, et al., "DNA Arrays for Analysis of Gene Expression", *Methods of Enzymology*, 303: 179-205, 1999.

Fambrough, et al., "Diverse Signaling Pathways Activated by Growth Factor Receptors Induce Broadly Overlapping, Rather than Independent, Sets of Genes", *Cell*, 97: 727-741, 1999.

Ferrando, et al., "Gene Expression Signatures Define Novel Oncogenic Pathways in T Cell Acute Lymphoblastic Leukemia", *Cancer Cell*, 1: 75-87, 2002.

Galitski, et al., "Ploidy Regulation of Gene Expression", *Science*, 285: 251-254, 1999.

Garber, et al., "Diversity of Gene Expression in Adenocarcinoma of the Lung", *Proc. Natl. Acad. Sci. USA*, 98: 13784-13789, 2001.

Golub, et al., "Molecular Classification of Cancer: Class Discovery and Class Prediction by Gene Expression Monitoring", *Science*, 286: 531-537, 1999.

Gruvberger, et al., "Estrogen Receptor Status in Breast Cancer is Associated with Remarkably Distinct Gene Expression Patterns", *Cancer Res.* 61: 5979-5984, 2001.

Guelstein, et al., "Monoclonal Antibody Mapping of Keratins 8 and 17 and of Vimentin in Normal Human Mammary Gland, Benign Tumors, Dysplasias and Breast Cancer", *Int. J. Cancer*, 42: 147-153, 1988.

Guerin, et al., "Overexpression of Either C-Myc or C-ErbB-2/Neu Proto-Oncogenes in Human Breast Carcinomas: Correlation with Poor Prognosis", *Oncogene Research*, 3: 21-31, 1988.

Gusterson, et al., "Distribution of Myoepithelial Cells and Basement Membrane Proteins in the Normal Breast and in Benign and Malignant Breast Disease", *Cancer Research*, 42: 4763-4770, 1982.

Hailey, et al., "Neutralizing Anti-Insulin-Like Growth Factor Receptor 1 Antibodies Inhibit Receptor Function and Induce Receptor Degradation in Tumor Cells", *Molecular Cancer Therapeutics*, 1: 1349-153, 2002.

Han, et al., "Distinct Cadherin Profiles in Special Variant Carcinomas and Other Tumors of the Breast", *Human Pathology*, 30(9): 1035-1039, 1999.

Hayes, et al., "Prognosis Factors in Breast Cancer: Current and New Predictors of Metastasis", *J. Mamm. Gland Bio. Neo.* 6: 375-392, 2001.

Hedenfalk, et al., "Gene-Expression Profiles in Hereditary Breast Cancer", *N. Engl. J. Med.* 344: 539-548, 2001.

Heintz, et al., "Amplification of the c-erb B-2 Oncogene and Prognosis of Breast Adenocarcinoma", *Arch Pathol Lab Med*-114: 160-163, 1990.

Heyer, et al., "Exploring Expression Data: Identification and Analysis of Coexpressed Genes", *Genome Res.* 9: 1106-1115, 1999.

Hippo, et al., "Global Gene Expression Analysis of Gastric Cancer by Oligonucleotide Microarrays", *Cancer Res.* 62: 233-240, 2002.

Hoch, et al., "Gata-3 is Expressed in Association with Estrogen Receptor in Breast Cancer", *Int. J. Cancer (Pred. Oncol).* 84: 122-128, 1999.

Hofmann, et al., "Relation Between Resistance of Philadelphia-Chromosome-Positive Acute Lymphoblastic Leukaemia to the Tyrosine Kinase Inhibitor ST1571 and Gene-Expression Profiles: A Gene-Expression Study" *Lancet*, 359: 481-486, 2002.

Iyer, et al., "The Transcriptional Program in the Response of Human Fibroblasts to Serum", *Science*, 283: 83-87, 1999.

Jazaeri, et al., "Gene Expression Profiles of BRCA1-Linked, BRCA-2-Linked, and Sporadic Ovarian Cancers", *J. Natl Cancer Inst.* 94: 990-1000, 2002.

Kallioniemi, et al., "Tissue Microarray Technology for High-Throughput Molecular Profiling of Cancer", *Human Molecular Genetics*, 10(7): 657-662, 2001.

Kaplan, et al., "Nonparametric Estimation from Incomplete Observations", *J. Am. Stat. Assn.* 53: 457-481, 1958.

Khan, et al., "Gene Expression Profiling of Alveolar Rhabdomyosarcoma with cDNA Microarrays", *Cancer Research*, 58: 5009-5013, 1998.

LaTulippe, et al., "Comprehensive Gene Expression Analysis of Prostate Cancer Reveals Distinct Transcriptional Programs Associated with Metastatic Disease", *Cancer Res.* 62: 4499-4506, 2002.

Leek, et al., "bcl-1 in Normal Human Breast and Carcinoma, Association with Oestrogen Receptor-Positive, Epidermal Growth Factor Receptor-Negative Tumours and in Situ Cancer", *Br. J. Cancer*, 69: 135-139, 1994.

Li, et al., "Identification of a Human Mitotic Checkpoint Gene: hsMAD2", *Science*, 274: 246-248, 1996.

Lin, et al., "Molecular Diagnosis of Colorectal Tumors by Expression Profiles of 50 Genes Expressed Differentially in Adenomas and Carcinomas", *Oncogene*, 21: 4120-4128, 2002.

MacDonald, et al., "Expression Profiling of Medulloblastoma: PDGFRA and the RAS/MAPK Pathway as Therapeutic Targets for Metastatic Disease" *Nature Genet.* 29: 143-152, 2001.

Malzahn, et al., "Biological and Prognostic Significance of Stratified Epithelial Cytokeratins in Infiltrating Ductal Breast Carcinomas", *Virchows Arch*, 433: 119-129, 1998.

Mantel, et al., "Statistical Aspects of the Analysis of Data from Retrospective Studies of Disease", *Journal of the National Cancer Institute*, 22: 719-748, 1959.

Miettinen, et al., "Endothelial Cell Markers CD31, CD34, and BNH9 Antibody to H- and Y-Antigens—Evaluation of Their Specificity and Sensitivity in the Diagnosis of Vascular Tumors and Comparison with Von Willebrand Factor", *Modern Pathology*, 7(1): 82-90, 1994.

Moog-Lutz, et al., "MLN64 Exhibits Homology with the Steroidogenic Acute Regulatory Protein (Star) and Is Over-Expressed in Human Breast Carcinomas", *Int. J. Cancer*: 71: 183-191, 1997.

Nagle, et al., "Characterization of Breast Carcinomas by Two Monoclonal Antibodies Distinguishing Myoepithelial from Luminal Epithelial Cells", *The Journal of Histochemistry and Cytochemistry*, 34(7): 869-881, 1986.

NIH National Institutes of Health Consensus Development Conference Statement: Adjuvant Therapy for Breast Cancer, Nov. 1-3, 2000, *J. Nat. Cancer Inst. Monographs*, 30: 5-15, 2001.

Nielsen, et al., "Immunohistochemical and Clinical Characterization of the Basal-Like Subtype of Invasive Breast Carcinoma" *Clinical Cancer Research*, 10: 5367-5374, 2004.

Osborne, et al., "The Value of Estrogen and Progesterone Receptors in the Treatment of Breast Cancer", *Cancer*, 46: 2884-2888, 1980.

Pauletti, et al., "Detection and Quantitation of HER-2/Neu Gene Amplification in Human Breast Cancer Archival Material Using Fluorescence in Situ Hybridization", *Oncogene*, 13: 63-72, 1996.

Perou, et al., "Distinctive Gene Expression Patterns in Human Mammary Epithelial Cells and Breast Cancers", *Proc. Natl. Acad. Sci. USA*, 96: 9212-9217, 1999.

Perou, et al., "Molecular Portraits of Human Breast Tumours" *Nature*, 406: 747-752, 2000.

Pollack, et al., "Genome-Wide Analysis of DNA Copy-Number Changes Using cDNA Microarrays", *Nature Genetics*, 23: 41-46, 1999.

Pomeroy, et al., "Prediction of Central Nervous System Embryonal Tumour Outcome Based on Gene Expression", *Nature*, 415: 436-442, 2002.

Prud'Homme, et al., "Cloning of a Gene Expressed in Human Breast Cancer and Regulated by Estrogen in MCF-7 Cells", *DNA*, 4(1): 11-21, 1985.

Ravdin, et al., "A Demonstration that Breast Cancer Recurrence can be Predicted by Neural Network Analysis", *Breast Cancer Res. Treat.* 21: 47-53, 1992.

Rhodes, et al., "Large-Scale Meta-Analysis of Cancer Microarray Data Identifies Common Transcriptional Profiles of Neoplastic Transformation and Progression", *Proc. Natl. Acad. Sci. USA*, 101(25): 9309-9314, 2004.

Ring, et al., "Microarrays and Molecular Markers for Tumor Classification", *Genome Biology*, 3(5): 1-6, 2002.

Ring, et al., "Predictors of Response to Systemic Therapy in Breast Cancer", *Forum*, 12(1): 19-32, 2002.

Ronnov-Jessen, et al., "Cellular Changes Involved in Conversion of Normal to Malignant Breast: Importance of the Stromal Reaction", *Physiological Reviews*, 76(1): 69-125, 1996.

Rosenwald, et al., "The Use of Molecular Profiling to Predict Survival After Chemotherapy for Diffuse Large-B-Cell Lymphoma", *N. Engl. J. Med.* 346: 1937-47, 2002.

Ross, et al., "Systematic Variation in Gene Expression Patterns in Human Cancer Cell Lines", *Nature Genetics*, 24: 227-235, 2000.

Segal, et al., "A Comparison of Estimated Proportional Hazards Models and Regression Trees", *Stat. Med.* 8: 539, 550, 1989.

Shimoyama, et al., "Cadherin Cell-Adhesion Molecules in Human Epithelial Tissues and Carcinomas", *Cancer Research*, 49: 2128-2133, 1989.

Shipp, et al., "Diffuse Large B-Cell Lymphoma Outcome Prediction by Gene-Expression Profiling and Supervised Machine Learning", *Nature Med.*, 8: 68-74, 2002.

Singh, et al., "Gene Expression Correlates of Clinical Prostate Cancer Behavior", *Cancer Cell*, 1: 203-209, 2002.

Slamon, et al., "Studies of the HER-2/Neu Proto-Oncogene in Human Breast and Ovarian Cancer", *Science*, 244: 707-712, 1989.

Soler, et al., "P-Cadherin Expression in Breast Carcinoma Indicates Poor Survival", *Cancer*, 86: 1263-1272, 1999.

Sorlie, et al., "Gene Expression Patterns of Breast Carcinomas Distinguish Tumor Subclasses with Clinical Implications", *Proc. Natl. Acad. Sci. USA*, 98: 10869-10874, 2001.

Sorlie, et al., "Repeated Observation of Breast Tumor Subtypes in Independent Gene Expression Data Sets", *Proc. Natl. Acad. Sci. USA*, 100(14): 8418-8423, 2003.

Spellman, et al., "Comprehensive Identification of Cell Cycle-Regulated Genes of the Yeast *Saccharomyces cerevisiae* by Microarray Hybridization", *Molecular Biology of the Cell*, 9: 3273-3297, 1998.

Srinivas, et al., "Proteomics for Cancer Biomarker Discovery", *Clinical Chemistry*, 48(8): 1160-1169, 2002.

Stein, et al., "The SH2 Domain Protein GRB-7 is Co-Amplified, Overexpressed and in a Tight Complex with HER2 in Breast Cancer", *The EMBO Journal*, 13(6): 1331-1340, 1994.

Takimoto, et al., "Clinical Applications of the Camptothecins", *Biochimica et Biophysica Acta*, 1400: 107-119, 1998.

Takahashi, et al., "Gene Expression Profiling of Clear Cell Renal Cell Carcinoma: Gene Identification and Prognostic Classification", *Proc. Natl. Acad. Sci. USA*, 98: 9754-9759, 2001.

Tontonoz, et al., "mPPARγ2: Tissue-Specific Regulator of an Adipocyte Enhancer", *Genes & Development*, 8: 1224-1234, 1994.

Torenbeek, et al., "Value of a Panel of Antibodies to Identify the Primary Origin of Adenocarcinomas Presenting as Bladder Carcinoma", *Histopathology*, 32: 20-27, 1998.

Torhorst, et al., "Tissue Microarrays for Rapid Linking of Molecular Changes to Clinical Endpoints", *American Journal of Pathology*, 159(6): 2249-2256, 2001.

Van De Rijn, Matt., "Expression of Cytokeratins 17 and 5 Identifies a Group of Breast Carcinomas with Poor Clinical Outcome", *American Journal of Pathology*, 161(6): 1991-1996, 2002.

Van't Veer, et al., "Gene Expression Profiling Predicts Clinical Outcome of Breast Cancer", *Nature*, 415: 530-536, 2002.

Wang, et al., "Monitoring Gene Expression Profile Changes in Ovarian Carcinomas Using cDNA Microarray", *Gene*, 229: 101-108, 1999.

Welsh, et al., "Analysis of Gene Expression Identifies Candidate Markers and Pharmacological Targets in Prostate Cancer", *Cancer Res.* 61: 5974-5978, 2001.

Welsh, et al., "Analysis of Gene Expression Profiles in Normal and Neoplastic Ovarian Tissue Samples Identifies Candidate Molecular Markers of Epithelial Ovarian Cancer", *Proc. Natl. Acad. Sci. USA*, 98: 1176-1181, 2001.

West, et al., "Predicting the Clinical Status of Human Breast Cancer by Using Gene Expression Profiles", *Proc. Natl. Acad. Sci. USA*, 98: 11462-11467, 2001.

Wolf, et al., "Prognostic Significance of Polo-Like Kinase (PLK) Expression in Non-Small Cell Lung Cancer", *Oncogene*, 14: 543-549, 1997.

Yang, et al., "Combining SSH and cDNA Microarrays for Rapid Identification of Differentially Expressed Genes", *Nucleic Acids Research*, 27(6): 1517-1523, 1999.

Yeoh, et al., "Classification, Subtype Discovery, and Prediction of Outcome in Pediatric Acute Lymphoblastic Leukemia by Gene Expression Profiling", *Cancer Cell*, 1: 133-143, 2002.

Zhou, et al., "Tumour Amplified Kinase STK15/BTAK Induces Centrosome Amplification, Aneuploidy and Transformation", *Nature Genetics*, 20: 189-193, 1998.

Zou, et al., "Application of cDNA Microarrays to Generate a Molecular Taxonomy Capable of Distinguishing Between Colon Cancer and Normal Colon", *Oncogene*, 21: 4855-4862, 2002.

International Search Report issued for corresponding PCT application PCT/US2004/026005.

Ring et al., "Novel prognostic immunohistochemical biomarker panel for estrogen receptor-positive breast cancer", US National Library of Medicine(NLM), Bethesda, MD, US, Jul. 1, 2006. XP002403235, Database accession No. NLM16809728 abstract.

International Search Report, PCT/US2006/005601, date of mailing Sep. 11, 2006.

\* cited by examiner

Breast ER+

Breast ER-

Ovarian Tree Panel

SEQUENCE LISTING

```
<160> NUMBER OF SEQ ID NOS: 409

<210> SEQ ID NO 1
<211> LENGTH: 588
<212> TYPE: PRT
<213> ORGANISM: Homo sapiens

<400> SEQUENCE: 1

Met Glu Ala Ala Asp Ala Ser Arg Ser Asn Gly Ser Ser Pro Glu Ala
1               5                   10                  15

Arg Asp Ala Arg Ser Pro Ser Gly Pro Ser Gly Ser Leu Glu Asn Gly
            20                  25                  30

Thr Lys Ala Asp Gly Lys Asp Ala Lys Thr Thr Asn Gly His Gly Gly
        35                  40                  45

Glu Ala Ala Glu Gly Lys Ser Leu Gly Ser Ala Leu Lys Pro Gly Glu
    50                  55                  60

Gly Arg Ser Ala Leu Phe Ala Gly Asn Glu Trp Arg Arg Pro Ile Ile
65                  70                  75                  80

Gln Phe Val Glu Ser Gly Asp Asp Lys Asn Ser Asn Tyr Phe Ser Met
                85                  90                  95

Asp Ser Met Glu Gly Lys Arg Ser Pro Tyr Ala Gly Leu Gln Leu Gly
            100                 105                 110

Ala Ala Lys Lys Pro Pro Val Thr Phe Ala Glu Lys Gly Glu Leu Arg
        115                 120                 125

Lys Ser Ile Phe Ser Glu Ser Arg Lys Pro Thr Val Ser Ile Met Glu
    130                 135                 140

Pro Gly Glu Thr Arg Arg Asn Ser Tyr Pro Arg Ala Asp Thr Gly Leu
145                 150                 155                 160
```

```
Phe Ser Arg Ser Lys Ser Gly Ser Glu Glu Val Leu Cys Asp Ser Cys
                165                 170                 175
Ile Gly Asn Lys Gln Lys Ala Val Lys Ser Cys Leu Val Cys Gln Ala
            180                 185                 190
Ser Phe Cys Glu Leu His Leu Lys Pro His Leu Glu Gly Ala Ala Phe
        195                 200                 205
Arg Asp His Gln Leu Leu Glu Pro Ile Arg Asp Phe Glu Ala Arg Lys
    210                 215                 220
Cys Pro Val His Gly Lys Thr Met Glu Leu Phe Cys Gln Thr Asp Gln
225                 230                 235                 240
Thr Cys Ile Cys Tyr Leu Cys Met Phe Gln Glu His Lys Asn His Ser
                245                 250                 255
Thr Val Thr Val Glu Glu Ala Lys Ala Glu Lys Glu Thr Glu Leu Ser
            260                 265                 270
Leu Gln Lys Glu Gln Leu Gln Leu Lys Ile Ile Glu Ile Glu Asp Glu
        275                 280                 285
Ala Glu Lys Trp Gln Lys Glu Lys Asp Arg Ile Lys Ser Phe Thr Thr
    290                 295                 300
Asn Glu Lys Ala Ile Leu Glu Gln Asn Phe Arg Asp Leu Val Arg Asp
305                 310                 315                 320
Leu Glu Lys Gln Lys Glu Glu Val Arg Ala Ala Leu Glu Gln Arg Glu
                325                 330                 335
Gln Asp Ala Val Asp Gln Val Lys Val Ile Met Asp Ala Leu Asp Glu
            340                 345                 350
Arg Ala Lys Val Leu His Glu Asp Lys Gln Thr Arg Glu Gln Leu His
        355                 360                 365
Ser Ile Ser Asp Ser Val Leu Phe Leu Gln Glu Phe Gly Ala Leu Met
    370                 375                 380
Ser Asn Tyr Ser Leu Pro Pro Leu Pro Thr Tyr His Val Leu Leu
385                 390                 395                 400
Glu Gly Glu Gly Leu Gly Gln Ser Leu Gly Asn Phe Lys Asp Asp Leu
                405                 410                 415
Leu Asn Val Cys Met Arg His Val Glu Lys Met Cys Lys Ala Asp Leu
            420                 425                 430
Ser Arg Asn Phe Ile Glu Arg Asn His Met Glu Asn Gly Gly Asp His
        435                 440                 445
Arg Tyr Val Asn Asn Tyr Thr Asn Ser Phe Gly Gly Glu Trp Ser Ala
    450                 455                 460
Pro Asp Thr Met Lys Arg Tyr Ser Met Tyr Leu Thr Pro Lys Gly Gly
465                 470                 475                 480
Val Arg Thr Ser Tyr Gln Pro Ser Ser Pro Gly Arg Phe Thr Lys Glu
                485                 490                 495
Thr Thr Gln Lys Asn Phe Asn Asn Leu Tyr Gly Thr Lys Gly Asn Tyr
            500                 505                 510
Thr Ser Arg Val Trp Glu Tyr Ser Ser Ile Gln Asn Ser Asp Asn
        515                 520                 525
Asp Leu Pro Val Val Gln Gly Ser Ser Phe Ser Leu Lys Gly Tyr
    530                 535                 540
Pro Ser Leu Met Arg Ser Gln Ser Pro Lys Ala Gln Pro Gln Thr Trp
545                 550                 555                 560
Lys Ser Gly Lys Gln Thr Met Leu Ser His Tyr Arg Pro Phe Tyr Val
                565                 570                 575
```

-continued

```
Asn Lys Gly Asn Gly Ile Gly Ser Asn Glu Ala Pro
        580                 585

<210> SEQ ID NO 2
<211> LENGTH: 568
<212> TYPE: PRT
<213> ORGANISM: Homo sapiens

<400> SEQUENCE: 2

Met Pro Ser Thr Asp Leu Leu Met Leu Lys Ala Phe Glu Pro Tyr Leu
1               5                   10                  15

Glu Ile Leu Glu Val Tyr Ser Thr Lys Ala Lys Asn Tyr Val Asn Gly
            20                  25                  30

His Cys Thr Lys Tyr Glu Pro Trp Gln Leu Ile Ala Trp Ser Val Val
        35                  40                  45

Trp Thr Leu Leu Ile Val Trp Gly Tyr Glu Phe Val Phe Gln Pro Glu
    50                  55                  60

Ser Leu Trp Ser Arg Phe Lys Lys Cys Phe Lys Leu Thr Arg Lys
65                  70                  75                  80

Met Pro Ile Ile Gly Arg Lys Ile Gln Asp Lys Leu Asn Lys Thr Lys
                85                  90                  95

Asp Asp Ile Ser Lys Asn Met Ser Phe Leu Lys Val Asp Lys Glu Tyr
            100                 105                 110

Val Lys Ala Leu Pro Ser Gln Gly Leu Ser Ser Ser Ala Val Leu Glu
        115                 120                 125

Lys Leu Lys Glu Tyr Ser Ser Met Asp Ala Phe Trp Gln Glu Gly Arg
    130                 135                 140

Ala Ser Gly Thr Val Tyr Ser Gly Glu Glu Lys Leu Thr Glu Leu Leu
145                 150                 155                 160

Val Lys Ala Tyr Gly Asp Phe Ala Trp Ser Asn Pro Leu His Pro Asp
                165                 170                 175

Ile Phe Pro Gly Leu Arg Lys Ile Glu Ala Glu Ile Val Arg Ile Ala
            180                 185                 190

Cys Ser Leu Phe Asn Gly Gly Pro Asp Ser Cys Gly Cys Val Thr Ser
        195                 200                 205

Gly Gly Thr Glu Ser Ile Leu Met Ala Cys Lys Ala Tyr Arg Asp Leu
    210                 215                 220

Ala Phe Glu Lys Gly Ile Lys Thr Pro Glu Ile Val Ala Pro Gln Ser
225                 230                 235                 240

Ala His Ala Ala Phe Asn Lys Ala Ser Tyr Phe Gly Met Lys Ile
                245                 250                 255

Val Arg Val Pro Leu Thr Lys Met Met Glu Val Asp Val Arg Ala Met
            260                 265                 270

Arg Arg Ala Ile Ser Arg Asn Thr Ala Met Leu Val Cys Ser Thr Pro
        275                 280                 285

Gln Phe Pro His Gly Val Ile Asp Pro Val Pro Glu Val Ala Lys Leu
    290                 295                 300

Ala Val Lys Tyr Lys Ile Pro Leu His Val Asp Ala Cys Leu Gly Gly
305                 310                 315                 320

Phe Leu Ile Val Phe Met Glu Lys Ala Gly Tyr Pro Leu Glu His Pro
                325                 330                 335

Phe Asp Phe Arg Val Lys Gly Val Thr Ser Ile Ser Ala Asp Thr His
            340                 345                 350

Lys Tyr Gly Tyr Ala Pro Lys Gly Ser Ser Leu Val Leu Tyr Ser Asp
        355                 360                 365
```

```
Lys Lys Tyr Arg Asn Tyr Gln Phe Phe Val Asp Thr Asp Trp Gln Gly
    370                 375                 380

Gly Ile Tyr Ala Ser Pro Thr Ile Ala Gly Ser Arg Pro Gly Gly Ile
385                 390                 395                 400

Ser Ala Ala Cys Trp Ala Ala Leu Met His Phe Gly Glu Asn Gly Tyr
                    405                 410                 415

Val Glu Ala Thr Lys Gln Ile Ile Lys Thr Ala Arg Phe Leu Lys Ser
                420                 425                 430

Glu Leu Glu Asn Ile Lys Gly Ile Phe Val Phe Gly Asn Pro Gln Leu
                435                 440                 445

Ser Val Ile Ala Leu Gly Ser Arg Asp Phe Asp Ile Tyr Arg Leu Ser
450                 455                 460

Asn Leu Met Thr Ala Lys Gly Trp Asn Leu Asn Gln Leu Gln Phe Pro
465                 470                 475                 480

Pro Ser Ile His Phe Cys Ile Thr Leu Leu His Ala Arg Lys Arg Val
                485                 490                 495

Ala Ile Gln Phe Leu Lys Asp Ile Arg Glu Ser Val Thr Gln Ile Met
                500                 505                 510

Lys Asn Pro Lys Ala Lys Thr Thr Gly Met Gly Ala Ile Tyr Gly Met
                515                 520                 525

Ala Gln Thr Thr Val Asp Arg Asn Met Val Ala Glu Leu Ser Ser Val
                530                 535                 540

Phe Leu Asp Ser Leu Tyr Ser Thr Asp Thr Val Thr Gln Gly Ser Gln
545                 550                 555                 560

Met Asn Gly Ser Pro Lys Pro His
                565

<210> SEQ ID NO 3
<211> LENGTH: 507
<212> TYPE: PRT
<213> ORGANISM: Homo sapiens

<400> SEQUENCE: 3

Met Ala Gly Ala Gly Pro Lys Arg Arg Ala Leu Ala Ala Pro Ala Ala
1               5                   10                  15

Glu Glu Lys Glu Glu Ala Arg Glu Lys Met Leu Ala Ala Lys Ser Ala
                20                  25                  30

Asp Gly Ser Ala Pro Ala Gly Glu Gly Glu Gly Val Thr Leu Gln Arg
            35                  40                  45

Asn Ile Thr Leu Leu Asn Gly Val Ala Ile Ile Val Gly Thr Ile Ile
        50                  55                  60

Gly Ser Gly Ile Phe Val Thr Pro Thr Gly Val Leu Lys Glu Ala Gly
65                  70                  75                  80

Ser Pro Gly Leu Ala Leu Val Val Trp Ala Ala Cys Gly Val Phe Ser
                85                  90                  95

Ile Val Gly Ala Leu Cys Tyr Ala Glu Leu Gly Thr Thr Ile Ser Lys
                100                 105                 110

Ser Gly Gly Asp Tyr Ala Tyr Met Leu Glu Val Tyr Gly Ser Leu Pro
            115                 120                 125

Ala Phe Leu Lys Leu Trp Ile Glu Leu Leu Ile Ile Arg Pro Ser Ser
        130                 135                 140

Gln Tyr Ile Val Ala Leu Val Phe Ala Thr Tyr Leu Leu Lys Pro Leu
145                 150                 155                 160

Phe Pro Thr Cys Pro Val Pro Glu Glu Ala Ala Lys Leu Val Ala Cys
```

```
                    165                 170                 175
Leu Cys Val Leu Leu Thr Ala Val Asn Cys Tyr Ser Val Lys Ala
                180                 185                 190
Ala Thr Arg Val Gln Asp Ala Phe Ala Ala Lys Leu Leu Ala Leu
                195                 200                 205
Ala Leu Ile Ile Leu Leu Gly Phe Val Gln Ile Gly Lys Gly Asp Val
                210                 215                 220
Ser Asn Leu Asp Pro Asn Phe Ser Phe Glu Gly Thr Lys Leu Asp Val
225                 230                 235                 240
Gly Asn Ile Val Leu Ala Leu Tyr Ser Gly Leu Phe Ala Tyr Gly Gly
                245                 250                 255
Trp Asn Tyr Leu Asn Phe Val Thr Glu Glu Met Ile Asn Pro Tyr Arg
                260                 265                 270
Asn Leu Pro Leu Ala Ile Ile Ile Ser Leu Pro Ile Val Thr Leu Val
                275                 280                 285
Tyr Val Leu Thr Asn Leu Ala Tyr Phe Thr Thr Leu Ser Thr Glu Gln
                290                 295                 300
Met Leu Ser Ser Glu Ala Val Ala Val Asp Phe Gly Asn Tyr His Leu
305                 310                 315                 320
Gly Val Met Ser Trp Ile Ile Pro Val Phe Val Gly Leu Ser Cys Phe
                325                 330                 335
Gly Ser Val Asn Gly Ser Leu Phe Thr Ser Ser Arg Leu Phe Phe Val
                340                 345                 350
Gly Ser Arg Glu Gly His Leu Pro Ser Ile Leu Ser Met Ile His Pro
                355                 360                 365
Gln Leu Leu Thr Pro Val Pro Ser Leu Val Phe Thr Cys Val Met Thr
                370                 375                 380
Leu Leu Tyr Ala Phe Ser Lys Asp Ile Phe Ser Val Ile Asn Phe Phe
385                 390                 395                 400
Ser Phe Phe Asn Trp Leu Cys Val Ala Leu Ala Ile Ile Gly Met Ile
                405                 410                 415
Trp Leu Arg His Arg Lys Pro Glu Leu Glu Arg Pro Ile Lys Val Asn
                420                 425                 430
Leu Ala Leu Pro Val Phe Phe Ile Leu Ala Cys Leu Phe Leu Ile Ala
                435                 440                 445
Val Ser Phe Trp Lys Thr Pro Val Glu Cys Gly Ile Gly Phe Thr Ile
                450                 455                 460
Ile Leu Ser Gly Leu Pro Val Tyr Phe Phe Gly Val Trp Trp Lys Asn
465                 470                 475                 480
Lys Pro Lys Trp Leu Leu Gln Gly Ile Phe Ser Thr Thr Val Leu Cys
                485                 490                 495
Gln Lys Leu Met Gln Val Val Pro Gln Glu Thr
                500                 505

<210> SEQ ID NO 4
<211> LENGTH: 513
<212> TYPE: PRT
<213> ORGANISM: Homo sapiens

<400> SEQUENCE: 4

Met Ala Met Glu Ile Asp Ser Arg Pro Gly Gly Leu Pro Gly Ser Ser
1               5                   10                  15
Cys Asn Leu Gly Ala Ala Arg Glu His Met Gln Ala Val Thr Arg Asn
                20                  25                  30
```

-continued

```
Tyr Ile Thr His Pro Arg Val Thr Tyr Arg Thr Val Cys Ser Val Asn
        35                  40                  45

Gly Pro Leu Val Val Leu Asp Arg Val Lys Phe Ala Gln Tyr Ala Glu
    50                  55                  60

Ile Val His Phe Thr Leu Pro Asp Gly Thr Gln Arg Ser Gly Gln Val
 65                  70                  75                  80

Leu Glu Val Ala Gly Thr Lys Ala Ile Val Gln Val Phe Glu Gly Thr
                85                  90                  95

Ser Gly Ile Asp Ala Arg Lys Thr Thr Cys Glu Phe Thr Gly Asp Ile
            100                 105                 110

Leu Arg Thr Pro Val Ser Glu Asp Met Leu Gly Arg Val Phe Asn Gly
        115                 120                 125

Ser Gly Lys Pro Ile Asp Lys Gly Pro Val Val Met Ala Glu Asp Phe
    130                 135                 140

Leu Asp Ile Asn Gly Gln Pro Ile Asn Pro His Ser Arg Ile Tyr Pro
145                 150                 155                 160

Glu Glu Met Ile Gln Thr Gly Ile Ser Pro Ile Asp Val Met Asn Ser
                165                 170                 175

Ile Ala Arg Gly Gln Lys Ile Pro Ile Phe Ser Ala Ala Gly Leu Pro
            180                 185                 190

His Asn Glu Ile Ala Ala Gln Ile Cys Arg Gln Ala Gly Leu Val Lys
        195                 200                 205

Lys Ser Lys Ala Val Leu Asp Tyr His Asp Asn Phe Ala Ile Val
    210                 215                 220

Phe Ala Ala Met Gly Val Asn Met Glu Thr Ala Arg Phe Phe Lys Ser
225                 230                 235                 240

Asp Phe Glu Gln Asn Gly Thr Met Gly Asn Val Cys Leu Phe Leu Asn
                245                 250                 255

Leu Ala Asn Asp Pro Thr Ile Glu Arg Ile Ile Thr Pro Arg Leu Ala
            260                 265                 270

Leu Thr Thr Ala Glu Phe Leu Ala Tyr Gln Cys Glu Lys His Val Leu
        275                 280                 285

Val Ile Leu Thr Asp Met Ser Ser Tyr Ala Glu Ala Leu Arg Glu Val
    290                 295                 300

Ser Ala Ala Arg Glu Glu Val Pro Gly Arg Arg Gly Phe Pro Gly Tyr
305                 310                 315                 320

Met Tyr Thr Asp Leu Ala Thr Ile Tyr Glu Arg Ala Gly Arg Val Glu
                325                 330                 335

Gly Arg Gly Gly Ser Ile Thr Gln Ile Pro Ile Leu Thr Met Pro Asn
            340                 345                 350

Asp Asp Ile Thr His Pro Ile Pro Asp Leu Thr Gly Phe Ile Thr Glu
        355                 360                 365

Gly Gln Ile Tyr Val Asp Arg Gln Leu His Asn Arg Gln Ile Tyr Pro
    370                 375                 380

Pro Ile Asn Val Leu Pro Ser Leu Ser Arg Leu Met Lys Ser Ala Ile
385                 390                 395                 400

Gly Glu Gly Met Thr Arg Lys Asp His Gly Asp Val Ser Asn Gln Leu
                405                 410                 415

Tyr Ala Cys Tyr Ala Ile Gly Lys Asp Val Gln Ala Met Lys Ala Val
            420                 425                 430

Val Gly Glu Glu Ala Leu Thr Ser Glu Asp Leu Leu Tyr Leu Glu Phe
        435                 440                 445

Leu Gln Lys Phe Glu Lys Asn Phe Ile Asn Gln Gly Pro Tyr Glu Asn
```

-continued

```
               450                 455                 460
Arg Ser Val Phe Glu Ser Leu Asp Leu Gly Trp Lys Leu Leu Arg Ile
465                 470                 475                 480

Phe Pro Lys Glu Met Leu Lys Arg Ile Pro Gln Ala Val Ile Asp Glu
                485                 490                 495

Phe Tyr Ser Arg Glu Gly Ala Leu Gln Asp Leu Ala Pro Asp Thr Ala
                500                 505                 510

Leu

<210> SEQ ID NO 5
<211> LENGTH: 772
<212> TYPE: PRT
<213> ORGANISM: Homo sapiens

<400> SEQUENCE: 5

Met Tyr Pro Gln Gly Arg His Pro Ala Pro His Gln Pro Gly Gln Pro
1               5                   10                  15

Gly Phe Lys Phe Thr Val Ala Glu Ser Cys Asp Arg Ile Lys Asp Glu
                20                  25                  30

Phe Gln Phe Leu Gln Ala Gln Tyr His Ser Leu Lys Val Glu Tyr Asp
            35                  40                  45

Lys Leu Ala Asn Glu Lys Thr Glu Met Gln Arg His Tyr Val Met Tyr
50                  55                  60

Tyr Glu Met Ser Tyr Gly Leu Asn Ile Glu Met His Lys Gln Thr Glu
65                  70                  75                  80

Ile Ala Lys Arg Leu Asn Thr Ile Leu Ala Gln Ile Met Pro Phe Leu
                85                  90                  95

Ser Gln Glu His Gln Gln Val Ala Gln Ala Val Glu Arg Ala Lys
            100                 105                 110

Gln Val Thr Met Thr Glu Leu Asn Ala Ile Ile Gly Gln Gln Gln Leu
            115                 120                 125

Gln Ala Gln His Leu Ser His Ala Thr His Gly Pro Pro Val Gln Leu
        130                 135                 140

Pro Pro His Pro Ser Gly Leu Gln Pro Pro Gly Ile Pro Pro Val Thr
145                 150                 155                 160

Gly Ser Ser Ser Gly Leu Leu Ala Leu Gly Ala Leu Gly Ser Gln Ala
                165                 170                 175

His Leu Thr Val Lys Asp Glu Lys Asn His His Glu Leu Asp His Arg
            180                 185                 190

Glu Arg Glu Ser Ser Ala Asn Asn Ser Val Ser Pro Ser Glu Ser Leu
        195                 200                 205

Arg Ala Ser Glu Lys His Arg Gly Ser Ala Asp Tyr Ser Met Glu Ala
    210                 215                 220

Lys Lys Arg Lys Val Glu Glu Lys Asp Ser Leu Ser Arg Tyr Asp Ser
225                 230                 235                 240

Asp Gly Asp Lys Ser Asp Asp Leu Val Val Asp Val Ser Asn Glu Asp
                245                 250                 255

Pro Ala Thr Pro Arg Val Ser Pro Ala His Ser Pro Pro Glu Asn Gly
            260                 265                 270

Leu Asp Lys Ala Arg Ser Leu Lys Lys Asp Ala Pro Thr Ser Pro Ala
        275                 280                 285

Ser Val Ala Ser Ser Ser Ser Thr Pro Ser Ser Lys Thr Lys Asp Leu
    290                 295                 300

Gly His Asn Asp Lys Ser Ser Thr Pro Gly Leu Lys Ser Asn Thr Pro
```

-continued

```
              305                 310                 315                 320
Thr Pro Arg Asn Asp Ala Pro Thr Pro Gly Thr Ser Thr Thr Pro Gly
                325                 330                 335

Leu Arg Ser Met Pro Gly Lys Pro Pro Gly Met Asp Pro Ile Gly Ile
                340                 345                 350

Met Ala Ser Ala Leu Arg Thr Pro Ile Ser Ile Thr Ser Ser Tyr Ala
                355                 360                 365

Ala Pro Phe Ala Met Met Ser His His Glu Met Asn Gly Ser Leu Thr
                370                 375                 380

Ser Pro Gly Ala Tyr Ala Gly Leu His Asn Ile Pro Pro Gln Met Ser
385                 390                 395                 400

Ala Ala Ala Ala Ala Ala Ala Ala Tyr Gly Arg Ser Pro Met Val
                    405                 410                 415

Ser Phe Gly Ala Val Gly Phe Asp Pro His Pro Met Arg Ala Thr
                420                 425                 430

Gly Leu Pro Ser Ser Leu Ala Ser Ile Pro Gly Gly Lys Pro Ala Tyr
                435                 440                 445

Ser Phe His Val Ser Ala Asp Gly Gln Met Gln Pro Val Pro Phe Pro
                450                 455                 460

His Asp Ala Leu Ala Gly Pro Gly Ile Pro Arg His Ala Arg Gln Ile
465                 470                 475                 480

Asn Thr Leu Ser His Gly Gly Val Val Cys Ala Val Thr Ile Ser Asn
                485                 490                 495

Pro Ser Arg His Val Tyr Thr Gly Gly Lys Gly Cys Val Lys Ile Trp
                500                 505                 510

Asp Ile Ser Gln Pro Gly Ser Lys Ser Pro Ile Ser Gln Leu Asp Cys
                515                 520                 525

Leu Asn Arg Asp Asn Tyr Met Arg Ser Cys Lys Leu His Pro Asp Gly
                530                 535                 540

Arg Thr Leu Ile Val Gly Gly Glu Gly Ser Thr Leu Thr Ile Trp Asp
545                 550                 555                 560

Leu Ala Ser Pro Thr Pro Arg Ile Lys Ala Glu Leu Thr Ser Ser Ala
                565                 570                 575

Pro Ala Cys Tyr Ala Leu Ala Ile Ser Pro Asp Ala Lys Val Cys Phe
                580                 585                 590

Ser Cys Cys Ser Asp Gly Asn Ile Ala Val Trp Asp Leu His Asn Gln
                595                 600                 605

Thr Leu Val Arg Gln Phe Gln Gly His Thr Asp Gly Ala Ser Cys Ile
                610                 615                 620

Asp Ile Ser His Asp Gly Thr Lys Leu Trp Thr Gly Gly Leu Asp Asn
625                 630                 635                 640

Thr Val Arg Ser Trp Asp Leu Arg Glu Gly Arg Gln Leu Gln Gln His
                645                 650                 655

Asp Phe Thr Ser Gln Ile Phe Ser Leu Gly Tyr Cys Pro Thr Gly Glu
                660                 665                 670

Trp Leu Ala Val Gly Met Glu Ser Ser Asn Val Glu Val Leu His His
                675                 680                 685

Thr Lys Pro His Lys Tyr Gln Leu His Leu His Glu Ser Cys Val Leu
                690                 695                 700

Ser Leu Lys Phe Ala Tyr Cys Gly Lys Trp Phe Val Ser Thr Gly Lys
705                 710                 715                 720

Asp Asn Leu Leu Asn Ala Trp Arg Thr Pro Tyr Gly Ala Ser Ile Ser
                725                 730                 735
```

-continued

```
Gln Ser Lys Glu Ser Ser Val Leu Ser Cys Asp Ile Ser Ala Asp
            740                 745                 750
Asp Lys Tyr Ile Val Thr Gly Ser Gly Asp Lys Lys Ala Thr Val Tyr
        755                 760                 765
Glu Val Ile Tyr
    770

<210> SEQ ID NO 6
<211> LENGTH: 501
<212> TYPE: PRT
<213> ORGANISM: Homo sapiens

<400> SEQUENCE: 6

Met Val Arg Lys Pro Val Val Ser Thr Ile Ser Lys Gly Gly Tyr Leu
1               5                   10                  15
Gln Gly Asn Val Asn Gly Arg Leu Pro Ser Leu Gly Asn Lys Glu Pro
            20                  25                  30
Pro Gly Gln Glu Lys Val Gln Leu Lys Arg Lys Val Thr Leu Leu Arg
        35                  40                  45
Gly Val Ser Ile Ile Ile Gly Thr Ile Ile Gly Ala Gly Ile Phe Ile
    50                  55                  60
Ser Pro Lys Gly Val Leu Gln Asn Thr Gly Ser Val Gly Met Ser Leu
65                  70                  75                  80
Thr Ile Trp Thr Val Cys Gly Val Leu Ser Leu Phe Gly Ala Leu Ser
                85                  90                  95
Tyr Ala Glu Leu Gly Thr Thr Ile Lys Lys Ser Gly Gly His Tyr Thr
            100                 105                 110
Tyr Ile Leu Glu Val Phe Gly Pro Leu Pro Ala Phe Val Arg Val Trp
        115                 120                 125
Val Glu Leu Leu Ile Ile Arg Pro Ala Ala Thr Ala Val Ile Ser Leu
    130                 135                 140
Ala Phe Gly Arg Tyr Ile Leu Glu Pro Phe Phe Ile Gln Cys Glu Ile
145                 150                 155                 160
Pro Glu Leu Ala Ile Lys Leu Ile Thr Ala Val Gly Ile Thr Val Val
                165                 170                 175
Met Val Leu Asn Ser Met Ser Val Ser Trp Ser Ala Arg Ile Gln Ile
            180                 185                 190
Phe Leu Thr Phe Cys Lys Leu Thr Ala Ile Leu Ile Ile Ile Val Pro
        195                 200                 205
Gly Val Met Gln Leu Ile Lys Gly Gln Thr Gln Asn Phe Lys Asp Ala
    210                 215                 220
Phe Ser Gly Arg Asp Ser Ser Ile Thr Arg Leu Pro Leu Ala Phe Tyr
225                 230                 235                 240
Tyr Gly Met Tyr Ala Tyr Ala Gly Trp Phe Tyr Leu Asn Phe Val Thr
                245                 250                 255
Glu Glu Val Glu Asn Pro Glu Lys Thr Ile Pro Leu Ala Ile Cys Ile
            260                 265                 270
Ser Met Ala Ile Val Thr Ile Gly Tyr Val Leu Thr Asn Val Ala Tyr
        275                 280                 285
Phe Thr Thr Ile Asn Ala Glu Glu Leu Leu Leu Ser Asn Ala Val Ala
    290                 295                 300
Val Thr Phe Ser Glu Arg Leu Leu Gly Asn Phe Ser Leu Ala Val Pro
305                 310                 315                 320
Ile Phe Val Ala Leu Ser Cys Phe Gly Ser Met Asn Gly Gly Val Phe
```

-continued

```
            325                 330                 335
Ala Val Ser Arg Leu Phe Tyr Val Ala Ser Arg Glu Gly His Leu Pro
            340                 345                 350

Glu Ile Leu Ser Met Ile His Val Arg Lys His Thr Pro Leu Pro Ala
            355                 360                 365

Val Ile Val Leu His Pro Leu Thr Met Ile Met Leu Phe Ser Gly Asp
            370                 375                 380

Leu Asp Ser Leu Leu Asn Phe Leu Ser Phe Ala Arg Trp Leu Phe Ile
385                 390                 395                 400

Gly Leu Ala Val Ala Gly Leu Ile Tyr Leu Arg Tyr Lys Cys Pro Asp
                405                 410                 415

Met His Arg Pro Phe Lys Val Pro Leu Phe Ile Pro Ala Leu Phe Ser
                420                 425                 430

Phe Thr Cys Leu Phe Met Val Ala Leu Ser Leu Tyr Ser Asp Pro Phe
            435                 440                 445

Ser Thr Gly Ile Gly Phe Val Ile Thr Leu Thr Gly Val Pro Ala Tyr
            450                 455                 460

Tyr Leu Phe Ile Ile Trp Asp Lys Lys Pro Arg Trp Phe Arg Ile Met
465                 470                 475                 480

Ser Glu Lys Ile Thr Arg Thr Leu Gln Ile Ile Leu Glu Val Val Pro
                485                 490                 495

Glu Glu Asp Lys Leu
                500

<210> SEQ ID NO 7
<211> LENGTH: 529
<212> TYPE: PRT
<213> ORGANISM: Homo sapiens

<400> SEQUENCE: 7

Met Glu His Arg Ile Val Gly Pro Gly Pro Tyr Arg Ala Thr Arg Leu
1               5                   10                  15

Trp Asn Glu Thr Val Glu Leu Phe Arg Ala Lys Met Pro Leu Arg Lys
            20                  25                  30

His Arg Cys Arg Phe Lys Ser Tyr Glu His Cys Phe Thr Ala Ala Glu
        35                  40                  45

Ala Val Asp Trp Leu His Glu Leu Leu Arg Cys Ser Gln Asn Phe Gly
    50                  55                  60

Pro Glu Val Thr Arg Lys Gln Thr Val Gln Leu Leu Lys Lys Phe Leu
65                  70                  75                  80

Lys Asn His Val Ile Glu Asp Ile Lys Gly Lys Trp Gly Glu Glu Asp
                85                  90                  95

Phe Glu Asp Asn Arg His Leu Tyr Arg Phe Pro Ser Ser Pro Leu
            100                 105                 110

Lys Pro Tyr Pro Lys Lys Pro Pro Asn Gln Lys Asp Val Ile Lys Phe
        115                 120                 125

Pro Glu Trp Asn Asp Leu Pro Pro Gly Thr Ser Gln Glu Asn Ile Pro
    130                 135                 140

Val Arg Pro Val Met Asn Ser Glu Met Trp Tyr Lys Arg His Ser
145                 150                 155                 160

Ile Ala Ile Gly Glu Val Pro Ala Cys Arg Leu Val His Arg Arg Gln
                165                 170                 175

Leu Thr Glu Ala Asn Val Glu Glu Ile Trp Lys Ser Met Thr Leu Ser
            180                 185                 190
```

```
Tyr Leu Gln Lys Ile Leu Gly Leu Asp Ser Leu Glu Glu Val Leu Asp
            195                 200                 205

Val Lys Leu Val Asn Ser Lys Phe Ile Ile His Asn Val Tyr Ser Val
210                 215                 220

Ser Lys Gln Gly Val Val Ile Leu Asp Asp Lys Ser Lys Glu Leu Pro
225                 230                 235                 240

His Trp Val Leu Ser Ala Met Lys Cys Leu Ala Asn Trp Pro Asn Cys
            245                 250                 255

Ser Asp Leu Lys Gln Pro Met Tyr Leu Gly Phe Glu Lys Asp Val Phe
            260                 265                 270

Lys Thr Ile Ala Asp Tyr Tyr Gly His Leu Lys Glu Pro Leu Leu Thr
            275                 280                 285

Phe His Leu Phe Asp Ala Phe Val Ser Val Leu Gly Leu Leu Gln Lys
            290                 295                 300

Glu Lys Val Ala Val Glu Ala Phe Gln Ile Cys Cys Leu Leu Leu Pro
305                 310                 315                 320

Pro Glu Asn Arg Arg Lys Leu Gln Leu Leu Met Arg Met Met Ala Arg
                325                 330                 335

Ile Cys Leu Asn Lys Glu Met Pro Pro Leu Cys Asp Gly Phe Gly Thr
            340                 345                 350

Arg Thr Leu Met Val Gln Thr Phe Ser Arg Cys Ile Leu Cys Ser Lys
            355                 360                 365

Asp Glu Val Asp Leu Asp Glu Leu Leu Ala Ala Arg Leu Val Thr Phe
370                 375                 380

Leu Met Asp Asn Tyr Gln Glu Ile Leu Lys Val Pro Leu Ala Leu Gln
385                 390                 395                 400

Thr Ser Ile Glu Glu Arg Val Ala His Leu Arg Arg Val Gln Ile Lys
                405                 410                 415

Tyr Pro Gly Ala Asp Met Asp Ile Thr Leu Ser Ala Pro Ser Phe Cys
            420                 425                 430

Arg Gln Ile Ser Pro Glu Glu Phe Glu Tyr Gln Arg Ser Tyr Gly Ser
            435                 440                 445

Gln Glu Pro Leu Ala Ala Leu Glu Glu Val Ile Thr Asp Ala Lys
            450                 455                 460

Leu Ser Asn Lys Glu Lys Lys Lys Leu Lys Gln Phe Gln Lys Ser
465                 470                 475                 480

Tyr Pro Glu Val Tyr Gln Glu Arg Phe Pro Thr Pro Glu Ser Ala Ala
            485                 490                 495

Leu Leu Phe Pro Glu Lys Pro Lys Pro Gln Leu Leu Met Trp
            500                 505                 510

Ala Leu Lys Lys Pro Phe Gln Pro Phe Gln Arg Thr Arg Ser Phe Arg
            515                 520                 525

Met
```

<210> SEQ ID NO 8
<211> LENGTH: 696
<212> TYPE: PRT
<213> ORGANISM: Homo sapiens

<400> SEQUENCE: 8

```
Met Lys Phe Ala Glu His Leu Ser Ala His Ile Thr Pro Glu Trp Arg
1               5                   10                  15

Lys Gln Tyr Ile Gln Tyr Glu Ala Phe Lys Asp Met Leu Tyr Ser Ala
            20                  25                  30
```

-continued

```
Gln Asp Gln Ala Pro Ser Val Glu Val Thr Asp Glu Asp Thr Val Lys
        35                  40                  45

Arg Tyr Phe Ala Lys Phe Glu Glu Lys Phe Gln Thr Cys Glu Lys
 50                  55                  60

Glu Leu Ala Lys Ile Asn Thr Phe Tyr Ser Lys Leu Ala Glu Ala
 65                  70                  75                  80

Gln Arg Arg Phe Ala Thr Leu Gln Asn Glu Leu Gln Ser Ser Leu Asp
                    85                  90                  95

Ala Gln Lys Glu Ser Thr Gly Val Thr Thr Leu Arg Gln Arg Lys
            100                 105                 110

Pro Val Phe His Leu Ser His Glu Arg Val Gln His Arg Asn Ile
                115                 120                 125

Lys Asp Leu Lys Leu Ala Phe Ser Glu Phe Tyr Leu Ser Leu Ile Leu
    130                 135                 140

Leu Gln Asn Tyr Gln Asn Leu Asn Phe Thr Gly Phe Arg Lys Ile Leu
145                 150                 155                 160

Lys Lys His Asp Lys Ile Leu Glu Thr Ser Arg Gly Ala Asp Trp Arg
                165                 170                 175

Val Ala His Val Glu Val Ala Pro Phe Tyr Thr Cys Lys Lys Ile Asn
                180                 185                 190

Gln Leu Ile Ser Glu Thr Glu Ala Val Val Thr Asn Glu Leu Glu Asp
                195                 200                 205

Gly Asp Arg Gln Lys Ala Met Lys Arg Leu Arg Val Pro Pro Leu Gly
    210                 215                 220

Ala Ala Gln Pro Ala Pro Ala Trp Thr Thr Phe Arg Val Gly Leu Phe
225                 230                 235                 240

Cys Gly Ile Phe Ile Val Leu Asn Ile Thr Leu Val Leu Ala Ala Val
                245                 250                 255

Phe Lys Leu Glu Thr Asp Arg Ser Ile Trp Pro Leu Ile Arg Ile Tyr
                260                 265                 270

Arg Gly Gly Phe Leu Leu Ile Glu Phe Leu Phe Leu Leu Gly Ile Asn
                275                 280                 285

Thr Tyr Gly Trp Arg Gln Ala Gly Val Asn His Val Leu Ile Phe Glu
                290                 295                 300

Leu Asn Pro Arg Ser Asn Leu Ser His Gln His Leu Phe Glu Ile Ala
305                 310                 315                 320

Gly Phe Leu Gly Ile Leu Trp Cys Leu Ser Leu Leu Ala Cys Phe Phe
                325                 330                 335

Ala Pro Ile Ser Val Ile Pro Thr Tyr Val Tyr Pro Leu Ala Leu Tyr
                340                 345                 350

Gly Phe Met Val Phe Leu Ile Asn Pro Thr Lys Thr Phe Tyr Tyr
                355                 360                 365

Lys Ser Arg Phe Trp Leu Leu Lys Leu Leu Phe Arg Val Phe Thr Ala
    370                 375                 380

Pro Phe His Lys Val Gly Phe Ala Asp Phe Trp Leu Ala Asp Gln Leu
385                 390                 395                 400

Asn Ser Leu Ser Val Ile Leu Met Asp Leu Glu Tyr Met Ile Cys Phe
                405                 410                 415

Tyr Ser Leu Glu Leu Lys Trp Asp Glu Ser Lys Gly Leu Leu Pro Asn
                420                 425                 430

Asn Ser Glu Glu Ser Gly Ile Cys His Lys Tyr Thr Tyr Gly Val Arg
            435                 440                 445

Ala Ile Val Gln Cys Ile Pro Ala Trp Leu Arg Phe Ile Gln Cys Leu
```

```
                450                 455                 460
Arg Arg Tyr Arg Asp Thr Lys Arg Ala Phe Pro His Leu Val Asn Ala
465                 470                 475                 480

Gly Lys Tyr Ser Thr Thr Phe Phe Met Val Thr Phe Ala Ala Leu Tyr
                485                 490                 495

Ser Thr His Lys Glu Arg Gly His Ser Asp Thr Met Val Phe Phe Tyr
                500                 505                 510

Leu Trp Ile Val Phe Tyr Ile Ile Ser Ser Cys Tyr Thr Leu Ile Trp
                515                 520                 525

Asp Leu Lys Met Asp Trp Gly Leu Phe Asp Lys Asn Ala Gly Glu Asn
530                 535                 540

Thr Phe Leu Arg Glu Glu Ile Val Tyr Pro Gln Lys Ala Tyr Tyr Tyr
545                 550                 555                 560

Cys Ala Ile Ile Glu Asp Val Ile Leu Arg Phe Ala Trp Thr Ile Gln
                565                 570                 575

Ile Ser Ile Thr Ser Thr Thr Leu Leu Pro His Ser Gly Asp Ile Ile
                580                 585                 590

Ala Thr Val Phe Ala Pro Leu Glu Val Phe Arg Arg Phe Val Trp Asn
                595                 600                 605

Phe Phe Arg Leu Glu Asn Glu His Leu Asn Asn Cys Gly Glu Phe Arg
                610                 615                 620

Ala Val Arg Asp Ile Ser Val Ala Pro Leu Asn Ala Asp Asp Gln Thr
625                 630                 635                 640

Leu Leu Glu Gln Met Met Asp Gln Asp Gly Val Arg Asn Arg Gln
                645                 650                 655

Lys Asn Arg Ser Trp Lys Tyr Asn Gln Ser Ile Ser Leu Arg Arg Pro
                660                 665                 670

Arg Leu Ala Ser Gln Ser Lys Ala Arg Asp Thr Lys Val Leu Ile Glu
                675                 680                 685

Asp Thr Asp Asp Glu Ala Asn Thr
                690                 695

<210> SEQ ID NO 9
<211> LENGTH: 231
<212> TYPE: PRT
<213> ORGANISM: Homo sapiens

<400> SEQUENCE: 9

Met Ser Gly Arg Ser Val Arg Ala Glu Thr Arg Ser Arg Ala Lys Asp
1               5                   10                  15

Asp Ile Lys Arg Val Met Ala Ala Ile Glu Lys Val Arg Lys Trp Glu
                20                  25                  30

Lys Lys Trp Val Thr Val Gly Asp Thr Ser Leu Arg Ile Tyr Lys Trp
                35                  40                  45

Val Pro Val Thr Glu Pro Lys Val Asp Asp Lys Asn Lys Asn Lys Lys
                50                  55                  60

Lys Gly Lys Asp Glu Lys Cys Gly Ser Glu Val Thr Thr Pro Glu Asn
65                  70                  75                  80

Ser Ser Ser Pro Gly Met Met Asp Met His Asp Asp Asn Ser Asn Gln
                85                  90                  95

Ser Ser Ile Ala Asp Ala Ser Pro Ile Lys Gln Glu Asn Ser Ser Asn
                100                 105                 110

Ser Ser Pro Ala Pro Glu Pro Asn Ser Ala Val Pro Ser Asp Gly Thr
                115                 120                 125
```

```
Glu Ala Lys Val Asp Glu Ala Gln Ala Asp Gly Lys Glu His Pro Gly
        130                 135                 140

Ala Glu Asp Ala Ser Asp Glu Gln Asn Ser Gln Ser Ser Met Glu His
145                 150                 155                 160

Ser Met Asn Ser Ser Glu Lys Val Asp Arg Gln Pro Ser Gly Asp Ser
                165                 170                 175

Gly Leu Ala Ala Glu Thr Ser Ala Ile Ser Gln Val Pro Arg Ser Arg
            180                 185                 190

Ser Gln Arg Gly Ser Gln Ile Gly Arg Glu Pro Ile Gly Leu Ser Gly
        195                 200                 205

Asp Leu Glu Gly Val Pro Pro Ser Lys Lys Met Lys Leu Glu Ala Ser
    210                 215                 220

Gln Gln Asn Ser Glu Glu Met
225                 230
```

<210> SEQ ID NO 10
<211> LENGTH: 2649
<212> TYPE: PRT
<213> ORGANISM: Homo sapiens

<400> SEQUENCE: 10

```
Met His Ser Ser Tyr Ser Tyr Arg Ser Ser Asp Ser Val Phe Ser
1               5                   10                  15

Asn Thr Thr Ser Thr Arg Thr Ser Leu Asp Ser Asn Glu Asn Leu Leu
                20                  25                  30

Leu Val His Cys Gly Pro Thr Leu Ile Asn Ser Cys Ile Ser Phe Gly
            35                  40                  45

Ser Glu Ser Phe Asp Gly His Arg Leu Glu Met Leu Gln Gln Ile Ala
    50                  55                  60

Asn Arg Val Gln Arg Asp Ser Val Ile Cys Glu Asp Lys Leu Ile Leu
65                  70                  75                  80

Ala Gly Asn Ala Leu Gln Ser Asp Ser Lys Arg Leu Glu Ser Gly Val
                85                  90                  95

Gln Phe Gln Asn Glu Ala Glu Ile Ala Gly Tyr Ile Leu Glu Cys Glu
                100                 105                 110

Asn Leu Leu Arg Gln His Val Ile Asp Val Gln Ile Leu Ile Asp Gly
            115                 120                 125

Lys Tyr Tyr Gln Ala Asp Gln Leu Val Gln Arg Val Ala Lys Leu Arg
    130                 135                 140

Asp Glu Ile Met Ala Leu Arg Asn Glu Cys Ser Ser Val Tyr Ser Lys
145                 150                 155                 160

Gly Arg Ile Leu Thr Thr Glu Gln Thr Lys Leu Met Ile Ser Gly Ile
                165                 170                 175

Thr Gln Ser Leu Asn Ser Gly Phe Ala Gln Thr Leu His Pro Ser Leu
            180                 185                 190

Thr Ser Gly Leu Thr Gln Ser Leu Thr Pro Ser Leu Thr Ser Ser Ser
        195                 200                 205

Met Thr Ser Gly Leu Ser Ser Gly Met Thr Ser Arg Leu Thr Pro Ser
    210                 215                 220

Val Thr Pro Ala Tyr Thr Pro Gly Phe Pro Ser Gly Leu Val Pro Asn
225                 230                 235                 240

Phe Ser Ser Gly Val Glu Pro Asn Ser Leu Gln Thr Leu Lys Leu Met
                245                 250                 255

Gln Ile Arg Lys Pro Leu Leu Lys Ser Ser Leu Leu Asp Gln Asn Leu
            260                 265                 270
```

-continued

Thr Glu Glu Glu Ile Asn Met Lys Phe Val Gln Asp Leu Leu Asn Trp
            275                 280                 285

Val Asp Glu Met Gln Val Gln Leu Asp Arg Thr Glu Trp Gly Ser Asp
    290                 295                 300

Leu Pro Ser Val Glu Ser His Leu Glu Asn His Lys Asn Val His Arg
305                 310                 315                 320

Ala Ile Glu Glu Phe Glu Ser Ser Leu Lys Glu Ala Lys Ile Ser Glu
                325                 330                 335

Ile Gln Met Thr Ala Pro Leu Lys Leu Thr Tyr Ala Glu Lys Leu His
            340                 345                 350

Arg Leu Glu Ser Gln Tyr Ala Lys Leu Leu Asn Thr Ser Arg Asn Gln
        355                 360                 365

Glu Arg His Leu Asp Thr Leu His Asn Phe Val Ser Arg Ala Thr Asn
    370                 375                 380

Glu Leu Ile Trp Leu Asn Glu Lys Glu Glu Glu Val Ala Tyr Asp
385                 390                 395                 400

Trp Ser Glu Arg Asn Thr Asn Ile Ala Arg Lys Lys Asp Tyr His Ala
                405                 410                 415

Glu Leu Met Arg Glu Leu Asp Gln Lys Glu Asn Ile Lys Ser Val
            420                 425                 430

Gln Glu Ile Ala Glu Gln Leu Leu Leu Glu Asn His Pro Ala Arg Leu
        435                 440                 445

Thr Ile Glu Ala Tyr Arg Ala Ala Met Gln Thr Gln Trp Ser Trp Ile
    450                 455                 460

Leu Gln Leu Cys Gln Cys Val Glu Gln His Ile Lys Glu Asn Thr Ala
465                 470                 475                 480

Tyr Phe Glu Phe Phe Asn Asp Ala Lys Glu Ala Thr Asp Tyr Leu Arg
                485                 490                 495

Asn Leu Lys Asp Ala Ile Gln Arg Lys Tyr Ser Cys Asp Arg Ser Ser
            500                 505                 510

Ser Ile His Lys Leu Glu Asp Leu Val Gln Glu Ser Met Glu Glu Lys
        515                 520                 525

Glu Glu Leu Leu Gln Tyr Lys Ser Thr Ile Ala Asn Leu Met Gly Lys
    530                 535                 540

Ala Lys Thr Ile Ile Gln Leu Lys Pro Arg Asn Ser Asp Cys Pro Leu
545                 550                 555                 560

Lys Thr Ser Ile Pro Ile Lys Ala Ile Cys Asp Tyr Arg Gln Ile Glu
                565                 570                 575

Ile Thr Ile Tyr Lys Asp Asp Glu Cys Val Leu Ala Asn Asn Ser His
            580                 585                 590

Arg Ala Lys Trp Lys Val Ile Ser Pro Thr Gly Asn Glu Ala Met Val
        595                 600                 605

Pro Ser Val Cys Phe Thr Val Pro Pro Asn Lys Glu Ala Val Asp
    610                 615                 620

Leu Ala Asn Arg Ile Glu Gln Gln Tyr Gln Asn Val Leu Thr Leu Trp
625                 630                 635                 640

His Glu Ser His Ile Asn Met Lys Ser Val Val Ser Trp His Tyr Leu
                645                 650                 655

Ile Asn Glu Ile Asp Arg Ile Arg Ala Ser Asn Val Ala Ser Ile Lys
            660                 665                 670

Thr Met Leu Pro Gly Glu His Gln Gln Val Leu Ser Asn Leu Gln Ser
        675                 680                 685

-continued

Arg Phe Glu Asp Phe Leu Glu Asp Ser Gln Glu Ser Gln Val Phe Ser
690             695             700

Gly Ser Asp Ile Thr Gln Leu Glu Lys Glu Val Asn Val Cys Lys Gln
705             710             715             720

Tyr Tyr Gln Glu Leu Leu Lys Ser Ala Glu Arg Glu Gln Glu Glu
    725             730             735

Ser Val Tyr Asn Leu Tyr Ile Ser Glu Val Arg Asn Ile Arg Leu Arg
        740             745             750

Leu Glu Asn Cys Glu Asp Arg Leu Ile Arg Gln Ile Arg Thr Pro Leu
        755             760             765

Glu Arg Asp Asp Leu His Glu Ser Val Phe Arg Ile Thr Glu Gln Glu
    770             775             780

Lys Leu Lys Lys Glu Leu Glu Arg Leu Lys Asp Asp Leu Gly Thr Ile
785             790             795             800

Thr Asn Lys Cys Glu Glu Phe Phe Ser Gln Ala Ala Ser Ser Ser
            805             810             815

Val Pro Thr Leu Arg Ser Glu Leu Asn Val Val Leu Gln Asn Met Asn
        820             825             830

Gln Val Tyr Ser Met Ser Ser Thr Tyr Ile Asp Lys Leu Lys Thr Val
            835             840             845

Asn Leu Val Leu Lys Asn Thr Gln Ala Ala Glu Ala Leu Val Lys Leu
850             855             860

Tyr Glu Thr Lys Leu Cys Glu Glu Ala Val Ile Ala Asp Lys Asn
865             870             875             880

Asn Ile Glu Asn Leu Ile Ser Thr Leu Lys Gln Trp Arg Ser Glu Val
            885             890             895

Asp Glu Lys Arg Gln Val Phe His Ala Leu Glu Asp Glu Leu Gln Lys
        900             905             910

Ala Lys Ala Ile Ser Asp Glu Met Phe Lys Thr Tyr Lys Glu Arg Asp
        915             920             925

Leu Asp Phe Asp Trp His Lys Glu Lys Ala Asp Gln Leu Val Glu Arg
930             935             940

Trp Gln Asn Val His Val Gln Ile Asp Asn Arg Leu Arg Asp Leu Glu
945             950             955             960

Gly Ile Gly Lys Ser Leu Lys Tyr Tyr Arg Asp Thr Tyr His Pro Leu
            965             970             975

Asp Asp Trp Ile Gln Gln Val Glu Thr Thr Gln Arg Lys Ile Gln Glu
        980             985             990

Asn Gln Pro Glu Asn Ser Lys Thr Leu Ala Thr Gln Leu Asn Gln Gln
        995             1000            1005

Lys Met Leu Val Ser Glu Ile Glu Met Lys Gln Ser Lys Met Asp
    1010            1015            1020

Glu Cys Gln Lys Tyr Ala Glu Gln Tyr Ser Ala Thr Val Lys Asp
    1025            1030            1035

Tyr Glu Leu Gln Thr Met Thr Tyr Arg Ala Met Val Asp Ser Gln
    1040            1045            1050

Gln Lys Ser Pro Val Lys Arg Arg Arg Met Gln Ser Ser Ala Asp
    1055            1060            1065

Leu Ile Ile Gln Glu Phe Met Asp Leu Arg Thr Arg Tyr Thr Ala
    1070            1075            1080

Leu Val Thr Leu Met Thr Gln Tyr Ile Lys Phe Ala Gly Asp Ser
    1085            1090            1095

Leu Lys Arg Leu Glu Glu Glu Ile Lys Arg Cys Lys Glu Thr

-continued

```
            1100                1105                 1110
Ser Glu His Gly Ala Tyr Ser Asp Leu Leu Gln Arg Gln Lys Ala
    1115                1120                1125

Thr Val Leu Glu Asn Ser Lys Leu Thr Gly Lys Ile Ser Glu Leu
    1130                1135                1140

Glu Arg Met Val Ala Glu Leu Lys Lys Gln Lys Ser Arg Val Glu
    1145                1150                1155

Glu Glu Leu Pro Lys Val Arg Glu Ala Ala Glu Asn Glu Leu Arg
    1160                1165                1170

Lys Gln Gln Arg Asn Val Glu Asp Ile Ser Leu Gln Lys Ile Arg
    1175                1180                1185

Ala Glu Ser Glu Ala Lys Gln Tyr Arg Arg Glu Leu Glu Thr Ile
    1190                1195                1200

Val Arg Glu Lys Glu Ala Ala Glu Arg Glu Leu Glu Arg Val Arg
    1205                1210                1215

Gln Leu Thr Ile Glu Ala Glu Ala Lys Arg Ala Ala Val Glu Glu
    1220                1225                1230

Asn Leu Leu Asn Phe Arg Asn Gln Leu Glu Glu Asn Thr Phe Thr
    1235                1240                1245

Arg Arg Thr Leu Glu Asp His Leu Lys Arg Lys Asp Leu Ser Leu
    1250                1255                1260

Asn Asp Leu Glu Gln Gln Lys Asn Lys Leu Met Glu Glu Leu Arg
    1265                1270                1275

Arg Lys Arg Asp Asn Glu Glu Glu Leu Leu Lys Leu Ile Lys Gln
    1280                1285                1290

Met Glu Lys Asp Leu Ala Phe Gln Lys Gln Val Ala Glu Lys Gln
    1295                1300                1305

Leu Lys Glu Lys Gln Lys Ile Glu Leu Glu Ala Arg Arg Lys Ile
    1310                1315                1320

Thr Glu Ile Gln Tyr Thr Cys Arg Glu Asn Ala Leu Pro Val Cys
    1325                1330                1335

Pro Ile Thr Gln Ala Thr Ser Cys Arg Ala Val Thr Gly Leu Gln
    1340                1345                1350

Gln Glu His Asp Lys Gln Lys Ala Glu Glu Leu Lys Gln Gln Val
    1355                1360                1365

Asp Glu Leu Thr Ala Ala Asn Arg Lys Ala Glu Gln Asp Met Arg
    1370                1375                1380

Glu Leu Thr Tyr Glu Leu Asn Ala Leu Gln Leu Glu Lys Thr Ser
    1385                1390                1395

Ser Glu Glu Lys Ala Arg Leu Leu Lys Asp Lys Leu Asp Glu Thr
    1400                1405                1410

Asn Asn Thr Leu Arg Cys Leu Lys Leu Glu Leu Glu Arg Lys Asp
    1415                1420                1425

Gln Ala Glu Lys Gly Tyr Ser Gln Gln Leu Arg Glu Leu Gly Arg
    1430                1435                1440

Gln Leu Asn Gln Thr Thr Gly Lys Ala Glu Glu Ala Met Gln Glu
    1445                1450                1455

Ala Ser Asp Leu Lys Lys Ile Lys Arg Asn Tyr Gln Leu Glu Leu
    1460                1465                1470

Glu Ser Leu Asn His Glu Lys Gly Lys Leu Gln Arg Glu Val Asp
    1475                1480                1485

Arg Ile Thr Arg Ala His Ala Val Ala Glu Lys Asn Ile Gln His
    1490                1495                1500
```

-continued

```
Leu Asn Ser Gln Ile His Ser Phe Arg Asp Glu Lys Glu Leu Glu
1505                1510                1515

Arg Leu Gln Ile Cys Gln Arg Lys Ser Asp His Leu Lys Glu Gln
1520                1525                1530

Phe Glu Lys Ser His Glu Gln Leu Leu Gln Asn Ile Lys Ala Glu
1535                1540                1545

Lys Glu Asn Asn Asp Lys Ile Gln Arg Leu Asn Glu Glu Leu Glu
1550                1555                1560

Lys Ser Asn Glu Cys Ala Glu Met Leu Lys Gln Lys Val Glu Glu
1565                1570                1575

Leu Thr Arg Gln Asn Asn Glu Thr Lys Leu Met Met Gln Arg Ile
1580                1585                1590

Gln Ala Glu Ser Glu Asn Ile Val Leu Glu Lys Gln Thr Ile Gln
1595                1600                1605

Gln Arg Cys Glu Ala Leu Lys Ile Gln Ala Asp Gly Phe Lys Asp
1610                1615                1620

Gln Leu Arg Ser Thr Asn Glu His Leu His Lys Gln Thr Lys Thr
1625                1630                1635

Glu Gln Asp Phe Gln Arg Lys Ile Lys Cys Leu Glu Glu Asp Leu
1640                1645                1650

Ala Lys Ser Gln Asn Leu Val Ser Glu Phe Lys Gln Lys Cys Asp
1655                1660                1665

Gln Gln Asn Ile Ile Ile Gln Asn Thr Lys Lys Glu Val Arg Asn
1670                1675                1680

Leu Asn Ala Glu Leu Asn Ala Ser Lys Glu Glu Lys Arg Arg Gly
1685                1690                1695

Glu Gln Lys Val Gln Leu Gln Gln Ala Gln Val Gln Glu Leu Asn
1700                1705                1710

Asn Arg Leu Lys Lys Val Gln Asp Glu Leu His Leu Lys Thr Ile
1715                1720                1725

Glu Glu Gln Met Thr His Arg Lys Met Val Leu Phe Gln Glu Glu
1730                1735                1740

Ser Gly Lys Phe Lys Gln Ser Ala Glu Glu Phe Arg Lys Lys Met
1745                1750                1755

Glu Lys Leu Met Glu Ser Lys Val Ile Thr Glu Asn Asp Ile Ser
1760                1765                1770

Gly Ile Arg Leu Asp Phe Val Ser Leu Gln Gln Glu Asn Ser Arg
1775                1780                1785

Ala Gln Glu Asn Ala Lys Leu Cys Glu Thr Asn Ile Lys Glu Leu
1790                1795                1800

Glu Arg Gln Leu Gln Gln Tyr Arg Glu Gln Met Gln Gln Gly Gln
1805                1810                1815

His Met Glu Ala Asn His Tyr Gln Lys Cys Gln Lys Leu Glu Asp
1820                1825                1830

Glu Leu Ile Ala Gln Lys Arg Glu Val Glu Asn Leu Lys Gln Lys
1835                1840                1845

Met Asp Gln Gln Ile Lys Glu His Glu His Gln Leu Val Leu Leu
1850                1855                1860

Gln Cys Glu Ile Gln Lys Lys Ser Thr Ala Lys Asp Cys Thr Phe
1865                1870                1875

Lys Pro Asp Phe Glu Met Thr Val Lys Glu Cys Gln His Ser Gly
1880                1885                1890
```

-continued

```
Glu Leu Ser Ser Arg Asn Thr Gly His Leu His Pro Thr Pro Arg
    1895            1900            1905

Ser Pro Leu Leu Arg Trp Thr Gln Glu Pro Gln Pro Leu Glu Glu
    1910            1915            1920

Lys Trp Gln His Arg Val Val Glu Gln Ile Pro Lys Glu Val Gln
    1925            1930            1935

Phe Gln Pro Pro Gly Ala Pro Leu Glu Lys Glu Lys Ser Gln Gln
    1940            1945            1950

Cys Tyr Ser Glu Tyr Phe Ser Gln Thr Ser Thr Glu Leu Gln Ile
    1955            1960            1965

Thr Phe Asp Glu Thr Asn Pro Ile Thr Arg Leu Ser Glu Ile Glu
    1970            1975            1980

Lys Ile Arg Asp Gln Ala Leu Asn Asn Ser Arg Pro Pro Val Arg
    1985            1990            1995

Tyr Gln Asp Asn Ala Cys Glu Met Glu Leu Val Lys Val Leu Thr
    2000            2005            2010

Pro Leu Glu Ile Ala Lys Asn Lys Gln Tyr Asp Met His Thr Glu
    2015            2020            2025

Val Thr Thr Leu Lys Gln Glu Lys Asn Pro Val Pro Ser Ala Glu
    2030            2035            2040

Glu Trp Met Leu Glu Gly Cys Arg Ala Ser Gly Gly Leu Lys Lys
    2045            2050            2055

Gly Asp Phe Leu Lys Lys Gly Leu Glu Pro Glu Thr Phe Gln Asn
    2060            2065            2070

Phe Asp Gly Asp His Ala Cys Ser Val Arg Asp Asp Glu Phe Lys
    2075            2080            2085

Phe Gln Gly Leu Arg His Thr Val Thr Ala Arg Gln Leu Val Glu
    2090            2095            2100

Ala Lys Leu Leu Asp Met Arg Thr Ile Glu Gln Leu Arg Leu Gly
    2105            2110            2115

Leu Lys Thr Val Glu Glu Val Gln Lys Thr Leu Asn Lys Phe Leu
    2120            2125            2130

Thr Lys Ala Thr Ser Ile Ala Gly Leu Tyr Leu Glu Ser Thr Lys
    2135            2140            2145

Glu Lys Ile Ser Phe Ala Ser Ala Ala Glu Arg Ile Ile Ile Asp
    2150            2155            2160

Lys Met Val Ala Leu Ala Phe Leu Glu Ala Gln Ala Ala Thr Gly
    2165            2170            2175

Phe Ile Ile Asp Pro Ile Ser Gly Gln Thr Tyr Ser Val Glu Asp
    2180            2185            2190

Ala Val Leu Lys Gly Val Val Asp Pro Glu Phe Arg Ile Arg Leu
    2195            2200            2205

Leu Glu Ala Glu Lys Ala Ala Val Gly Tyr Ser Tyr Ser Ser Lys
    2210            2215            2220

Thr Leu Ser Val Phe Gln Ala Met Glu Asn Arg Met Leu Asp Arg
    2225            2230            2235

Gln Lys Gly Lys His Ile Leu Glu Ala Gln Ile Ala Ser Gly Gly
    2240            2245            2250

Val Ile Asp Pro Val Arg Gly Ile Arg Val Pro Pro Glu Ile Ala
    2255            2260            2265

Leu Gln Gln Gly Leu Leu Asn Asn Ala Ile Leu Gln Phe Leu His
    2270            2275            2280

Glu Pro Ser Ser Asn Thr Arg Val Phe Pro Asn Pro Asn Asn Lys
```

```
                    2285                2290                2295
Gln Ala Leu Tyr Tyr Ser Glu Leu Leu Arg Met Cys Val Phe Asp
                2300                2305                2310
Val Glu Ser Gln Cys Phe Leu Phe Pro Phe Gly Glu Arg Asn Ile
                2315                2320                2325
Ser Asn Leu Asn Val Lys Lys Thr His Arg Ile Ser Val Val Asp
                2330                2335                2340
Thr Lys Thr Gly Ser Glu Leu Thr Val Tyr Glu Ala Phe Gln Arg
                2345                2350                2355
Asn Leu Ile Glu Lys Ser Ile Tyr Leu Glu Leu Ser Gly Gln Gln
                2360                2365                2370
Tyr Gln Trp Lys Glu Ala Met Phe Phe Glu Ser Tyr Gly His Ser
                2375                2380                2385
Ser His Met Leu Thr Asp Thr Lys Thr Gly Leu His Phe Asn Ile
                2390                2395                2400
Asn Glu Ala Ile Glu Gln Gly Thr Ile Asp Lys Ala Leu Val Lys
                2405                2410                2415
Lys Tyr Gln Glu Gly Leu Ile Thr Leu Thr Glu Leu Ala Asp Ser
                2420                2425                2430
Leu Leu Ser Arg Leu Val Pro Lys Lys Asp Leu His Ser Pro Val
                2435                2440                2445
Ala Gly Tyr Trp Leu Thr Ala Ser Gly Glu Arg Ile Ser Val Leu
                2450                2455                2460
Lys Ala Ser Arg Arg Asn Leu Val Asp Arg Ile Thr Ala Leu Arg
                2465                2470                2475
Cys Leu Glu Ala Gln Val Ser Thr Gly Gly Ile Ile Asp Pro Leu
                2480                2485                2490
Thr Gly Lys Lys Tyr Arg Val Ala Glu Ala Leu His Arg Gly Leu
                2495                2500                2505
Val Asp Glu Gly Phe Ala Gln Gln Leu Arg Gln Cys Glu Leu Val
                2510                2515                2520
Ile Thr Gly Ile Gly His Pro Ile Thr Asn Lys Met Met Ser Val
                2525                2530                2535
Val Glu Ala Val Asn Ala Asn Ile Ile Asn Lys Glu Met Gly Ile
                2540                2545                2550
Arg Cys Leu Glu Phe Gln Tyr Leu Thr Gly Gly Leu Ile Glu Pro
                2555                2560                2565
Gln Val His Ser Arg Leu Ser Ile Glu Glu Ala Leu Gln Val Gly
                2570                2575                2580
Ile Ile Asp Val Leu Ile Ala Thr Lys Leu Lys Asp Gln Lys Ser
                2585                2590                2595
Tyr Val Arg Asn Ile Ile Cys Pro Gln Thr Lys Arg Lys Leu Thr
                2600                2605                2610
Tyr Lys Glu Ala Leu Glu Lys Ala Asp Phe Asp Phe His Thr Gly
                2615                2620                2625
Leu Lys Leu Leu Glu Val Ser Glu Pro Leu Met Thr Gly Ile Ser
                2630                2635                2640
Ser Leu Tyr Tyr Ser Ser
        2645

<210> SEQ ID NO 11
<211> LENGTH: 13
<212> TYPE: PRT
<213> ORGANISM: Homo sapiens
```

```
<400> SEQUENCE: 11

Asp Tyr Ile Ser Lys Ser Lys Glu Asp Val Lys Leu Lys
1               5                   10

<210> SEQ ID NO 12
<211> LENGTH: 15
<212> TYPE: PRT
<213> ORGANISM: Homo sapiens

<400> SEQUENCE: 12

Glu Lys Arg Thr Asn Gly Leu Arg Arg Thr Pro Lys Gln Val Asp
1               5                   10                  15

<210> SEQ ID NO 13
<211> LENGTH: 20
<212> TYPE: PRT
<213> ORGANISM: Homo sapiens

<400> SEQUENCE: 13

Thr Glu Glu Ser Ile Asn Asp Glu Asp Ile Tyr Lys Gly Leu Pro Asp
1               5                   10                  15

Leu Ile Asp Glu
            20

<210> SEQ ID NO 14
<211> LENGTH: 19
<212> TYPE: PRT
<213> ORGANISM: Homo sapiens

<400> SEQUENCE: 14

Ser Lys Thr Ile Asn Pro Gln Val Ser Lys Thr Glu Tyr Lys Glu Leu
1               5                   10                  15

Leu Gln Glu

<210> SEQ ID NO 15
<211> LENGTH: 15
<212> TYPE: PRT
<213> ORGANISM: Homo sapiens

<400> SEQUENCE: 15

Asp Asp Asn Ala Thr Thr Asn Ala Ile Asp Glu Leu Lys Glu Cys
1               5                   10                  15

<210> SEQ ID NO 16
<211> LENGTH: 15
<212> TYPE: PRT
<213> ORGANISM: Homo sapiens

<400> SEQUENCE: 16

Asn Gln Thr Asp Glu Thr Leu Ser Asn Val Glu Val Phe Met Gln
1               5                   10                  15

<210> SEQ ID NO 17
<211> LENGTH: 19
<212> TYPE: PRT
<213> ORGANISM: Homo sapiens

<400> SEQUENCE: 17

Ser Ser Asp Asp Gly Ile Arg Pro Leu Pro Glu Tyr Ser Thr Glu Lys
1               5                   10                  15

His Lys Lys
```

<210> SEQ ID NO 18
<211> LENGTH: 15
<212> TYPE: PRT
<213> ORGANISM: Homo sapiens

<400> SEQUENCE: 18

Asn Lys Thr Lys Lys Lys Lys Ser Ser Arg Leu Pro Pro Glu Lys
1               5                   10                  15

<210> SEQ ID NO 19
<211> LENGTH: 17
<212> TYPE: PRT
<213> ORGANISM: Homo sapiens

<400> SEQUENCE: 19

Asp Gly Lys Ser Lys Asp Lys Pro Pro Lys Arg Lys Lys Ala Asp Thr
1               5                   10                  15

Glu

<210> SEQ ID NO 20
<211> LENGTH: 18
<212> TYPE: PRT
<213> ORGANISM: Homo sapiens

<400> SEQUENCE: 20

Lys Asn Lys Glu Pro Leu Thr Lys Lys Gly Glu Thr Lys Thr Ala Glu
1               5                   10                  15

Arg Asp

<210> SEQ ID NO 21
<211> LENGTH: 17
<212> TYPE: PRT
<213> ORGANISM: Homo sapiens

<400> SEQUENCE: 21

Lys Leu Thr Cys Thr Asp Leu Asp Ser Ser Pro Arg Ser Phe Arg Tyr
1               5                   10                  15

Ser

<210> SEQ ID NO 22
<211> LENGTH: 17
<212> TYPE: PRT
<213> ORGANISM: Homo sapiens

<400> SEQUENCE: 22

Glu Val Asp Tyr Glu Asn Pro Ser Asn Leu Ala Ala Gly Asn Lys Tyr
1               5                   10                  15

Thr

<210> SEQ ID NO 23
<211> LENGTH: 20
<212> TYPE: PRT
<213> ORGANISM: Homo sapiens

<400> SEQUENCE: 23

Lys Thr Leu Gln Val Phe Asn Pro Leu Arg Phe Ser Arg Glu Asn Ser
1               5                   10                  15

Glu Lys Ile His
            20

<210> SEQ ID NO 24

```
<211> LENGTH: 15
<212> TYPE: PRT
<213> ORGANISM: Homo sapiens

<400> SEQUENCE: 24

Gln His Phe Ala Ile Ile Glu Cys Lys Val Ala Val Ala Leu Thr
1               5                   10                  15

<210> SEQ ID NO 25
<211> LENGTH: 17
<212> TYPE: PRT
<213> ORGANISM: Homo sapiens

<400> SEQUENCE: 25

Arg Lys Phe Leu Ala Pro Asp His Ser Arg Pro Pro Gln Pro Val Arg
1               5                   10                  15

Gln

<210> SEQ ID NO 26
<211> LENGTH: 16
<212> TYPE: PRT
<213> ORGANISM: Homo sapiens

<400> SEQUENCE: 26

Val Leu Pro Leu Lys Asn Ile Leu Asp Glu Ile Lys Lys Pro Lys Asn
1               5                   10                  15

<210> SEQ ID NO 27
<211> LENGTH: 17
<212> TYPE: PRT
<213> ORGANISM: Homo sapiens

<400> SEQUENCE: 27

Tyr Glu Leu Cys Arg Glu Val Arg Arg Arg Met Val Gln Gly Lys
1               5                   10                  15

Thr

<210> SEQ ID NO 28
<211> LENGTH: 18
<212> TYPE: PRT
<213> ORGANISM: Homo sapiens

<400> SEQUENCE: 28

Met Ala Lys Ala Glu Val Lys Leu Ala Ile Phe Gly Arg Ala Gly Val
1               5                   10                  15

Gly Lys

<210> SEQ ID NO 29
<211> LENGTH: 15
<212> TYPE: PRT
<213> ORGANISM: Homo sapiens

<400> SEQUENCE: 29

Lys Asn Thr Glu Ile Ser Phe Lys Leu Gly Val Glu Phe Asp Glu
1               5                   10                  15

<210> SEQ ID NO 30
<211> LENGTH: 15
<212> TYPE: PRT
<213> ORGANISM: Homo sapiens

<400> SEQUENCE: 30

His Leu Gln Lys Trp Asp Gly Gln Glu Thr Thr Leu Val Arg Glu
```

-continued

```
                1               5                  10                 15

<210> SEQ ID NO 31
<211> LENGTH: 19
<212> TYPE: PRT
<213> ORGANISM: Homo sapiens

<400> SEQUENCE: 31

Thr Lys Pro Thr Thr Ile Ile Glu Lys Asn Gly Asp Ile Leu Thr Leu
1               5                  10                 15

Lys Thr His

<210> SEQ ID NO 32
<211> LENGTH: 19
<212> TYPE: PRT
<213> ORGANISM: Homo sapiens

<400> SEQUENCE: 32

Leu Gln Gln Met Ala Ala Lys Asp Arg Gly Thr Thr Lys Glu Val Glu
1               5                  10                 15

Glu Val Ser

<210> SEQ ID NO 33
<211> LENGTH: 20
<212> TYPE: PRT
<213> ORGANISM: Homo sapiens

<400> SEQUENCE: 33

Lys Arg Lys Ile Ser Phe Ala Ser Ile Glu Ile Ser Ser Asp Asn Val
1               5                  10                 15

Asp Tyr Ser Asp
            20

<210> SEQ ID NO 34
<211> LENGTH: 21
<212> TYPE: PRT
<213> ORGANISM: Homo sapiens

<400> SEQUENCE: 34

Asp Gly Asn Asp Val Glu Phe Thr Trp Leu Arg Gly Asn Asp Ser Val
1               5                  10                 15

Arg Gly Leu Glu His
            20

<210> SEQ ID NO 35
<211> LENGTH: 19
<212> TYPE: PRT
<213> ORGANISM: Homo sapiens

<400> SEQUENCE: 35

Gln Arg Gln Gln Ile Ala Lys Ser Phe Lys Ala Gln Phe Gly Lys Asp
1               5                  10                 15

Leu Thr Glu

<210> SEQ ID NO 36
<211> LENGTH: 20
<212> TYPE: PRT
<213> ORGANISM: Homo sapiens

<400> SEQUENCE: 36

Arg Glu Ile Met Lys Ala Tyr Glu Glu Asp Tyr Gly Ser Ser Leu Glu
1               5                  10                 15
```

```
Glu Asp Ile Gln
        20

<210> SEQ ID NO 37
<211> LENGTH: 18
<212> TYPE: PRT
<213> ORGANISM: Homo sapiens

<400> SEQUENCE: 37

Glu Glu Tyr Glu Lys Ile Ala Asn Lys Ser Ile Glu Asp Ser Ile Lys
1               5                   10                  15

Ser Glu

<210> SEQ ID NO 38
<211> LENGTH: 21
<212> TYPE: PRT
<213> ORGANISM: Homo sapiens

<400> SEQUENCE: 38

Glu Gly Gly Ser Leu Val Pro Ala Ala Arg Gln Gln His Cys Thr Gln
1               5                   10                  15

Val Arg Ser Arg Arg
        20

<210> SEQ ID NO 39
<211> LENGTH: 15
<212> TYPE: PRT
<213> ORGANISM: Homo sapiens

<400> SEQUENCE: 39

Arg Lys Ala Gly Lys Ser Lys Lys Ser Ser Arg Lys Glu Ala Glu
1               5                   10                  15

<210> SEQ ID NO 40
<211> LENGTH: 16
<212> TYPE: PRT
<213> ORGANISM: Homo sapiens

<400> SEQUENCE: 40

Lys Thr His Glu Lys Tyr Gly Trp Val Thr Pro Pro Val Ser Asp Gly
1               5                   10                  15

<210> SEQ ID NO 41
<211> LENGTH: 15
<212> TYPE: PRT
<213> ORGANISM: Homo sapiens

<400> SEQUENCE: 41

Met Asp Leu Glu Gly Asp Arg Asn Gly Gly Ala Lys Lys Lys Asn
1               5                   10                  15

<210> SEQ ID NO 42
<211> LENGTH: 19
<212> TYPE: PRT
<213> ORGANISM: Homo sapiens

<400> SEQUENCE: 42

Asn Leu Glu Asp Leu Met Ser Asn Ile Thr Asn Arg Ser Asp Ile Asn
1               5                   10                  15

Asp Thr Gly

<210> SEQ ID NO 43
```

```
<211> LENGTH: 15
<212> TYPE: PRT
<213> ORGANISM: Homo sapiens

<400> SEQUENCE: 43

Arg Gly Ser Gln Ala Gln Asp Arg Lys Leu Ser Thr Lys Glu Ala
1               5                   10                  15

<210> SEQ ID NO 44
<211> LENGTH: 18
<212> TYPE: PRT
<213> ORGANISM: Homo sapiens

<400> SEQUENCE: 44

Met Asp Leu Glu Ala Ala Lys Asn Gly Thr Ala Trp Arg Pro Thr Ser
1               5                   10                  15

Ala Glu

<210> SEQ ID NO 45
<211> LENGTH: 17
<212> TYPE: PRT
<213> ORGANISM: Homo sapiens

<400> SEQUENCE: 45

Asn Phe Ser Phe Pro Val Asn Phe Ser Leu Ser Leu Leu Asn Pro Gly
1               5                   10                  15

Lys

<210> SEQ ID NO 46
<211> LENGTH: 16
<212> TYPE: PRT
<213> ORGANISM: Homo sapiens

<400> SEQUENCE: 46

Lys Asn Ser Gln Met Cys Gln Lys Ser Leu Asp Val Glu Thr Asp Gly
1               5                   10                  15

<210> SEQ ID NO 47
<211> LENGTH: 13
<212> TYPE: PRT
<213> ORGANISM: Homo sapiens

<400> SEQUENCE: 47

Met Ala Leu Arg Gly Phe Cys Ser Ala Asp Gly Ser Asp
1               5                   10

<210> SEQ ID NO 48
<211> LENGTH: 16
<212> TYPE: PRT
<213> ORGANISM: Homo sapiens

<400> SEQUENCE: 48

Lys Asn Trp Lys Lys Glu Cys Ala Lys Thr Arg Lys Gln Pro Val Lys
1               5                   10                  15

<210> SEQ ID NO 49
<211> LENGTH: 16
<212> TYPE: PRT
<213> ORGANISM: Homo sapiens

<400> SEQUENCE: 49

Asp Ser Ile Glu Arg Arg Pro Val Lys Asp Gly Gly Gly Thr Asn Ser
1               5                   10                  15
```

-continued

```
<210> SEQ ID NO 50
<211> LENGTH: 20
<212> TYPE: PRT
<213> ORGANISM: Homo sapiens

<400> SEQUENCE: 50

Met Leu Glu Lys Phe Cys Asn Ser Thr Phe Trp Asn Ser Ser Phe Leu
1               5                   10                  15

Asp Ser Pro Glu
            20

<210> SEQ ID NO 51
<211> LENGTH: 15
<212> TYPE: PRT
<213> ORGANISM: Homo sapiens

<400> SEQUENCE: 51

Ser Ile Leu Cys Gly Thr Phe Gln Phe Gln Thr Leu Ile Arg Thr
1               5                   10                  15

<210> SEQ ID NO 52
<211> LENGTH: 14
<212> TYPE: PRT
<213> ORGANISM: Homo sapiens

<400> SEQUENCE: 52

Glu Asn Asn Glu Ser Ser Asn Asn Pro Ser Ser Ile Ala Ser
1               5                   10

<210> SEQ ID NO 53
<211> LENGTH: 16
<212> TYPE: PRT
<213> ORGANISM: Homo sapiens

<400> SEQUENCE: 53

Gln Glu Val Lys Pro Asn Pro Leu Gln Asp Ala Asn Ile Cys Ser Arg
1               5                   10                  15

<210> SEQ ID NO 54
<211> LENGTH: 16
<212> TYPE: PRT
<213> ORGANISM: Homo sapiens

<400> SEQUENCE: 54

Asp Glu Ile Ser Gln Arg Asn Arg Gln Leu Pro Ser Asp Gly Lys Lys
1               5                   10                  15

<210> SEQ ID NO 55
<211> LENGTH: 18
<212> TYPE: PRT
<213> ORGANISM: Homo sapiens

<400> SEQUENCE: 55

Val Gln Asp Phe Thr Ala Phe Trp Asp Lys Ala Ser Glu Thr Pro Thr
1               5                   10                  15

Leu Gln

<210> SEQ ID NO 56
<211> LENGTH: 18
<212> TYPE: PRT
<213> ORGANISM: Homo sapiens

<400> SEQUENCE: 56
```

```
Met Asp Ala Leu Cys Gly Ser Gly Glu Leu Gly Ser Lys Phe Trp Asp
1               5                   10                  15

Ser Asn

<210> SEQ ID NO 57
<211> LENGTH: 15
<212> TYPE: PRT
<213> ORGANISM: Homo sapiens

<400> SEQUENCE: 57

Arg Lys Gln Glu Lys Gln Thr Ala Arg His Lys Ala Ser Ala Ala
1               5                   10                  15

<210> SEQ ID NO 58
<211> LENGTH: 13
<212> TYPE: PRT
<213> ORGANISM: Homo sapiens

<400> SEQUENCE: 58

Asp Pro Gln Ser Val Glu Arg Lys Thr Ile Ser Pro Gly
1               5                   10

<210> SEQ ID NO 59
<211> LENGTH: 19
<212> TYPE: PRT
<213> ORGANISM: Homo sapiens

<400> SEQUENCE: 59

Met Lys Asp Ile Asp Ile Gly Lys Glu Tyr Ile Ile Pro Ser Pro Gly
1               5                   10                  15

Tyr Arg Ser

<210> SEQ ID NO 60
<211> LENGTH: 18
<212> TYPE: PRT
<213> ORGANISM: Homo sapiens

<400> SEQUENCE: 60

Arg Asp Arg Glu Asp Ser Lys Phe Arg Arg Thr Arg Pro Leu Glu Cys
1               5                   10                  15

Gln Asp

<210> SEQ ID NO 61
<211> LENGTH: 15
<212> TYPE: PRT
<213> ORGANISM: Homo sapiens

<400> SEQUENCE: 61

Ser Lys His Glu Ser Ser Asp Val Asn Cys Arg Arg Leu Glu Arg
1               5                   10                  15

<210> SEQ ID NO 62
<211> LENGTH: 20
<212> TYPE: PRT
<213> ORGANISM: Homo sapiens

<400> SEQUENCE: 62

Met Ala Ala Pro Ala Glu Pro Cys Ala Gly Gln Gly Val Trp Asn Gln
1               5                   10                  15

Thr Glu Pro Glu
            20
```

```
<210> SEQ ID NO 63
<211> LENGTH: 17
<212> TYPE: PRT
<213> ORGANISM: Homo sapiens

<400> SEQUENCE: 63

Asp Pro Gly Val Val Asp Ser Ser Ser Gly Ser Ala Ala Gly Lys
1               5                   10                  15

Ser

<210> SEQ ID NO 64
<211> LENGTH: 13
<212> TYPE: PRT
<213> ORGANISM: Homo sapiens

<400> SEQUENCE: 64

His Thr Leu Val Ala Glu Asn Ala Met Asn Ala Glu Lys
1               5                   10

<210> SEQ ID NO 65
<211> LENGTH: 15
<212> TYPE: PRT
<213> ORGANISM: Homo sapiens

<400> SEQUENCE: 65

Gln Glu Val Leu Ser Lys Ile Gln His Gly Thr Ile Ile Ser
1               5                   10                  15

<210> SEQ ID NO 66
<211> LENGTH: 14
<212> TYPE: PRT
<213> ORGANISM: Homo sapiens

<400> SEQUENCE: 66

Thr Asn Ser Ser Leu Asn Gln Asn Met Thr Asn Gly Thr Arg
1               5                   10

<210> SEQ ID NO 67
<211> LENGTH: 18
<212> TYPE: PRT
<213> ORGANISM: Homo sapiens

<400> SEQUENCE: 67

Met Ser Asp Ser Val Ile Leu Arg Ser Ile Lys Lys Phe Gly Glu Glu
1               5                   10                  15

Asn Asp

<210> SEQ ID NO 68
<211> LENGTH: 15
<212> TYPE: PRT
<213> ORGANISM: Homo sapiens

<400> SEQUENCE: 68

Gly Ala Asp Asp Pro Ser Ser Val Thr Ala Glu Glu Ile Gln Arg
1               5                   10                  15

<210> SEQ ID NO 69
<211> LENGTH: 14
<212> TYPE: PRT
<213> ORGANISM: Homo sapiens

<400> SEQUENCE: 69

Asn Ala Val Ala Ser Pro Glu Phe Pro Pro Arg Phe Asn Thr
1               5                   10
```

```
<210> SEQ ID NO 70
<211> LENGTH: 18
<212> TYPE: PRT
<213> ORGANISM: Homo sapiens

<400> SEQUENCE: 70

Lys Pro Asn Gly Ile Tyr Arg Lys Leu Met Asn Lys Gln Ser Phe Ile
1               5                   10                  15

Ser Ala

<210> SEQ ID NO 71
<211> LENGTH: 13
<212> TYPE: PRT
<213> ORGANISM: Homo sapiens

<400> SEQUENCE: 71

Met Ala Ser Ser Arg Cys Pro Ala Pro Arg Gly Cys Arg
1               5                   10

<210> SEQ ID NO 72
<211> LENGTH: 10
<212> TYPE: PRT
<213> ORGANISM: Homo sapiens

<400> SEQUENCE: 72

Gln Gly Gly Ser Gly Asn Pro Val Arg Arg
1               5                   10

<210> SEQ ID NO 73
<211> LENGTH: 17
<212> TYPE: PRT
<213> ORGANISM: Homo sapiens

<400> SEQUENCE: 73

Glu Phe Val Gly Asp Gly Ile Tyr Asn Asn Thr Met Gly His Val His
1               5                   10                  15

Ser

<210> SEQ ID NO 74
<211> LENGTH: 16
<212> TYPE: PRT
<213> ORGANISM: Homo sapiens

<400> SEQUENCE: 74

Met Pro Leu Ala Phe Cys Gly Ser Glu Asn His Ser Ala Ala Tyr Arg
1               5                   10                  15

<210> SEQ ID NO 75
<211> LENGTH: 18
<212> TYPE: PRT
<213> ORGANISM: Homo sapiens

<400> SEQUENCE: 75

Asp His Leu Gly Lys Glu Asn Asp Val Phe Gln Pro Lys Thr Gln Phe
1               5                   10                  15

Leu Gly

<210> SEQ ID NO 76
<211> LENGTH: 16
<212> TYPE: PRT
<213> ORGANISM: Homo sapiens
```

```
<400> SEQUENCE: 76

Glu Ile Arg Glu Glu Gln Cys Ala Pro His Glu Pro Thr Pro Gln Gly
1               5                   10                  15

<210> SEQ ID NO 77
<211> LENGTH: 12
<212> TYPE: PRT
<213> ORGANISM: Homo sapiens

<400> SEQUENCE: 77

Met Ser Leu Ser Phe Cys Gly Asn Asn Ile Ser Ser
1               5                   10

<210> SEQ ID NO 78
<211> LENGTH: 18
<212> TYPE: PRT
<213> ORGANISM: Homo sapiens

<400> SEQUENCE: 78

Gln Arg Val Asn Glu Thr Gln Asn Gly Thr Asn Asn Thr Thr Gly Ile
1               5                   10                  15

Ser Glu

<210> SEQ ID NO 79
<211> LENGTH: 19
<212> TYPE: PRT
<213> ORGANISM: Homo sapiens

<400> SEQUENCE: 79

Asp Glu Ile Gly Asp Asp Ser Trp Arg Thr Gly Glu Ser Ser Leu Pro
1               5                   10                  15

Phe Glu Ser

<210> SEQ ID NO 80
<211> LENGTH: 21
<212> TYPE: PRT
<213> ORGANISM: Homo sapiens

<400> SEQUENCE: 80

Met Val Lys Val Thr Phe Asn Ser Ala Leu Ala Gln Lys Glu Ala Lys
1               5                   10                  15

Lys Asp Glu Pro Lys
            20

<210> SEQ ID NO 81
<211> LENGTH: 16
<212> TYPE: PRT
<213> ORGANISM: Homo sapiens

<400> SEQUENCE: 81

Gln Thr Ile Glu Glu Asn Ile Lys Ile Phe Glu Glu Glu Val Glu
1               5                   10                  15

<210> SEQ ID NO 82
<211> LENGTH: 21
<212> TYPE: PRT
<213> ORGANISM: Homo sapiens

<400> SEQUENCE: 82

His Asp Lys Glu Thr Tyr Lys Leu Gln Arg Arg Glu Thr Ile Lys Gly
1               5                   10                  15

Ile Gln Lys Arg Glu
```

```
<210> SEQ ID NO 83
<211> LENGTH: 20
<212> TYPE: PRT
<213> ORGANISM: Homo sapiens

<400> SEQUENCE: 83

His Lys Lys Glu Thr Glu Ser Asp Gln Asp Asp Glu Ile Glu Lys Thr
1               5                   10                  15
Asp Arg Arg Gln
            20

<210> SEQ ID NO 84
<211> LENGTH: 20
<212> TYPE: PRT
<213> ORGANISM: Homo sapiens

<400> SEQUENCE: 84

Glu Gly Phe Lys Val Lys Thr Lys Lys Glu Ile Arg His Val Glu Lys
1               5                   10                  15
Lys Ser His Ser
            20

<210> SEQ ID NO 85
<211> LENGTH: 20
<212> TYPE: PRT
<213> ORGANISM: Homo sapiens

<400> SEQUENCE: 85

Met Ala His Ala Ala Ser Gln Leu Lys Lys Asn Arg Asp Leu Glu Ile
1               5                   10                  15
Asn Ala Glu Glu
            20

<210> SEQ ID NO 86
<211> LENGTH: 18
<212> TYPE: PRT
<213> ORGANISM: Homo sapiens

<400> SEQUENCE: 86

Glu Arg Ala Leu Ala Ala Ala Gln Arg Cys His Lys Lys Val Met Lys
1               5                   10                  15
Glu Arg

<210> SEQ ID NO 87
<211> LENGTH: 15
<212> TYPE: PRT
<213> ORGANISM: Homo sapiens

<400> SEQUENCE: 87

Thr Ala Gly Met Lys Asp Leu Leu Ser Val Phe Gln Ala Tyr Gln
1               5                   10                  15

<210> SEQ ID NO 88
<211> LENGTH: 16
<212> TYPE: PRT
<213> ORGANISM: Homo sapiens

<400> SEQUENCE: 88

Asp Pro Pro Arg Thr Val Leu Gln Ala Pro Lys Glu Trp Val Cys Leu
1               5                   10                  15
```

```
<210> SEQ ID NO 89
<211> LENGTH: 20
<212> TYPE: PRT
<213> ORGANISM: Homo sapiens

<400> SEQUENCE: 89

Met Glu Ala Ala Asp Ala Ser Arg Ser Asn Gly Ser Ser Pro Glu Ala
1               5                   10                  15

Arg Asp Ala Arg
            20

<210> SEQ ID NO 90
<211> LENGTH: 17
<212> TYPE: PRT
<213> ORGANISM: Homo sapiens

<400> SEQUENCE: 90

Glu Leu His Leu Lys Pro His Leu Glu Gly Ala Ala Phe Arg Asp His
1               5                   10                  15

Gln

<210> SEQ ID NO 91
<211> LENGTH: 18
<212> TYPE: PRT
<213> ORGANISM: Homo sapiens

<400> SEQUENCE: 91

Glu Gly Glu Gly Leu Gly Gln Ser Leu Gly Asn Phe Lys Asp Asp Leu
1               5                   10                  15

Leu Asn

<210> SEQ ID NO 92
<211> LENGTH: 17
<212> TYPE: PRT
<213> ORGANISM: Homo sapiens

<400> SEQUENCE: 92

Glu Leu His Leu Lys Pro His Leu Glu Gly Ala Ala Phe Arg Asp His
1               5                   10                  15

Gln

<210> SEQ ID NO 93
<211> LENGTH: 17
<212> TYPE: PRT
<213> ORGANISM: Homo sapiens

<400> SEQUENCE: 93

Gly Ser Glu Glu Arg Gly Ala Gly Arg Gly Ser Ser Gly Gly Arg Glu
1               5                   10                  15

Glu

<210> SEQ ID NO 94
<211> LENGTH: 18
<212> TYPE: PRT
<213> ORGANISM: Homo sapiens

<400> SEQUENCE: 94

Lys Ile Trp Ser Leu Ala Glu Thr Ala Thr Ser Pro Asp Asn Pro Arg
1               5                   10                  15

Arg Ser
```

<210> SEQ ID NO 95
<211> LENGTH: 20
<212> TYPE: PRT
<213> ORGANISM: Homo sapiens

<400> SEQUENCE: 95

Lys Lys Leu Leu Lys Thr Ala Phe Gln Pro Val Pro Arg Arg Pro Gln
1               5                   10                  15

Asn His Leu Asp
            20

<210> SEQ ID NO 96
<211> LENGTH: 21
<212> TYPE: PRT
<213> ORGANISM: Homo sapiens

<400> SEQUENCE: 96

Arg Arg Ser Ser Thr Thr His Val Lys Gln Ala Ile Asn Lys Met Leu
1               5                   10                  15

Thr Lys Ile Ser Ser
            20

<210> SEQ ID NO 97
<211> LENGTH: 20
<212> TYPE: PRT
<213> ORGANISM: Homo sapiens

<400> SEQUENCE: 97

Met Arg Arg Lys Asn Thr Cys Gln Asn Phe Met Glu Tyr Phe Cys Ile
1               5                   10                  15

Ser Leu Ala Phe
            20

<210> SEQ ID NO 98
<211> LENGTH: 21
<212> TYPE: PRT
<213> ORGANISM: Homo sapiens

<400> SEQUENCE: 98

Asn Glu Thr Ile Leu Tyr Phe Pro Phe Ser Ser His Ser Ser Tyr Thr
1               5                   10                  15

Val Arg Ser Lys Lys
            20

<210> SEQ ID NO 99
<211> LENGTH: 19
<212> TYPE: PRT
<213> ORGANISM: Homo sapiens

<400> SEQUENCE: 99

Lys Val Gln Ile Pro Ala Tyr Ile Glu Met Asn Ile Pro Leu Val Ile
1               5                   10                  15

Leu Cys Gln

<210> SEQ ID NO 100
<211> LENGTH: 18
<212> TYPE: PRT
<213> ORGANISM: Homo sapiens

<400> SEQUENCE: 100

Met Leu Thr Glu Leu Glu Lys Ala Leu Asn Ser Ile Ile Asp Val Tyr
1               5                   10                  15

His Lys

<210> SEQ ID NO 101
<211> LENGTH: 22
<212> TYPE: PRT
<213> ORGANISM: Homo sapiens

<400> SEQUENCE: 101

Arg Asp Asp Leu Lys Lys Leu Leu Glu Thr Glu Cys Pro Gln Tyr Ile
1               5                   10                  15

Arg Lys Lys Gly Ala Asp
            20

<210> SEQ ID NO 102
<211> LENGTH: 17
<212> TYPE: PRT
<213> ORGANISM: Homo sapiens

<400> SEQUENCE: 102

Lys Met Gly Val Ala Ala His Lys Lys Ser His Glu Glu Ser His Lys
1               5                   10                  15

Glu

<210> SEQ ID NO 103
<211> LENGTH: 17
<212> TYPE: PRT
<213> ORGANISM: Homo sapiens

<400> SEQUENCE: 103

Pro Glu Ser Arg Lys Asp Pro Ser Gly Ala Ser Asn Pro Ser Ala Asp
1               5                   10                  15

Ser

<210> SEQ ID NO 104
<211> LENGTH: 15
<212> TYPE: PRT
<213> ORGANISM: Homo sapiens

<400> SEQUENCE: 104

His Gly Leu Ala Pro His Glu Ser Gln Leu His Leu Lys Gly Asp
1               5                   10                  15

<210> SEQ ID NO 105
<211> LENGTH: 18
<212> TYPE: PRT
<213> ORGANISM: Homo sapiens

<400> SEQUENCE: 105

Glu Gln Gln His Lys Leu Asp Phe Lys Ala Tyr Glu Gln Ala Leu Gln
1               5                   10                  15

Tyr Ser

<210> SEQ ID NO 106
<211> LENGTH: 15
<212> TYPE: PRT
<213> ORGANISM: Homo sapiens

<400> SEQUENCE: 106

His Gly Leu Ala Pro His Glu Ser Gln Leu His Leu Lys Gly Asp
1               5                   10                  15

```
<210> SEQ ID NO 107
<211> LENGTH: 20
<212> TYPE: PRT
<213> ORGANISM: Homo sapiens

<400> SEQUENCE: 107

Glu Glu Tyr Val Gly Leu Ser Ala Asn Gln Cys Ala Val Pro Ala Lys
1               5                   10                  15

Asp Arg Val Asp
            20

<210> SEQ ID NO 108
<211> LENGTH: 15
<212> TYPE: PRT
<213> ORGANISM: Homo sapiens

<400> SEQUENCE: 108

Arg Val Asp Cys Gly Tyr Pro His Val Thr Pro Lys Glu Cys Asn
1               5                   10                  15

<210> SEQ ID NO 109
<211> LENGTH: 15
<212> TYPE: PRT
<213> ORGANISM: Homo sapiens

<400> SEQUENCE: 109

Val Pro Trp Cys Phe Lys Pro Leu Gln Glu Ala Glu Cys Thr Phe
1               5                   10                  15

<210> SEQ ID NO 110
<211> LENGTH: 15
<212> TYPE: PRT
<213> ORGANISM: Homo sapiens

<400> SEQUENCE: 110

Val Pro Trp Cys Phe Lys Pro Leu Gln Glu Ala Glu Cys Thr Phe
1               5                   10                  15

<210> SEQ ID NO 111
<211> LENGTH: 16
<212> TYPE: PRT
<213> ORGANISM: Homo sapiens

<400> SEQUENCE: 111

Lys Lys Glu Pro Val Thr Thr Arg Gln Val Arg Thr Ile Val Glu Glu
1               5                   10                  15

<210> SEQ ID NO 112
<211> LENGTH: 17
<212> TYPE: PRT
<213> ORGANISM: Homo sapiens

<400> SEQUENCE: 112

Gln Asp Gly Lys Val Ile Ser Ser Arg Glu Gln Val His Gln Thr Thr
1               5                   10                  15

Arg

<210> SEQ ID NO 113
<211> LENGTH: 15
<212> TYPE: PRT
<213> ORGANISM: Homo sapiens

<400> SEQUENCE: 113

Ser Ser Ser Ile Lys Gly Ser Ser Gly Leu Gly Gly Gly Ser Ser
```

-continued

```
1               5                   10                  15

<210> SEQ ID NO 114
<211> LENGTH: 20
<212> TYPE: PRT
<213> ORGANISM: Homo sapiens

<400> SEQUENCE: 114

Asp His Asn His Ala Ala Ser Gly Lys Asn Lys Arg Lys Ala Leu Cys
1               5                   10                  15

Pro Asp His Asp
            20

<210> SEQ ID NO 115
<211> LENGTH: 21
<212> TYPE: PRT
<213> ORGANISM: Homo sapiens

<400> SEQUENCE: 115

Glu Glu Pro Ala Met Glu Met Lys Arg Gly Pro Leu Phe Ser His Leu
1               5                   10                  15

Ser Ser Gln Asn Ile
            20

<210> SEQ ID NO 116
<211> LENGTH: 16
<212> TYPE: PRT
<213> ORGANISM: Homo sapiens

<400> SEQUENCE: 116

Gln Arg Tyr Ser Arg Glu Glu Leu Lys Asp Ala Gly Val Ala Thr Leu
1               5                   10                  15

<210> SEQ ID NO 117
<211> LENGTH: 22
<212> TYPE: PRT
<213> ORGANISM: Homo sapiens

<400> SEQUENCE: 117

Met Asp Ile Glu Ala Tyr Leu Glu Arg Ile Gly Tyr Lys Lys Ser Arg
1               5                   10                  15

Asn Lys Leu Asp Leu Glu
            20

<210> SEQ ID NO 118
<211> LENGTH: 22
<212> TYPE: PRT
<213> ORGANISM: Homo sapiens

<400> SEQUENCE: 118

Gln Met Trp Gln Pro Leu Glu Leu Ile Ser Gly Lys Asp Gln Pro Gln
1               5                   10                  15

Val Pro Cys Val Phe Arg
            20

<210> SEQ ID NO 119
<211> LENGTH: 20
<212> TYPE: PRT
<213> ORGANISM: Homo sapiens

<400> SEQUENCE: 119

Phe Asn Ile Ser Leu Gln Arg Lys Leu Val Pro Lys His Gly Asp Arg
1               5                   10                  15
```

```
Phe Phe Thr Ile
            20

<210> SEQ ID NO 120
<211> LENGTH: 20
<212> TYPE: PRT
<213> ORGANISM: Homo sapiens

<400> SEQUENCE: 120

Gln Pro Pro Phe Leu Cys Gln Trp Gly Arg His Gln Pro Ser Trp Lys
1               5                   10                  15

Pro Leu Met Asn
            20

<210> SEQ ID NO 121
<211> LENGTH: 20
<212> TYPE: PRT
<213> ORGANISM: Homo sapiens

<400> SEQUENCE: 121

Glu Lys Thr His Gly Leu Val Val Glu Asn Gln Glu Leu Arg Gln Arg
1               5                   10                  15

Leu Gly Met Asp
            20

<210> SEQ ID NO 122
<211> LENGTH: 21
<212> TYPE: PRT
<213> ORGANISM: Homo sapiens

<400> SEQUENCE: 122

Arg Gln Arg Leu Thr His Leu Ser Pro Glu Glu Lys Ala Leu Arg Arg
1               5                   10                  15

Lys Leu Lys Asn Arg
            20

<210> SEQ ID NO 123
<211> LENGTH: 16
<212> TYPE: PRT
<213> ORGANISM: Homo sapiens

<400> SEQUENCE: 123

Arg Glu His Met Gln Ala Val Thr Arg Asn Tyr Ile Thr His Pro Arg
1               5                   10                  15

<210> SEQ ID NO 124
<211> LENGTH: 13
<212> TYPE: PRT
<213> ORGANISM: Homo sapiens

<400> SEQUENCE: 124

Lys Lys Ser Lys Ala Val Leu Asp Tyr His Asp Asp Asn
1               5                   10

<210> SEQ ID NO 125
<211> LENGTH: 19
<212> TYPE: PRT
<213> ORGANISM: Homo sapiens

<400> SEQUENCE: 125

Asp Glu Phe Tyr Ser Arg Glu Gly Arg Leu Gln Asp Leu Ala Pro Asp
1               5                   10                  15
```

-continued

Thr Ala Leu

<210> SEQ ID NO 126
<211> LENGTH: 18
<212> TYPE: PRT
<213> ORGANISM: Homo sapiens

<400> SEQUENCE: 126

Arg Tyr Ala Phe Asp Phe Ala Arg Asp Lys Asp Gln Arg Ser Leu Asp
1               5                   10                  15

Ile Asp

<210> SEQ ID NO 127
<211> LENGTH: 19
<212> TYPE: PRT
<213> ORGANISM: Homo sapiens

<400> SEQUENCE: 127

Ser Val Phe Tyr Gln Tyr Leu Glu Gln Ser Lys Tyr Arg Val Met Asn
1               5                   10                  15

Lys Asp Gln

<210> SEQ ID NO 128
<211> LENGTH: 22
<212> TYPE: PRT
<213> ORGANISM: Homo sapiens

<400> SEQUENCE: 128

Glu Asp Gly Ala Trp Pro Val Leu Leu Asp Glu Phe Val Glu Trp Gln
1               5                   10                  15

Lys Val Arg Gln Thr Ser
            20

<210> SEQ ID NO 129
<211> LENGTH: 19
<212> TYPE: PRT
<213> ORGANISM: Homo sapiens

<400> SEQUENCE: 129

Ser Phe Lys Ser Pro Gln Val Tyr Leu Lys Glu Glu Glu Lys Asn
1               5                   10                  15

Glu Lys Arg

<210> SEQ ID NO 130
<211> LENGTH: 17
<212> TYPE: PRT
<213> ORGANISM: Homo sapiens

<400> SEQUENCE: 130

Arg Lys Lys Gln Gln Glu Ala Gln Gly Glu Lys Ala Ser Arg Tyr Ile
1               5                   10                  15

Glu

<210> SEQ ID NO 131
<211> LENGTH: 20
<212> TYPE: PRT
<213> ORGANISM: Homo sapiens

<400> SEQUENCE: 131

Glu Asp Ile Gly Ile Thr Val Asp Thr Val Leu Ile Leu Glu Glu Lys
1               5                   10                  15

-continued

Glu Gln Thr Asn
        20

<210> SEQ ID NO 132
<211> LENGTH: 18
<212> TYPE: PRT
<213> ORGANISM: Homo sapiens

<400> SEQUENCE: 132

Asp Phe Arg Cys Glu Glu Gly Gln Glu Glu Gly Gly Cys Leu Pro Arg
1               5                   10                  15

Pro Gln

<210> SEQ ID NO 133
<211> LENGTH: 21
<212> TYPE: PRT
<213> ORGANISM: Homo sapiens

<400> SEQUENCE: 133

Asp Gly Thr Ser Phe Ala Glu Glu Val Glu Lys Pro Thr Lys Cys Gly
1               5                   10                  15

Cys Ala Leu Cys Ala
        20

<210> SEQ ID NO 134
<211> LENGTH: 18
<212> TYPE: PRT
<213> ORGANISM: Homo sapiens

<400> SEQUENCE: 134

Lys Ala Phe Arg Gly Ala Thr Asp Leu Lys Asn Leu Arg Leu Asp Lys
1               5                   10                  15

Asn Gln

<210> SEQ ID NO 135
<211> LENGTH: 19
<212> TYPE: PRT
<213> ORGANISM: Homo sapiens

<400> SEQUENCE: 135

Met Asn Leu Leu Asp Pro Phe Met Lys Met Thr Asp Glu Gln Glu Lys
1               5                   10                  15

Gly Leu Ser

<210> SEQ ID NO 136
<211> LENGTH: 18
<212> TYPE: PRT
<213> ORGANISM: Homo sapiens

<400> SEQUENCE: 136

Asn Thr Phe Pro Lys Gly Glu Pro Asp Leu Lys Lys Glu Ser Glu Glu
1               5                   10                  15

Asp Lys

<210> SEQ ID NO 137
<211> LENGTH: 19
<212> TYPE: PRT
<213> ORGANISM: Homo sapiens

<400> SEQUENCE: 137

Lys Asn Gly Gln Ala Glu Ala Glu Glu Ala Thr Glu Gln Thr His Ile
1               5                   10                  15

Ser Pro Asn

<210> SEQ ID NO 138
<211> LENGTH: 18
<212> TYPE: PRT
<213> ORGANISM: Homo sapiens

<400> SEQUENCE: 138

Gln Ala Ser Ser Leu Arg Leu Glu Pro Gly Arg Ala Asn Asp Gly Asp
1               5                   10                  15

Trp His

<210> SEQ ID NO 139
<211> LENGTH: 20
<212> TYPE: PRT
<213> ORGANISM: Homo sapiens

<400> SEQUENCE: 139

Glu Leu Lys Gly Phe Ala Glu Arg Leu Gln Arg Asn Glu Ser Gly Leu
1               5                   10                  15

Asp Ser Gly Arg
            20

<210> SEQ ID NO 140
<211> LENGTH: 17
<212> TYPE: PRT
<213> ORGANISM: Homo sapiens

<400> SEQUENCE: 140

Arg Ser Gly Lys Ser Gln Pro Ser Tyr Ile Pro Phe Leu Leu Arg Glu
1               5                   10                  15

Glu

<210> SEQ ID NO 141
<211> LENGTH: 22
<212> TYPE: PRT
<213> ORGANISM: Homo sapiens

<400> SEQUENCE: 141

Arg Arg Ser Asp Tyr Ala Lys Val Ala Lys Ile Phe Tyr Asn Leu Ser
1               5                   10                  15

Ile Gln Ser Phe Asp Asp
            20

<210> SEQ ID NO 142
<211> LENGTH: 19
<212> TYPE: PRT
<213> ORGANISM: Homo sapiens

<400> SEQUENCE: 142

Lys Asn Phe Thr Met Asn Glu Lys Leu Lys Lys Phe Phe Asn Val Leu
1               5                   10                  15

Thr Thr Asn

<210> SEQ ID NO 143
<211> LENGTH: 20
<212> TYPE: PRT
<213> ORGANISM: Homo sapiens

<400> SEQUENCE: 143

Glu Phe Phe Val Asn Glu Ala Arg Lys Asn Asn His His Phe Lys Ser

```
1               5                   10                  15
Glu Ser Glu Glu
            20

<210> SEQ ID NO 144
<211> LENGTH: 19
<212> TYPE: PRT
<213> ORGANISM: Homo sapiens

<400> SEQUENCE: 144

Lys Asn Thr Gln Ala Ala Glu Ala Leu Val Lys Leu Tyr Glu Thr Lys
1               5                   10                  15

Leu Cys Glu

<210> SEQ ID NO 145
<211> LENGTH: 17
<212> TYPE: PRT
<213> ORGANISM: Homo sapiens

<400> SEQUENCE: 145

Gln Glu Asn Gln Pro Glu Asn Ser Lys Thr Leu Ala Thr Gln Leu Asn
1               5                   10                  15

Gln

<210> SEQ ID NO 146
<211> LENGTH: 19
<212> TYPE: PRT
<213> ORGANISM: Homo sapiens

<400> SEQUENCE: 146

Lys Gln Met Glu Lys Asp Leu Ala Phe Gln Lys Gln Val Ala Glu Lys
1               5                   10                  15

Gln Leu Lys

<210> SEQ ID NO 147
<211> LENGTH: 17
<212> TYPE: PRT
<213> ORGANISM: Homo sapiens

<400> SEQUENCE: 147

Glu Phe Val Glu Gln Leu Arg Lys Glu Gly Val Phe Ala Lys Glu Val
1               5                   10                  15

Arg

<210> SEQ ID NO 148
<211> LENGTH: 18
<212> TYPE: PRT
<213> ORGANISM: Homo sapiens

<400> SEQUENCE: 148

Asp Arg His Pro Gln Ala Leu Glu Ala Ala Gln Ala Glu Leu Gln Gln
1               5                   10                  15

His Asp

<210> SEQ ID NO 149
<211> LENGTH: 20
<212> TYPE: PRT
<213> ORGANISM: Homo sapiens

<400> SEQUENCE: 149

Arg Glu Val Arg Gln Leu Thr Leu Arg Lys Leu Gln Glu Leu Ser Ser
```

```
1               5                   10                  15
Lys Ala Asp Glu
            20
```

<210> SEQ ID NO 150
<211> LENGTH: 19
<212> TYPE: PRT
<213> ORGANISM: Homo sapiens

<400> SEQUENCE: 150

```
Ala Tyr Ile Arg Glu Gly His Glu Lys Gln Ala Asp Ile Met Ile Phe
1               5                   10                  15

Phe Ala Glu
```

<210> SEQ ID NO 151
<211> LENGTH: 18
<212> TYPE: PRT
<213> ORGANISM: Homo sapiens

<400> SEQUENCE: 151

```
Asp Glu Ala Ser Leu Glu Pro Gly Tyr Pro Lys His Ile Lys Glu Leu
1               5                   10                  15

Gly Arg
```

<210> SEQ ID NO 152
<211> LENGTH: 16
<212> TYPE: PRT
<213> ORGANISM: Homo sapiens

<400> SEQUENCE: 152

```
Arg Gly Ser Phe Met Gly Ser Asp Glu Val Phe Thr Tyr Phe Tyr Lys
1               5                   10                  15
```

<210> SEQ ID NO 153
<211> LENGTH: 20
<212> TYPE: PRT
<213> ORGANISM: Homo sapiens

<400> SEQUENCE: 153

```
Arg Gln Glu His Cys Met Ser Glu His Phe Lys Asn Arg Pro Ala Cys
1               5                   10                  15

Leu Gly Ala Arg
            20
```

<210> SEQ ID NO 154
<211> LENGTH: 19
<212> TYPE: PRT
<213> ORGANISM: Homo sapiens

<400> SEQUENCE: 154

```
Gln Gly His Lys Trp Gly Glu Ser Pro Ser Gln Gly Thr Gln Ala Gly
1               5                   10                  15

Ala Gly Lys
```

<210> SEQ ID NO 155
<211> LENGTH: 21
<212> TYPE: PRT
<213> ORGANISM: Homo sapiens

<400> SEQUENCE: 155

```
Arg Ala Cys Gly Lys Arg Val Ser Glu Gly Asp Arg Asn Gly Ser Gly
1               5                   10                  15
```

```
Gly Gly Lys Trp Gly
            20

<210> SEQ ID NO 156
<211> LENGTH: 16
<212> TYPE: PRT
<213> ORGANISM: Homo sapiens

<400> SEQUENCE: 156

Met Val Glu Ala Phe Cys Ala Thr Trp Lys Leu Thr Asn Ser Gln Asn
1               5                  10                  15

<210> SEQ ID NO 157
<211> LENGTH: 15
<212> TYPE: PRT
<213> ORGANISM: Homo sapiens

<400> SEQUENCE: 157

Gln Val Gly Asn Val Thr Lys Pro Thr Val Ile Ile Ser Gln Glu
1               5                  10                  15

<210> SEQ ID NO 158
<211> LENGTH: 14
<212> TYPE: PRT
<213> ORGANISM: Homo sapiens

<400> SEQUENCE: 158

Lys Val Val Ile Arg Thr Leu Ser Thr Phe Lys Asn Thr Glu
1               5                  10

<210> SEQ ID NO 159
<211> LENGTH: 19
<212> TYPE: PRT
<213> ORGANISM: Homo sapiens

<400> SEQUENCE: 159

Arg Ala Val Phe Arg Glu Ala Glu Val Thr Leu Glu Ala Gly Gly Ala
1               5                  10                  15

Glu Gln Glu

<210> SEQ ID NO 160
<211> LENGTH: 17
<212> TYPE: PRT
<213> ORGANISM: Homo sapiens

<400> SEQUENCE: 160

Gln Glu Pro Ala Leu Phe Ser Thr Asp Asn Asp Phe Thr Val Arg
1               5                  10                  15

Asn

<210> SEQ ID NO 161
<211> LENGTH: 15
<212> TYPE: PRT
<213> ORGANISM: Homo sapiens

<400> SEQUENCE: 161

Gln Lys Tyr Glu Ala His Val Pro Glu Asn Ala Val Gly His Glu
1               5                  10                  15

<210> SEQ ID NO 162
<211> LENGTH: 14
<212> TYPE: PRT
<213> ORGANISM: Homo sapiens
```

<400> SEQUENCE: 162

Lys Lys Ile Ile Glu Lys Met Leu Asn Ser Asp Lys Ser Asn
1               5                   10

<210> SEQ ID NO 163
<211> LENGTH: 20
<212> TYPE: PRT
<213> ORGANISM: Homo sapiens

<400> SEQUENCE: 163

Gly Lys Pro Gly Asn Gln Asn Ser Lys Asn Glu Pro Pro Lys Lys Arg
1               5                   10                  15

Glu Arg Glu Arg
            20

<210> SEQ ID NO 164
<211> LENGTH: 14
<212> TYPE: PRT
<213> ORGANISM: Homo sapiens

<400> SEQUENCE: 164

Gln Ala Glu Ala Pro Leu Val Pro Leu Ser Arg Gln Asn Lys
1               5                   10

<210> SEQ ID NO 165
<211> LENGTH: 13
<212> TYPE: PRT
<213> ORGANISM: Homo sapiens

<400> SEQUENCE: 165

Asn Cys Phe Leu Thr Glu Arg Lys Ala Gln Pro Asp Glu
1               5                   10

<210> SEQ ID NO 166
<211> LENGTH: 15
<212> TYPE: PRT
<213> ORGANISM: Homo sapiens

<400> SEQUENCE: 166

Lys Gln Val Asp Leu Glu Asn Val Trp Leu Asp Phe Ile Arg Glu
1               5                   10                  15

<210> SEQ ID NO 167
<211> LENGTH: 15
<212> TYPE: PRT
<213> ORGANISM: Homo sapiens

<400> SEQUENCE: 167

Glu Phe Asp Thr Val Asp Leu Ser Ala Val Asp Val His Pro Asn
1               5                   10                  15

<210> SEQ ID NO 168
<211> LENGTH: 18
<212> TYPE: PRT
<213> ORGANISM: Homo sapiens

<400> SEQUENCE: 168

Asn Lys Glu Val Tyr His Glu Lys Asp Ile Lys Val Phe Phe Asp Lys
1               5                   10                  15

Ala Lys

<210> SEQ ID NO 169

<211> LENGTH: 17
<212> TYPE: PRT
<213> ORGANISM: Homo sapiens

<400> SEQUENCE: 169

Lys Arg Gly Ile Glu Glu Arg Ile Gln Glu Glu Ser Gly Phe Leu Ile
1               5                   10                  15

Glu

<210> SEQ ID NO 170
<211> LENGTH: 17
<212> TYPE: PRT
<213> ORGANISM: Homo sapiens

<400> SEQUENCE: 170

Asp Arg Val Ile Gly Lys Asn Arg Gln Pro Lys Phe Glu Asp Arg Thr
1               5                   10                  15

Lys

<210> SEQ ID NO 171
<211> LENGTH: 16
<212> TYPE: PRT
<213> ORGANISM: Homo sapiens

<400> SEQUENCE: 171

Asn Pro Gln His Phe Leu Asp Asp Lys Gly Gln Phe Lys Lys Ser Asp
1               5                   10                  15

<210> SEQ ID NO 172
<211> LENGTH: 18
<212> TYPE: PRT
<213> ORGANISM: Homo sapiens

<400> SEQUENCE: 172

Arg His Cys Ile Leu Gly Glu Trp Leu Pro Ile Leu Ile Met Ala Val
1               5                   10                  15

Phe Asn

<210> SEQ ID NO 173
<211> LENGTH: 16
<212> TYPE: PRT
<213> ORGANISM: Homo sapiens

<400> SEQUENCE: 173

Lys Gln Arg Glu Leu Ala Gly Asn Thr Met Thr Val Ser Tyr Met Ser
1               5                   10                  15

<210> SEQ ID NO 174
<211> LENGTH: 21
<212> TYPE: PRT
<213> ORGANISM: Homo sapiens

<400> SEQUENCE: 174

Arg Asn Ala His Gly Ser Cys Leu His Ala Ser Thr Ala Asn Gly Ser
1               5                   10                  15

Ile Leu Ala Gly Leu
            20

<210> SEQ ID NO 175
<211> LENGTH: 16
<212> TYPE: PRT
<213> ORGANISM: Homo sapiens

<400> SEQUENCE: 175

Glu Leu Met Glu Lys Glu Val Glu Pro Glu Gly Ser Lys Arg Thr Asp
1               5                   10                  15

<210> SEQ ID NO 176
<211> LENGTH: 15
<212> TYPE: PRT
<213> ORGANISM: Homo sapiens

<400> SEQUENCE: 176

Lys Ala Arg Ser Phe Cys Lys Thr His Ala Arg Leu Phe Lys Lys
1               5                   10                  15

<210> SEQ ID NO 177
<211> LENGTH: 16
<212> TYPE: PRT
<213> ORGANISM: Homo sapiens

<400> SEQUENCE: 177

Lys Asn Lys Arg Leu Ser Gly Met Glu Glu Trp Ile Glu Gly Glu Lys
1               5                   10                  15

<210> SEQ ID NO 178
<211> LENGTH: 17
<212> TYPE: PRT
<213> ORGANISM: Homo sapiens

<400> SEQUENCE: 178

Glu Gly Ser Thr Asp Leu Pro Leu Ala Pro Glu Ser Arg Val Asp Pro
1               5                   10                  15

Glu

<210> SEQ ID NO 179
<211> LENGTH: 15
<212> TYPE: PRT
<213> ORGANISM: Homo sapiens

<400> SEQUENCE: 179

Lys Val Ala Gln Gln Gln Arg His Leu Glu Lys Gln His Leu Arg
1               5                   10                  15

<210> SEQ ID NO 180
<211> LENGTH: 20
<212> TYPE: PRT
<213> ORGANISM: Homo sapiens

<400> SEQUENCE: 180

Asp His Lys His Leu Asp His Glu Val Ala Lys Pro Ala Arg Arg Lys
1               5                   10                  15

Arg Leu Pro Glu
            20

<210> SEQ ID NO 181
<211> LENGTH: 17
<212> TYPE: PRT
<213> ORGANISM: Homo sapiens

<400> SEQUENCE: 181

Lys Leu Thr Ile Glu Ser Thr Pro Phe Asn Val Ala Glu Gly Lys Glu
1               5                   10                  15

Cys

```
<210> SEQ ID NO 182
<211> LENGTH: 21
<212> TYPE: PRT
<213> ORGANISM: Homo sapiens

<400> SEQUENCE: 182

Lys Ser Asp Leu Val Asn Glu Glu Ala Thr Gly Gln Phe Arg Val Tyr
1               5                   10                  15

Pro Glu Leu Pro Lys
            20

<210> SEQ ID NO 183
<211> LENGTH: 18
<212> TYPE: PRT
<213> ORGANISM: Homo sapiens

<400> SEQUENCE: 183

Lys Pro Val Glu Asp Lys Asp Ala Val Ala Phe Thr Cys Glu Pro Glu
1               5                   10                  15

Ala Gln

<210> SEQ ID NO 184
<211> LENGTH: 22
<212> TYPE: PRT
<213> ORGANISM: Homo sapiens

<400> SEQUENCE: 184

Asp Glu Lys Leu Ile Ser Leu Ile Cys Arg Ala Val Lys Ala Thr Phe
1               5                   10                  15

Asn Pro Ala Gln Asp Lys
            20

<210> SEQ ID NO 185
<211> LENGTH: 19
<212> TYPE: PRT
<213> ORGANISM: Homo sapiens

<400> SEQUENCE: 185

Lys Asp Lys Trp Asp Glu Leu Lys Glu Ala Gly Val Ser Asp Met Lys
1               5                   10                  15

Leu Gly Asp

<210> SEQ ID NO 186
<211> LENGTH: 23
<212> TYPE: PRT
<213> ORGANISM: Homo sapiens

<400> SEQUENCE: 186

Asp Ser Trp Ile Val Pro Leu Asp Asn Leu Thr Lys Asp Asp Leu Asp
1               5                   10                  15

Glu Glu Glu Asp Thr His Leu
            20

<210> SEQ ID NO 187
<211> LENGTH: 20
<212> TYPE: PRT
<213> ORGANISM: Homo sapiens

<400> SEQUENCE: 187

Arg Lys Arg Val Leu Glu Ala Lys Glu Leu Ala Leu Gln Pro Lys Asp
1               5                   10                  15

Asp Ile Val Asp
```

```
                    20

<210> SEQ ID NO 188
<211> LENGTH: 21
<212> TYPE: PRT
<213> ORGANISM: Homo sapiens

<400> SEQUENCE: 188

Arg His Gly Val Ser His Lys Val Asp Asp Ser Ser Gly Ser Ile Gly
1               5                   10                  15

Arg Arg Tyr Ala Arg
            20

<210> SEQ ID NO 189
<211> LENGTH: 20
<212> TYPE: PRT
<213> ORGANISM: Homo sapiens

<400> SEQUENCE: 189

Glu Ala Arg Tyr Pro Leu Phe Glu Gly Gln Glu Thr Gly Lys Lys Glu
1               5                   10                  15

Thr Ile Glu Glu
            20

<210> SEQ ID NO 190
<211> LENGTH: 18
<212> TYPE: PRT
<213> ORGANISM: Homo sapiens

<400> SEQUENCE: 190

Glu Ala Leu Tyr Pro Gln Arg Arg Ser Tyr Thr Ser Glu Asp Glu Ala
1               5                   10                  15

Trp Lys

<210> SEQ ID NO 191
<211> LENGTH: 19
<212> TYPE: PRT
<213> ORGANISM: Homo sapiens

<400> SEQUENCE: 191

Asp Tyr Tyr Lys Val Pro Arg Glu Arg Arg Ser Ser Thr Ala Lys Pro
1               5                   10                  15

Glu Val Glu

<210> SEQ ID NO 192
<211> LENGTH: 19
<212> TYPE: PRT
<213> ORGANISM: Homo sapiens

<400> SEQUENCE: 192

Asp Lys Tyr Asp Val Pro His Asp Lys Ile Gly Lys Ile Phe Lys Lys
1               5                   10                  15

Cys Lys Lys

<210> SEQ ID NO 193
<211> LENGTH: 21
<212> TYPE: PRT
<213> ORGANISM: Homo sapiens

<400> SEQUENCE: 193

Asp Pro Asp Gln Tyr Asn Phe Ser Ser Ser Glu Leu Gly Gly Asp Phe
1               5                   10                  15
```

```
Glu Phe Met Asp Asp
        20

<210> SEQ ID NO 194
<211> LENGTH: 15
<212> TYPE: PRT
<213> ORGANISM: Homo sapiens

<400> SEQUENCE: 194

Glu Tyr Ile Arg Gln Leu Pro Pro Asn Phe Pro Tyr Arg Asp Asp
1               5                   10                  15

<210> SEQ ID NO 195
<211> LENGTH: 20
<212> TYPE: PRT
<213> ORGANISM: Homo sapiens

<400> SEQUENCE: 195

Asp Thr Thr Val Leu Leu Pro Pro Tyr Asp Asp Ala Thr Val Asn Gly
1               5                   10                  15

Ala Ala Lys Glu
        20

<210> SEQ ID NO 196
<211> LENGTH: 14
<212> TYPE: PRT
<213> ORGANISM: Homo sapiens

<400> SEQUENCE: 196

Arg Arg Glu Glu Val Thr Lys Lys His Gln Tyr Glu Ile Arg
1               5                   10

<210> SEQ ID NO 197
<211> LENGTH: 19
<212> TYPE: PRT
<213> ORGANISM: Homo sapiens

<400> SEQUENCE: 197

Lys Glu Ser Arg Tyr Val His Asp Lys His Phe Glu Val Leu His Ser
1               5                   10                  15

Asp Leu Glu

<210> SEQ ID NO 198
<211> LENGTH: 15
<212> TYPE: PRT
<213> ORGANISM: Homo sapiens

<400> SEQUENCE: 198

Asp Phe Phe Asp Arg Phe Met Leu Thr Gln Lys Asp Ile Asn Lys
1               5                   10                  15

<210> SEQ ID NO 199
<211> LENGTH: 19
<212> TYPE: PRT
<213> ORGANISM: Homo sapiens

<400> SEQUENCE: 199

Glu Ser Lys His Phe Thr Arg Asp Leu Met Glu Lys Leu Lys Gly Arg
1               5                   10                  15

Thr Ser Arg

<210> SEQ ID NO 200
```

```
<211> LENGTH: 17
<212> TYPE: PRT
<213> ORGANISM: Homo sapiens

<400> SEQUENCE: 200

Glu Thr Asp Arg Leu Pro Arg Cys Val Arg Ser Thr Ala Arg Leu Ala
1               5                   10                  15

Arg

<210> SEQ ID NO 201
<211> LENGTH: 20
<212> TYPE: PRT
<213> ORGANISM: Homo sapiens

<400> SEQUENCE: 201

Glu Ser Arg Trp Lys Asp Ile Arg Ala Arg Ile Phe Leu Ile Ala Ser
1               5                   10                  15

Lys Glu Leu Glu
            20

<210> SEQ ID NO 202
<211> LENGTH: 12
<212> TYPE: PRT
<213> ORGANISM: Homo sapiens

<400> SEQUENCE: 202

Ser Glu Trp Arg Ser Ser Gly Glu Gln Ala Gly Arg
1               5                   10

<210> SEQ ID NO 203
<211> LENGTH: 16
<212> TYPE: PRT
<213> ORGANISM: Homo sapiens

<400> SEQUENCE: 203

Lys Cys Lys Cys Lys Phe Gly Gln Lys Ser Gly His His Pro Gly Glu
1               5                   10                  15

<210> SEQ ID NO 204
<211> LENGTH: 23
<212> TYPE: PRT
<213> ORGANISM: Homo sapiens

<400> SEQUENCE: 204

Lys Val Thr Leu Gly Leu Leu Val Phe Leu Ala Gly Phe Pro Val Leu
1               5                   10                  15

Asp Ala Asn Asp Leu Glu Asp
            20

<210> SEQ ID NO 205
<211> LENGTH: 21
<212> TYPE: PRT
<213> ORGANISM: Homo sapiens

<400> SEQUENCE: 205

Lys Val Ala Lys Glu Ser Asp Ser Val Phe Val Leu Lys Ile Tyr His
1               5                   10                  15

Leu Arg Gln Glu Asp
            20

<210> SEQ ID NO 206
<211> LENGTH: 19
<212> TYPE: PRT
```

<213> ORGANISM: Homo sapiens

<400> SEQUENCE: 206

Glu Arg Glu Lys Thr Val Thr Gly Glu Phe Ile Asp Lys Glu Ser Lys
1               5                   10                  15

Arg Pro Lys

<210> SEQ ID NO 207
<211> LENGTH: 18
<212> TYPE: PRT
<213> ORGANISM: Homo sapiens

<400> SEQUENCE: 207

Lys Arg Ala Glu Asp Thr Ala Gly Gln Thr Ala Leu Thr Val Met Arg
1               5                   10                  15

Pro Asp

<210> SEQ ID NO 208
<211> LENGTH: 19
<212> TYPE: PRT
<213> ORGANISM: Homo sapiens

<400> SEQUENCE: 208

Lys Val Ala Arg Lys Val Arg Ala Leu Tyr Asp Phe Glu Ala Val Glu
1               5                   10                  15

Asp Asn Glu

<210> SEQ ID NO 209
<211> LENGTH: 18
<212> TYPE: PRT
<213> ORGANISM: Homo sapiens

<400> SEQUENCE: 209

Glu Thr Glu Val Ala Ala Val Asp Lys Leu Asn Val Ile Asp Asp
1               5                   10                  15

Val Glu

<210> SEQ ID NO 210
<211> LENGTH: 19
<212> TYPE: PRT
<213> ORGANISM: Homo sapiens

<400> SEQUENCE: 210

Glu Ile Lys Lys Ser Glu Pro Glu Pro Val Tyr Ile Asp Glu Asp Lys
1               5                   10                  15

Met Asp Arg

<210> SEQ ID NO 211
<211> LENGTH: 18
<212> TYPE: PRT
<213> ORGANISM: Homo sapiens

<400> SEQUENCE: 211

Asp Glu Glu Cys Gly Thr Asp Glu Tyr Cys Ala Ser Pro Thr Arg Gly
1               5                   10                  15

Gly Asp

<210> SEQ ID NO 212
<211> LENGTH: 20
<212> TYPE: PRT
<213> ORGANISM: Homo sapiens -continued

```
<400> SEQUENCE: 212

Arg Gly Glu Ile Glu Glu Thr Ile Thr Glu Ser Phe Gly Asn Asp His
1               5                   10                  15

Ser Thr Leu Asp
            20

<210> SEQ ID NO 213
<211> LENGTH: 22
<212> TYPE: PRT
<213> ORGANISM: Homo sapiens

<400> SEQUENCE: 213

Met Asp Leu Arg Arg Arg Asp Tyr His Met Glu Arg Pro Leu Leu Asn
1               5                   10                  15

Gln Glu His Leu Glu Glu
            20

<210> SEQ ID NO 214
<211> LENGTH: 16
<212> TYPE: PRT
<213> ORGANISM: Homo sapiens

<400> SEQUENCE: 214

Asp Thr Asp Ile Tyr Arg Asp Val Ala Glu Tyr Ser Glu Ala Lys Glu
1               5                   10                  15

<210> SEQ ID NO 215
<211> LENGTH: 24
<212> TYPE: PRT
<213> ORGANISM: Homo sapiens

<400> SEQUENCE: 215

Glu Phe Tyr Ser Asp Ala Leu Lys Gln Arg Cys Gly Val Asp Val Asp
1               5                   10                  15

Phe Leu Ile Ser Gln Lys Lys Lys
            20

<210> SEQ ID NO 216
<211> LENGTH: 20
<212> TYPE: PRT
<213> ORGANISM: Homo sapiens

<400> SEQUENCE: 216

Asp Ala His Gln Ala Arg Val Leu Ile Gly Phe Glu Gly Asp Ile Leu
1               5                   10                  15

Ile Val Ser Glu
            20

<210> SEQ ID NO 217
<211> LENGTH: 18
<212> TYPE: PRT
<213> ORGANISM: Homo sapiens

<400> SEQUENCE: 217

Glu Arg Arg Ile Cys Glu Cys Pro Asp Gly Phe His Gly Pro His Cys
1               5                   10                  15

Glu Lys

<210> SEQ ID NO 218
<211> LENGTH: 19
<212> TYPE: PRT
```

-continued

<213> ORGANISM: Homo sapiens

<400> SEQUENCE: 218

Lys Arg Tyr Glu Ala Ser Leu Ile His Ala Leu Arg Pro Ala Gly Ala
1               5                   10                  15

Gln Leu Arg

<210> SEQ ID NO 219
<211> LENGTH: 18
<212> TYPE: PRT
<213> ORGANISM: Homo sapiens

<400> SEQUENCE: 219

Asp Ile Lys Met Ile Leu Lys Met Val Gln Leu Asp Ser Ile Glu Asp
1               5                   10                  15

Leu Glu

<210> SEQ ID NO 220
<211> LENGTH: 19
<212> TYPE: PRT
<213> ORGANISM: Homo sapiens

<400> SEQUENCE: 220

Lys Arg Lys Val Asp Gly Leu Ser Thr Glu Ala Glu Gln Pro Phe Ile
1               5                   10                  15

Pro Val Glu

<210> SEQ ID NO 221
<211> LENGTH: 20
<212> TYPE: PRT
<213> ORGANISM: Homo sapiens

<400> SEQUENCE: 221

Lys Glu Gly Ala Cys Asp Glu Leu Phe Ser Tyr Leu Ile Glu Lys Val
1               5                   10                  15

Lys Arg Lys Lys
            20

<210> SEQ ID NO 222
<211> LENGTH: 15
<212> TYPE: PRT
<213> ORGANISM: Homo sapiens

<400> SEQUENCE: 222

Arg Leu Arg Lys Lys Ala Phe Ala Asn Pro Glu Asp Ala Leu Arg
1               5                   10                  15

<210> SEQ ID NO 223
<211> LENGTH: 16
<212> TYPE: PRT
<213> ORGANISM: Homo sapiens

<400> SEQUENCE: 223

Arg Ser Asp Pro Asp Val Glu Arg Cys Leu Arg Ala His Arg Asn Asp
1               5                   10                  15

<210> SEQ ID NO 224
<211> LENGTH: 17
<212> TYPE: PRT
<213> ORGANISM: Homo sapiens

<400> SEQUENCE: 224

```
Arg Val Ala His Thr Val Ala Tyr Leu Gly Lys Leu Arg Ala Pro Ile
1               5                   10                  15

Arg

<210> SEQ ID NO 225
<211> LENGTH: 13
<212> TYPE: PRT
<213> ORGANISM: Homo sapiens

<400> SEQUENCE: 225

Lys Arg Arg Ala Leu Ala Ala Pro Ala Ala Glu Glu Lys
1               5                   10

<210> SEQ ID NO 226
<211> LENGTH: 20
<212> TYPE: PRT
<213> ORGANISM: Homo sapiens

<400> SEQUENCE: 226

Glu Ala Arg Glu Lys Met Leu Ala Ala Lys Ser Ala Asp Gly Ser Ala
1               5                   10                  15

Pro Ala Gly Glu
            20

<210> SEQ ID NO 227
<211> LENGTH: 16
<212> TYPE: PRT
<213> ORGANISM: Homo sapiens

<400> SEQUENCE: 227

Met Ile Trp Leu Arg His Arg Lys Pro Glu Leu Glu Arg Pro Ile Lys
1               5                   10                  15

<210> SEQ ID NO 228
<211> LENGTH: 14
<212> TYPE: PRT
<213> ORGANISM: Homo sapiens

<400> SEQUENCE: 228

Lys Pro Asn Lys Ala Leu Lys Val Lys Lys Glu Ala Gly Glu
1               5                   10

<210> SEQ ID NO 229
<211> LENGTH: 22
<212> TYPE: PRT
<213> ORGANISM: Homo sapiens

<400> SEQUENCE: 229

Lys Arg Val Thr Gln Lys Glu Glu Leu Glu Arg Gln Arg Val Glu Leu
1               5                   10                  15

Gln Gln Glu Val Glu Lys
            20

<210> SEQ ID NO 230
<211> LENGTH: 12
<212> TYPE: PRT
<213> ORGANISM: Homo sapiens

<400> SEQUENCE: 230

Arg Leu Glu Leu Asp Ala Leu Arg Ser Lys Tyr Glu
1               5                   10

<210> SEQ ID NO 231
```

```
<211> LENGTH: 21
<212> TYPE: PRT
<213> ORGANISM: Homo sapiens

<400> SEQUENCE: 231

Lys Met His Thr Asp Gly Arg Ser Cys Leu Glu Arg Glu Asp Thr Val
1               5                   10                  15

Leu Glu Val Thr Glu
            20

<210> SEQ ID NO 232
<211> LENGTH: 18
<212> TYPE: PRT
<213> ORGANISM: Homo sapiens

<400> SEQUENCE: 232

Lys Lys Gly Phe Lys Leu Leu Thr Asp Glu Lys Ser Cys Gln Asp Val
1               5                   10                  15

Asp Glu

<210> SEQ ID NO 233
<211> LENGTH: 21
<212> TYPE: PRT
<213> ORGANISM: Homo sapiens

<400> SEQUENCE: 233

Lys Arg Thr Glu Lys Arg Leu Arg Lys Ala Ile Arg Thr Leu Arg Lys
1               5                   10                  15

Ala Val His Arg Glu
            20

<210> SEQ ID NO 234
<211> LENGTH: 17
<212> TYPE: PRT
<213> ORGANISM: Homo sapiens

<400> SEQUENCE: 234

Arg Val Glu Gly Pro Gln Thr Glu Ser Lys Asn Glu Ala Ser Ser Arg
1               5                   10                  15

Asp

<210> SEQ ID NO 235
<211> LENGTH: 19
<212> TYPE: PRT
<213> ORGANISM: Homo sapiens

<400> SEQUENCE: 235

Glu Glu Thr Lys Ser Thr Glu Thr Glu Thr Gly Ser Arg Val Gly Lys
1               5                   10                  15

Leu Pro Glu

<210> SEQ ID NO 236
<211> LENGTH: 21
<212> TYPE: PRT
<213> ORGANISM: Homo sapiens

<400> SEQUENCE: 236

Lys Trp Glu Asn Phe Lys Leu Glu Ile Asn Glu Lys Asn Ser Trp Lys
1               5                   10                  15

Leu Phe Gln Phe Asp
            20
```

-continued

```
<210> SEQ ID NO 237
<211> LENGTH: 17
<212> TYPE: PRT
<213> ORGANISM: Homo sapiens

<400> SEQUENCE: 237

Asp Lys Gly Tyr Leu Thr Lys Glu Asp Leu Arg Val Leu Met Glu Lys
1               5                   10                  15

Glu

<210> SEQ ID NO 238
<211> LENGTH: 20
<212> TYPE: PRT
<213> ORGANISM: Homo sapiens

<400> SEQUENCE: 238

Lys Asp Pro Leu Ala Val Asp Lys Ile Met Lys Asp Leu Asp Gln Cys
1               5                   10                  15

Arg Asp Gly Lys
            20

<210> SEQ ID NO 239
<211> LENGTH: 23
<212> TYPE: PRT
<213> ORGANISM: Homo sapiens

<400> SEQUENCE: 239

Glu Glu Asp Leu Lys Glu Val Leu Arg Ser Glu Ala Gly Ile Glu Leu
1               5                   10                  15

Ile Ile Glu Asp Asp Ile Arg
            20

<210> SEQ ID NO 240
<211> LENGTH: 21
<212> TYPE: PRT
<213> ORGANISM: Homo sapiens

<400> SEQUENCE: 240

Met Ser Arg Arg Thr Arg Cys Glu Asp Leu Asp Glu Leu His Tyr Gln
1               5                   10                  15

Asp Thr Asp Ser Asp
            20

<210> SEQ ID NO 241
<211> LENGTH: 20
<212> TYPE: PRT
<213> ORGANISM: Homo sapiens

<400> SEQUENCE: 241

Arg Arg Ser Pro Ile Lys Lys Val Arg Lys Ser Leu Ala Leu Asp Ile
1               5                   10                  15

Val Asp Glu Asp
            20

<210> SEQ ID NO 242
<211> LENGTH: 17
<212> TYPE: PRT
<213> ORGANISM: Homo sapiens

<400> SEQUENCE: 242

Glu Asp Tyr Lys Asn Thr Ala Glu Trp Leu Leu Ser His Thr Lys His
1               5                   10                  15
```

Arg

<210> SEQ ID NO 243
<211> LENGTH: 22
<212> TYPE: PRT
<213> ORGANISM: Homo sapiens

<400> SEQUENCE: 243

Asp Glu Arg Phe Gly Asp Arg Phe Pro Ala Met Ser Asp Ala Tyr Asp
1               5                   10                  15

Arg Thr Met Arg Gln Arg
            20

<210> SEQ ID NO 244
<211> LENGTH: 16
<212> TYPE: PRT
<213> ORGANISM: Homo sapiens

<400> SEQUENCE: 244

Lys Val Ile Met Asp Tyr Glu Ser Leu Glu Lys Ala Asn His Glu Glu
1               5                   10                  15

<210> SEQ ID NO 245
<211> LENGTH: 22
<212> TYPE: PRT
<213> ORGANISM: Homo sapiens

<400> SEQUENCE: 245

Asp Gln Asp Arg Lys Ser Arg Leu Met Gly Leu Glu Ala Leu Lys Ser
1               5                   10                  15

His Ile Met Ala Ala Lys
            20

<210> SEQ ID NO 246
<211> LENGTH: 20
<212> TYPE: PRT
<213> ORGANISM: Homo sapiens

<400> SEQUENCE: 246

Lys Gly Val Ile Val Asp Lys Asp Phe Ser His Pro Gln Met Pro Lys
1               5                   10                  15

Lys Val Glu Asp
            20

<210> SEQ ID NO 247
<211> LENGTH: 17
<212> TYPE: PRT
<213> ORGANISM: Homo sapiens

<400> SEQUENCE: 247

Arg Met Ile Leu Lys Ile Asp Asp Ile Arg Lys Pro Gly Glu Ser Glu
1               5                   10                  15

Glu

<210> SEQ ID NO 248
<211> LENGTH: 20
<212> TYPE: PRT
<213> ORGANISM: Homo sapiens

<400> SEQUENCE: 248

Arg Leu Gln Pro Glu Phe Lys Pro Lys Gln Leu Glu Gly Thr Met Ala
1               5                   10                  15

Asn Cys Glu Arg
            20

<210> SEQ ID NO 249
<211> LENGTH: 20
<212> TYPE: PRT
<213> ORGANISM: Homo sapiens

<400> SEQUENCE: 249

Lys Phe Met Gln Ala Ser Glu Asp Leu Leu Lys Glu His Tyr Val Asp
1               5                   10                  15

Leu Lys Asp Arg
            20

<210> SEQ ID NO 250
<211> LENGTH: 21
<212> TYPE: PRT
<213> ORGANISM: Homo sapiens

<400> SEQUENCE: 250

Asp Ser Val Glu Ser Ala Glu Lys Glu Ile Gly Leu Trp Phe His Pro
1               5                   10                  15

Glu Glu Leu Val Asp
            20

<210> SEQ ID NO 251
<211> LENGTH: 18
<212> TYPE: PRT
<213> ORGANISM: Homo sapiens

<400> SEQUENCE: 251

Lys Ser Pro Pro Glu Ser Glu Asn Lys Glu Gln Leu Glu Ala Arg Arg
1               5                   10                  15

Arg Arg

<210> SEQ ID NO 252
<211> LENGTH: 18
<212> TYPE: PRT
<213> ORGANISM: Homo sapiens

<400> SEQUENCE: 252

Arg Asp Gly Arg Lys Val Thr Val Ile Glu Arg Asp Leu Lys Glu Pro
1               5                   10                  15

Asp Arg

<210> SEQ ID NO 253
<211> LENGTH: 17
<212> TYPE: PRT
<213> ORGANISM: Homo sapiens

<400> SEQUENCE: 253

Asp His Leu Lys Glu Pro Phe Leu Glu Ala Thr Asp Asn Ser His Leu
1               5                   10                  15

Arg

<210> SEQ ID NO 254
<211> LENGTH: 19
<212> TYPE: PRT
<213> ORGANISM: Homo sapiens

<400> SEQUENCE: 254

-continued

Asp Leu Glu Val Lys Asp Trp Met Gln Lys Lys Arg Arg Gly Leu Arg
1               5                   10                  15

Asn Ser Arg

<210> SEQ ID NO 255
<211> LENGTH: 24
<212> TYPE: PRT
<213> ORGANISM: Homo sapiens

<400> SEQUENCE: 255

Glu Tyr His Lys Val His Gln Met Met Arg Glu Gln Ser Ile Leu Ser
1               5                   10                  15

Pro Ser Pro Tyr Glu Gly Tyr Arg
            20

<210> SEQ ID NO 256
<211> LENGTH: 23
<212> TYPE: PRT
<213> ORGANISM: Homo sapiens

<400> SEQUENCE: 256

Arg His Gln Leu Leu Cys Phe Lys Glu Asp Cys Gln Ala Val Phe Gln
1               5                   10                  15

Asp Leu Glu Gly Val Glu Lys
            20

<210> SEQ ID NO 257
<211> LENGTH: 16
<212> TYPE: PRT
<213> ORGANISM: Homo sapiens

<400> SEQUENCE: 257

Gly Pro Asp Ile Leu Arg Thr Tyr Ser Gly Ala Phe Val Cys Leu Glu
1               5                   10                  15

<210> SEQ ID NO 258
<211> LENGTH: 12
<212> TYPE: PRT
<213> ORGANISM: Homo sapiens

<400> SEQUENCE: 258

Cys Ser Leu Gly Leu Ala Leu Arg Arg Trp Arg Pro
1               5                   10

<210> SEQ ID NO 259
<211> LENGTH: 20
<212> TYPE: PRT
<213> ORGANISM: Homo sapiens

<400> SEQUENCE: 259

Arg Tyr Leu Thr Leu Asp Ile Phe Ala Gly Pro Pro Asn Tyr Pro Phe
1               5                   10                  15

Ser Asp Glu Tyr
            20

<210> SEQ ID NO 260
<211> LENGTH: 20
<212> TYPE: PRT
<213> ORGANISM: Homo sapiens

<400> SEQUENCE: 260

His Tyr Phe Asn Ser Asp Ser Phe Ala Ser His Pro Asn Tyr Pro Tyr
1               5                   10                  15

Ser Asp Glu Tyr
          20

<210> SEQ ID NO 261
<211> LENGTH: 20
<212> TYPE: PRT
<213> ORGANISM: Homo sapiens

<400> SEQUENCE: 261

Arg Tyr Val Val Met Asp Phe Leu Met Asp His Pro Asp Tyr Pro Phe
1               5                   10                  15

Ser Asp Glu Tyr
          20

<210> SEQ ID NO 262
<211> LENGTH: 17
<212> TYPE: PRT
<213> ORGANISM: Homo sapiens

<400> SEQUENCE: 262

Asp Pro Ala Lys Val Gln Ser Leu Val Asp Thr Ile Arg Glu Asp Pro
1               5                   10                  15

Asp

<210> SEQ ID NO 263
<211> LENGTH: 17
<212> TYPE: PRT
<213> ORGANISM: Homo sapiens

<400> SEQUENCE: 263

Arg Glu Thr Ile Pro Ala Lys Leu Val Gln Ser Thr Leu Ser Asp Leu
1               5                   10                  15

Arg

<210> SEQ ID NO 264
<211> LENGTH: 17
<212> TYPE: PRT
<213> ORGANISM: Homo sapiens

<400> SEQUENCE: 264

Ser Asp Thr Thr Glu Glu Leu Thr Val Ile Lys Ser Ser Leu Lys Asp
1               5                   10                  15

Glu

<210> SEQ ID NO 265
<211> LENGTH: 16
<212> TYPE: PRT
<213> ORGANISM: Homo sapiens

<400> SEQUENCE: 265

His Ser Arg Ser Ser Leu Met Pro Leu Arg Asn Asp Val Asp Lys Arg
1               5                   10                  15

<210> SEQ ID NO 266
<211> LENGTH: 20
<212> TYPE: PRT
<213> ORGANISM: Homo sapiens

<400> SEQUENCE: 266

Asp Ala Asn Thr Cys Gly Glu Asp Lys Gly Ser Arg Arg Lys Phe Leu
1               5                   10                  15

Asp Gly Asp Glu
        20

<210> SEQ ID NO 267
<211> LENGTH: 20
<212> TYPE: PRT
<213> ORGANISM: Homo sapiens

<400> SEQUENCE: 267

Gln Leu Glu Glu Met Thr Glu Leu Glu Ser Pro Lys Cys Lys Arg Gln
1               5                   10                  15

Glu Asn Glu Gln
        20

<210> SEQ ID NO 268
<211> LENGTH: 20
<212> TYPE: PRT
<213> ORGANISM: Homo sapiens

<400> SEQUENCE: 268

Gln Ala Asp Gly Ala Ala Ser Ala Pro Thr Glu Glu Glu Glu Glu Val
1               5                   10                  15

Val Lys Asp Arg
        20

<210> SEQ ID NO 269
<211> LENGTH: 20
<212> TYPE: PRT
<213> ORGANISM: Homo sapiens

<400> SEQUENCE: 269

Ser Gly Asp Ser Leu Glu Thr Lys Glu Asp Gln Lys Met Ser Pro Lys
1               5                   10                  15

Ala Thr Glu Glu
        20

<210> SEQ ID NO 270
<211> LENGTH: 20
<212> TYPE: PRT
<213> ORGANISM: Homo sapiens

<400> SEQUENCE: 270

Lys Ile Arg Leu Pro Glu Arg Glu Lys Pro Asp Arg Glu Arg Asn Ala
1               5                   10                  15

Arg Arg Glu Pro
        20

<210> SEQ ID NO 271
<211> LENGTH: 20
<212> TYPE: PRT
<213> ORGANISM: Homo sapiens

<400> SEQUENCE: 271

Arg Gly Thr Lys Cys Leu Arg Arg Glu Ala Pro Arg Trp Asp Ala Pro
1               5                   10                  15

Leu Arg Asp Pro
        20

<210> SEQ ID NO 272
<211> LENGTH: 20
<212> TYPE: PRT
<213> ORGANISM: Homo sapiens

```
<400> SEQUENCE: 272

Gly Thr Arg Ser Arg Ser His Thr Ser Glu Gly Arg Thr Ser Arg Ser
1               5                   10                  15
His Thr Ser Glu
            20

<210> SEQ ID NO 273
<211> LENGTH: 18
<212> TYPE: PRT
<213> ORGANISM: Homo sapiens

<400> SEQUENCE: 273

Glu Glu Thr Thr Ala Asp Gly Arg Lys Thr Gln Thr Val Cys Asn Phe
1               5                   10                  15
Thr Asp

<210> SEQ ID NO 274
<211> LENGTH: 16
<212> TYPE: PRT
<213> ORGANISM: Homo sapiens

<400> SEQUENCE: 274

Ala Lys Arg Lys Arg Ser Ala Pro Glu Lys Ser Ser Gly Asp Val Pro
1               5                   10                  15

<210> SEQ ID NO 275
<211> LENGTH: 20
<212> TYPE: PRT
<213> ORGANISM: Homo sapiens

<400> SEQUENCE: 275

Arg Val Asp Arg Pro Gly Ser Arg Tyr Asp Val Ser Arg Leu Gly Arg
1               5                   10                  15
Gly Lys Arg Ser
            20

<210> SEQ ID NO 276
<211> LENGTH: 17
<212> TYPE: PRT
<213> ORGANISM: Homo sapiens

<400> SEQUENCE: 276

Glu Thr Val Asp Lys Leu Leu Lys Gly Tyr Asp Ile Arg Leu Arg Pro
1               5                   10                  15
Asp

<210> SEQ ID NO 277
<211> LENGTH: 20
<212> TYPE: PRT
<213> ORGANISM: Homo sapiens

<400> SEQUENCE: 277

Ala Pro Gly Gly Ala Glu Asp Leu Glu Asp Thr Gln Phe Pro Ser Glu
1               5                   10                  15
Glu Ala Arg Glu
            20

<210> SEQ ID NO 278
<211> LENGTH: 20
<212> TYPE: PRT
<213> ORGANISM: Homo sapiens
```

-continued

```
<400> SEQUENCE: 278

Arg Lys Ser Ser Arg Thr Leu Lys Lys Gly Pro Arg Gln Asp Pro Ser
1               5                   10                  15

Ala Ile Val Glu
            20

<210> SEQ ID NO 279
<211> LENGTH: 20
<212> TYPE: PRT
<213> ORGANISM: Homo sapiens

<400> SEQUENCE: 279

Gly Ser Glu Ser Gly Asp Ser Asp Glu Ser Glu Ser Lys Ser Glu Gln
1               5                   10                  15

Arg Thr Lys Arg
            20

<210> SEQ ID NO 280
<211> LENGTH: 20
<212> TYPE: PRT
<213> ORGANISM: Homo sapiens

<400> SEQUENCE: 280

Glu Ala Asp Ser Gly Asp Ala Arg Arg Leu Pro Arg Ala Arg Gly Glu
1               5                   10                  15

Arg Arg Arg His
            20

<210> SEQ ID NO 281
<211> LENGTH: 19
<212> TYPE: PRT
<213> ORGANISM: Homo sapiens

<400> SEQUENCE: 281

Arg Leu Glu Arg Pro Gln Asp Arg Asp Thr Pro Val Gln Asn Lys Arg
1               5                   10                  15

Arg Arg Ser

<210> SEQ ID NO 282
<211> LENGTH: 19
<212> TYPE: PRT
<213> ORGANISM: Homo sapiens

<400> SEQUENCE: 282

Asp Arg Val Glu Asp Val Met Met Glu Arg Glu Ser Gln Phe Lys Glu
1               5                   10                  15

Lys Gln Glu

<210> SEQ ID NO 283
<211> LENGTH: 17
<212> TYPE: PRT
<213> ORGANISM: Homo sapiens

<400> SEQUENCE: 283

Asp Glu Ala Phe Lys Arg Leu Gln Gly Lys Arg Asn Arg Gly Arg Glu
1               5                   10                  15

Glu

<210> SEQ ID NO 284
<211> LENGTH: 15
<212> TYPE: PRT
```

```
<213> ORGANISM: Homo sapiens

<400> SEQUENCE: 284

Arg Phe Gln Glu Glu Ile Lys Glu Asn Thr Lys Asn Asp Lys Gln
1               5                   10                  15

<210> SEQ ID NO 285
<211> LENGTH: 19
<212> TYPE: PRT
<213> ORGANISM: Homo sapiens

<400> SEQUENCE: 285

Lys Arg Asp Lys Glu Gly Val Arg Trp Thr Lys Cys Asn Lys Lys Thr
1               5                   10                  15

Leu Thr Asp

<210> SEQ ID NO 286
<211> LENGTH: 19
<212> TYPE: PRT
<213> ORGANISM: Homo sapiens

<400> SEQUENCE: 286

Lys Glu Gly Ser Leu Leu Ser Lys Gln Glu Glu Ser Lys Ala Ala Phe
1               5                   10                  15

Gly Glu Glu

<210> SEQ ID NO 287
<211> LENGTH: 19
<212> TYPE: PRT
<213> ORGANISM: Homo sapiens

<400> SEQUENCE: 287

Glu Ser Asp Ala Gly Lys Glu Lys Leu Pro Lys Met Arg Leu Pro Thr
1               5                   10                  15

Arg Ser Asp

<210> SEQ ID NO 288
<211> LENGTH: 19
<212> TYPE: PRT
<213> ORGANISM: Homo sapiens

<400> SEQUENCE: 288

Glu Arg Asp Lys Gly Lys Thr Val Glu Val Gly Arg Ala Tyr Phe Glu
1               5                   10                  15

Thr Glu Lys

<210> SEQ ID NO 289
<211> LENGTH: 15
<212> TYPE: PRT
<213> ORGANISM: Homo sapiens

<400> SEQUENCE: 289

Glu Lys Phe Arg Val Glu Lys Asp Lys Leu Val Pro Glu Lys Arg
1               5                   10                  15

<210> SEQ ID NO 290
<211> LENGTH: 18
<212> TYPE: PRT
<213> ORGANISM: Homo sapiens

<400> SEQUENCE: 290

Glu Asn Tyr Glu Asp Asp Asp Leu Val Asn Ser Asp Glu Val Met Lys
1               5                   10                  15
```

```
1               5                   10                  15
Lys Pro

<210> SEQ ID NO 291
<211> LENGTH: 17
<212> TYPE: PRT
<213> ORGANISM: Homo sapiens

<400> SEQUENCE: 291

Pro Lys Ala Asp Glu Ile Arg Thr Leu Val Lys Asp Met Trp Asp Thr
1               5                   10                  15
Arg

<210> SEQ ID NO 292
<211> LENGTH: 19
<212> TYPE: PRT
<213> ORGANISM: Homo sapiens

<400> SEQUENCE: 292

Arg Lys Arg Cys Leu Glu Asp Ser Glu Asp Phe Gly Val Lys Lys Ala
1               5                   10                  15
Arg Thr Glu

<210> SEQ ID NO 293
<211> LENGTH: 19
<212> TYPE: PRT
<213> ORGANISM: Homo sapiens

<400> SEQUENCE: 293

Glu Pro Lys Ser Phe Leu Cys Arg Leu Cys Cys Gln Glu Asp Pro Glu
1               5                   10                  15
Leu Asp Ser

<210> SEQ ID NO 294
<211> LENGTH: 18
<212> TYPE: PRT
<213> ORGANISM: Homo sapiens

<400> SEQUENCE: 294

Glu Glu Tyr Asp Arg Glu Ser Lys Ser Ser Asp Asp Val Asp Tyr Arg
1               5                   10                  15
Gly Ser

<210> SEQ ID NO 295
<211> LENGTH: 16
<212> TYPE: PRT
<213> ORGANISM: Homo sapiens

<400> SEQUENCE: 295

Glu Gln Arg Ala Arg Trp Glu Arg Lys Arg Ala Cys Thr Ala Arg Glu
1               5                   10                  15

<210> SEQ ID NO 296
<211> LENGTH: 17
<212> TYPE: PRT
<213> ORGANISM: Homo sapiens

<400> SEQUENCE: 296

Glu Arg Lys Gln Leu Glu Cys Glu Gln Val Leu Gln Lys Leu Ala Lys
1               5                   10                  15
Glu
```

<210> SEQ ID NO 297
<211> LENGTH: 19
<212> TYPE: PRT
<213> ORGANISM: Homo sapiens

<400> SEQUENCE: 297

Arg Asn Ser Glu Thr Lys Val Arg Arg Ser Thr Arg Leu Gln Lys Asp
1               5                   10                  15

Leu Glu Asn

<210> SEQ ID NO 298
<211> LENGTH: 16
<212> TYPE: PRT
<213> ORGANISM: Homo sapiens

<400> SEQUENCE: 298

Ser Asp Tyr Gln Val Ile Ser Asp Arg Gln Thr Pro Lys Lys Asp Glu
1               5                   10                  15

<210> SEQ ID NO 299
<211> LENGTH: 15
<212> TYPE: PRT
<213> ORGANISM: Homo sapiens

<400> SEQUENCE: 299

Asp Ile Glu Gly Lys Leu Pro Gln Thr Glu Gln Glu Leu Lys Glu
1               5                   10                  15

<210> SEQ ID NO 300
<211> LENGTH: 19
<212> TYPE: PRT
<213> ORGANISM: Homo sapiens

<400> SEQUENCE: 300

Asp Asp Val Asn Tyr Lys Met His Phe Arg Met Ile Asn Glu Gln Gln
1               5                   10                  15

Val Glu Asp

<210> SEQ ID NO 301
<211> LENGTH: 17
<212> TYPE: PRT
<213> ORGANISM: Homo sapiens

<400> SEQUENCE: 301

Glu Asn Pro Leu Pro Glu Arg Pro Arg Glu Lys Glu Glu Pro Val Val
1               5                   10                  15

Arg

<210> SEQ ID NO 302
<211> LENGTH: 19
<212> TYPE: PRT
<213> ORGANISM: Homo sapiens

<400> SEQUENCE: 302

Arg Glu Gln Ser Glu Gly Val Gly Ala Arg Val Arg Arg Ser Ile Gly
1               5                   10                  15

Arg Pro Glu

<210> SEQ ID NO 303
<211> LENGTH: 19
<212> TYPE: PRT

```
<213> ORGANISM: Homo sapiens

<400> SEQUENCE: 303

Pro Arg Ala Val Ala Gly Lys Glu Glu Glu Asp Ser Asp Pro Glu Lys
1               5                   10                  15

Ala Leu Arg

<210> SEQ ID NO 304
<211> LENGTH: 17
<212> TYPE: PRT
<213> ORGANISM: Homo sapiens

<400> SEQUENCE: 304

Glu Lys Ala Asp Thr Asp Met Glu Gly Ser Val Asp Thr Arg Gln Glu
1               5                   10                  15

Lys

<210> SEQ ID NO 305
<211> LENGTH: 19
<212> TYPE: PRT
<213> ORGANISM: Homo sapiens

<400> SEQUENCE: 305

Arg Val Gln Asn His Asp Asn Pro Lys Trp Glu Ala Lys Lys Glu Asn
1               5                   10                  15

Ile Ser Lys

<210> SEQ ID NO 306
<211> LENGTH: 19
<212> TYPE: PRT
<213> ORGANISM: Homo sapiens

<400> SEQUENCE: 306

Arg Ser Pro Pro Ala Lys Gly Ala Thr Gly Pro Glu Glu Gln Ser Asp
1               5                   10                  15

Ser Leu Lys

<210> SEQ ID NO 307
<211> LENGTH: 19
<212> TYPE: PRT
<213> ORGANISM: Homo sapiens

<400> SEQUENCE: 307

Arg Glu Glu Asp Phe Lys Ala Thr Glu Ile Ile Glu Pro Ser Lys Gln
1               5                   10                  15

Asp Lys Pro

<210> SEQ ID NO 308
<211> LENGTH: 15
<212> TYPE: PRT
<213> ORGANISM: Homo sapiens

<400> SEQUENCE: 308

Asp Lys Thr Cys Met Lys Trp Ser Thr Asn Ser Cys Gly Ala Gln
1               5                   10                  15

<210> SEQ ID NO 309
<211> LENGTH: 14
<212> TYPE: PRT
<213> ORGANISM: Homo sapiens

<400> SEQUENCE: 309
```

-continued

Asp Ala Asn Leu Ser Lys Asn Gly Gly Leu Glu Val Trp Leu
1               5                   10

<210> SEQ ID NO 310
<211> LENGTH: 10
<212> TYPE: PRT
<213> ORGANISM: Homo sapiens

<400> SEQUENCE: 310

Glu Pro Phe Leu Pro Lys Leu Leu Thr Lys
1               5                   10

<210> SEQ ID NO 311
<211> LENGTH: 19
<212> TYPE: PRT
<213> ORGANISM: Homo sapiens

<400> SEQUENCE: 311

Arg Lys Ser Glu Ala Gly Ser Gly Ala Ala Ser Ser Ser Gly Glu Asp
1               5                   10                  15

Lys Glu Asn

<210> SEQ ID NO 312
<211> LENGTH: 19
<212> TYPE: PRT
<213> ORGANISM: Homo sapiens

<400> SEQUENCE: 312

Asp Asp Ile Tyr Asp Pro Thr Tyr Lys Asp Lys Glu Gly Pro Ser Pro
1               5                   10                  15

Lys Val Glu

<210> SEQ ID NO 313
<211> LENGTH: 19
<212> TYPE: PRT
<213> ORGANISM: Homo sapiens

<400> SEQUENCE: 313

Gln Ser Asp Glu Ala Lys Asn Asn Met Lys Gly Leu Pro Glu Leu Glu
1               5                   10                  15

Lys Lys Asp

<210> SEQ ID NO 314
<211> LENGTH: 19
<212> TYPE: PRT
<213> ORGANISM: Homo sapiens

<400> SEQUENCE: 314

Ser Arg Pro Gln Gly Leu Thr Glu Ala Glu Gln Arg Glu Leu Glu Gln
1               5                   10                  15

Glu Ala Lys

<210> SEQ ID NO 315
<211> LENGTH: 14
<212> TYPE: PRT
<213> ORGANISM: Homo sapiens

<400> SEQUENCE: 315

Arg Val Gln Gln Lys Gly Thr Ser Glu Thr Asp Thr Ile Cys
1               5                   10

<210> SEQ ID NO 316
<211> LENGTH: 16
<212> TYPE: PRT
<213> ORGANISM: Homo sapiens

<400> SEQUENCE: 316

Val Arg Leu Ser Pro Leu Ala Glu Arg Gln Leu Gln Val Gln Trp Glu
1               5                   10                  15

<210> SEQ ID NO 317
<211> LENGTH: 19
<212> TYPE: PRT
<213> ORGANISM: Homo sapiens

<400> SEQUENCE: 317

Arg Arg Ser Leu Gly Val Ser Val Arg Ser Trp Asp Glu Leu Pro Asp
1               5                   10                  15

Glu Lys Arg

<210> SEQ ID NO 318
<211> LENGTH: 17
<212> TYPE: PRT
<213> ORGANISM: Homo sapiens

<400> SEQUENCE: 318

Asp Glu Gly Leu Gly Pro Asp Pro His Arg Asp Arg Leu Arg Ser
1               5                   10                  15

Lys

<210> SEQ ID NO 319
<211> LENGTH: 18
<212> TYPE: PRT
<213> ORGANISM: Homo sapiens

<400> SEQUENCE: 319

Ser Gly Lys Arg Ser Ser Asp Gly Ser Leu Ser His Glu Glu Asp Leu
1               5                   10                  15

Ala Lys

<210> SEQ ID NO 320
<211> LENGTH: 19
<212> TYPE: PRT
<213> ORGANISM: Homo sapiens

<400> SEQUENCE: 320

Ser Gln Glu Arg Ser Asp Ser Pro Glu Ile Cys His Tyr Glu Lys Ser
1               5                   10                  15

Phe His Lys

<210> SEQ ID NO 321
<211> LENGTH: 17
<212> TYPE: PRT
<213> ORGANISM: Homo sapiens

<400> SEQUENCE: 321

Lys Val Asn Pro Glu Pro Thr His Glu Ile Arg Cys Asn Ser Glu Val
1               5                   10                  15

Lys

<210> SEQ ID NO 322
<211> LENGTH: 16
<212> TYPE: PRT

```
<213> ORGANISM: Homo sapiens

<400> SEQUENCE: 322

Ser Asp Gly Arg Gly Arg Pro Ala Phe Pro Phe Ser Cys Pro Arg Gln
1               5                   10                  15

<210> SEQ ID NO 323
<211> LENGTH: 15
<212> TYPE: PRT
<213> ORGANISM: Homo sapiens

<400> SEQUENCE: 323

Gly Ser Lys Glu Asp Phe Asp Ser Leu Leu Gln Ser Ala Lys Lys
1               5                   10                  15

<210> SEQ ID NO 324
<211> LENGTH: 18
<212> TYPE: PRT
<213> ORGANISM: Homo sapiens

<400> SEQUENCE: 324

Gln Lys Glu Glu Lys Thr Trp His Glu Ala Leu Arg Ser Cys Gln Ala
1               5                   10                  15

Asp Asn

<210> SEQ ID NO 325
<211> LENGTH: 17
<212> TYPE: PRT
<213> ORGANISM: Homo sapiens

<400> SEQUENCE: 325

Glu Lys Ala Glu Glu Gly Pro Arg Lys Arg Glu Pro Ala Pro Leu Asp
1               5                   10                  15

Lys

<210> SEQ ID NO 326
<211> LENGTH: 14
<212> TYPE: PRT
<213> ORGANISM: Homo sapiens

<400> SEQUENCE: 326

Glu Gln Asn Arg Asp Arg Ile Leu Thr Pro Glu Asn Arg Lys
1               5                   10

<210> SEQ ID NO 327
<211> LENGTH: 14
<212> TYPE: PRT
<213> ORGANISM: Homo sapiens

<400> SEQUENCE: 327

Arg Asp Trp Tyr Ile Gly Leu Val Ser Asp Glu Lys Trp Lys
1               5                   10

<210> SEQ ID NO 328
<211> LENGTH: 17
<212> TYPE: PRT
<213> ORGANISM: Homo sapiens

<400> SEQUENCE: 328

Asp Ser Tyr Leu Lys Thr Arg Ser Pro Val Thr Phe Leu Ser Asp Leu
1               5                   10                  15

Arg
```

```
<210> SEQ ID NO 329
<211> LENGTH: 17
<212> TYPE: PRT
<213> ORGANISM: Homo sapiens

<400> SEQUENCE: 329

Lys Cys Arg Gly Glu Thr Val Ala Lys Glu Ile Ser Glu Ala Met Lys
1               5                   10                  15
Ser

<210> SEQ ID NO 330
<211> LENGTH: 17
<212> TYPE: PRT
<213> ORGANISM: Homo sapiens

<400> SEQUENCE: 330

Lys Pro Pro Gln Glu Thr Glu Lys Gly His Ser Ala Cys Glu Pro Glu
1               5                   10                  15
Asn

<210> SEQ ID NO 331
<211> LENGTH: 14
<212> TYPE: PRT
<213> ORGANISM: Homo sapiens

<400> SEQUENCE: 331

Glu Arg Arg Ala Gly Ser Gly Ala Arg Asp Ala Glu Arg Glu
1               5                   10

<210> SEQ ID NO 332
<211> LENGTH: 16
<212> TYPE: PRT
<213> ORGANISM: Homo sapiens

<400> SEQUENCE: 332

Ser Glu Gln Lys Ala Asp Pro Pro Ala Thr Glu Lys Thr Leu Leu Glu
1               5                   10                  15

<210> SEQ ID NO 333
<211> LENGTH: 19
<212> TYPE: PRT
<213> ORGANISM: Homo sapiens

<400> SEQUENCE: 333

Glu Ala Glu Trp Ser Gln Gly Val Gln Gly Thr Leu Arg Ile Lys Lys
1               5                   10                  15
Tyr Leu Thr

<210> SEQ ID NO 334
<211> LENGTH: 17
<212> TYPE: PRT
<213> ORGANISM: Homo sapiens

<400> SEQUENCE: 334

Glu Glu Ser Lys Ser Ile Thr Glu Gly Leu Leu Thr Gln Lys Gln Tyr
1               5                   10                  15
Glu

<210> SEQ ID NO 335
<211> LENGTH: 16
<212> TYPE: PRT
<213> ORGANISM: Homo sapiens
```

```
<400> SEQUENCE: 335

Gln Asn Phe Lys Asp Ala Phe Ser Gly Arg Asp Ser Ser Ile Thr Arg
1               5                   10                  15

<210> SEQ ID NO 336
<211> LENGTH: 15
<212> TYPE: PRT
<213> ORGANISM: Homo sapiens

<400> SEQUENCE: 336

Thr Glu Asp Val Asp Glu Phe Arg Asn Lys Leu Gln Gly Glu Arg
1               5                   10                  15

<210> SEQ ID NO 337
<211> LENGTH: 20
<212> TYPE: PRT
<213> ORGANISM: Homo sapiens

<400> SEQUENCE: 337

Lys Gly Asp Val Ser Asn Leu Asp Pro Asn Phe Ser Phe Glu Gly Thr
1               5                   10                  15

Lys Leu Asp Val
            20

<210> SEQ ID NO 338
<211> LENGTH: 18
<212> TYPE: PRT
<213> ORGANISM: Homo sapiens

<400> SEQUENCE: 338

Glu Lys Thr Gly Val Cys Pro Glu Leu Gln Ala Asp Gln Asn Cys Thr
1               5                   10                  15

Gln Glu

<210> SEQ ID NO 339
<211> LENGTH: 14
<212> TYPE: PRT
<213> ORGANISM: Homo sapiens

<400> SEQUENCE: 339

Pro Asn Asp Lys Glu Gly Ser Cys Pro Gln Val Asn Ile Asn
1               5                   10

<210> SEQ ID NO 340
<211> LENGTH: 15
<212> TYPE: PRT
<213> ORGANISM: Homo sapiens

<400> SEQUENCE: 340

Arg Asp Gln Cys Gln Val Asp Thr Gln Cys Pro Gly Gln Met Lys
1               5                   10                  15

<210> SEQ ID NO 341
<211> LENGTH: 20
<212> TYPE: PRT
<213> ORGANISM: Homo sapiens

<400> SEQUENCE: 341

Asp Glu Glu Asp Lys Leu Arg His Phe Arg Glu Cys Phe Tyr Ile Pro
1               5                   10                  15

Lys Ile Gln Asp
            20
```

-continued

<210> SEQ ID NO 342
<211> LENGTH: 21
<212> TYPE: PRT
<213> ORGANISM: Homo sapiens

<400> SEQUENCE: 342

Lys Pro Arg Glu Gly Glu Glu Thr Leu Arg Ile Glu Asp Ile Leu Glu
1               5                   10                  15

Val Ile Glu Lys Glu
            20

<210> SEQ ID NO 343
<211> LENGTH: 21
<212> TYPE: PRT
<213> ORGANISM: Homo sapiens

<400> SEQUENCE: 343

Glu Glu Arg Gly Cys Gln Leu Thr Ile Thr Phe Ser Val Pro Asn Lys
1               5                   10                  15

Asp Val Phe Gln Glu
            20

<210> SEQ ID NO 344
<211> LENGTH: 16
<212> TYPE: PRT
<213> ORGANISM: Homo sapiens

<400> SEQUENCE: 344

Asn Lys Ile Thr Thr Glu Phe Phe Asp Pro Leu Phe Val Glu Gln Lys
1               5                   10                  15

<210> SEQ ID NO 345
<211> LENGTH: 18
<212> TYPE: PRT
<213> ORGANISM: Homo sapiens

<400> SEQUENCE: 345

Phe Ser Ile Ser Asp Asn Asn Lys Thr Pro Arg Tyr Thr Tyr Asn Gly
1               5                   10                  15

Ala Thr

<210> SEQ ID NO 346
<211> LENGTH: 18
<212> TYPE: PRT
<213> ORGANISM: Homo sapiens

<400> SEQUENCE: 346

Glu Asp Phe Lys Thr Thr Asn Pro Ser Lys Gln Phe Asp Lys Asn Ala
1               5                   10                  15

Tyr Val

<210> SEQ ID NO 347
<211> LENGTH: 20
<212> TYPE: PRT
<213> ORGANISM: Homo sapiens

<400> SEQUENCE: 347

Glu Gly Asp Ala Lys Gly Leu Lys Glu Gly Glu Thr Pro Gly Asn Phe
1               5                   10                  15

Met Glu Asp Glu
            20

```
<210> SEQ ID NO 348
<211> LENGTH: 19
<212> TYPE: PRT
<213> ORGANISM: Homo sapiens

<400> SEQUENCE: 348

Glu Trp Cys Phe Cys Phe Trp Arg Glu Lys Pro Pro Cys Leu Ala Glu
1               5                   10                  15

Leu Glu Arg

<210> SEQ ID NO 349
<211> LENGTH: 16
<212> TYPE: PRT
<213> ORGANISM: Homo sapiens

<400> SEQUENCE: 349

Glu Glu Glu Gly Glu Ala Gly Glu Ala Asp Asp Gly Gly Tyr Ile Trp
1               5                   10                  15

<210> SEQ ID NO 350
<211> LENGTH: 13
<212> TYPE: PRT
<213> ORGANISM: Homo sapiens

<400> SEQUENCE: 350

Asp Lys Asp Pro Gln Lys Met Tyr Ala Thr Ile Tyr Glu
1               5                   10

<210> SEQ ID NO 351
<211> LENGTH: 15
<212> TYPE: PRT
<213> ORGANISM: Homo sapiens

<400> SEQUENCE: 351

Lys Lys Cys Asp Tyr Trp Ile Arg Thr Phe Val Pro Gly Cys Gln
1               5                   10                  15

<210> SEQ ID NO 352
<211> LENGTH: 15
<212> TYPE: PRT
<213> ORGANISM: Homo sapiens

<400> SEQUENCE: 352

Glu Asn Phe Ile Arg Phe Ser Lys Tyr Leu Gly Leu Pro Glu Asn
1               5                   10                  15

<210> SEQ ID NO 353
<211> LENGTH: 15
<212> TYPE: PRT
<213> ORGANISM: Homo sapiens

<400> SEQUENCE: 353

Asp Asp Ser Asp Gln Asp Ser Cys Arg Leu Ser Ile Asp Ser Gln
1               5                   10                  15

<210> SEQ ID NO 354
<211> LENGTH: 15
<212> TYPE: PRT
<213> ORGANISM: Homo sapiens

<400> SEQUENCE: 354

Arg Gln His Tyr Pro Glu Ala Tyr Ala Ser Pro Ser His Thr Lys
1               5                   10                  15
```

<210> SEQ ID NO 355
<211> LENGTH: 19
<212> TYPE: PRT
<213> ORGANISM: Homo sapiens

<400> SEQUENCE: 355

Asn Thr Pro Leu Gly Arg Asn Leu Ser Thr His Gln Thr Tyr Pro Val
1               5                   10                  15

Val Ala Asp

<210> SEQ ID NO 356
<211> LENGTH: 15
<212> TYPE: PRT
<213> ORGANISM: Homo sapiens

<400> SEQUENCE: 356

Arg Leu Val Ser Cys Pro Gly Pro Leu Asp Gln Asp Gln Gln Glu
1               5                   10                  15

<210> SEQ ID NO 357
<211> LENGTH: 19
<212> TYPE: PRT
<213> ORGANISM: Homo sapiens

<400> SEQUENCE: 357

Lys Met Ser Pro Glu Asp Ile Arg Lys Trp Asn Val Thr Ser Leu Glu
1               5                   10                  15

Thr Leu Lys

<210> SEQ ID NO 358
<211> LENGTH: 20
<212> TYPE: PRT
<213> ORGANISM: Homo sapiens

<400> SEQUENCE: 358

Ser Pro Glu Glu Leu Ser Ser Val Pro Pro Ser Ser Ile Trp Ala Val
1               5                   10                  15

Arg Pro Gln Asp
            20

<210> SEQ ID NO 359
<211> LENGTH: 17
<212> TYPE: PRT
<213> ORGANISM: Homo sapiens

<400> SEQUENCE: 359

Glu Glu Gln Asn Lys Leu Val His Gly Gly Pro Cys Asp Lys Thr Ser
1               5                   10                  15

His

<210> SEQ ID NO 360
<211> LENGTH: 16
<212> TYPE: PRT
<213> ORGANISM: Homo sapiens

<400> SEQUENCE: 360

Glu Leu Ile Gln Pro Leu Pro Leu Glu Arg Asp Cys Ser Ala Asn Thr
1               5                   10                  15

<210> SEQ ID NO 361
<211> LENGTH: 14

```
<212> TYPE: PRT
<213> ORGANISM: Homo sapiens

<400> SEQUENCE: 361

Gly Lys Thr Ala Asp Gly Asp Phe Pro Asp Thr Ile Gln Cys
1               5                   10

<210> SEQ ID NO 362
<211> LENGTH: 20
<212> TYPE: PRT
<213> ORGANISM: Homo sapiens

<400> SEQUENCE: 362

Arg Glu Gln Trp Pro Glu Arg Arg Arg Cys His Arg Leu Glu Asn Gly
1               5                   10                  15

Cys Gly Asn Ala
            20

<210> SEQ ID NO 363
<211> LENGTH: 16
<212> TYPE: PRT
<213> ORGANISM: Homo sapiens

<400> SEQUENCE: 363

Lys Val Asn Ser Ala Gly Asp Ala Ile Gly Leu Gln Pro Asp Ala Arg
1               5                   10                  15

<210> SEQ ID NO 364
<211> LENGTH: 20
<212> TYPE: PRT
<213> ORGANISM: Homo sapiens

<400> SEQUENCE: 364

Gln Gln Leu Lys Val Ile Asp Asn Gln Arg Glu Leu Ser Arg Leu Ser
1               5                   10                  15

Arg Glu Leu Glu
            20

<210> SEQ ID NO 365
<211> LENGTH: 18
<212> TYPE: PRT
<213> ORGANISM: Homo sapiens

<400> SEQUENCE: 365

Lys Gln Gln Asp Gly Pro Thr Lys Thr His Lys Leu Glu Lys Leu Met
1               5                   10                  15

Ile Arg

<210> SEQ ID NO 366
<211> LENGTH: 19
<212> TYPE: PRT
<213> ORGANISM: Homo sapiens

<400> SEQUENCE: 366

Glu Leu Arg Val Leu Ser Lys Ala Asn Ala Ile Val Pro Gly Leu Ser
1               5                   10                  15

Gly Gly Glu

<210> SEQ ID NO 367
<211> LENGTH: 20
<212> TYPE: PRT
<213> ORGANISM: Homo sapiens
```

```
<400> SEQUENCE: 367

Arg Arg Gly Gly Glu Gly Gly Glu Glu Asn Pro Ser Ala Ala Lys Gly
1               5                   10                  15

His Leu Met Gly
            20

<210> SEQ ID NO 368
<211> LENGTH: 14
<212> TYPE: PRT
<213> ORGANISM: Homo sapiens

<400> SEQUENCE: 368

Met Pro Glu Val Ser Ser Lys Gly Ala Thr Ile Ser Lys Lys
1               5                   10

<210> SEQ ID NO 369
<211> LENGTH: 11
<212> TYPE: PRT
<213> ORGANISM: Homo sapiens

<400> SEQUENCE: 369

Gly Phe Lys Lys Ala Val Val Lys Thr Gln Lys
1               5                   10

<210> SEQ ID NO 370
<211> LENGTH: 12
<212> TYPE: PRT
<213> ORGANISM: Homo sapiens

<400> SEQUENCE: 370

Lys Glu Gly Lys Lys Arg Lys Arg Thr Arg Lys Glu
1               5                   10

<210> SEQ ID NO 371
<211> LENGTH: 20
<212> TYPE: PRT
<213> ORGANISM: Homo sapiens

<400> SEQUENCE: 371

Gln Arg Ile Lys Glu Gln Ala Ser Lys Ile Ser Glu Ala Asp Lys Ser
1               5                   10                  15

Lys Pro Lys Phe
            20

<210> SEQ ID NO 372
<211> LENGTH: 21
<212> TYPE: PRT
<213> ORGANISM: Homo sapiens

<400> SEQUENCE: 372

His Ala Lys Thr Lys Glu Lys Leu Glu Val Thr Trp Glu Lys Met Ser
1               5                   10                  15

Lys Ser Lys His Asn
            20

<210> SEQ ID NO 373
<211> LENGTH: 18
<212> TYPE: PRT
<213> ORGANISM: Homo sapiens

<400> SEQUENCE: 373

Lys Ser Pro Gln Pro Gln Leu Leu Ser Asn Lys Glu Lys Ala Glu Ala
1               5                   10                  15
```

Arg Lys

<210> SEQ ID NO 374
<211> LENGTH: 16
<212> TYPE: PRT
<213> ORGANISM: Homo sapiens

<400> SEQUENCE: 374

Met Leu Phe Glu Gln Gly Gln Gln Ala Leu Glu Leu Pro Glu Cys Thr
1               5                   10                  15

<210> SEQ ID NO 375
<211> LENGTH: 20
<212> TYPE: PRT
<213> ORGANISM: Homo sapiens

<400> SEQUENCE: 375

Lys Asp Gln Lys Ala Lys Gly Ile Leu His Ser Pro Ala Ser Gln Ser
1               5                   10                  15

Pro Glu Arg Ser
            20

<210> SEQ ID NO 376
<211> LENGTH: 16
<212> TYPE: PRT
<213> ORGANISM: Homo sapiens

<400> SEQUENCE: 376

His Ser Ser Gln Gly Arg Leu Pro Glu Ala Pro Lys Leu Thr His Leu
1               5                   10                  15

<210> SEQ ID NO 377
<211> LENGTH: 18
<212> TYPE: PRT
<213> ORGANISM: Homo sapiens

<400> SEQUENCE: 377

Lys Arg Gly Ala Arg Arg Gly Gly Trp Lys Arg Lys Met Pro Ser Thr
1               5                   10                  15

Asp Leu

<210> SEQ ID NO 378
<211> LENGTH: 16
<212> TYPE: PRT
<213> ORGANISM: Homo sapiens

<400> SEQUENCE: 378

Lys Ile Val Arg Val Pro Leu Thr Lys Met Met Glu Val Asp Val Arg
1               5                   10                  15

<210> SEQ ID NO 379
<211> LENGTH: 19
<212> TYPE: PRT
<213> ORGANISM: Homo sapiens

<400> SEQUENCE: 379

Gln Phe Leu Lys Asp Ile Arg Glu Ser Val Thr Gln Ile Met Lys Asn
1               5                   10                  15

Pro Lys Ala

<210> SEQ ID NO 380
<211> LENGTH: 18

```
<212> TYPE: PRT
<213> ORGANISM: Homo sapiens

<400> SEQUENCE: 380

Ser Lys Gln Gly Val Val Ile Leu Asp Asp Lys Ser Lys Glu Leu Pro
1               5                   10                  15

His Trp

<210> SEQ ID NO 381
<211> LENGTH: 20
<212> TYPE: PRT
<213> ORGANISM: Homo sapiens

<400> SEQUENCE: 381

Val Gln Thr Phe Ser Arg Cys Ile Leu Cys Ser Lys Asp Glu Val Asp
1               5                   10                  15

Leu Asp Glu Leu
            20

<210> SEQ ID NO 382
<211> LENGTH: 16
<212> TYPE: PRT
<213> ORGANISM: Homo sapiens

<400> SEQUENCE: 382

Leu Lys Lys Pro Phe Gln Pro Phe Gln Arg Thr Arg Ser Phe Arg Met
1               5                   10                  15

<210> SEQ ID NO 383
<211> LENGTH: 20
<212> TYPE: PRT
<213> ORGANISM: Homo sapiens

<400> SEQUENCE: 383

Met Ile Pro Gly Gly Leu Ser Glu Ala Lys Pro Ala Thr Pro Glu Ile
1               5                   10                  15

Gln Glu Ile Val
            20

<210> SEQ ID NO 384
<211> LENGTH: 15
<212> TYPE: PRT
<213> ORGANISM: Homo sapiens

<400> SEQUENCE: 384

Asn Glu Thr Tyr Gly Lys Leu Glu Ala Val Gln Tyr Lys Thr Gln
1               5                   10                  15

<210> SEQ ID NO 385
<211> LENGTH: 20
<212> TYPE: PRT
<213> ORGANISM: Homo sapiens

<400> SEQUENCE: 385

Asp Leu Val Leu Thr Gly Tyr Gln Val Asp Lys Asn Lys Asp Asp Glu
1               5                   10                  15

Leu Thr Gly Phe
            20

<210> SEQ ID NO 386
<211> LENGTH: 18
<212> TYPE: PRT
<213> ORGANISM: Homo sapiens
```

```
<400> SEQUENCE: 386

Leu Lys Lys Pro Gln Asp Ser Gln Leu Glu Glu Gly Lys Pro Gly Tyr
1               5                   10                  15

Leu Asp

<210> SEQ ID NO 387
<211> LENGTH: 17
<212> TYPE: PRT
<213> ORGANISM: Homo sapiens

<400> SEQUENCE: 387

Lys Ala Lys Arg Leu Gln Lys Gln Pro Glu Gly Glu Glu Pro Glu Met
1               5                   10                  15

Glu

<210> SEQ ID NO 388
<211> LENGTH: 22
<212> TYPE: PRT
<213> ORGANISM: Homo sapiens

<400> SEQUENCE: 388

Lys Asp Arg Pro Ser Phe Ser Glu Ile Ala Ser Ala Leu Gly Asp Ser
1               5                   10                  15

Thr Val Asp Ser Lys Pro
            20

<210> SEQ ID NO 389
<211> LENGTH: 21
<212> TYPE: PRT
<213> ORGANISM: Homo sapiens

<400> SEQUENCE: 389

Glu Ala Val Val Thr Asn Glu Leu Glu Asp Gly Asp Arg Gln Lys Ala
1               5                   10                  15

Met Lys Arg Leu Arg
            20

<210> SEQ ID NO 390
<211> LENGTH: 18
<212> TYPE: PRT
<213> ORGANISM: Homo sapiens

<400> SEQUENCE: 390

Arg Arg Tyr Arg Asp Thr Lys Arg Ala Phe Pro His Leu Val Asn Ala
1               5                   10                  15

Gly Lys

<210> SEQ ID NO 391
<211> LENGTH: 18
<212> TYPE: PRT
<213> ORGANISM: Homo sapiens

<400> SEQUENCE: 391

Lys Ala Arg Asp Thr Lys Val Leu Ile Glu Asp Thr Asp Asp Glu Ala
1               5                   10                  15

Asn Thr

<210> SEQ ID NO 392
<211> LENGTH: 20
<212> TYPE: PRT
```

```
<213> ORGANISM: Homo sapiens

<400> SEQUENCE: 392

Tyr Arg Asn Pro Tyr Val Glu Ala Glu Tyr Phe Pro Thr Lys Pro Met
1               5                   10                  15

Phe Val Ile Ala
            20

<210> SEQ ID NO 393
<211> LENGTH: 20
<212> TYPE: PRT
<213> ORGANISM: Homo sapiens

<400> SEQUENCE: 393

Lys Lys Phe Pro Arg Phe Arg Asn Arg Glu Leu Glu Ala Thr Arg Arg
1               5                   10                  15

Gln Arg Met Asp
            20

<210> SEQ ID NO 394
<211> LENGTH: 14
<212> TYPE: PRT
<213> ORGANISM: Homo sapiens

<400> SEQUENCE: 394

Ser Gly Asn Thr Ala Ile Asn Tyr Lys His Ser Ser Ile Pro
1               5                   10

<210> SEQ ID NO 395
<211> LENGTH: 20
<212> TYPE: PRT
<213> ORGANISM: Homo sapiens

<400> SEQUENCE: 395

Arg Lys Ser Val Lys Arg Met Lys Glu Ser Arg Leu Glu Asp Thr Gln
1               5                   10                  15

Lys His Arg Val
            20

<210> SEQ ID NO 396
<211> LENGTH: 19
<212> TYPE: PRT
<213> ORGANISM: Homo sapiens

<400> SEQUENCE: 396

Glu Val Ala Glu Lys Arg Arg Lys Ala Leu Tyr Glu Ala Leu Lys Glu
1               5                   10                  15

Asn Glu Lys

<210> SEQ ID NO 397
<211> LENGTH: 18
<212> TYPE: PRT
<213> ORGANISM: Homo sapiens

<400> SEQUENCE: 397

Cys Val Asn Gly Glu Ile Glu Gly Leu Asn Asp Thr Phe Lys Glu Leu
1               5                   10                  15

Glu Phe

<210> SEQ ID NO 398
<211> LENGTH: 17
<212> TYPE: PRT
```

<213> ORGANISM: Homo sapiens

<400> SEQUENCE: 398

Arg Glu Leu Arg Glu Val Leu Arg Thr Val Glu Thr Lys Ala Thr Gln
1               5                   10                  15
Asn

<210> SEQ ID NO 399
<211> LENGTH: 18
<212> TYPE: PRT
<213> ORGANISM: Homo sapiens

<400> SEQUENCE: 399

Arg Asp Thr Glu Asp Gln Glu Asp Gln Val Asp Pro Arg Leu Ile Asp
1               5                   10                  15
Gly Lys

<210> SEQ ID NO 400
<211> LENGTH: 16
<212> TYPE: PRT
<213> ORGANISM: Homo sapiens

<400> SEQUENCE: 400

Lys Asn His His Glu Leu Asp His Arg Glu Arg Glu Ser Ser Ala Asn
1               5                   10                  15

<210> SEQ ID NO 401
<211> LENGTH: 15
<212> TYPE: PRT
<213> ORGANISM: Homo sapiens

<400> SEQUENCE: 401

Glu Tyr Arg Asn Gln Thr Asn Leu Pro Thr Glu Asn Val Asp Lys
1               5                   10                  15

<210> SEQ ID NO 402
<211> LENGTH: 16
<212> TYPE: PRT
<213> ORGANISM: Homo sapiens

<400> SEQUENCE: 402

Gln Arg Gly Ser Gln Ile Gly Arg Glu Pro Ile Gly Leu Ser Gly Asp
1               5                   10                  15

<210> SEQ ID NO 403
<211> LENGTH: 16
<212> TYPE: PRT
<213> ORGANISM: Homo sapiens

<400> SEQUENCE: 403

Glu Lys Ile His Leu Asp Asp Ala Asn Glu Ser Asp His Phe Glu Asn
1               5                   10                  15

<210> SEQ ID NO 404
<211> LENGTH: 16
<212> TYPE: PRT
<213> ORGANISM: Homo sapiens

<400> SEQUENCE: 404

Lys Ala Arg Ala Ala Val Ser Pro Gln Lys Arg Lys Ser Asp Gly Pro
1               5                   10                  15

<210> SEQ ID NO 405

-continued

<211> LENGTH: 17
<212> TYPE: PRT
<213> ORGANISM: Homo sapiens

<400> SEQUENCE: 405

Arg Gln Ile Pro Ala Pro Gln Gly Ala Val Leu Val Gln Arg Glu Lys
1               5                   10                  15

Asp

<210> SEQ ID NO 406
<211> LENGTH: 18
<212> TYPE: PRT
<213> ORGANISM: Homo sapiens

<400> SEQUENCE: 406

Ser Val Lys Glu Gln Val Glu Lys Ile Ile Cys Asn Leu Lys Pro Ala
1               5                   10                  15

Leu Lys

<210> SEQ ID NO 407
<211> LENGTH: 20
<212> TYPE: PRT
<213> ORGANISM: Homo sapiens

<400> SEQUENCE: 407

Asp Leu Ala Gly His Asp Met Gly His Glu Ser Lys Arg Met His Ile
1               5                   10                  15

Glu Lys Asp Glu
            20

<210> SEQ ID NO 408
<211> LENGTH: 20
<212> TYPE: PRT
<213> ORGANISM: Homo sapiens

<400> SEQUENCE: 408

Glu Lys Gln Val Gln Leu Glu Lys Thr Glu Leu Lys Met Asp Phe Leu
1               5                   10                  15

Arg Glu Arg Glu
            20

<210> SEQ ID NO 409
<211> LENGTH: 19
<212> TYPE: PRT
<213> ORGANISM: Homo sapiens

<400> SEQUENCE: 409

Glu Ala Asp Arg Ser Gly Gly Arg Thr Asp Ala Glu Arg Thr Ile Gln
1               5                   10                  15

Asp Gly Arg

REAGENTS AND METHODS FOR USE IN CANCER DIAGNOSIS, CLASSIFICATION AND THERAPY

PRIORITY INFORMATION

The present application claims the benefit of U.S. Ser. No. 60/680,924, filed May 12, 2005, the entire contents of which are hereby incorporated by reference.

GOVERNMENT SUPPORT

This invention was made with government support under Grant Number CA083591, awarded by NIA. The government has certain rights in the invention.

BACKGROUND OF THE INVENTION

A major challenge of cancer treatment is the selection of therapeutic regimens that maximize efficacy and minimize toxicity for a given patient. A related challenge lies in the attempt to provide accurate diagnostic, prognostic and predictive information. At present, tumors are generally classified under the tumor-node-metastasis (TNM) system. This system, which uses the size of the tumor, the presence or absence of tumor in regional lymph nodes, and the presence or absence of distant metastases, to assign a stage to the tumor is described in the *AJCC Cancer Staging Manual*, Lippincott, 5th ed., pp. 171-180 (1997). The assigned stage is used as a basis for selection of appropriate therapy and for prognostic purposes. In addition to the TNM parameters, morphologic appearance is used to further classify tumors into tumor types and thereby aid in selection of appropriate therapy. However, this approach has serious limitations. Tumors with similar histopathologic appearance can exhibit significant variability in terms of clinical course and response to therapy. For example, some tumors are rapidly progressive while others are not. Some tumors respond readily to hormonal therapy or chemotherapy while others are resistant.

Assays for cell surface markers, e.g., using immunohistochemistry, have provided means for dividing certain tumor types into subclasses. For example, one factor considered in prognosis and treatment decisions for breast cancer is the presence or absence of the estrogen receptor (ER) in tumor samples. ER-positive breast cancers typically respond much more readily to hormonal therapies such as tamoxifen, which acts as an anti-estrogen in breast tissue, than ER-negative tumors. Though useful, these analyses only in part predict the clinical behavior of breast tumors. There is phenotypic diversity present in cancers that current diagnostic tools fail to detect. As a consequence, there is still much controversy over how to stratify patients amongst potential treatments in order to optimize outcome (e.g., for breast cancer see "NIH Consensus Development Conference Statement: Adjuvant Therapy for Breast Cancer, Nov. 1-3, 2000", *J. Nat. Cancer Inst. Monographs*, 30:5-15, 2001 and Di Leo et al., *Int. J. Clin. Oncol.* 7:245-253, 2002).

Each year, over 25,000 patients are diagnosed with epithelial ovarian or primary peritoneal carcinoma, the majority being advanced stage. Surgical debulking followed by platinum based chemotherapy remains the mainstay of treatment, with about 40% of patients achieving optimal debulking with initial surgery. This is important as response rates to primary chemotherapy approach 70% with optimal debulking compared to only 30% with suboptimal debulking and respective improvements in survival. Despite this, prediction of response to chemotherapy remains problematic. Some patients recur or progress early on in their disease despite otherwise reassuring prognostic factors, while others with presumed poor prognosis have remarkable durable responses. Thus, reliable predictive markers for response to therapy are lacking.

There clearly exists a need for improved methods and reagents for classifying tumors. Once these methods and reagents are available, clinical studies can be performed that will allow the identification of classes or subclasses of patients having different prognosis and/or responses to therapy. Such prognostic tools will allow more rationally based choices governing the aggressiveness of therapeutic interventions; such predictive tools will also be useful for directing patients into appropriate treatment protocols.

SUMMARY OF THE INVENTION

The invention encompasses the realization that particular panels of tumor sample binding agents ("interaction partners") can be used to provide new insights into the biology of cancer. Among other things, the present invention provides methods and reagents for classifying tumors and for identifying new tumor classes and subclasses. The invention further provides methods for correlating tumor class or subclass with therapeutic regimen or outcome, for identifying appropriate (new or known) therapies for particular classes or subclasses, and for predicting outcomes based on class or subclass. The invention further provides new therapeutic agents and methods for the treatment of cancer.

For example, the present invention provides methods for identifying suitable panels of interaction partners (e.g., without limitation antibodies) whose binding is correlated with any of a variety of desirable aspects such as tumor class or subclass, tumor source (e.g., primary tumor versus metastases), likely prognosis, responsiveness to therapy, etc. Specifically, collections of interaction partners are selected and their activity in binding to a variety of different tumors, normal tissues and/or cell lines is assessed. Data are collected for multiple interaction partners to multiple samples and correlations with interesting or desirable features are assessed. As described herein, the detection of individual interaction partners or panels thereof that bind differentially with different tumors provides new methods of use in cancer prognosis and treatment selection. In addition, these interaction partners provide new therapies for treating cancer.

As described in further detail below, the invention employs methods for grouping interaction partners within a panel into subsets by determining their binding patterns across a collection of samples obtained from different tumor tissues, normal tissues and/or cell lines. The invention also groups the tumor samples into classes or subclasses based on similarities in their binding to a panel of interaction partners. This two-dimensional grouping approach permits the association of particular classes of tumors with particular subsets of interaction partners that, for example, show relatively high binding to tumors within that class. Correlation with clinical information indicates that the tumor classes have clinical significance in terms of prognosis or response to chemotherapy.

BRIEF DESCRIPTION OF APPENDICES A-G

This patent application refers to material comprising tables and data presented as appendices.

Appendix A is a table that lists the antibodies included in the breast, lung, colon or ovarian panels that are discussed in the Examples. The table is split into two parts. The first part includes the antibody ID, parent gene name, NCBI Entrez GeneID and UniGeneID (note that the priority application U.S. Ser. No. 60/680,924 makes reference to LocusLinkIDs that have since been superceded by Entrez GeneIDs that use the exact same reference numbers). The second part includes the antibody ID, parent gene name, known aliases for the parent gene, peptides that were used in preparing antibodies (or the commercial source of the antibody) and antibody titer. Using the parent gene name, NCBI Entrez GeneID, UniGeneID, and/or known aliases for the parent gene, a skilled person can readily obtain the nucleotide (and corresponding amino acid) sequences for each and every one of the parent genes that are listed in Appendix A from a public database (e.g., GenBank, Swiss-Prot or any future derivative of these). The nucleotide and corresponding amino acid sequences for each and every one of the parent genes that are listed in Appendix A are hereby incorporated by reference from these public databases. Antibodies with AGI IDs that begin with s5 or s6 were obtained from commercial sources as indicated. The third and fourth columns of Appendix A indicate whether the antibodies of the breast cancer classification panel were identified by staining with the Russian breast cohort (Example 2) and/or the HH breast cohort (Example 3). The fifth and sixth columns indicate whether the antibodies of the lung cancer classification panel were identified by staining with the Russian lung cohort (Example 4) and/or the HH lung cohort (Example 5). The seventh column indicates the antibodies of the colon cancer classification panel. These were all identified by staining with the Russian colon cohort (Example 6). The eight, ninth and tenth columns indicate whether the antibodies of the ovarian cancer classification panel were identified by staining with the Stanford ovarian cohort (Example 16), the UAB ovarian cohort (Example 17), and/or the Russian ovarian cohort (Example 18).

Appendix B includes breast IHC images, colon IHC images and lung IHC images. An actual copy of Appendix B is not included with this application but can be found in related case U.S. Ser. No. 10/915,059 filed Aug. 10, 2004 (published as US 2005-0112622 on May 26, 2005), the entire contents of which are hereby incorporated by reference.

Appendix C is a table that lists exemplary antibodies whose binding patterns have been shown to correlate with tumor prognosis in breast cancer patients. The results are grouped into four categories that have been clinically recognized to be of significance: all patients, ER+ patients, ER- patients, and ER+/lymph node metastases negative (ER+/node-) patients. Scoring methods 1-3 use the following schemes: method 1 (0=negative; 1=weak; 2=strong); method 2 (0=negative; 1=weak or strong); and method 3 (0=negative or weak; 1=strong). This table was prepared using samples from the HH breast cohort as described in Example 10.

Appendix D is a table that lists exemplary antibodies whose binding patterns have been shown to correlate with tumor prognosis in lung cancer patients. The results are grouped into three categories that have been clinically recognized to be of significance: all patients, adenocarcinoma patients, and squamous cell carcinoma patients. Scoring methods 1-3 use the following schemes: method 1 (0=negative; 1=weak; 2=strong); method 2 (0=negative; 1=weak or strong); and method 3 (0=negative or weak; 1=strong).

Appendix E is a table that lists exemplary antibodies whose binding patterns have been shown to correlate with tumor prognosis in breast cancer patients. The results are grouped into four categories that have been clinically recognized to be of significance: all patients, ER+ patients, ER- patients, and ER+/lymph node metastases negative (ER+/node-) patients. Scoring methods 1-3 use the following schemes: method 1 (0=negative; 1=weak; 2=strong); method 2 (0=negative; 1=weak or strong); and method 3 (0=negative or weak; 1=strong). This table was prepared using samples from the HH breast cohort as described in Example 12. Appendix E differs from Appendix C because of further analysis.

Appendix F is a table that lists exemplary antibodies whose binding patterns have been shown to correlate with tumor prognosis in lung cancer patients. The results are grouped into two categories that have been clinically recognized to be of significance: all patients and adenocarcinoma patients. Scoring methods 1-3 use the following schemes: method 1 (0=negative; 1=weak; 2=strong); method 2 (0=negative; 1=weak or strong); and method 3 (0=negative or weak; 1=strong). This table was prepared using samples from the HH and UAB lung cohorts as described in Example 13. The p-values and hazard ratios that were obtained with each cohort are shown. The antibodies listed have a prognostic p-value of less than 0.2 in both cohorts.

Appendix G is a table that lists exemplary antibodies whose binding patterns have been shown to correlate with tumor prognosis in ovarian cancer patients. Scoring methods 1-3 use the following schemes: method 1 (0=negative; 1=weak; 2=strong); method 2 (0=negative; 1=weak or strong); and method 3 (0=negative or weak; 1=strong). The p-values and hazard ratios are shown and were obtained as described in Example 19.

staining with a prognostic panel of antibodies from Appendix C and (B) the Nottingham Prognostic Index (NPI). In each case the patients were placed into one of three prognostic groups, namely "poor" (bottom curve), "moderate" (middle curve) and "good" (top curve).

Figure 5A:
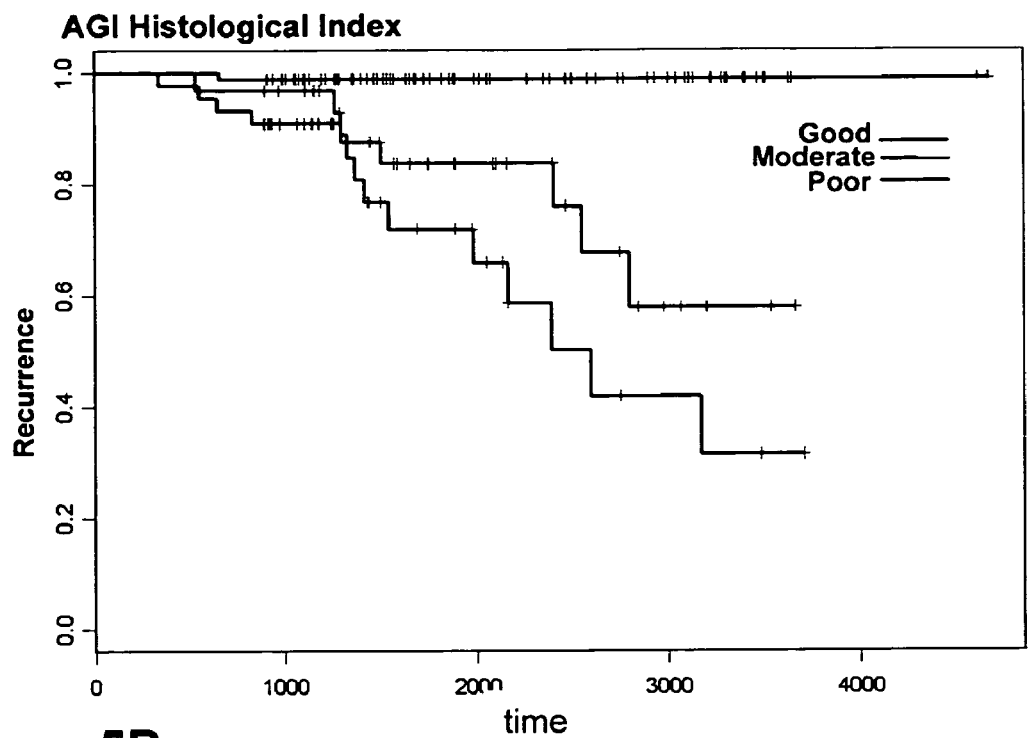
Figure 5B:
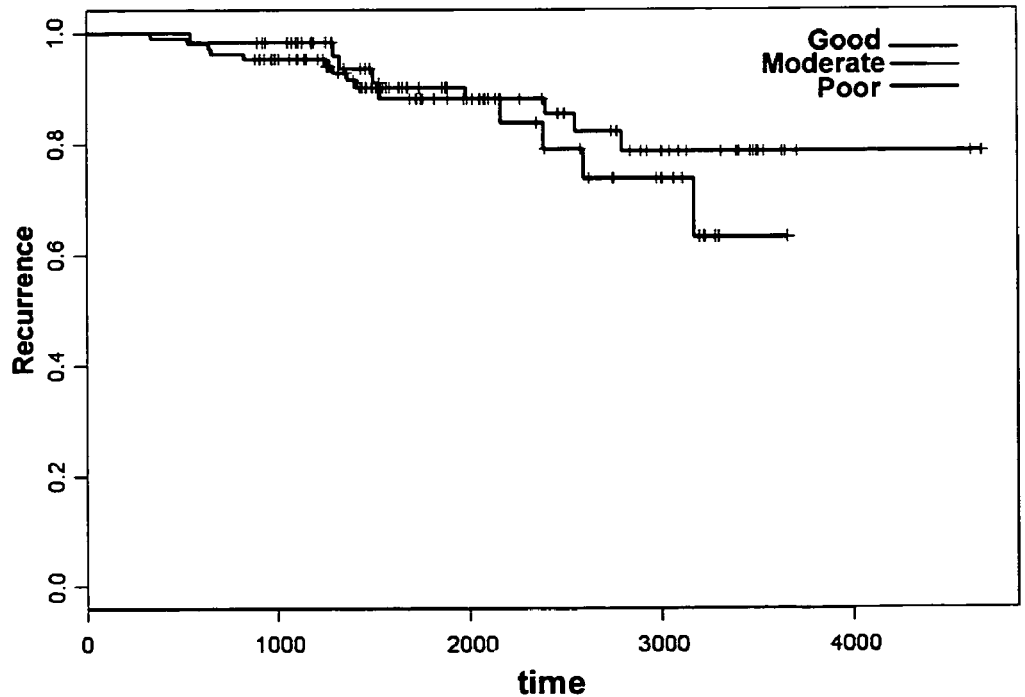

FIG. 5 shows Kaplan-Meier curves that were generated for ER+/node− patients after prognostic classification based on (A) staining with a prognostic panel of antibodies from Appendix C and (B) the Nottingham Prognostic Index (NPI). In each case the patients were placed into one of three prognostic groups, namely "poor" (bottom curve), "moderate" (middle curve) and "good" (top curve). Note that under the NPI scheme ER+/node− patients are never categorized as having a "poor" prognosis. For this reason, FIG. 5B only includes curves for patients with a "moderate" or "good" prognosis.

Figure 6:
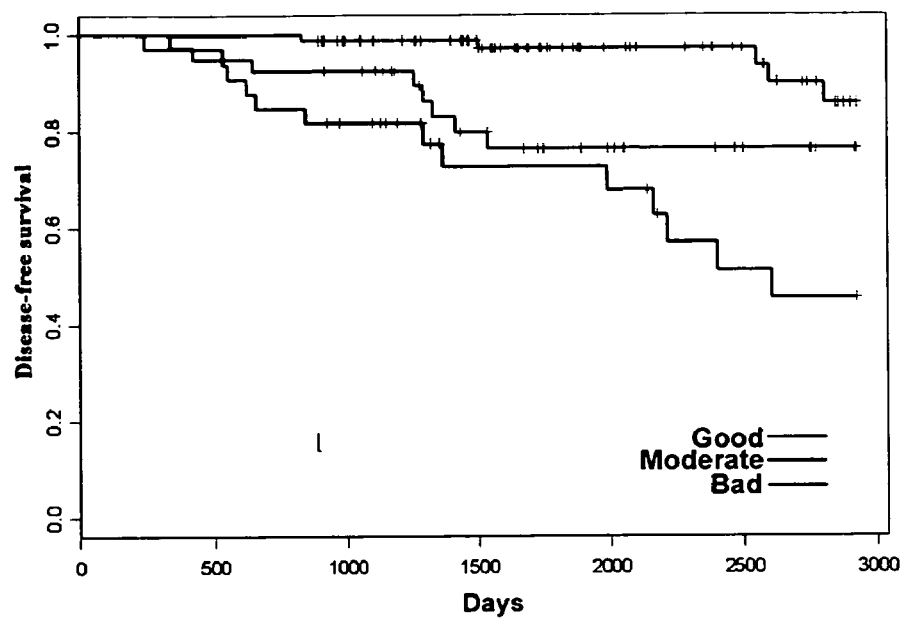

FIG. 6 shows Kaplan-Meier curves that were generated for ER+/node− patients after prognostic classification based on staining with the exemplary prognostic panel of antibodies from Table 5. In each case the patients were placed into one of three prognostic groups, namely "bad" (bottom curve), "moderate" (middle curve) and "good" (top curve).

Figure 7:
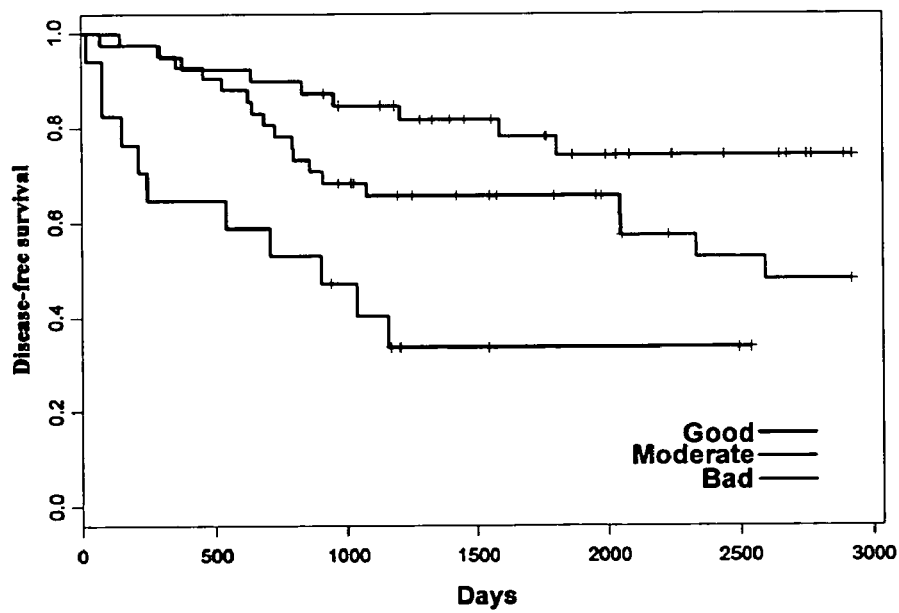

FIG. 7 shows Kaplan-Meier curves that were generated for ER− patients after prognostic classification based on staining with the exemplary prognostic panel of antibodies from Table 6. In each case the patients were placed into one of three prognostic groups, namely "bad" (bottom curve), "moderate" (middle curve) and "good" (top curve).

Figure 8:
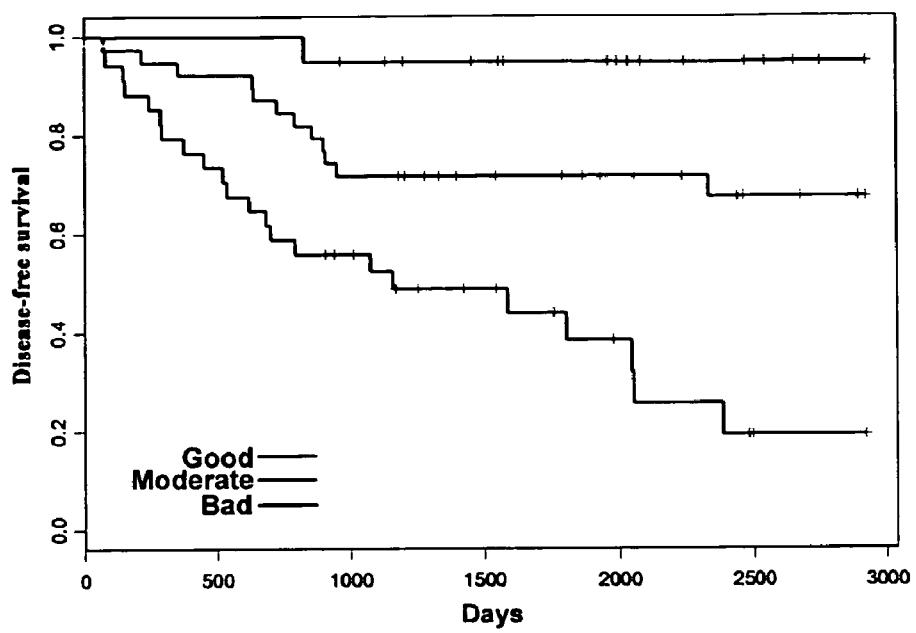

FIG. 8 shows Kaplan-Meier curves that were generated for ER− patients after prognostic classification based on staining with the exemplary prognostic panel of antibodies from Table 7. In each case the patients were placed into one of three prognostic groups, namely "bad" (bottom curve), "moderate" (middle curve) and "good" (top curve).

Figure 9:
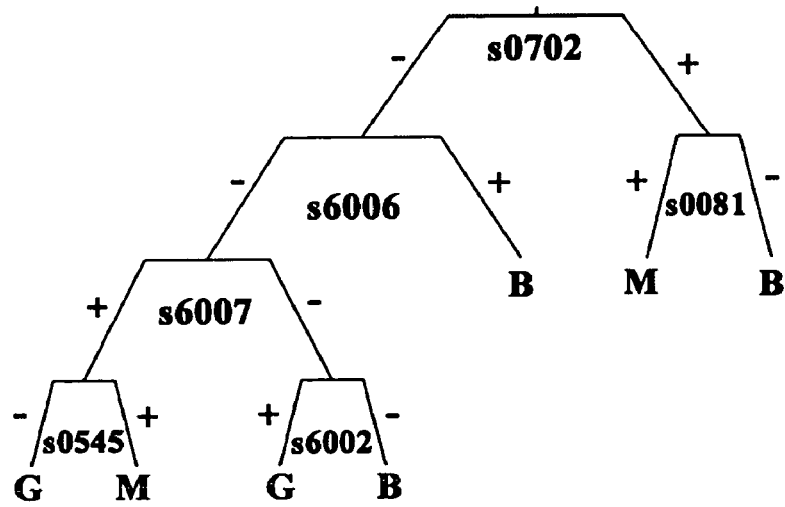

FIG. 9 shows a dendrogram for the tree panel of Table 8 that may be used for the prognostic classification of ER+/node− patients. If a patient is positive for staining at a given node his or her prognosis decision tree follows the branch marked with a "+". Conversely if a patient is negative for staining at a given node his or her prognosis decision tree follows the branch marked "−". This is done until a terminus is reached.

Figure 10:
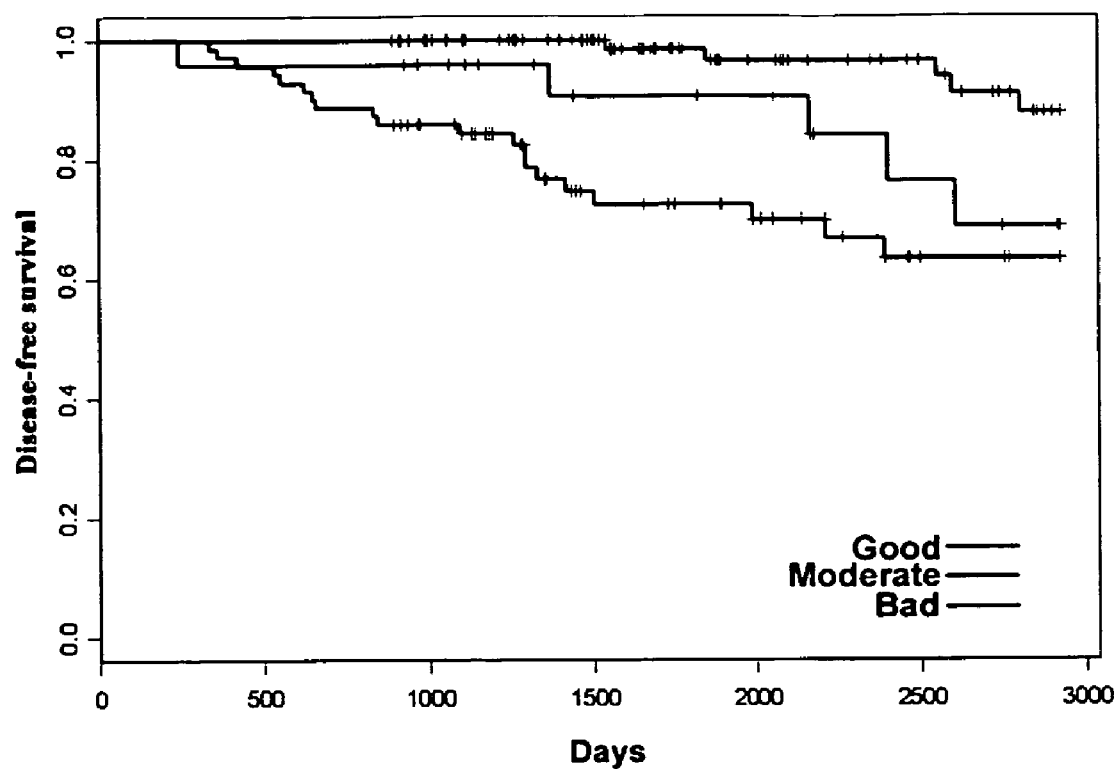

FIG. 10 shows Kaplan-Meier curves that were generated for ER+/node− patients after prognostic classification based on staining with the exemplary prognostic panel of antibodies from Table 8. In each case the patients were placed into one of three prognostic groups, namely "bad" (bottom curve), "moderate" (middle curve) and "good" (top curve).

Figure 11:
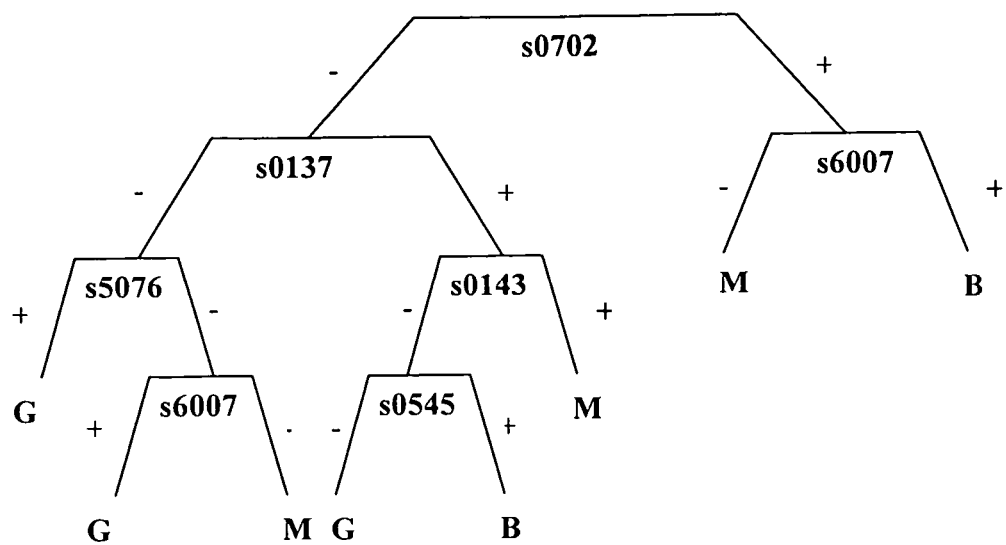
Figure 11:
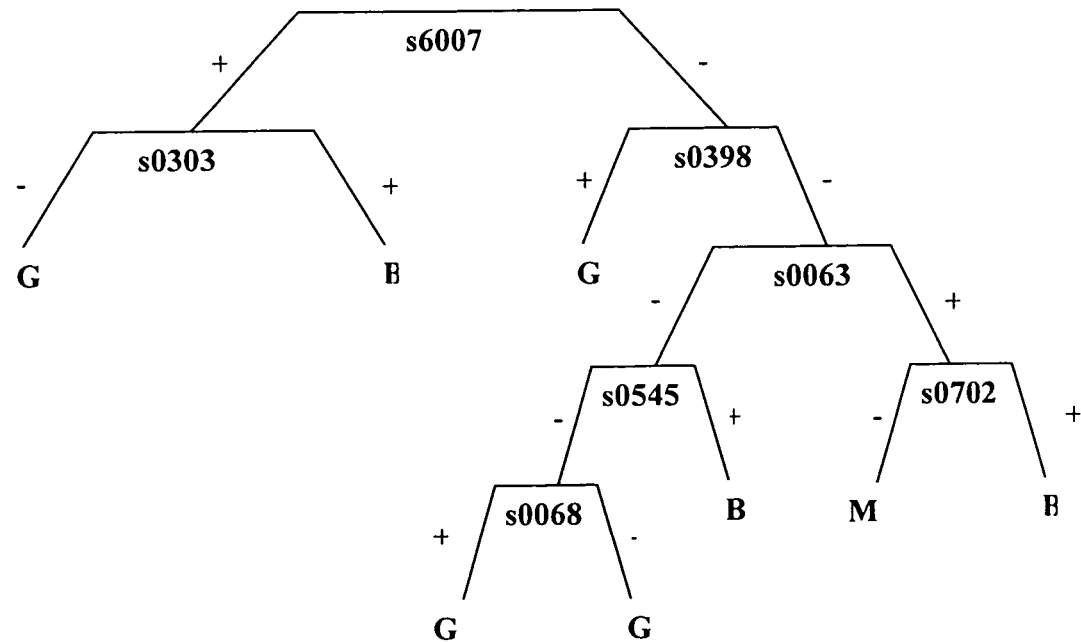

FIG. 11 shows a dendrogram for the tree panels of Table 9 that may be used for the prognostic classification of ER+ and ER− patients. If a patient is positive for staining at a given node his or her prognosis decision tree follows the branch marked with a "+". Conversely if a patient is negative for staining at a given node his or her prognosis decision tree follows the branch marked "−". This is done until a terminus is reached.

Figure 12:
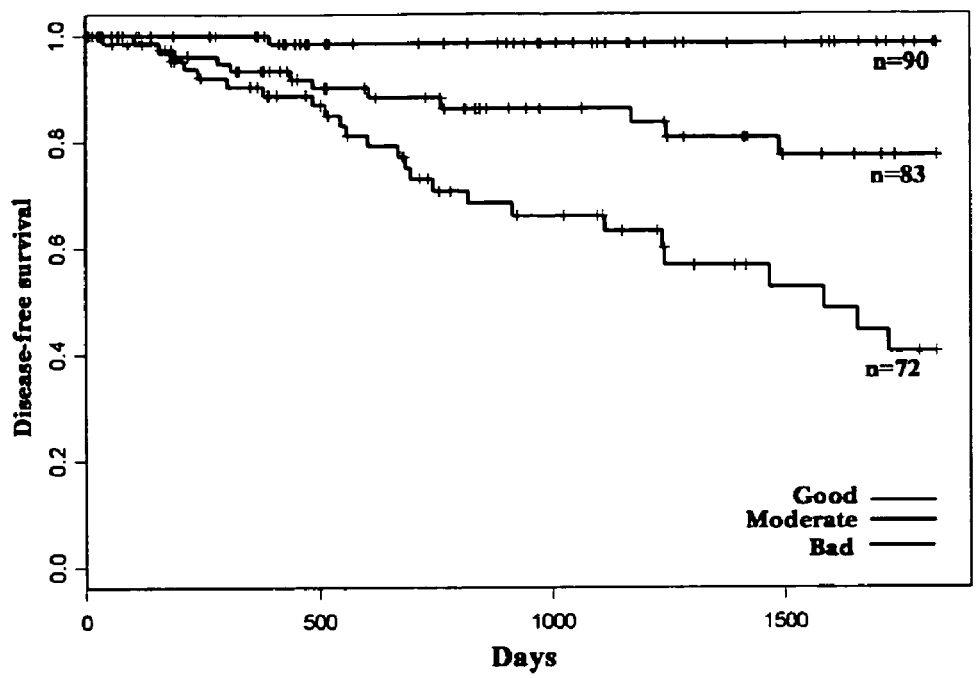

FIG. 12 shows Kaplan-Meier curves that were generated for combined lung cancer patients (HH cohort) after prognostic classification with the exemplary prognostic panels of antibodies from Tables 10 and 11. In each case the patients were placed into one of three prognostic groups, namely "bad" (bottom curve), "moderate" (middle curve) and "good" (top curve).

Figure 13:
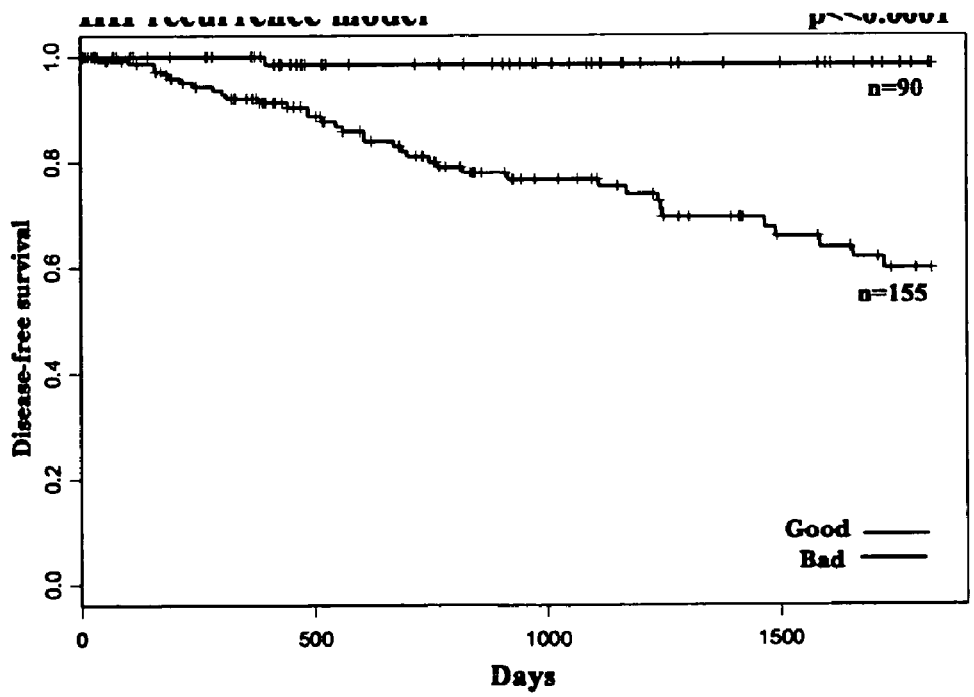

FIG. 13 shows the curves that were obtained when patients in the "moderate" and "bad" groups of FIG. 12 were combined into a single "bad" prognostic group.

Figure 14:
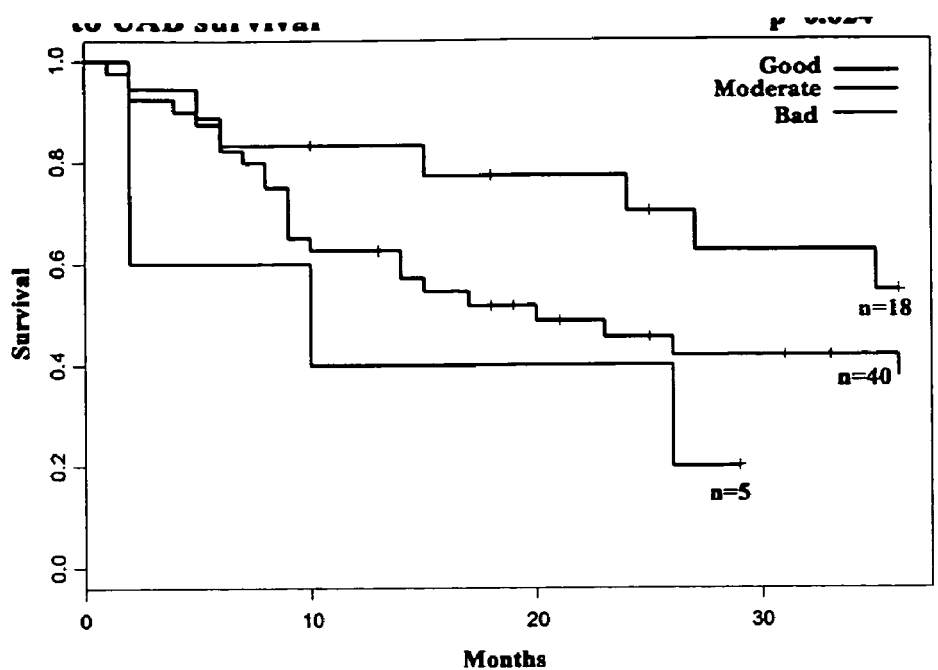

FIG. 14 shows Kaplan-Meier curves that were generated for combined lung cancer patients (UAB lung cohort) after prognostic classification with the exemplary prognostic panels of antibodies from Tables 10 and 11. In each case the patients were placed into one of three prognostic groups, namely "bad" (bottom curve), "moderate" (middle curve) and "good" (top curve).

Figure 15:
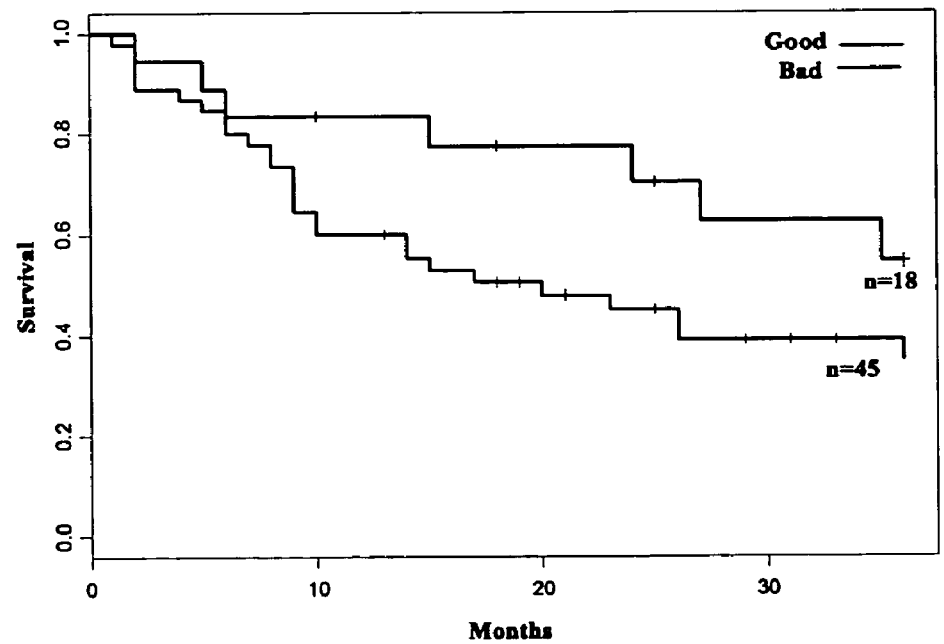

FIG. 15 shows the curves that were obtained when the patients in the "moderate" and "bad" groups of FIG. 14 were combined into a single "bad" prognostic group.

Figure 16:
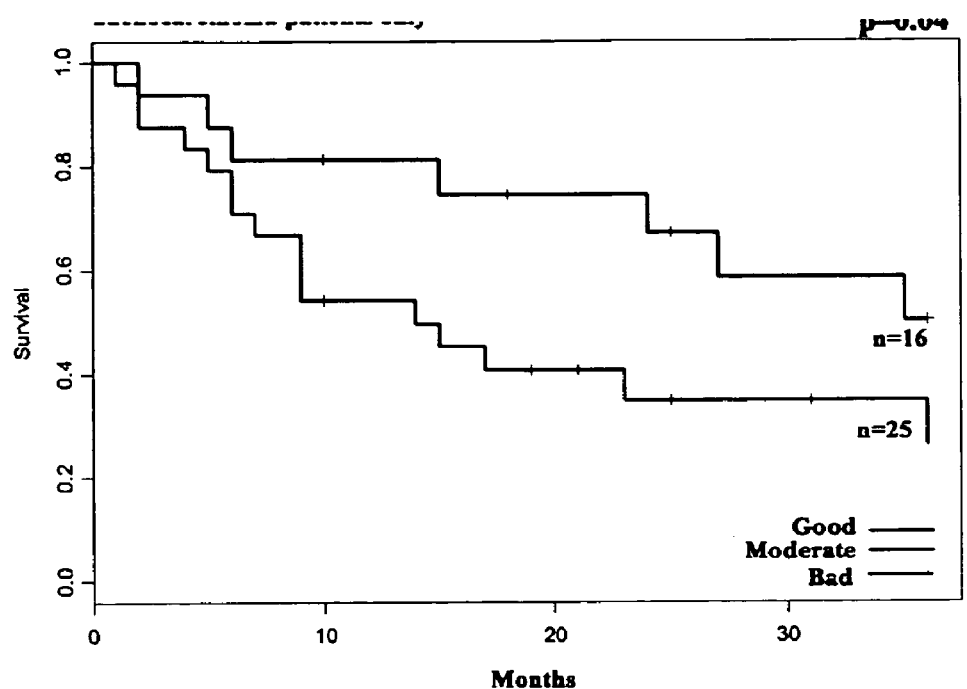

FIG. 16 shows Kaplan-Meier curves that were generated for adenocarcinoma patients (UAB cohort) after prognostic classification with the exemplary prognostic panels of antibodies from Table 11. In each case the patients were placed into one of three prognostic groups, namely "bad" (bottom curve), "moderate" (middle curve) and "good" (top curve).

Figure 17:
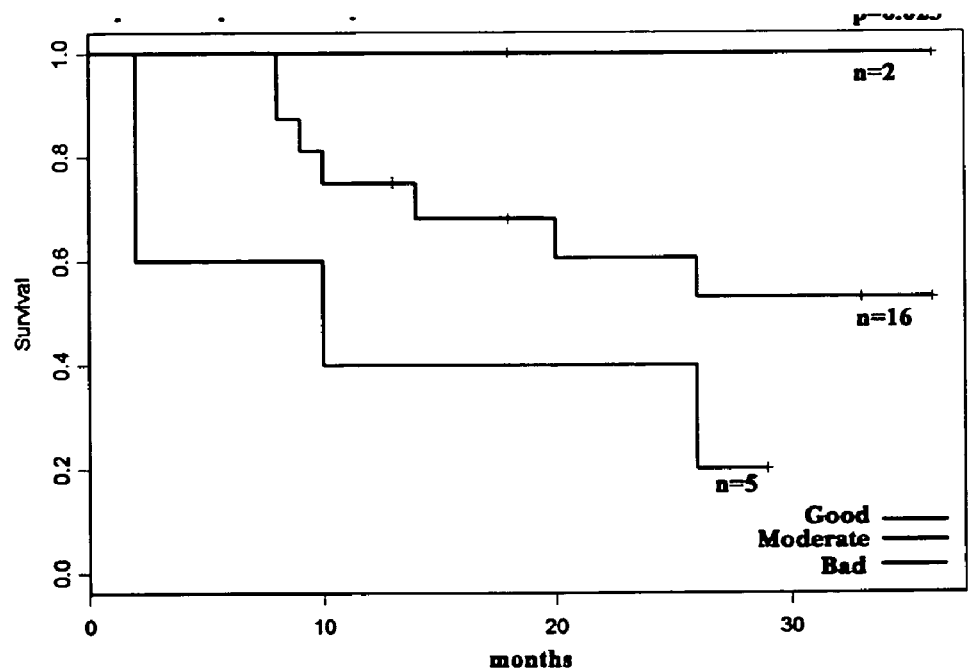

FIG. 17 shows Kaplan-Meier curves that were generated for squamous cell carcinoma patients (UAB lung cohort) after prognostic classification with the exemplary prognostic panels of antibodies from Table 10. In each case the patients were placed into one of three prognostic groups, namely "bad" (bottom curve), "moderate" (middle curve) and "good" (top curve).

Figure 18:
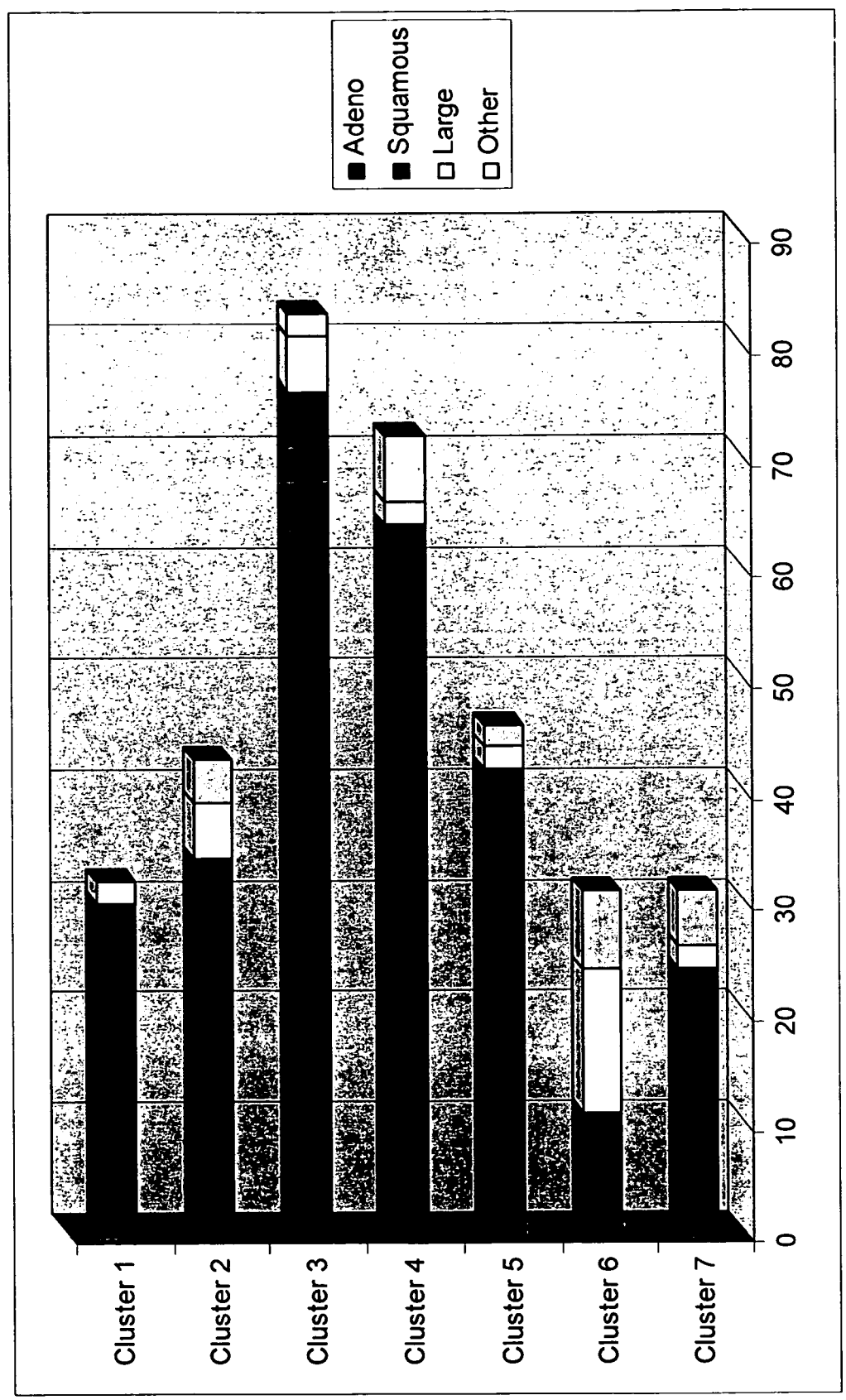

FIG. 18 shows the relative proportions of different lung cancer morphologies that were identified in seven sub-classes of patients in the HH lung cohort.

Figure 19:
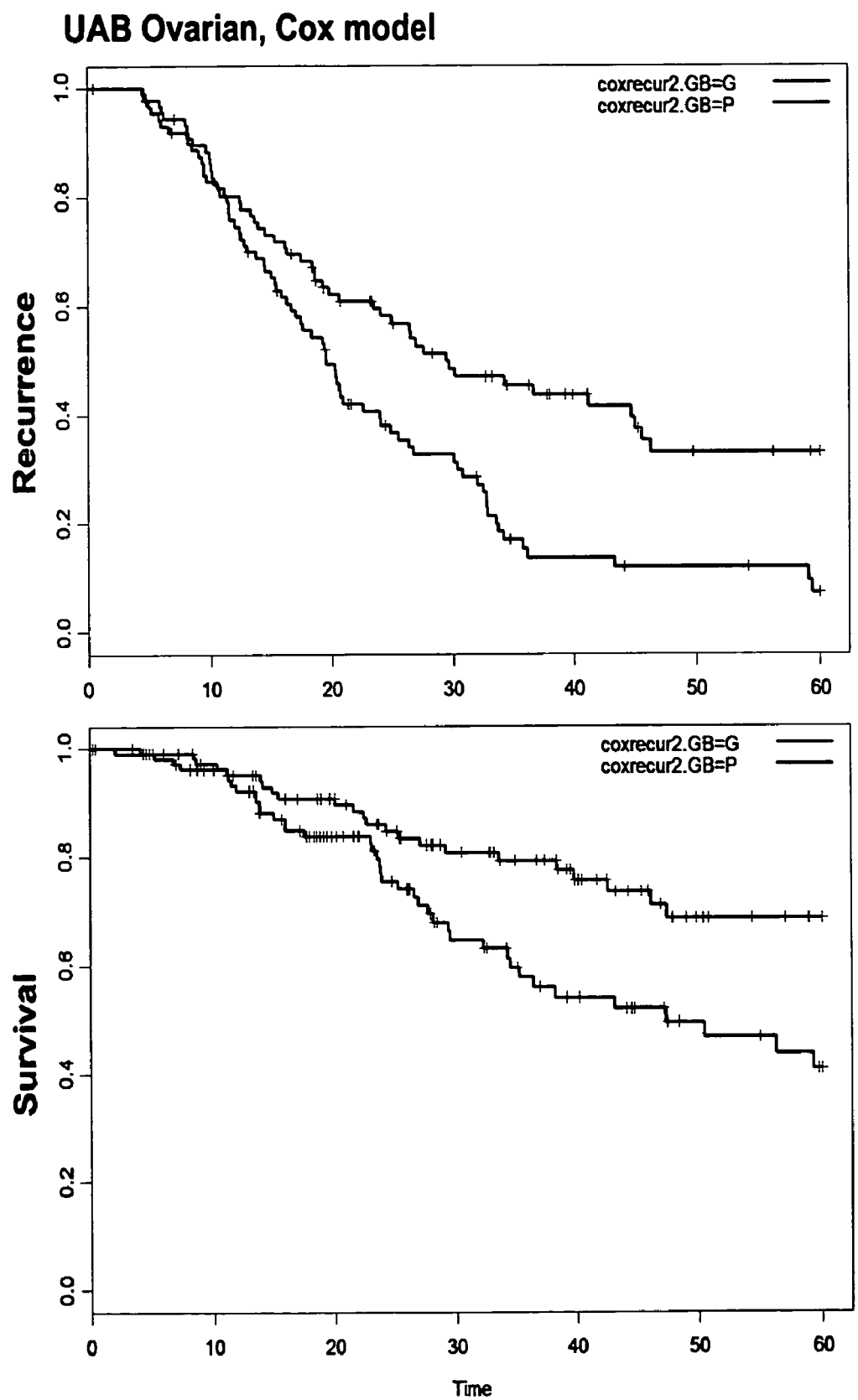

FIG. 19 shows Kaplan-Meier curves that were generated for ovarian cancer patients after prognostic classification based on staining with the exemplary prognostic panel of antibodies from Table 18. In each case the patients were placed into one of two prognostic groups, namely "poor" (bottom curve) and "good" (top curve).

Figure 20:
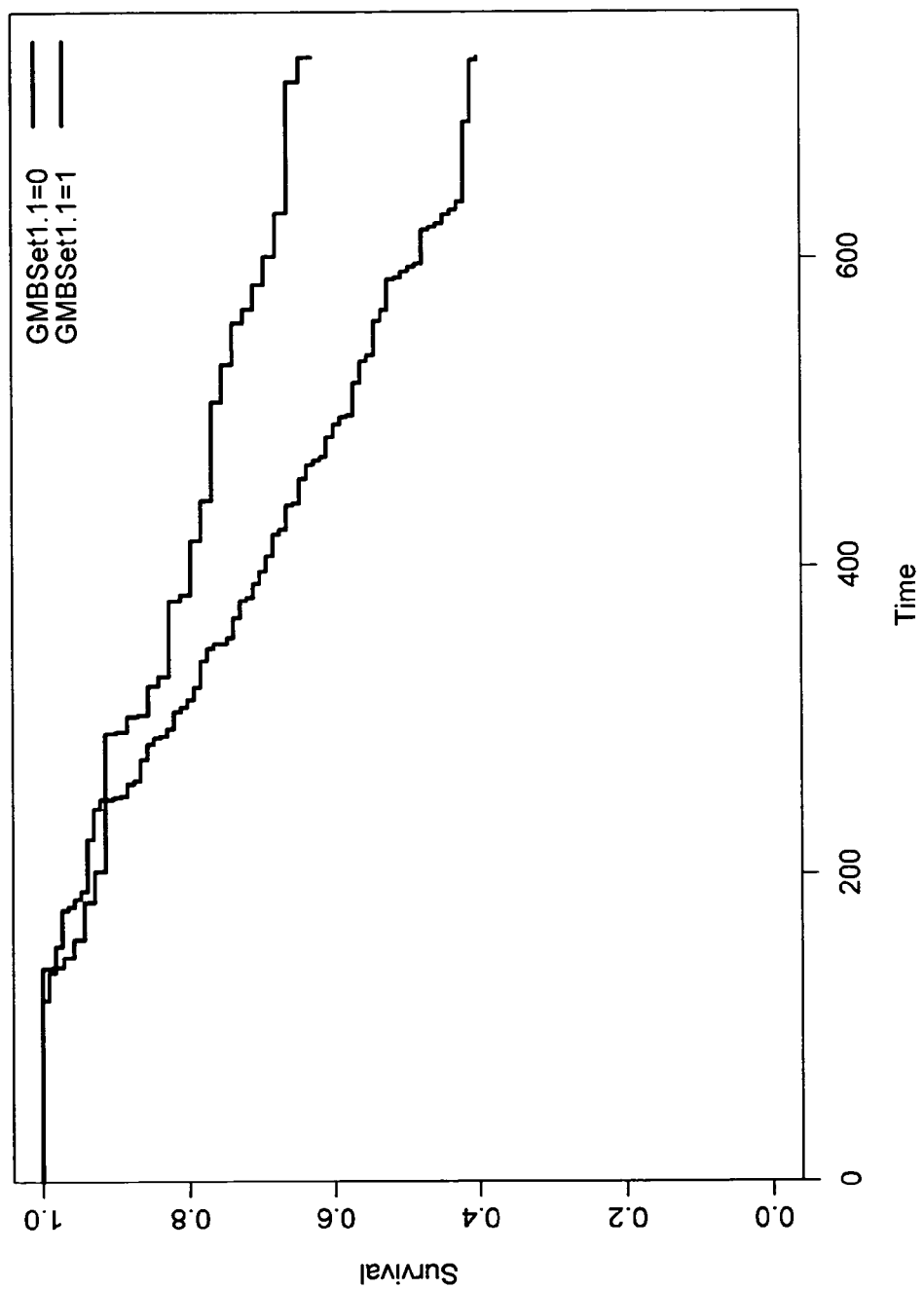

FIG. 20 shows Kaplan-Meier curves that were generated for ovarian cancer patients after prognostic classification based on staining with the exemplary prognostic panel of antibodies from Table 19. In each case the patients were placed into one of two prognostic groups, namely "poor" (bottom curve) and "good" (top curve).

Figure 21:
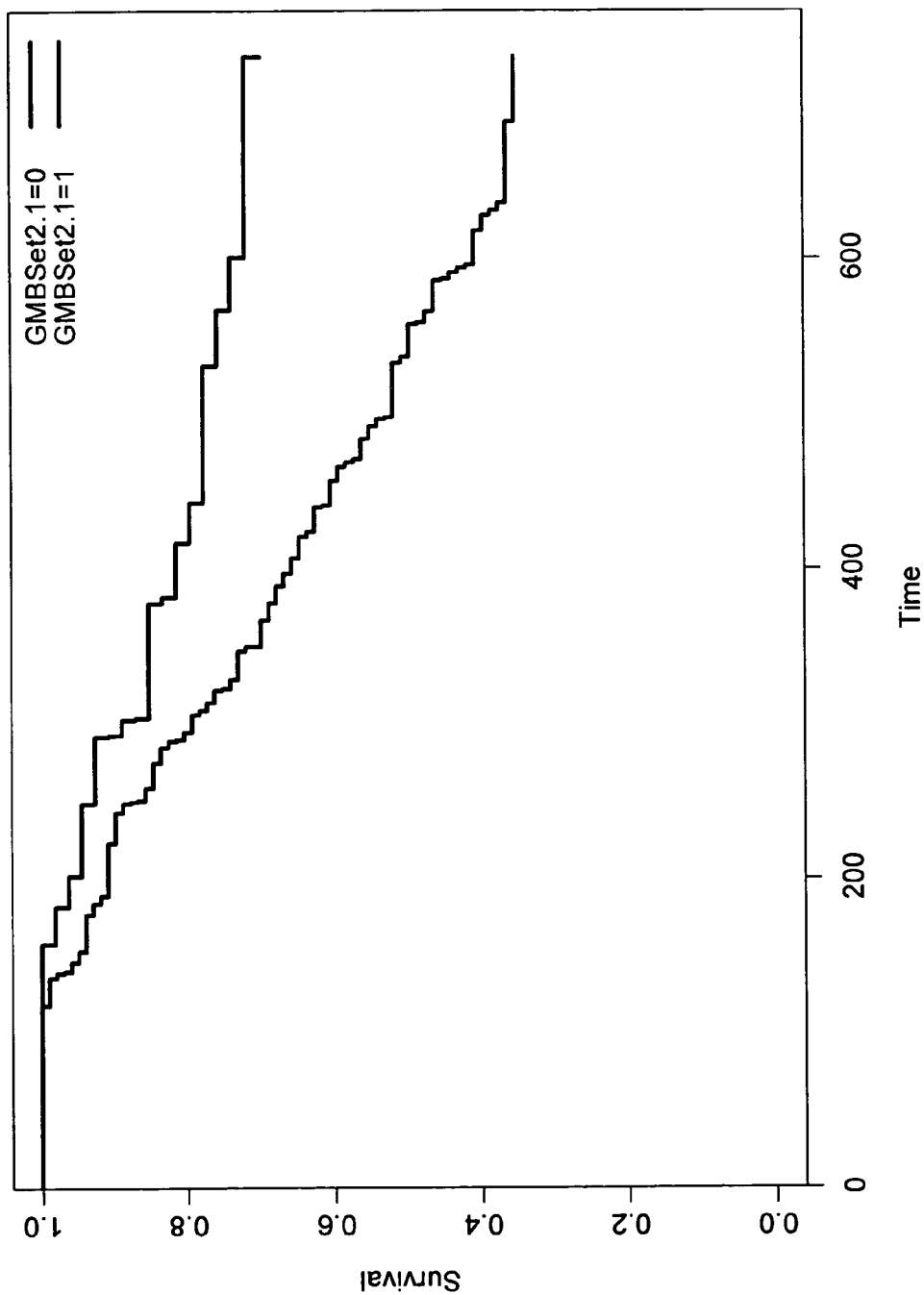

FIG. 21 shows Kaplan-Meier curves that were generated for ovarian cancer patients after prognostic classification based on staining with the exemplary prognostic panel of antibodies from Table 20. In each case the patients were placed into one of two prognostic groups, namely "poor" (bottom curve) and "good" (top curve).

Figure 22:
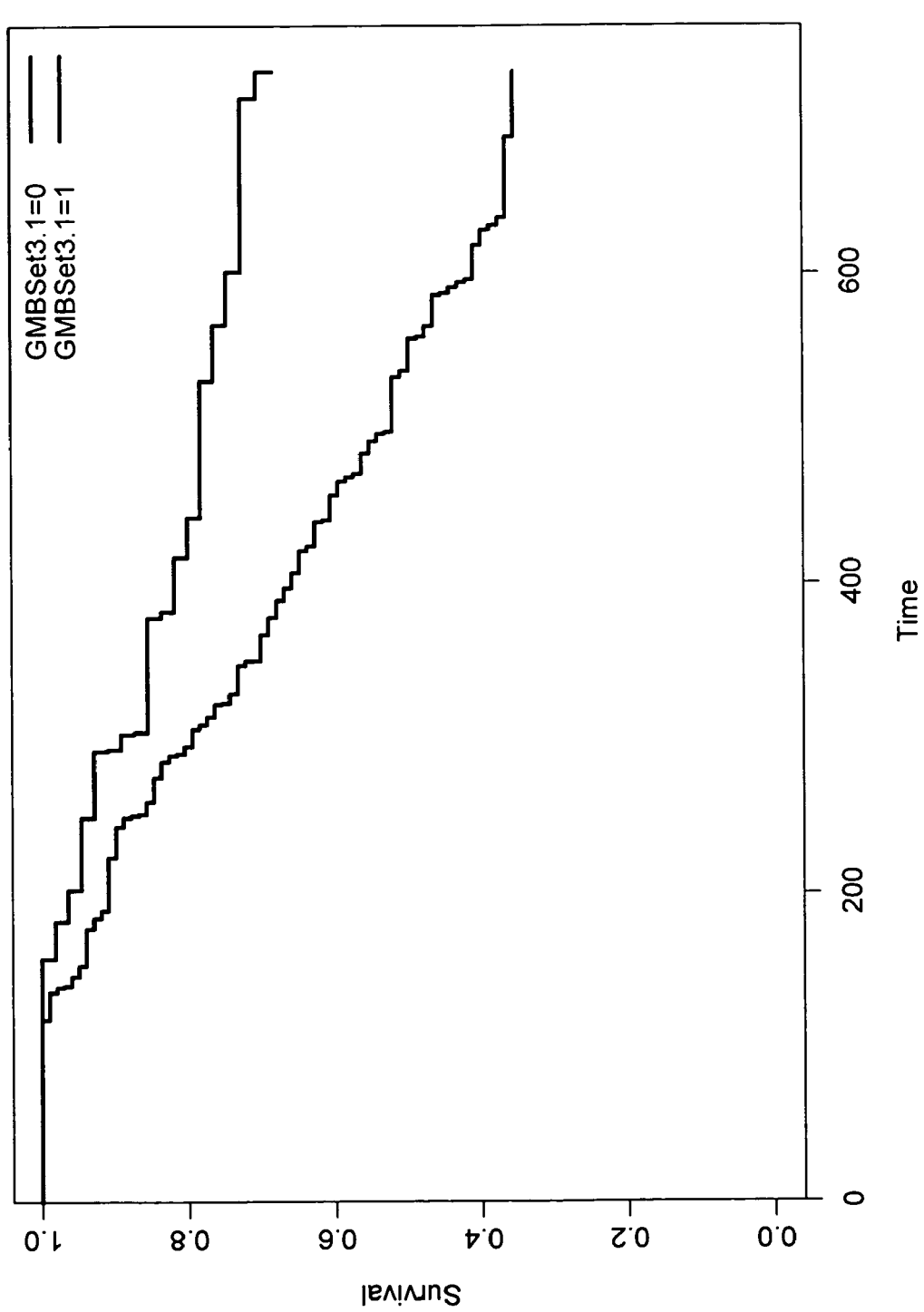

FIG. 22 shows Kaplan-Meier curves that were generated for ovarian cancer patients after prognostic classification based on staining with the exemplary prognostic panel of antibodies from Table 21. In each case the patients were placed into one of two prognostic groups, namely "poor" (bottom curve) and "good" (top curve).

Figure 23:
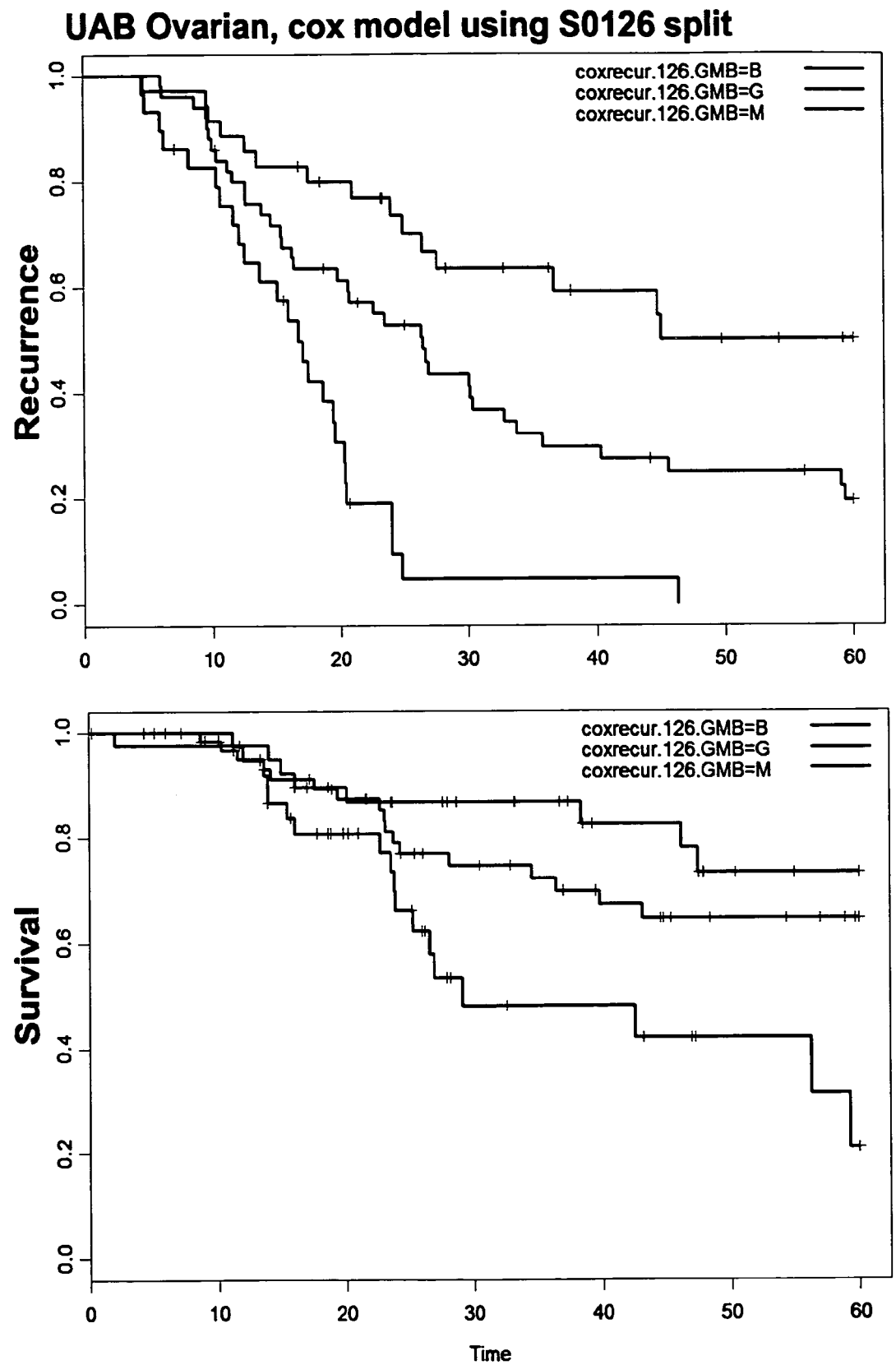

FIG. 23 shows Kaplan-Meier curves that were generated for ovarian cancer patients after prognostic classification with the exemplary prognostic panels of antibodies from Tables 22-23. In each case the patients were placed into one of three prognostic groups, namely "bad" (bottom curve), "moderate" (middle curve) and "good" (top curve).

Figure 24:
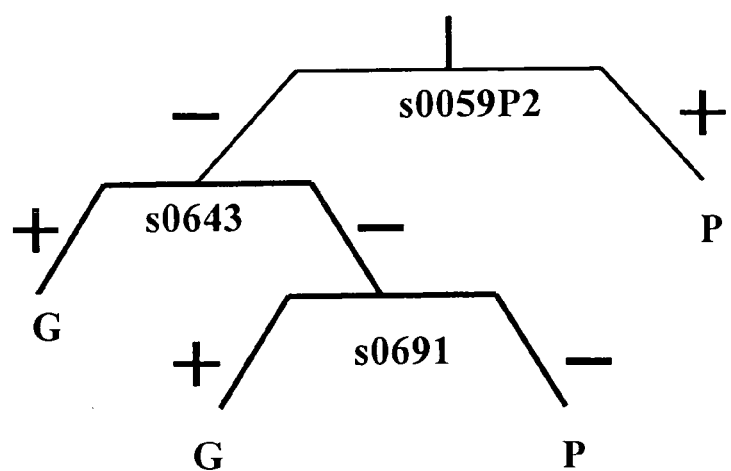

FIG. 24 shows a dendrogram for the tree panel of Table 24 that may be used for the prognostic classification of ovarian cancer patients. If a patient is positive for staining at a given node his or her prognosis decision tree follows the branch marked with a "+". Conversely if a patient is negative for staining at a given node his or her prognosis decision tree follows the branch marked "−". This is done until a terminus is reached.

Figure 25:
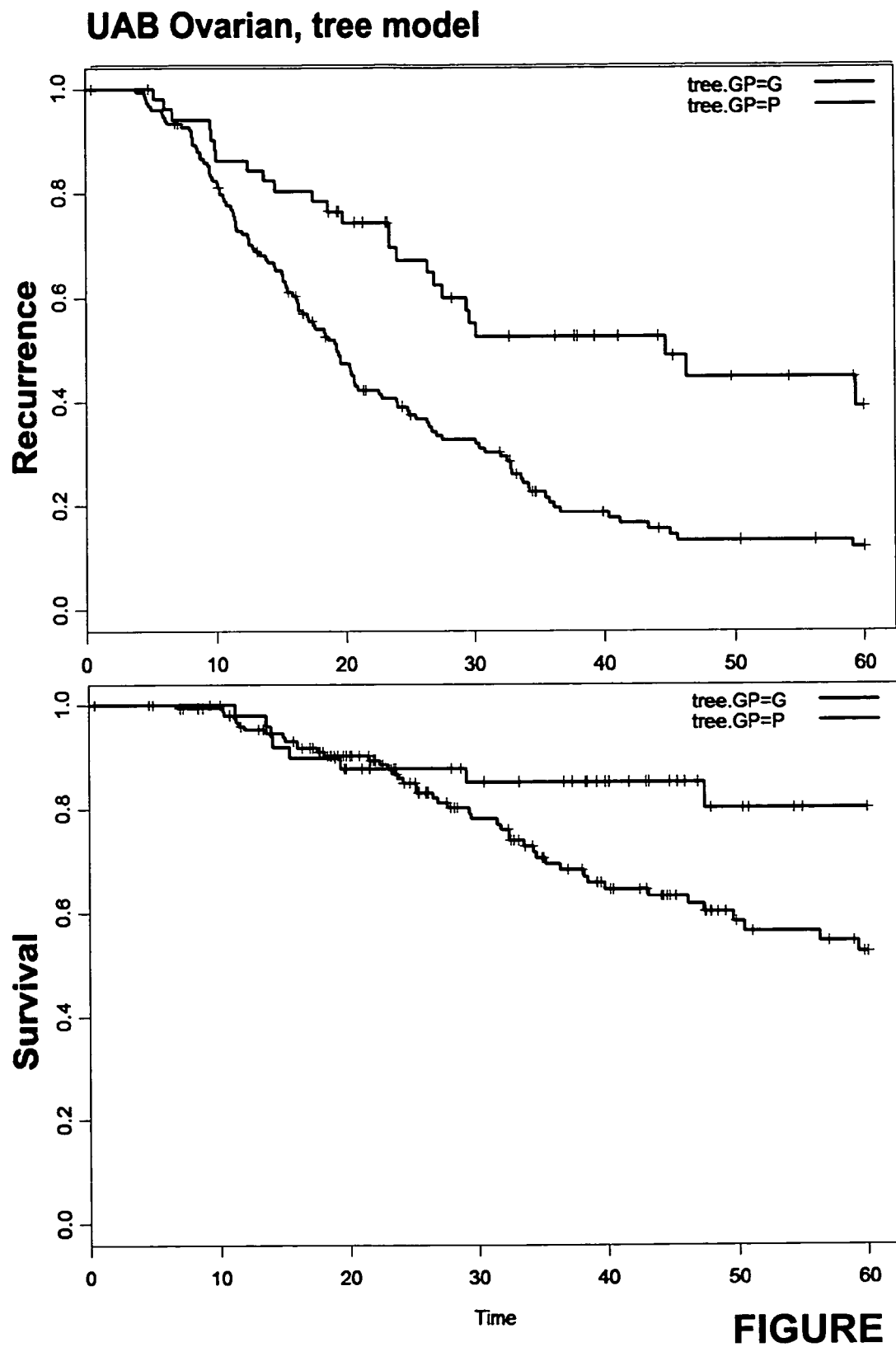

FIG. 25 shows Kaplan-Meier curves that were generated for ovarian cancer patients after prognostic classification based on staining with the exemplary prognostic panel of antibodies from Table 24 and FIG. 24. In each case the patients were placed into one of two prognostic groups, namely "poor" (bottom curve) and "good" (top curve).

DEFINITIONS

Associated—When an interaction partner and a tumor marker are physically "associated" with one another as described herein, they are linked by direct non-covalent interactions. Desirable non-covalent interactions include those of the type which occur between an immunoglobulin molecule and an antigen for which the immunoglobulin is specific, for example, ionic interactions, hydrogen bonds, van der Waals interactions, hydrophobic interactions, etc. The strength, or affinity of the physical association can be expressed in terms of the dissociation constant ($K_d$) of the interaction, wherein a smaller $K_d$ represents a greater affinity. The association properties of selected interaction partners and tumor markers can be quantified using methods well known in the art (e.g., see Davies et al., *Annual Rev. Biochem.* 59:439, 1990).

Classification panel—A "classification panel" of interaction partners is a set of interaction partners whose collective pattern of binding or lack of binding to a tumor sample, when taken together, is sufficient to classify the tumor sample as a member of a particular class or subclass of tumor, or as not a member of a particular class or subclass of tumor.

Correlation—"Correlation" refers to the degree to which one variable can be predicted from another variable, e.g., the degree to which a patient's therapeutic response can be predicted from the pattern of binding between a set of interaction partners and a tumor sample taken from that patient. A variety of statistical methods may be used to measure correlation between two variables, e.g., without limitation the student t-test, the Fisher exact test, the Pearson correlation coefficient, the Spearman correlation coefficient, the Chi squared test, etc. Results are traditionally given as a measured correlation coefficient with a p-value that provides a measure of the likelihood that the correlation arose by chance. A correlation with a p-value that is less than 0.05 is generally considered to be statistically significant. Preferred correlations have p-values that are less than 0.01, especially less than 0.001.

Interaction partner—An "interaction partner" is an entity that physically associates with a tumor marker. For example and without limitation, an interaction partner may be an antibody or a fragment thereof that physically associates with a tumor marker. In general, an interaction partner is said to "associate specifically" with a tumor marker if it associates at a detectable level with the tumor marker and does not associate detectably with unrelated molecular entities (e.g., other tumor markers) under similar conditions. Specific association between a tumor marker and an interaction partner will typically be dependent upon the presence of a particular structural feature of the target tumor marker such as an antigenic determinant or epitope recognized by the interaction partner. Generally, if an interaction partner is specific for epitope A, the presence of a molecular entity (e.g., a protein) containing epitope A or the presence of free unlabeled A in a reaction containing both free labeled A and the interaction partner thereto, will reduce the amount of labeled A that binds to the interaction partner. In general, it is to be understood that specificity need not be absolute. For example, it is well known in the art that antibodies frequently cross-react with other epitopes in addition to the target epitope. Such cross-reactivity may be acceptable depending upon the application for which the interaction partner is to be used. Thus the degree of specificity of an interaction partner will depend on the context in which it is being used. In general, an interaction partner exhibits specificity for a particular tumor marker if it favors binding with that partner above binding with other potential partners, e.g., other tumor markers. One of ordinary skill in the art will be able to select interaction partners having a sufficient degree of specificity to perform appropriately in any given application (e.g., for detection of a target tumor marker, for therapeutic purposes, etc.). It is also to be understood that specificity may be evaluated in the context of additional factors such as the affinity of the interaction partner for the target tumor marker versus the affinity of the interaction partner for other potential partners, e.g., other tumor markers. If an interaction partner exhibits a high affinity for a target tumor marker and low affinity for non-target molecules, the interaction partner will likely be an acceptable reagent for diagnostic purposes even if it lacks specificity. It will be appreciated that once the specificity of an interaction partner is established in one or more contexts, it may be employed in other, preferably similar, contexts without necessarily re-evaluating its specificity.

Predictive panel—A "predictive panel" of interaction partners is a set of interaction partners whose collective pattern of binding or lack of binding to a tumor sample, when taken together, has sufficient correlation to classify the tumor sample as being from a patient who is likely (or not) to respond to a given therapeutic regimen.

Prognostic panel—A "prognostic panel" of interaction partners is a set of interaction partners whose collective pattern of binding or lack of binding to a tumor sample, when taken together, has sufficient correlation to classify the tumor sample as being from a patient who is likely to have a given outcome. Generally, "outcome" may include, but is not limited to, the average life expectancy of the patient, the likelihood that the patient will survive for a given amount of time (e.g., 6 months, 1 year, 5 years, etc.), the likelihood of recurrence, the likelihood that the patient will be disease-free for a specified prolonged period of time, or the likelihood that the patient will be cured of the disease.

Response—The "response" of a tumor or a cancer to therapy may represent any detectable change, for example at the molecular, cellular, organellar, or organismal level. For instance, tumor size, patient life expectancy, recurrence, or the length of time the patient survives, etc., are all responses. Responses can be measured in any of a variety of ways, including for example non-invasive measuring of tumor size (e.g., CT scan, image-enhanced visualization, etc.), invasive measuring of tumor size (e.g., residual tumor resection, etc.), surrogate marker measurement (e.g., serum PSA, etc.), clinical course variance (e.g., measurement of patient quality of life, time to relapse, survival time, etc.).

Small molecule—A "small molecule" is a non-polymeric molecule. A small molecule can be synthesized in a laboratory (e.g., by combinatorial synthesis) or found in nature (e.g., a natural product). A small molecule is typically characterized in that it contains several carbon-carbon bonds and has a molecular weight of less than about 1500 Da, although this characterization is not intended to be limiting for the purposes of the present invention.

Tumor markers—"Tumor markers" are molecular entities that are detectable in tumor samples. Generally, tumor markers will be proteins that are present within the tumor sample, e.g., within the cytoplasm or membranes of tumor cells and/or secreted from such cells. According to the present invention, sets of tumor markers that correlate with tumor class or subclass are identified. Thus, subsequent tumor samples may be classified or subclassified based on the presence of these sets of tumor markers.

Tumor sample—As used herein the term "tumor sample" is taken broadly to include cell or tissue samples removed from a tumor, cells (or their progeny) derived from a tumor that may be located elsewhere in the body (e.g., cells in the bloodstream or at a site of metastasis), or any material derived by processing such a sample. Derived tumor samples may include, for example, nucleic acids or proteins extracted from the sample.

DETAILED DESCRIPTION OF CERTAIN PREFERRED EMBODIMENTS OF THE INVENTION

As noted above, the present invention provides techniques and reagents for the classification and subclassification, of tumors. Such classification (or subclassification) has many beneficial applications. For example, a particular tumor class or subclass may correlate with prognosis and/or susceptibility to a particular therapeutic regimen. As such, the classification or subclassification may be used as the basis for a prognostic or predictive kit and may also be used as the basis for identifying previously unappreciated therapies. Therapies that are effective against only a particular class or subclass of tumor may have been lost in studies whose data were not stratified by subclass; the present invention allows such data to be re-stratified, and allows additional studies to be performed, so that class- or subclass-specific therapies may be identified and/or implemented. Alternatively or additionally, the present invention allows identification and/or implementation of therapies that are targeted to genes identified as class- or subclass-specific.

Classification and Subclassification of Tumors

In general, according to the present invention, tumors are classified or subclassified on the basis of tumor markers whose presence is correlated with a particular class or subclass. In preferred embodiments, the tumor markers are detected via their physical association with an interaction partner. Included in the present invention are kits comprising sets of interaction partners that together can be used to identify or classify a particular tumor sample; such sets are generally referred to as "classification panels".

The present invention provides systems of identifying classification panels. In general, tumor samples are contacted with individual interaction partners, and binding between the interaction partners and their cognate tumor markers is detected. For example, panels of interaction partners that identify a particular class or subclass of tumor within tumor samples of a selected tissue of origin may be defined by contacting individual interaction partners with a variety of different tumor samples (e.g., from different patients) all of the same tissue of origin. Individual interaction partners may be selected for inclusion in the ultimate classification panel based on their binding to only a subset of the tumor samples (e.g., see Examples 1-4). Those of ordinary skill in the art, however, will appreciate that all that is required for a collection of interaction partners to operate effectively as a classification panel is that the combined binding characteristics of member interaction partners together are sufficient to classify a particular tumor sample.

The inventive process of identifying useful panels of interaction partners as described herein may itself result in the identification of new tumor classes or subclasses. That is, through the process of analyzing interaction partner binding patterns, investigators will often discover new tumor classes or subclasses to which sets of interaction partners bind. Thus, the processes (a) of defining classification panels of interaction partners for given tumor classes or subclasses; and (b) identifying new tumor classes or subclasses may well be experimentally interrelated. In general, the greater the number of tumor samples tested, the greater the likelihood that new classes or subclasses will be defined.

Often, when identifying sets of interaction partners that can act as a classification (or subclassification) panel, it will be desirable to obtain the largest set of tumor samples possible, and also to collect the largest amount of information possible about the individual samples. For example, the origin of the tumor, the gender of the patient, the age of the patient, the staging of the tumor (e.g., according to the TNM system), any microscopic or submicroscopic characteristics of the tumor that may have been determined, may be recorded. Those of ordinary skill in the art will appreciate that the more information that is known about a tumor sample, the more aspects of that sample are available for correlation with interaction partner binding.

The systems of the present invention have particular utility in classifying or subclassifying tumor samples that are not otherwise distinguishable from one another. Thus, in some embodiments, it will be desirable to analyze the largest collection of tumor samples that are most similar to one another.

When obtaining tumor samples for testing according to the present invention, it is generally preferred that the samples represent or reflect characteristics of a population of patients or samples. It may also be useful to handle and process the samples under conditions and according to techniques common to clinical laboratories. Although the present invention is not intended to be limited to the strategies used for processing tumor samples, we note that, in the field of pathology, it is often common to fix samples in buffered formalin, and then to dehydrate them by immersion in increasing concentrations of ethanol followed by xylene. Samples are then embedded into paraffin, which is then molded into a "paraffin block" that is a standard intermediate in histologic processing of tissue samples. The present inventors have found that many useful interaction partners display comparable binding regardless of the method of preparation of tumor samples; those of ordinary skill in the art can readily adjust observations to account for differences in preparation procedure.

In preferred embodiments of the invention, large numbers of tissue samples are analyzed simultaneously. In some embodiments, a tissue array is prepared. Tissue arrays may be constructed according to a variety of techniques. According to one procedure, a commercially-available mechanical device (e.g., the manual tissue arrayer MTA1 from Beecher Instruments of Sun Prairie, Wis.) is used to remove an 0.6-micron-diameter, full thickness "core" from a paraffin block (the donor block) prepared from each patient, and to insert the core into a separate paraffin block (the recipient block) in a designated location on a grid. In preferred embodiments, cores from as many as about 400 patients can be inserted into a single recipient block; preferably, core-to-core spacing is approximately 1 mm. The resulting tissue array may be processed into thin sections for staining with interaction partners according to standard methods applicable to paraffin embedded material. Depending upon the thickness of the donor blocks, as well as the dimensions of the clinical material, a single tissue array can yield about 50-150 slides containing >75% relevant tumor material for assessment with interaction partners. Construction of two or more parallel tissue arrays of cores from the same cohort of patient samples can provide relevant tumor material from the same set of patients in duplicate or more. Of course, in some cases, additional samples will be present in one array and not another.

The present inventors have found that it is often desirable to evaluate some aspects of the binding characteristics of potential interaction partners before or while assessing the desirability of including them in an interaction panel. For example, the inventors have found that it is often desirable to perform a titration study in which different concentrations of the interaction partner are contacted with a diverse set of tissue samples derived from a variety of different tissues (e.g., normal and/or tumor) in order to identify a concentration or titer at which differential binding is observed. This titer is referred to herein as a "discriminating titer". Such differential staining may be observed between different tissue samples and/or between different cell types within a given tissue sample.

In general, any tissue sample may be used for this purpose (e.g., samples obtained from the epididymis, esophagus, gall bladder, kidneys, liver, lungs, lymph nodes, muscles, ovaries, pancreas, parathyroid glands, placenta, prostate, saliva, skin, spleen, stomach, testis, thymus, thyroid, tonsils, uterus, etc.). For such titration studies, greater diversity among samples is often preferred. Without intending to limit the present invention, the inventors observe that useful titers for particular interaction partners can typically be defined in a study of approximately 40-70 different tissue samples from about 20-40 different tissues.

Binding studies (for titration, for assessment of inclusion in a panel, or during use of a panel) may be performed in any format that allows specific interaction to be detected. Where large numbers of samples are to be handled, it may be desirable to utilize arrayed and/or automated formats. Particularly preferred formats include tissue arrays as discussed above. The staining of large numbers of samples derived from a variety of tumors in a tissue array format allows excellent comparative assessment of differential staining between or among samples under identical conditions. According to the present invention, staining patterns that identify at least about 10% of samples as binding with a particular interaction partner, or at least about 20, 30, 40, 50% or more of samples, are likely to represent "real" differential staining patterns (i.e., real variations in binding with interaction partner and not experimental variations, for example, due to sample processing or day to day variation in staining techniques).

Any available technique may be used to detect binding between an interaction partner and a tumor sample. One powerful and commonly used technique is to have a detectable label associated (directly or indirectly) with the interaction partner. For example, commonly-used labels that often are associated with antibodies used in binding studies include fluorochromes, enzymes, gold, iodine, etc. Tissue staining by bound interaction partners is then assessed, preferably by a trained pathologist or cytotechnologist. For example, a scoring system may be utilized to designate whether the interaction partner does or does not bind to (e.g., stain) the sample, whether it stains the sample strongly or weakly and/or whether useful information could not be obtained (e.g., because the sample was lost, there was no tumor in the sample or the result was otherwise ambiguous). Those of ordinary skill in the art will recognize that the precise characteristics of the scoring system are not critical to the invention. For example, staining may be assessed qualitatively or quantitatively; more or less subtle gradations of staining may be defined; etc.

Whatever the format, and whatever the detection strategy, identification of a discriminating titer can simplify binding studies to assess the desirability of including a given interaction partner in a panel. In such studies, the interaction partner is contacted with a plurality of different tumor samples that preferably have at least one common trait (e.g., tissue of origin), and often have multiple common traits (e.g., tissue of origin, stage, microscopic characteristics, etc.). In some cases, it will be desirable to select a group of samples with at least one common trait and at least one different trait, so that a panel of interaction partners is defined that distinguishes the different trait. In other cases, it will be desirable to select a group of samples with no detectable different traits, so that a panel of interaction partners is defined that distinguishes among previously indistinguishable samples. Those of ordinary skill in the art will understand, however, that the present invention often will allow both of these goals to be accomplished even in studies of sample collections with varying degrees of similarity and difference.

According to the present invention, interaction partners that bind to tumor samples may be characterized by their ability to discriminate among tumor samples. Any of a variety of techniques may be used to identify discriminating interaction partners. To give but one example, the present inventors have found it useful to define a "consensus panel" of tissue samples for tumors of a particular tissue of origin (see Examples 2-6). Those of ordinary skill in the art will again appreciate that the precise parameters used to designate a particular sample as interpretable and reproducible are not critical to the invention. Interaction partners may then be classified based on their ability to discriminate among tissue samples in the consensus panel (see Examples 2-6).

Assessing Prognosis or Therapeutic Regimen

The present invention further provides systems for identifying panels of interaction partners whose binding correlates with factors beyond tumor class or subclass, such as likelihood of a particular favorable or unfavorable outcome, susceptibility (or lack thereof) to a particular therapeutic regimen, etc.

As mentioned in the background, current approaches to assigning prognostic probabilities and/or selecting appropriate therapeutic regimens for particular tumors generally utilize the tumor-node-metastasis (TNM) system. This system uses the size of the tumor, the presence or absence of tumor in regional lymph nodes and the presence or absence of distant metastases, to assign a stage to the tumor. The assigned stage is used as a basis for selection of appropriate therapy and for prognostic purposes.

The present invention provides new methods and systems for evaluating tumor prognosis and/or recommended therapeutic approaches. In particular, the present invention provides systems for identifying panels of interaction partners whose binding correlates with tumor prognosis or therapeutic outcome.

For example, interaction partners whose binding correlates with prognosis can be identified by evaluating their binding to a collection of tumor samples for which prognosis is known or knowable. That is, the strategies of the invention may be employed either to identify collections of interaction partners whose binding correlates with a known outcome, or may be employed to identify a differential staining pattern that is then correlated with outcome (which outcome may either be known in advance or determined over time).

In general, it is preferred that inventive binding analyses be performed on human tumor samples. However, it is not necessary that the human tumors grow in a human host. Particularly for studies in which long-term outcome data are of interest (especially prognostic or predictive studies), it can be particularly useful to analyze samples grown in vitro (e.g., cell lines) or, more preferably, in a non-human host (e.g., a rodent, a dog, a sheep, a pig, or other animal). For instance, Example 9 provides a description of an assay in which inventive techniques employing human tumor cells growing in a non-human host are employed to define and/or utilize a panel of interaction partners whose binding to tumor samples correlates with prognosis and/or responsiveness to therapy.

It will often be desirable, when identifying interaction partners whose binding correlates with prognosis, to collect information about treatment regimens that may have been applied to the tumor whose sample is being assessed, in order to control for effects attributable to tumor therapy. Prognostic panel binding may correlate with outcome independent of treatment (Hayes et al., *J. Mamm. Gland Bio. Neo.* 6:375, 2001). Many prognostic markers, however, have both prognostic and predictive character (e.g., Her2/Neu status). Many of the individual interaction partners that comprise a prognostic panel may likewise have predictive capability and/or be members of a predictive panel.

Those of ordinary skill in the art will appreciate that prognostic panels (or individual interaction partners) have greater clinical utility if their binding/lack thereof correlates with positive/negative outcomes that are well separated statistically.

The inventive strategies may also be applied to the identification of predictive panels of interaction partners (i.e., panels whose binding correlates with susceptibility to a particular therapy). As noted above, some prognostic panels may also have predictive capabilities.

Interaction partners to be included in predictive panels are identified in binding studies performed on tumor samples that do or do not respond to a particular therapy. As with the prognostic panels, predictive panels may be assembled based on tests of tumor samples whose responsiveness is already known, or on samples whose responsiveness is not known in advance. As with the prognostic studies discussed above, the source of the tumor samples is not essential and can include, for example, tumor cell lines whose responsiveness to particular chemical agents has been determined, tumor samples from animal models in which tumors have been artificially introduced and therapeutic responsiveness has been determined and/or samples from naturally-occurring (human or other animal) tumors for which outcome data (e.g., time of survival, responsiveness to therapy, etc.) are available. Panels of interaction partners whose binding to tumor samples correlates with any prognostic or therapeutic trend can be defined and utilized as described herein.

Once correlations between interaction partner binding and tumor behavior have been established, the defined prognostic or predictive panels can be used to evaluate and classify tumor samples from patients and can be relied upon, for example to guide selection of an effective therapeutic regimen. As with the tumor classification studies described above, the process of identifying interaction partner panels whose binding correlates with outcome may itself identify particular outcomes not previously appreciated as distinct.

Those of ordinary skill in the art will appreciate that it is likely that, in at least some instances, tumor class or subclass identity will itself correlate with prognosis or responsiveness. In such circumstances, it is possible that the same set of interaction partners can act as both a classification panel and a prognosis or predictive panel.

Tumor Elements Bound by Interaction Partners

The inventive strategies for identifying and utilizing interaction partner panels in classifying or analyzing tumor samples do not rely on any assumptions about the identity or characteristics of the tumor components bound by the interaction partners. So long as interaction partner binding within the relevant panel correlates with some feature of interest, the inventive teachings apply. In many if not most, cases, however, it is expected that binding will be with a protein expressed by tumor cells.

In some preferred embodiments of the invention, interaction partners bind to tumor markers that (a) are differentially expressed in tumor cells; (b) are members of protein families whose activities contribute to relevant biological events (e.g., gene families that have been implicated in cancer such as oncogenes, tumor suppressor genes, and genes that regulate apoptosis; gene families that have been implicated in drug resistance; etc.); (c) are present on or in the plasma membrane of the tumor cells; and/or (d) are the products of degradation of tumor components, which degradation products might be detectable in patient serum.

In fact, according to the present invention, interaction partners for analysis and use in inventive panels may sometimes be identified by first identifying a tumor-associated protein of interest, and then finding a potential interaction partner that binds with the protein. Binding by this potential interaction partner to tumor samples may then be assessed and utilized as described herein.

For example, as described in the Examples, the present inventors have successfully assembled classification panels comprised of antibodies that bind to tumor protein antigens. Candidate antigens were identified both through literature reviews of proteins that play a biological role in tumor initiation or progression, or that are known to be differentially expressed in tumors, and through gene expression studies that identified additional differentially expressed proteins.

Work by the present inventors, as well as by others, has already demonstrated that studies of gene expression patterns in large tumor cohorts can identify novel tumor classes (see, for example, Perou et al., *Nature* 406:747, 2000; Sorlie et al., *Proc Natl Acad. Sci. USA* 98:10869, 2001; van't Veer et al., *Nature* 415:530, 2002; West et al., *Proc Natl. Acad. Sci. USA* 98:11462, 2001; Hedenfalk et al., *N. Engl. J. Med.* 344:539, 2001; Gruvberger et al., *Cancer Res.* 61:5979, 2001; MacDonald et al., *Nature Genet.* 29:143, 2001; Pomeroy et al., *Nature* 415:436, 2002; Jazaeri et al., *J. Natl Cancer Inst* 94:990, 2002; Welsh et al., *Proc. Natl. Acad. Sci. USA* 98:1176, 2001; Wang et al., *Gene* 229:101, 1999; Beer et al., *Nature Med.* 8:816, 2002; Garber et al., *Proc Natl Acad Sci USA* 98:13784, 2001; Bhattacharjee et al., *Proc Natl Acad Sci USA* 98:13790, 2001; Zou et al., *Oncogene* 21:4855, 2002; Lin et al., *Oncogene* 21:4120, 2002; Alon et al., *Proc Natl Acad Sci USA* 96:6745, 1999; Takahashi et al., *Proc Natl Acad Sci USA* 98:9754, 2001; Singh et al., *Cancer Cell* 1:203, 2002; LaTulippe et al., *Cancer Res.* 62:4499, 2002; Welsh et al., *Cancer Res.* 61:5974, 2001; Dhanasekaran et al., *Nature* 412:822, 2001; Hippo et al., *Cancer Res.* 62:233, 2002; Yeoh et al., *Cancer Cell* 1:133, 2002; Hofmann et al., *Lancet* 359:481, 2002; Ferrando et al., *Cancer Cell* 1:75, 2002; Shipp et al., *Nature Med* 8:68, 2002; Rosenwald et al., *N. Engl. J. Med.* 346:1937, 2002; and Alizadeh et al., *Nature* 403:503, 2000, each of which is incorporated herein by reference).

The gene sets described in these publications are promising candidates for genes that are likely to encode tumor markers whose interaction partners are useful in tumor classification and subclassification according to the present invention. Of particular interest are gene sets differentially expressed in solid tumors.

Furthermore, in general, given that differentially expressed genes are likely to be responsible for the different phenotypic characteristics of tumors, the present invention recognizes that such genes will often encode tumor markers for which a useful interaction partner, that discriminates among tumor classes or subclasses, can likely be prepared. A differentially expressed gene is a gene whose transcript abundance varies between different samples, e.g., between different tumor samples, between normal versus tumor samples, etc. In general, the amount by which the expression varies and the number of samples in which the expression varies by that amount will depend upon the number of samples and the particular characteristics of the samples. One skilled in the art will be able to determine, based on knowledge of the samples, what constitutes a significant degree of differential expression. Such genes can be identified by any of a variety of techniques including, for instance, in situ hybridization, Northern blot, nucleic acid amplification techniques (e.g., PCR, quantitative PCR, the ligase chain reaction, etc.), and, most commonly, microarray analysis.

Furthermore, those of ordinary skill in the art will readily appreciate, reading the present disclosure, that the inventive processes described herein of identifying and/or using sets of interaction partners whose binding (or lack thereof) correlates with an interesting tumor feature (e.g., tumor type or subtype, patient outcome, responsiveness of tumor or patient to therapy, etc.) inherently identifies both interaction partners of interest and the tumor markers to which they bind. Thus, one important aspect of the present invention is the identification of tumor markers whose ability (or lack thereof) to associate with an interaction partner correlates with a tumor characteristic of interest. Such tumor markers are useful as targets for identification of new therapeutic reagents, as well as of additional interaction partners useful in the practice of the present invention. Thus, it is to be understood that discussions of interaction partners presented herein are typically not limited to a particular interaction partner compound or entity, but may be generalized to include any compound or entity that binds to the relevant tumor marker(s) with requisite specificity and affinity.

Preparation of Interaction Partners

In general, interaction partners are entities that physically associate with selected tumor markers. Thus, any entity that binds detectably to a tumor marker may be utilized as an interaction partner in accordance with the present invention, so long as it binds with an appropriate combination of affinity and specificity.

Particularly preferred interaction partners are antibodies, or fragments (e.g., F(ab) fragments, F(ab')$_2$ fragments, Fv fragments, or sFv fragments, etc.; see, for example, Inbar et al., *Proc. Nat. Acad. Sci. USA* 69:2659, 1972; Hochman et al., *Biochem.* 15:2706, 1976; and Ehrlich et al., *Biochem.* 19:4091, 1980; Huston et al., *Proc. Nat. Acad. Sci. USA* 85:5879, 1998; U.S. Pat. Nos. 5,091,513 and 5,132,405 to Huston et al.; and U.S. Pat. No. 4,946,778 to Ladner et al., each of which is incorporated herein by reference). In certain embodiments, interaction partners may be selected from libraries of mutant antibodies (or fragments thereof). For example, collections of antibodies that each include different point mutations may be screened for their association with a tumor marker of interest. Yet further, chimeric antibodies may be used as interaction partners, e.g., "humanized" or "veneered" antibodies as described in greater detail below.

It is to be understood that the present invention is not limited to using antibodies or antibody fragments as interaction partners of inventive tumor markers. In particular, the present invention also encompasses the use of synthetic interaction partners that mimic the functions of antibodies. Several approaches to designing and/or identifying antibody mimics have been proposed and demonstrated (e.g., see the reviews by Hsieh-Wilson et al., *Acc. Chem. Res.* 29:164, 2000 and Peczuh and Hamilton, *Chem. Rev.* 100:2479, 2000). For example, small molecules that bind protein surfaces in a fashion similar to that of natural proteins have been identified by screening synthetic libraries of small molecules or natural product isolates (e.g., see Gallop et al., *J. Med. Chem.* 37:1233, 1994; Gordon et al., *J. Med. Chem.* 37:1385, 1994; DeWitt et al., *Proc. Natl. Acad. Sci. U.S.A.* 90:6909, 1993; Bunin et al., *Proc. Natl. Acad. Sci. USA.* 91:4708, 1994; Virgilio and Ellman, *J. Am. Chem. Soc.* 116:11580, 1994; Wang et al., *J. Med. Chem.* 38:2995, 1995; and Kick and Ellman, *J. Med. Chem.* 38:1427, 1995). Similarly, combinatorial approaches have been successfully applied to screen libraries of peptides and polypeptides for their ability to bind a range of proteins (e.g., see Cull et al., *Proc. Natl. Acad. Sci. USA.* 89:1865, 1992; Mattheakis et al., *Proc. Natl. Acad. Sci. U.S.A.* 91:9022, 1994; Scott and Smith, *Science* 249:386, 1990; Devlin et al., *Science* 249:404, 1990; Corey et al., *Gene* 128:129, 1993; Bray et al., *Tetrahedron Lett.* 31:5811, 1990; Fodor et al., *Science* 251:767, 1991; Houghten et al., *Nature* 354:84, 1991; Lam et al., *Nature* 354:82, 1991; Blake and Litzi-Davis, *Bioconjugate Chem.* 3:510, 1992; Needels et al., *Proc. Natl. Acad. Sci. USA.* 90:10700, 1993; and Ohlmeyer et al., *Proc. Natl. Acad. Sci. U.S.A.* 90:10922, 1993). Similar approaches have also been used to study carbohydrate-protein interactions (e.g., see Oldenburg et al., *Proc. Natl. Acad. Sci. U.S.A.* 89:5393, 1992) and polynucleotide-protein interactions (e.g., see Ellington and Szostak, *Nature* 346:818, 1990 and Tuerk and Gold, *Science* 249:505, 1990). These approaches have also been extended to study interactions between proteins and unnatural biopolymers such as oligocarbamates, oligoureas, oligosulfones, etc. (e.g., see Zuckermann et al., *J. Am. Chem. Soc.* 114:10646, 1992; Simon et al., *Proc. Natl. Acad. Sci. USA.* 89:9367, 1992; Zuckermann et al., *J. Med. Chem.* 37:2678, 1994; Burgess et al., *Angew. Chem., Int. Ed. Engl.* 34:907, 1995; and Cho et al., *Science* 261:1303, 1993). Yet further, alternative protein scaffolds that are loosely based around the basic fold of antibody molecules have been suggested and may be used in the preparation of inventive interaction partners (e.g., see Ku and Schultz *Proc. Natl. Acad. Sci. USA.* 92:6552, 1995). Antibody mimics comprising a scaffold of a small molecule such as 3-aminomethylbenzoic acid and a substituent consisting of a single peptide loop have also been constructed. The peptide loop performs the binding function in these mimics (e.g., see Smythe et al., *J. Am. Chem. Soc.* 116:2725, 1994). A synthetic antibody mimic comprising multiple peptide loops built around a calixarene unit has also been described (e.g., see U.S. Pat. No. 5,770,380 to Hamilton et al.).

Detecting Association of Interaction Partners and Tumor Markers

Any available strategy or system may be utilized to detect association between an interaction partner and its cognate tumor marker. In certain embodiments, association can be detected by adding a detectable label to the interaction partner. In other embodiments, association can be detected by using a labeled secondary interaction partner that associates specifically with the primary interaction partner, e.g., as is well known in the art of antigen/antibody detection. The detectable label may be directly detectable or indirectly detectable, e.g., through combined action with one or more additional members of a signal producing system. Examples of directly detectable labels include radioactive, paramagnetic, fluorescent, light scattering, absorptive and colorimetric labels. Examples of indirectly detectable include chemiluminescent labels, e.g., enzymes that are capable of converting a substrate to a chromogenic product such as alkaline phosphatase, horseradish peroxidase and the like.

Once a labeled interaction partner has bound a tumor marker, the complex may be visualized or detected in a variety of ways, with the particular manner of detection being chosen based on the particular detectable label, where representative detection means include, e.g., scintillation counting, autoradiography, measurement of paramagnetism, fluorescence measurement, light absorption measurement, measurement of light scattering and the like.

In general, association between an interaction partner and its cognate tumor marker may be assayed by contacting the interaction partner with a tumor sample that includes the marker. Depending upon the nature of the sample, appropriate methods include, but are not limited to, immunohistochemistry (IHC), radioimmunoassay, ELISA, immunoblotting and fluorescence activates cell sorting (FACS). In the case where the polypeptide is to be detected in a tissue sample, e.g., a biopsy sample, IHC is a particularly appropriate detection method. Techniques for obtaining tissue and cell samples and performing IHC and FACS are well known in the art.

The inventive strategies for classifying and/or subclassifying tumor samples may be applied to samples of any type and of any tissue of origin. In certain preferred embodiments of the invention, the strategies are applied to solid tumors. Historically, researchers have encountered difficulty in defining solid tumor subtypes, given the challenges associated with defining their molecular characteristics. As demonstrated in the Examples, the present invention is particularly beneficial in this area. Particularly preferred solid tumors include, for example, breast, lung, colon, and ovarian tumors. The invention also encompasses the recognition that tumor markers that are secreted from the cells in which they are produced may be present in serum, enabling their detection through a blood test rather than requiring a biopsy specimen. An interaction partner that binds to such tumor markers represents a particularly preferred embodiment of the invention.

In general, the results of such an assay can be presented in any of a variety of formats. The results can be presented in a qualitative fashion. For example, the test report may indicate only whether or not a particular tumor marker was detected, perhaps also with an indication of the limits of detection. Additionally the test report may indicate the subcellular location of binding, e.g., nuclear versus cytoplasmic and/or the relative levels of binding in these different subcellular locations. The results may be presented in a semi-quantitative fashion. For example, various ranges may be defined and the ranges may be assigned a score (e.g., 0 to 5) that provides a certain degree of quantitative information. Such a score may reflect various factors, e.g., the number of cells in which the tumor marker is detected, the intensity of the signal (which may indicate the level of expression of the tumor marker), etc. The results may be presented in a quantitative fashion, e.g., as a percentage of cells in which the tumor marker is detected, as a concentration, etc. As will be appreciated by one of ordinary skill in the art, the type of output provided by a test will vary depending upon the technical limitations of the test and the biological significance associated with detection of the tumor marker. For example, in the case of certain tumor markers a purely qualitative output (e.g., whether or not the tumor marker is detected at a certain detection level) provides significant information. In other cases a more quantitative output (e.g., a ratio of the level of expression of the tumor marker in two samples) is necessary.

Identification of Novel Therapies

Predictive panels of interaction agents are useful according to the present invention not only to classify tumor samples obtained from cancer sufferers with respect to their likely responsiveness to known therapies, but also to identify potential new therapies or therapeutic agents that could be useful in the treatment of cancer.

For example, as noted above, the process of identifying or using inventive panels according to the present invention simultaneously identifies and/or characterizes tumor markers in or on the tumor cells that correlate with one or more selected tumor characteristics (e.g., tumor type or subtype, patient prognosis, and/or responsiveness of tumor or patient to therapy). Such tumor markers are attractive candidates for identification of new therapeutic agents (e.g., via screens to detect compounds or entities that bind to the tumor markers, preferably with at least a specified affinity and/or specificity, and/or via screens to detect compounds or entities that modulate (i.e., increase or decrease) expression, localization, modification, or activity of the tumor markers. In many instances, interaction partners themselves may prove to be useful therapeutics.

Thus the present invention provides interaction partners that are themselves useful therapeutic agents. For example, binding by an interaction partner, or a collection of interaction partners, to a cancer cell, might inhibit growth of that cell. Alternatively or additionally, interaction partners defined or prepared according to the present invention could be used to deliver a therapeutic agent to a cancer cell. In particular, interaction partners may be coupled to one or more therapeutic agents. Suitable agents in this regard include radionuclides and drugs. Preferred radionuclides include $^{90}$Y, $^{123}$I, $^{125}$I, $^{131}$I, $^{186}$Re, $^{188}$Re, $^{211}$At and $^{212}$Bi. Preferred drugs include chlorambucil, ifosphamide, meclorethamine, cyclophosphamide, carboplatin, cisplatin, procarbazine, decarbazine, carmustine, cytarabine, hydroxyurea, mercaptopurine, methotrexate, thioguanine, 5-fluorouracil, actinomycin D, bleomycin, daunorubicin, doxorubicin, etoposide, vinblastine, vincristine, L-asparginase, adrenocorticosteroids, canciclovir triphosphate, adenine arabinonucleoside triphosphate, 5-aziridinyl-4-hydroxylamino-2-nitrobenzamide, acrolein, phosphoramide mustard, 6-methylpurine, etoposide, methotrexate, benzoic acid mustard, cyanide and nitrogen mustard.

According to such embodiments, the therapeutic agent may be coupled with an interaction partner by direct or indirect covalent or non-covalent interactions. A direct interaction between a therapeutic agent and an interaction partner is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other. Indirect interactions might involve a linker group that is itself associated with both the therapeutic agent and the interaction partner. A linker group can function as a spacer to distance an interaction partner from an agent in order to avoid interference with association capabilities. A linker group can also serve to increase the chemical reactivity of a substituent on an agent or an interaction partner and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfydryl groups or oxidized carbohydrate residues. There are numerous references describing such methodology, e.g., U.S. Pat. No. 4,671,958, to Rodwell et al. It will further be appreciated that a therapeutic agent and an interaction partner may be coupled via non-covalent interactions, e.g., ligand/receptor type interactions. Any ligand/receptor pair with a sufficient stability and specificity to operate in the context of the invention may be employed to couple a therapeutic agent and an interaction partner. To give but an example, a therapeutic agent may be covalently linked with biotin and an interaction partner with avidin. The strong non-covalent binding of biotin to avidin would then allow for coupling of the therapeutic agent and the interaction partner. Typical ligand/receptor pairs include protein/co-factor and enzyme/substrate pairs. Besides the commonly used biotin/avidin pair, these include without limitation, biotin/streptavidin, digoxigenin/anti-digoxigenin, FK506/FK506-binding protein (FKBP), rapamycin/FKBP, cyclophilin/cyclosporin and glutathione/glutathione transferase pairs. Other suitable ligand/receptor pairs would be recognized by those skilled in the art, e.g., monoclonal antibodies paired with a epitope tag such as, without limitation, glutathione-5-transferase (GST), c-myc, FLAG® and maltose binding protein (MBP) and further those described in Kessler pp. 105-152 of *Advances in Mutagenesis* Ed. by Kessler, Springer-Verlag, 1990; *"Affinity Chromatography: Methods and Protocols (Methods in Molecular Biology)"* Ed. by Pascal Baillon, Humana Press, 2000; and *"Immobilized Affinity Ligand Techniques"* by Hermanson et al., Academic Press, 1992.

Where a therapeutic agent is more potent when free from the interaction partner, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710 to Spitler), by irradiation of a photolabile bond (e.g., U.S. Pat. No. 4,625,014 to Senter et al.), by hydrolysis of derivatized amino acid side chains (e.g., U.S. Pat. No. 4,638,045 to Kohn et al.), by serum complement-mediated hydrolysis (e.g., U.S. Pat. No. 4,671,958 to Rodwell et al.) and by acid-catalyzed hydrolysis (e.g., U.S. Pat. No. 4,569,789 to Blattler et al.).

In certain embodiments, it may be desirable to couple more than one therapeutic agent to an interaction partner. In one embodiment, multiple molecules of an agent are coupled to one interaction partner molecule. In another embodiment, more than one type of therapeutic agent may be coupled to one interaction partner molecule. Regardless of the particular embodiment, preparations with more than one agent may be prepared in a variety of ways. For example, more than one agent may be coupled directly to an interaction partner molecule, or linkers that provide multiple sites for attachment can be used.

Alternatively, a carrier can be used. A carrier may bear the agents in a variety of ways, including covalent bonding either directly or via a linker group. Suitable carriers include proteins such as albumins (e.g., U.S. Pat. No. 4,507,234 to Kato et al.), peptides, and polysaccharides such as aminodextran (e.g., U.S. Pat. No. 4,699,784 to Shih et al.). A carrier may also bear an agent by non-covalent bonding or by encapsulation, such as within a liposome vesicle (e.g., U.S. Pat. No. 4,429,008 to Martin et al. and U.S. Pat. No. 4,873,088 to Mayhew et al.). Carriers specific for radionuclide agents include radiohalogenated small molecules and chelating compounds. For example, U.S. Pat. No. 4,735,792 to Srivastava discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562 to Davison et al. discloses representative chelating compounds and their synthesis.

When interaction partners are themselves therapeutics, it will be understood that, in many cases, any interaction partner that binds with the same tumor marker may be so used.

In one preferred embodiment of the invention, the therapeutic agents (whether interaction partners or otherwise) are antibodies. As is well known in the art, when using an antibody or fragment thereof for therapeutic purposes it may prove advantageous to use a "humanized" or "veneered" version of an antibody of interest to reduce any potential immunogenic reaction. In general, "humanized" or "veneered" antibody molecules and fragments thereof minimize unwanted immunological responses toward antihuman antibody molecules which can limit the duration and effectiveness of therapeutic applications of those moieties in human recipients.

A number of "humanized" antibody molecules comprising an antigen binding portion derived from a non-human immunoglobulin have been described in the art, including chimeric antibodies having rodent variable regions and their associated complementarity-determining regions (CDRs) fused to human constant domains (e.g., see Winter et al., *Nature* 349: 293, 1991; Lobuglio et al., *Proc. Nat. Acad. Sci. USA* 86:4220, 1989; Shaw et al., *J. Immunol.* 138:4534, 1987; and Brown et al., *Cancer Res.* 47:3577, 1987), rodent CDRs grafted into a human supporting framework region (FR) prior to fusion with an appropriate human antibody constant domain (e.g., see Riechmann et al., *Nature* 332:323, 1988; Verhoeyen et al., *Science* 239:1534, 1988; and Jones et al. *Nature* 321:522, 1986) and rodent CDRs supported by recombinantly veneered rodent FRs (e.g., see European Patent Publication No. 519,596, published Dec. 23, 1992). It is to be understood that the invention also encompasses "fully human" antibodies produced using the XenoMouse™ technology (AbGenix Corp., Fremont, Calif.) according to the techniques described in U.S. Pat. No. 6,075,181.

Yet further, so-called "veneered" antibodies may be used that include "veneered FRs". The process of veneering involves selectively replacing FR residues from, e.g., a murine heavy or light chain variable region, with human FR residues in order to provide a xenogeneic molecule comprising an antigen binding portion which retains substantially all of the native FR polypeptide folding structure. Veneering techniques are based on the understanding that the antigen binding characteristics of an antigen binding portion are determined primarily by the structure and relative disposition of the heavy and light chain CDR sets within the antigen-association surface (e.g., see Davies et al., *Ann. Rev. Biochem.* 59:439, 1990). Thus, antigen association specificity can be preserved in a humanized antibody only wherein the CDR structures, their interaction with each other and their interaction with the rest of the variable region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

Preferably, interaction partners suitable for use as therapeutics (or therapeutic agent carriers) exhibit high specificity for the target tumor marker and low background binding to other tumor markers. In certain embodiments, monoclonal antibodies are preferred for therapeutic purposes.

Tumor markers that are expressed on the cell surface represent preferred targets for the development of therapeutic agents, particularly therapeutic antibodies. For example, cell surface proteins can be tentatively identified using sequence analysis based on the presence of a predicted transmembrane domain. Their presence on the cell surface can ultimately be confirmed using IHC.

Kits

Useful sets or panels of interaction partners according to the present invention may be prepared and packaged together in kits for use in classifying, diagnosing, or otherwise characterizing tumor samples, or for inhibiting tumor cell growth or otherwise treating cancer.

Any available technique may be utilized in the preparation of individual interaction partners for inclusion in kits. For example, protein or polypeptide interaction partners may be produced by cells (e.g., recombinantly or otherwise), may be chemically synthesized, or may be otherwise generated in vitro (e.g., via in vitro transcription and/or translation). Non-protein or polypeptide interaction partners (e.g., small molecules, etc.) may be synthesized, may be isolated from within or around cells that produce them, or may be otherwise generated.

When antibodies are used as interaction partners, these may be prepared by any of a variety of techniques known to those of ordinary skill in the art (e.g., see Harlow and Lane, *Antibodies: A Laboratory Manual*, Cold Spring Harbor Laboratory, 1988). For example, antibodies can be produced by cell culture techniques, including the generation of monoclonal antibodies, or via transfection of antibody genes into suitable bacterial or mammalian cell hosts, in order to allow for the production of recombinant antibodies. In one technique, an "immunogen" comprising an antigenic portion of a tumor marker of interest (or the tumor marker itself) is initially injected into any of a wide variety of mammals (e.g., mice, rats, rabbits, sheep or goats). In this step, a tumor marker (or an antigenic portion thereof) may serve as the immunogen without modification. Alternatively, particularly for relatively short tumor markers, a superior immune response may be elicited if the tumor marker is joined to a carrier protein, such as bovine serum albumin or keyhole limpet hemocyanin (KLH). The immunogen is injected into the animal host, preferably according to a predetermined schedule incorporating one or more booster immunizations and the animals are bled periodically. Polyclonal antibodies specific for the tumor marker may then be purified from such antisera by, for example, affinity chromatography using the tumor marker (or an antigenic portion thereof) coupled to a suitable solid support. An exemplary method is described in Example 7.

If desired for diagnostic or therapeutic kits, monoclonal antibodies specific for a tumor marker of interest may be prepared, for example, using the technique of Kohler and Milstein, *Eur. J. Immunol.* 6:511, 1976 and improvements thereto. Briefly, these methods involve the preparation of immortal cell lines capable of producing antibodies having the desired specificity (i.e., reactivity with the tumor marker of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the tumor marker. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation and extraction. The tumor marker of interest may be used in the purification process in, for example, an affinity chromatography step.

In addition to inventive interaction partners, preferred kits for use in accordance with the present invention may include, a reference sample, instructions for processing samples, performing the test, instructions for interpreting the results, buffers and/or other reagents necessary for performing the test. In certain embodiments the kit can comprise a panel of antibodies.

Pharmaceutical Compositions

As mentioned above, the present invention provides new therapies and methods for identifying these. In certain embodiments, an interaction partner may be a useful therapeutic agent. Alternatively or additionally, interaction partners defined or prepared according to the present invention bind to tumor markers that serve as targets for therapeutic agents. Also, inventive interaction partners may be used to deliver a therapeutic agent to a cancer cell. For example, interaction partners provided in accordance with the present invention may be coupled to one or more therapeutic agents.

In addition, as mentioned above, to the extent that a particular predictive panel correlates with responsiveness to a particular therapy because it detects changes that reflect inhibition (or inhibitability) of cancer cell growth, that panel could be used to evaluate therapeutic candidates (e.g., small molecule drugs) for their ability to induce the same or similar changes in different cells. In particular, binding by the panel could be assessed on cancer cells before and after exposure to candidate therapeutics; those candidates that induce expression of the tumor markers to which the panel binds are then identified.

The invention includes pharmaceutical compositions comprising these inventive therapeutic agents. In general, a pharmaceutical composition will include a therapeutic agent in addition to one or more inactive agents such as a sterile, biocompatible carrier including, but not limited to, sterile water, saline, buffered saline, or dextrose solution. The pharmaceutical compositions may be administered either alone or in combination with other therapeutic agents including other chemotherapeutic agents, hormones, vaccines and/or radiation therapy. By "in combination with", it is not intended to imply that the agents must be administered at the same time or formulated for delivery together, although these methods of delivery are within the scope of the invention. In general, each agent will be administered at a dose and on a time schedule determined for that agent. Additionally, the invention encompasses the delivery of the inventive pharmaceutical compositions in combination with agents that may improve their bioavailability, reduce or modify their metabolism, inhibit their excretion, or modify their distribution within the body.

The invention encompasses treating cancer by administering the pharmaceutical compositions of the invention. Although the pharmaceutical compositions of the present invention can be used for treatment of any subject (e.g., any animal) in need thereof, they are most preferably used in the treatment of humans.

The pharmaceutical compositions of this invention can be administered to humans and other animals by a variety of routes including oral, intravenous, intramuscular, intra-arterial, subcutaneous, intraventricular, transdermal, rectal, intravaginal, intraperitoneal, topical (as by powders, ointments, or drops), bucal, or as an oral or nasal spray or aerosol. In general the most appropriate route of administration will depend upon a variety of factors including the nature of the agent (e.g., its stability in the environment of the gastrointestinal tract), the condition of the patient (e.g., whether the patient is able to tolerate oral administration), etc. At present the intravenous route is most commonly used to deliver therapeutic antibodies. However, the invention encompasses the delivery of the inventive pharmaceutical composition by any appropriate route taking into consideration likely advances in the sciences of drug delivery.

General considerations in the formulation and manufacture of pharmaceutical agents may be found, for example, in *Remington's Pharmaceutical Sciences*, $19^{th}$ ed., Mack Publishing Co., Easton, Pa., 1995.

According to the methods of treatment of the present invention, cancer is treated or prevented in a patient such as a human or other mammal by administering to the patient a therapeutically effective amount of a therapeutic agent of the invention, in such amounts and for such time as is necessary to achieve the desired result. By a "therapeutically effective amount" of a therapeutic agent of the invention is meant a sufficient amount of the therapeutic agent to treat (e.g., to ameliorate the symptoms of, delay progression of, prevent recurrence of, cure, etc.) cancer at a reasonable benefit/risk ratio, which involves a balancing of the efficacy and toxicity of the therapeutic agent. In general, therapeutic efficacy and toxicity may be determined by standard pharmacological procedures in cell cultures or with experimental animals, e.g., by calculating the $ED_{50}$ (the dose that is therapeutically effective in 50% of the treated subjects) and the $LD_{50}$ (the dose that is lethal to 50% of treated subjects). The $ED_{50}/LD_{50}$ represents the therapeutic index of the agent. Although in general therapeutic agents having a large therapeutic index are preferred, as is well known in the art, a smaller therapeutic index may be acceptable in the case of a serious disease, particularly in the absence of alternative therapeutic options. Ultimate selection of an appropriate range of doses for administration to humans is determined in the course of clinical trials.

It will be understood that the total daily usage of the therapeutic agents and compositions of the present invention for any given patient will be decided by the attending physician within the scope of sound medical judgment. The specific therapeutically effective dose level for any particular patient will depend upon a variety of factors including the disorder being treated and the severity of the disorder; the activity of the specific therapeutic agent employed; the specific composition employed; the age, body weight, general health, sex and diet of the patient; the time of administration, route of administration and rate of excretion of the specific therapeutic agent employed; the duration of the treatment; drugs used in combination or coincidental with the specific therapeutic agent employed; and like factors well known in the medical arts.

The total daily dose of the therapeutic agents of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 0.1 µg to about 2000 mg of the therapeutic agent(s) of the invention per day in single or multiple doses.

EXEMPLIFICATION

Example 1

Selection of Candidate Genes and Identification of Potential Interaction Partners for Tumor Classification Panels The present inventors identified a collection of candidate genes that (a) were differentially expressed across a set of tumor samples in a manner that suggested they distinguish biologically distinct classes of tumors; (b) were members of a gene functional class that has been linked to cellular pathways implicated in tumor prognosis or drug resistance; (c) were known or thought to display an expression, localization, modification, or activity pattern that correlates with a relevant tumor feature; etc.

For example, differentially expressed genes were identified using microarrays as described in co-pending U.S. patent application Ser. No. 09/916,722, filed Jul. 26, 2001 entitled "REAGENTS AND METHODS FOR USE IN MANAGING BREAST CANCER", the entire contents of which are incorporated herein by reference. Other genes were typically selected on the basis of published data suggesting their possible implication in drug resistance, cancer prognosis, etc. A total of 730 candidate genes were identified as encoding proteins against which antibodies should be raised.

Rabbit polyclonal affinity-purified antibodies were then raised against 661 of these proteins as described in Example 7. Each antibody was initially tested over a range of dilutions on tissue arrays that included a set of normal tissues, tumor tissues and cell lines, so that, for each antibody, a discriminating titer was established at which differential staining across the diverse set was observed. The preparation and staining of tissue arrays is described in greater detail in Example 8. Of the 661 antibodies subjected to this analysis, 460 showed differential staining and were considered of sufficient interest for further analysis.

Example 2

Breast Cancer Classification Panel (Russian Breast Cohort)

The present inventors prepared an exemplary panel of antibodies for use in classifying breast tumors. 272 of the 460 differentially staining antibodies of Example 1 exhibited a reproducibly robust staining pattern on tissues relevant for this application. These antibodies were therefore applied (at appropriate titers) to a tissue array comprised of approximately 400 independent breast tumor samples from a cohort of breast cancer patients (the Russian breast cohort). Stained tissue samples were scored by a trained cytotechnologist or pathologist on a semi-quantitative scale in which 0=no stain on tumor cells; 1=no information; 2=weak staining of tumor cells; and 3=strong staining of tumor cells. Antibodies were included in a breast cancer classification panel if they stained greater than 10% and less than 90% of a defined "consensus panel" of the breast tumor tissue samples on at least two independent tissue arrays.

A given tissue sample was included in this "consensus panel" if at least 80% of the antibodies tested gave interpretable scores (i.e., a non-zero score) with that sample. Of the 400 breast tumor samples in the tissue array about 320 were included in the consensus panel. Also, in scoring antibody binding to the consensus panel, all scores represented a consensus score of replicate tissue arrays comprised of independent samples from the same sources. The consensus score was determined by computing the median (rounded down to an integer, where applicable) of all scores associated with a given antibody applied under identical conditions to the particular patient sample. In cases where the variance of the scores was greater than 2, the score was changed to 1 (i.e., no information). The data for each antibody was stored in an Oracle-based database that contained the semi-quantitative scores of tumor tissue staining and also contained links to both patient clinical information and stored images of the stained patient samples.

Through this analysis 90 of the 272 tested antibodies were selected for inclusion in an exemplary breast cancer classification panel (see Appendix A, e.g., S0021, S0022, S0039, etc.). It is to be understood that any sub-combination of these 90 antibodies may be used in constructing an inventive breast cancer classification panel. It will also be appreciated that additional antibodies may be added to or removed from an inventive breast cancer classification panel as more tumor markers are identified and/or more samples are tested (e.g., see Example 3).

Figure 1:
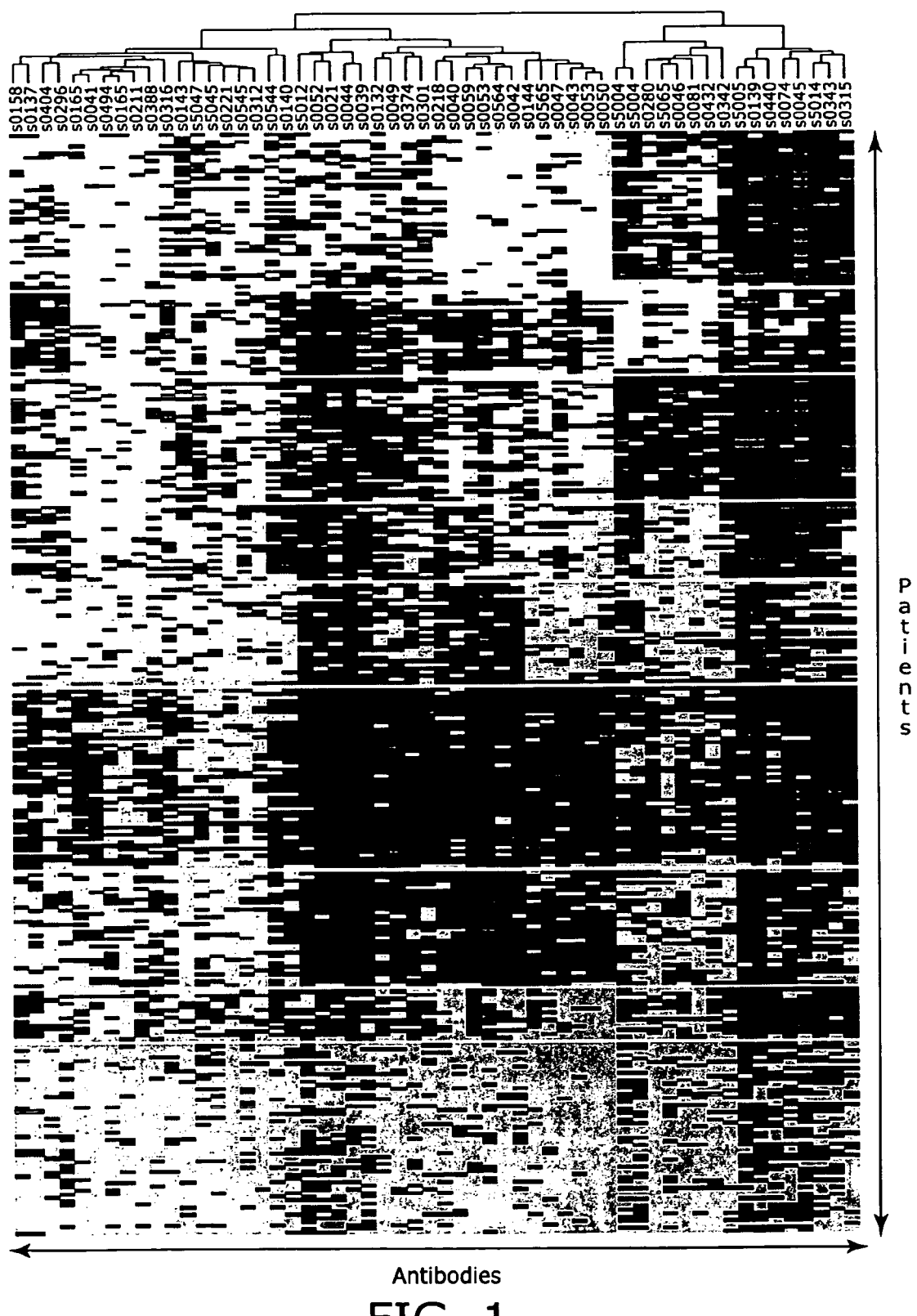
FIG. 1 depicts semi-quantitative immunohistochemistry (IHC) scoring of a 298 breast cancer patient cohort with an inventive breast cancer classification panel. The panel was prepared as described in Example 2—antibodies were used as interaction partners. The patients (rows) were classified using k-means clustering while the antibodies (columns) were organized using hierarchical clustering. Dark gray represents strong positive staining, black represents weak positive staining, while light gray represents the absence of staining and medium gray represents a lack of data. As illustrated in the Figure, nine groups of patients were identified by their consensus pattern of staining with the panel of antibodies.

FIG. 1 shows the pattern of reactivity observed with certain members of this panel of antibodies across samples from the Russian breast cohort. Dark gray represents strong positive staining, black represents weak positive staining, while light gray represents the absence of staining and medium gray represents a lack of data. Images of stained samples can be found in Appendix B (see right hand column of Appendix A for cross-references to corresponding antibodies).

The patients (rows) were classified using k-means clustering (as described, for example, in MacQueen in *Proceedings of the Fifth Berkeley Symposium on Mathematical Statistics and Probability* (Le Cam et al., Eds.; University of California Press, Berkeley, Calif.) 1:281, 1967; Heyer et al., *Genome Res.* 9:1106, 1999, each of which is incorporated herein by reference) while the antibodies (columns) were organized using hierarchical clustering (as described in, for example, Sokal et al., *Principles of Numerical Tazonomy* (Freeman & Co., San Francisco, Calif.), 1963; Eisen et al., *Proc. Natl. Acad. Sci. USA* 95:14863, 1998, each of which is incorporated herein by reference). As shown in FIG. 1, nine subclasses of breast cancer patients were identified by their consensus pattern of staining with this breast cancer classification panel.

Example 3

Breast Cancer Classification Panel (HH Breast Cohort)

In order to refine and expand the breast cancer classification panel of Example 2, the present inventors tested 109 of the 460 differentially staining antibodies of Example 1 on samples from a new cohort of 550 breast cancer patients (the Huntsville Hospital breast cohort or "HH breast" cohort, the characteristics of which are described in Example 10).

Antibodies were included in an updated breast cancer classification panel if they stained more than 10% and less than 90% of the particular consensus panel of tissue samples tested. Through this analysis 87 of the 109 tested antibodies were selected (see Appendix A, e.g., S0011, S0018, S0020, etc.).

Example 4

Lung Cancer Classification Panel (Russian Lung Cohort)

The present inventors also prepared an exemplary panel of antibodies for use in classifying lung tumors. 417 of the 460 differentially staining antibodies of Example 1 exhibited a reproducibly robust staining pattern on tissues relevant for this application. These antibodies were therefore applied (at the titers determined in Example 1) to a tissue array comprised of approximately 400 independent lung tumor tissues from a cohort of lung cancer patients (the Russian lung cohort). Stained tissue samples were scored by a trained cytotechnologist or pathologist as before and again antibodies were included in the classification panel if they stained greater than 10% and less than 90% of a defined "consensus panel" of tissue samples on at least two independent tissue arrays.

Through this analysis an exemplary lung cancer classification panel was generated that was made up of 106 of the 417 tested antibodies (see Appendix A, e.g., s0021, s0022, s0024, etc.). It is to be understood that any sub-combination of these 106 antibodies may be used in constructing an inventive lung cancer classification panel. It will also be appreciated that additional antibodies may be added to or removed from an inventive lung cancer classification panel as more tumor markers are identified and/or more samples are tested (e.g., see Example 5).

Figure 2:
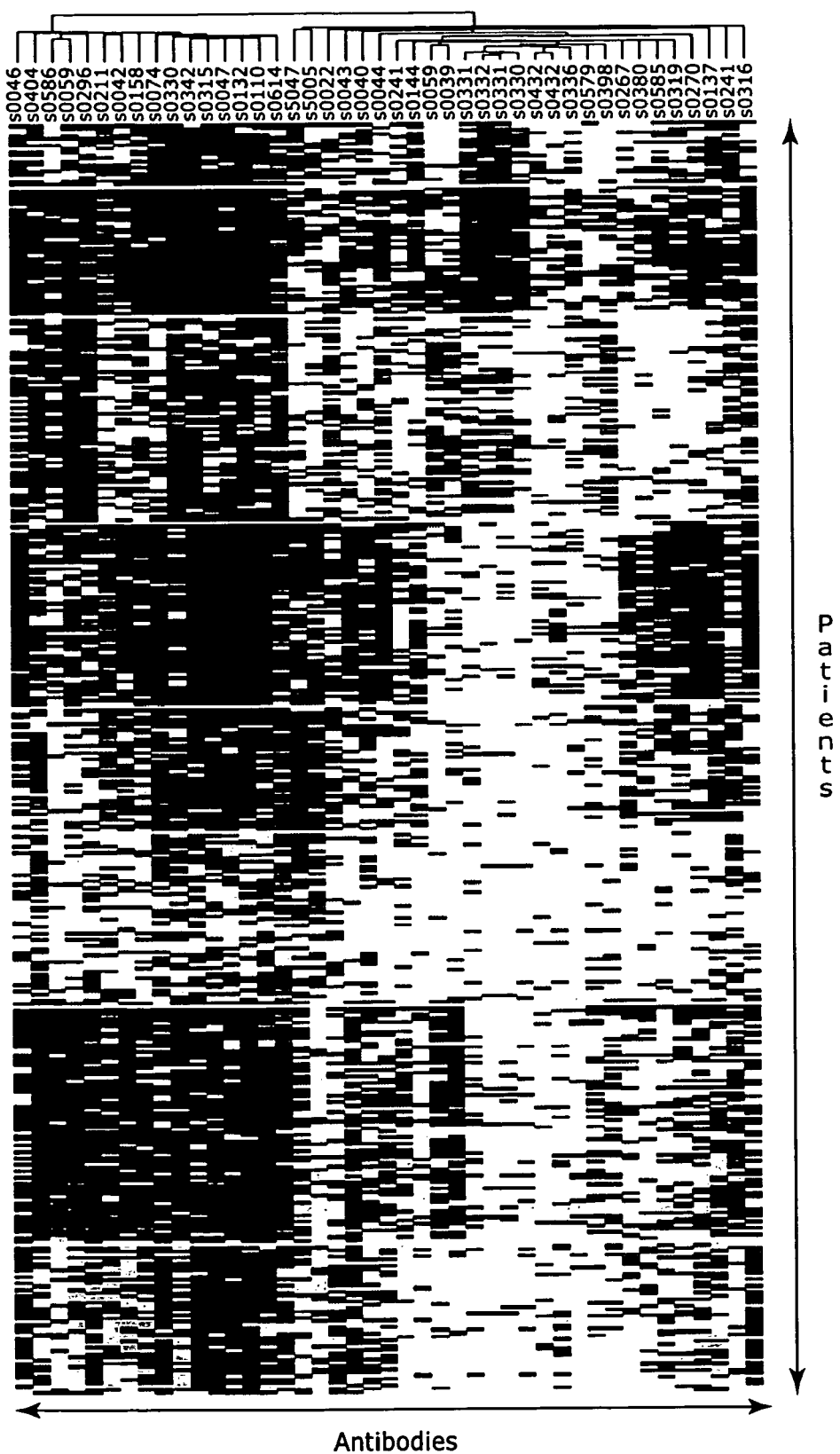
FIG. 2 depicts semi-quantitative immunohistochemistry (IHC) scoring of a 387 lung cancer patient cohort with an inventive lung cancer classification panel. The panel was prepared as described in Example 4—antibodies were used as interaction partners. The patients (rows) were classified using k-means clustering while the antibodies (columns) were organized using hierarchical clustering. Dark gray represents strong positive staining, black represents weak positive staining, while light gray represents the absence of staining and medium gray represents a lack of data. As illustrated in the Figure, eight groups of patients were identified by their consensus pattern of staining with the panel of antibodies.

FIG. 2 shows the pattern of reactivity observed with certain members of this panel of antibodies across samples from the Russian lung cohort. Dark gray represents strong positive staining, black represents weak positive staining, while light gray represents the absence of staining and medium gray represents a lack of data. Images of stained samples can be found in Appendix B (see right hand column of Appendix A for cross-references to corresponding antibodies).

The patients (rows) were again classified using k-means clustering while the antibodies (columns) were organized using hierarchical clustering. As shown in FIG. 2, eight subclasses of lung cancer patients were identified by their consensus pattern of staining with this lung cancer classification panel.

Example 5

Lung Cancer Classification Panel (HH Lung Cohort)

In order to refine and expand the lung cancer classification panel of Example 4, the present inventors tested 54 of the 460 differentially staining antibodies of Example 1 on samples from a new cohort of 379 lung cancer patients (the Huntsville Hospital lung cohort or "HH lung" cohort, the characteristics of which are described in Example 11).

Antibodies were included in an updated colon cancer classification panel if they stained more than 10% and less than 90% of the particular consensus panel of tissue samples tested. Through this analysis 39 of the 54 tested antibodies were selected (see Appendix A, e.g., S0021, S0022, S0046, etc.).

Example 6

Colon Cancer Classification Panel (Russian Colon Cohort)

The present inventors also prepared an exemplary panel of antibodies for use in classifying colon tumors. 382 of the 460 differentially staining antibodies of Example 1 exhibited a reproducibly robust staining pattern on tissues relevant for this application. These antibodies were therefore applied (at the titers determined in Example 1) to a tissue array comprised of approximately 400 independent colon tumor tissues from a cohort of colon cancer patients (the Russian colon cohort). Stained tissue samples were scored by a trained cytotechnologist or pathologist as before and again antibodies were included in the classification panel if they stained greater than 10% and less than 90% of a defined "consensus panel" of tissue samples on at least two independent tissue arrays.

Through this analysis a colon antibody classification panel was generated that was made up of 86 of the 382 tested antibodies (see Appendix A, e.g., S0022, S0036, S0039, etc.). It will be appreciated that any sub-combination of these 86 antibodies may be used in constructing an inventive colon cancer classification panel. It will also be appreciated that additional antibodies may be added to or removed from an inventive colon cancer classification panel as more tumor markers are identified and/or more samples are tested.

Figure 3:
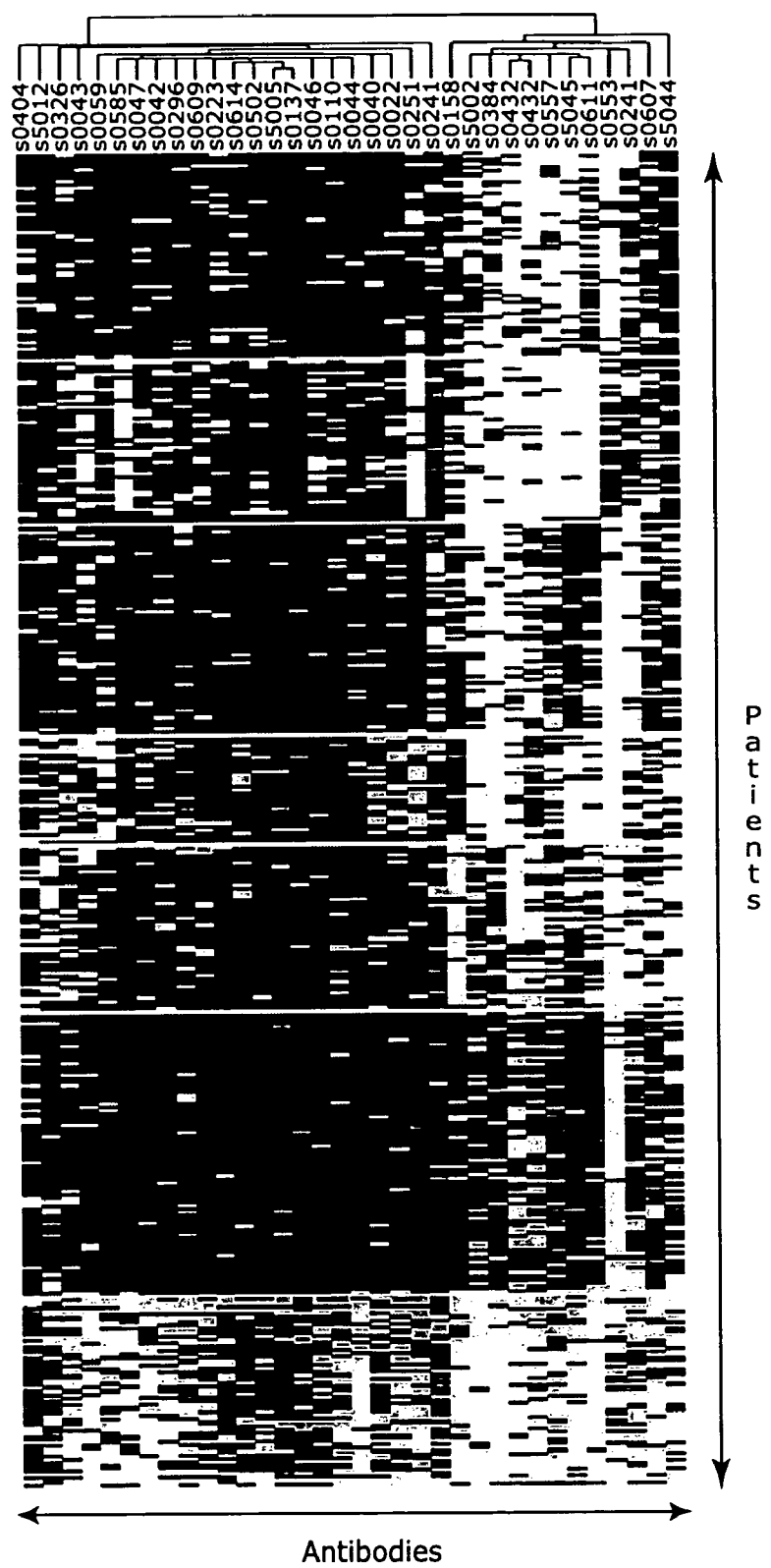
FIG. 3 depicts semi-quantitative immunohistochemistry (IHC) scoring of a 359 colon cancer patient cohort with an inventive colon cancer classification panel. The panel was prepared as described in Example 6—antibodies were used as interaction partners. The patients (rows) were classified using k-means clustering while the antibodies (columns) were organized using hierarchical clustering. Dark gray represents strong positive staining, black represents weak positive staining, while light gray represents the absence of staining and medium gray represents a lack of data. As illustrated in the Figure, seven groups of patients were identified by their consensus pattern of staining with the panel of antibodies.

FIG. 3 shows the pattern of reactivity observed with certain members of this panel of antibodies across samples from the Russian colon cohort. Dark gray represents strong positive staining, black represents weak positive staining, while light gray represents the absence of staining and medium gray represents a lack of data. Images of the stained samples can be found in Appendix B (see right hand column of Appendix A for cross-references to corresponding antibodies).

The patients (rows) were again classified using k-means clustering while the antibodies (columns) were organized using hierarchical clustering. As shown in FIG. 3, seven subclasses of patients were identified by their consensus pattern of staining with this exemplary colon cancer classification panel.

Example 7

Raising Antibodies

This example describes a method that was employed to generate the majority of the antibodies that were used in Examples 1-6. Similar methods may be used to generate an antibody that binds to any polypeptide of interest (e.g., to polypeptides that are or are derived from other tumor markers). In some cases, antibodies may be obtained from commercial sources (e.g., Chemicon, Dako, Oncogene Research Products, NeoMarkers, etc.) or other publicly available sources (e.g., Imperial Cancer Research Technology, etc.).

Materials and Solutions

Anisole (Cat. No. A4405, Sigma, St. Louis, Mo.)
2,2'-azino-di-(3-ethyl-benzthiazoline-sulfonic acid) (ABTS) (Cat. No. A6499, Molecular Probes, Eugene, Oreg.)
Activated maleimide Keyhole Limpet Hemocyanin (Cat. No. 77106, Pierce, Rockford, Ill.)
Keyhole Limpet Hemocyanin (Cat. No. 77600, Pierce, Rockford, Ill.)
Phosphoric Acid ($H_3PO_4$) (Cat. No. P6560, Sigma)
Glacial Acetic Acid (Cat No. BP1185-500, Fisher)
EDC (EDAC) (Cat No. 341006, Calbiochem)
25% Glutaraldehyde (Cat No. G-5882, Sigma)
Glycine (Cat No. G-8898, Sigma)
Biotin (Cat. No. B2643, Sigma)
Boric acid (Cat. No. B0252, Sigma)
Sepharose 4B (Cat. No. 17-0120-01, LKB/Pharmacia, Uppsala, Sweden)
Bovine Serum Albumin (LP) (Cat. No. 100 350, Boehringer Mannheim, Indianapolis, Ind.)
Cyanogen bromide (Cat. No. C6388, Sigma)
Dialysis tubing Spectra/Por Membrane MWCO: 6-8,000 (Cat. No. 132 665, Spectrum Industries, Laguna Hills, Calif.)
Dimethyl formamide (DMF) (Cat. No. 22705-6, Aldrich, Milwaukee, Wis.)
DIC (Cat. No. BP 592-500, Fisher)
Ethanedithiol (Cat. No. 39,802-0, Aldrich)
Ether (Cat. No. TX 1275-3, EM Sciences)
Ethylenediaminetetraacetatic acid (EDTA) (Cat. No. BP 120-1, Fisher, Springfield, N.J.)
1-ethyl-3-(3'dimethylaminopropyl)-carbodiimide, HCL (EDC) (Cat. no. 341-006, Calbiochem, San Diego, Calif.)
Freund's Adjuvant, complete (Cat. No. M-0638-50B, Lee Laboratories, Grayson, Ga.)
Freund's Adjuvant, incomplete (Cat. No. M-0639-50B, Lee Laboratories)
Fritted chromatography columns (Column part No. 12131011; Frit Part No. 12131029, Varian Sample Preparation Products, Harbor City, Calif.)
Gelatin from Bovine Skin (Cat. No. G9382, Sigma)
Goat anti-rabbit IgG, biotinylated (Cat. No. A 0418, Sigma)
HOBt (Cat. No. 01-62-0008, Calbiochem)
Horseradish peroxidase (HRP) (Cat. No. 814 393, Boehringer Mannheim)
HRP-Streptavidin (Cat. No. S 5512, Sigma)
Hydrochloric Acid (Cat. No. 71445-500, Fisher)
Hydrogen Peroxide 30% w/w (Cat. No. H1009, Sigma)
Methanol (Cat. No. A412-20, Fisher)
Microtiter plates, 96 well (Cat. No. 2595, Corning-Costar, Pleasanton, Calif.)
N-α-Fmoc protected amino acids from Calbiochem. See '97-'98 Catalog pp. 1-45.
N-α-Fmoc protected amino acids attached to Wang Resin from Calbiochem. See '97-'98 Catalog pp. 161-164.
NMP (Cat. No. CAS 872-50-4, Burdick and Jackson, Muskegon, Mich.)
Peptide (Synthesized by Research Genetics. Details given below)
Piperidine (Cat. No. 80640, Fluka, available through Sigma)
Sodium Bicarbonate (Cat. No. BP328-1, Fisher)
Sodium Borate (Cat. No. B9876, Sigma)
Sodium Carbonate (Cat. No. BP357-1, Fisher)
Sodium Chloride (Cat. No. BP 358-10, Fisher)
Sodium Hydroxide (Cat. No. SS 255-1, Fisher)
Streptavidin (Cat. No. 1 520, Boehringer Mannheim)
Thioanisole (Cat. No. T-2765, Sigma)
Trifluoroacetic acid (Cat. No. TX 1275-3, EM Sciences)
Tween-20 (Cat. No. BP 337-500, Fisher).
Wetbox (Rectangular Servin' Saver™ Part No. 3862, Rubbermaid, Wooster, Ohio)
BBS—Borate Buffered Saline with EDTA dissolved in distilled water (pH 8.2 to 8.4 with HCl or NaOH), 25 mM Sodium borate (Borax), 100 mM Boric Acid, 75 mM NaCl and 5 mM EDTA.

0.1 N HCl in saline as follows: concentrated HCl (8.3 ml/0.917 liter distilled water) and 0.154 M NaCl Glycine (pH 2.0 and pH 3.0) dissolved in distilled water and adjusted to the desired pH, 0.1 M glycine and 0.154 M NaCl.

5× Borate 1× Sodium Chloride dissolved in distilled water, 0.11 M NaCl, 60 mM Sodium Borate and 250 mM Boric Acid.

Substrate Buffer in distilled water adjusted to pH 4.0 with sodium hydroxide, 50 to 100 mM Citric Acid.

AA solution: HOBt is dissolved in NMP (8.8 grams HOBt to 1 liter NMP). Fmoc-N-a-amino at a concentration at 0.53 M.

DIC solution: 1 part DIC to 3 parts NMP.

Deprotecting solution: 1 part Piperidine to 3 parts DMF.

Reagent R: 2 parts anisole, 3 parts ethanedithiol, 5 parts thioanisole and 90 parts trifluoroacetic acid.

Equipment

MRX Plate Reader (Dynatech, Chantilly, Va.)

Hamilton Eclipse (Hamilton Instruments, Reno, Nev.)

Beckman TJ-6 Centrifuge (Model No. TJ-6, Beckman Instruments, Fullerton, Calif.)

Chart Recorder (Recorder 1 Part No. 18-1001-40, Pharmacia LKB Biotechnology)

UV Monitor (Uvicord SII Part No. 18-1004-50, Pharmacia LKB Biotechnology)

Amicon Stirred Cell Concentrator (Model 8400, Amicon, Beverly, Mass.)

30 kD MW cut-off filter (Cat. No. YM-30 Membranes Cat. No. 13742, Amicon)

Multi-channel Automated Pipettor (Cat. No. 4880, Corning Costar, Cambridge, Mass.)

pH Meter Corning 240 (Corning Science Products, Corning Glassworks, Corning, N.Y.)

ACT396 peptide synthesizer (Advanced ChemTech, Louisville, Ky.)

Vacuum dryer (Box from Labconco, Kansas City, Mo. and Pump from Alcatel, Laurel, Md.).

Lyophilizer (Unitop 600sl in tandem with Freezemobile 12, both from Virtis, Gardiner, N.Y.)

Peptide Selection

Peptides against which antibodies would be raised were selected from within the polypeptide sequence of interest using a program that uses the Hopp/Woods method (described in Hopp and Woods, *Mol. Immunol.* 20:483, 1983 and Hopp and Woods, *Proc. Nat. Acad. Sci. U.S.A.* 78:3824, 1981). The program uses a scanning window that identifies peptide sequences of 15-20 amino acids containing several putative antigenic epitopes as predicted by low solvent accessibility. This is in contrast to most implementations of the Hopp/Woods method, which identify single short (~6 amino acids) presumptive antigenic epitopes. Occasionally the predicted solvent accessibility was further assessed by PHD prediction of loop structures (described in Rost and Sander, *Proteins* 20:216, 1994). Preferred peptide sequences display minimal similarity with additional known human proteins. Similarity was determined by performing BLASTP alignments, using a wordsize of 2 (described in Altschul et al., *J. Mol. Biol.* 215:403, 1990). All alignments given an EXPECT value less than 1000 were examined and alignments with similarities of greater than 60% or more than four residues in an exact contiguous non-gapped alignment forced those peptides to be rejected. When it was desired to target regions of proteins exposed outside the cell membrane, extracellular regions of the protein of interest were determined from the literature or as defined by predicted transmembrane domains using a hidden Markov model (described in Krogh et al., *J. Mol. Biol.* 305:567, 2001). When the peptide sequence was in an extracellular domain, peptides were rejected if they contained N-linked glycosylation sites. As shown in Appendix A, one to three peptide sequences were selected for each polypeptide using this procedure.

Peptide Synthesis

The sequence of the desired peptide was provided to the peptide synthesizer. The C-terminal residue was determined and the appropriate Wang Resin was attached to the reaction vessel. The peptides were synthesized C-terminus to N-terminus by adding one amino acid at a time using a synthesis cycle. Which amino acid is added was controlled by the peptide synthesizer, which looks to the sequence of the peptide that was entered into its database. The synthesis steps were performed as follows:

Step 1—Resin Swelling: Added 2 ml DMF, incubated 30 minutes, drained DMF.

Step 2—Synthesis cycle (repeated over the length of the peptide)

2a—Deprotection: 1 ml deprotecting solution was added to the reaction vessel and incubated for 20 minutes.

2b—Wash Cycle

2c—Coupling: 750 ml of amino acid solution (changed as the sequence listed in the peptide synthesizer dictated) and 250 ml of DIC solution were added to the reaction vessel. The reaction vessel was incubated for thirty minutes and washed once. The coupling step was repeated once.

2d—Wash Cycle

Step 3—Final Deprotection: Steps 2a and 2b were performed one last time.

Resins were deswelled in methanol (rinsed twice in 5 ml methanol, incubated 5 minutes in 5 ml methanol, rinsed in 5 ml methanol) and then vacuum dried.

Peptide was removed from the resin by incubating 2 hours in reagent R and then precipitated into ether. Peptide was washed in ether and then vacuum dried. Peptide was resolubilized in diH$_2$0, frozen and lyophilized overnight.

Conjugation of Peptide with Keyhole Limpet Hemocyanin

Peptide (6 mg) was conjugated with Keyhole Limpet Hemocyanin (KLH). When the selected peptide included at least one cysteine, three aliquots (2 mg) were dissolved in PBS (2 ml) and coupled to KLH via glutaraldehyde, EDC or maleimide activated KLH (2 mg) in 2 ml of PBS for a total volume of 4 ml. When the peptide lacked cysteine, two aliquots (3 mg) were coupled via glutaraldehyde and EDC methods.

Maleimide coupling is accomplished by mixing 2 mg of peptide with 2 mg of maleimide-activated KLH dissolved in PBS (4 ml) and incubating 4 hr.

EDC coupling is accomplished by mixing 2 mg of peptide, 2 mg unmodified KLH, and 20 mg of EDC in 4 ml PBS (lowered to pH 5 by the addition of phosphoric acid), and incubating for 4 hours. The reaction is stopped by the slow addition of 1.33 ml acetic acid (pH 4.2). When using EDC to couple 3 mg of peptide, the amounts listed above are increased by a factor of 1.5.

Glutaraldehyde coupling occurs when 2 mg of peptide are mixed with 2 mg of KLH in 0.9 ml of PBS. 0.9 ml of 0.2% glutaraldehyde in PBS is added and mixed for one hour. 0.46 ml of 1 M glycine in PBS is added and mixed for one hour.

When using glutaraldehyde to couple 3 mg of peptide, the above amounts are increased by a factor of 1.5.

The conjugated aliquots were subsequently repooled, mixed for two hours, dialyzed in 1 liter PBS and lyophilized.

Immunization of Rabbits

Two New Zealand White Rabbits were injected with 250 µg (total) KLH conjugated peptide in an equal volume of complete Freund's adjuvant and saline in a total volume of 1 ml. 100 µg KLH conjugated peptide in an equal volume of incomplete Freund's Adjuvant and saline were then injected into three to four subcutaneous dorsal sites for a total volume of 1 ml two, six, eight and twelve weeks after the first immunization. The immunization schedule was as follows:

| Day 0 | Pre-immune bleed, primary immunization |
| --- | --- |
| Day 15 | 1st boost |
| Day 27 | 1st bleed |
| Day 44 | 2nd boost |
| Day 57 | 2nd bleed and 3rd boost |
| Day 69 | 3rd bleed |
| Day 84 | 4th boost |
| Day 98 | 4th bleed |

Collection of Rabbit Serum

The rabbits were bled (30 to 50 ml) from the auricular artery. The blood was allowed to clot at room temperature for 15 minutes and the serum was separated from the clot using an IEC DPR-6000 centrifuge at 5000 g. Cell-free serum was decanted gently into a clean test tube and stored at −20° C. for affinity purification.

Determination of Antibody Titer

All solutions with the exception of wash solution were added by the Hamilton Eclipse, a liquid handling dispenser. The antibody titer was determined in the rabbits using an ELISA assay with peptide on the solid phase. Flexible high binding ELISA plates were passively coated with peptide diluted in BBS (100 µl, 1 µg/well) and the plate was incubated at 4° C. in a wetbox overnight (air-tight container with moistened cotton balls). The plates were emptied and then washed three times with BBS containing 0.1% Tween-20 (BBS-TW) by repeated filling and emptying using a semi-automated plate washer. The plates were blocked by completely filling each well with BBS-TW containing 1% BSA and 0.1% gelatin (BBS-TW-BG) and incubating for 2 hours at room temperature. The plates were emptied and sera of both pre- and post-immune serum were added to wells. The first well contained sera at 1:50 in BBS. The sera were then serially titrated eleven more times across the plate at a ratio of 1:1 for a final (twelfth) dilution of 1:204,800. The plates were incubated overnight at 4° C. The plates were emptied and washed three times as described.

Biotinylated goat anti-rabbit IgG (100 µl) was added to each microtiter plate test well and incubated for four hours at room temperature. The plates were emptied and washed three times. Horseradish peroxidase-conjugated Streptavidin (100 µl diluted 1:10,000 in BBS-TW-BG) was added to each well and incubated for two hours at room temperature. The plates were emptied and washed three times. The ABTS was prepared fresh from stock by combining 10 ml of citrate buffer (0.1 M at pH 4.0), 0.2 ml of the stock solution (15 mg/ml in water) and 10 µl of 30% hydrogen peroxide. The ABTS solution (100 µl) was added to each well and incubated at room temperature. The plates were read at 414 nm, 20 minutes following the addition of substrate.

Preparation of Peptide Affinity Purification Column:

The affinity column was prepared by conjugating 5 mg of peptide to 10 ml of cyanogen bromide-activated Sepharose 4B and 5 mg of peptide to hydrazine-Sepharose 4B. Briefly, 100 µl of DMF was added to peptide (5 mg) and the mixture was vortexed until the contents were completely wetted. Water was then added (900 µl) and the contents were vortexed until the peptide dissolved. Half of the dissolved peptide (500 µl) was added to separate tubes containing 10 ml of cyanogen-bromide activated Sepharose 4B in 0.1 ml of borate buffered saline at pH 8.4 (BBS) and 10 ml of hydrazine-Sepharose 4B in 0.1 M carbonate buffer adjusted to pH 4.5 using excess EDC in citrate buffer pH 6.0. The conjugation reactions were allowed to proceed overnight at room temperature. The conjugated Sepharose was pooled and loaded onto fritted columns, washed with 10 ml of BBS, blocked with 10 ml of 1 M glycine and washed with 10 ml 0.1 M glycine adjusted to pH 2.5 with HCl and re-neutralized in BBS. The column was washed with enough volume for the optical density at 280 nm to reach baseline.

Affinity Purification of Antibodies

The peptide affinity column was attached to a UV monitor and chart recorder. The titered rabbit antiserum was thawed and pooled. The serum was diluted with one volume of BBS and allowed to flow through the columns at 10 ml per minute. The non-peptide immunoglobulins and other proteins were washed from the column with excess BBS until the optical density at 280 nm reached baseline. The columns were disconnected and the affinity purified column was eluted using a stepwise pH gradient from pH 7.0 to 1.0. The elution was monitored at 280 nm and fractions containing antibody (pH 3.0 to 1.0) were collected directly into excess 0.5 M BBS. Excess buffer (0.5 M BBS) in the collection tubes served to neutralize the antibodies collected in the acidic fractions of the pH gradient.

The entire procedure was repeated with "depleted" serum to ensure maximal recovery of antibodies. The eluted material was concentrated using a stirred cell apparatus and a membrane with a molecular weight cutoff of 30 kD. The concentration of the final preparation was determined using an optical density reading at 280 nm. The concentration was determined using the following formula: mg/ml $OD_{280}/1.4$.

It will be appreciated that in certain embodiments, additional steps may be used to purify antibodies of the invention. In particular, it may prove advantageous to repurify antibodies, e.g., against one of the peptides that was used in generating the antibodies. It is to be understood that the present invention encompasses antibodies that have been prepared with such additional purification or repurification steps. It will also be appreciated that the purification process may affect the binding between samples and the inventive antibodies.

Example 8

Preparing and Staining Tissue Arrays

This example describes a method that was employed to prepare the tissue arrays that were used in Examples 1-6. This example also describes how the antibody staining was performed.

Tissue arrays were prepared by inserting full-thickness cores from a large number of paraffin blocks (donor blocks) that contain fragments of tissue derived from many different patients and/or different tissues or fragments of tissues from a single patient, into a virgin paraffin block (recipient block)

in a grid pattern at designated locations in a grid. A standard slide of the paraffin embedded tissue (donor block) was then made which contained a thin section of the specimen amenable to H & E staining. A trained pathologist, or the equivalent versed in evaluating tumor and normal tissue, designated the region of interest for sampling on the tissue array (e.g., a tumor area as opposed to stroma). A commercially available tissue arrayer from Beecher Instruments was then used to remove a core from the donor block which was then inserted into the recipient block at a designated location. The process was repeated until all donor blocks had been inserted into the recipient block. The recipient block was then thin-sectioned to yield 50-300 slides containing cores from all cases inserted into the block.

The selected antibodies were then used to perform immunohistochemical staining using the DAKO Envision+, Peroxidase IHC kit (DAKO Corp., Carpenteria, Calif.) with DAB substrate according to the manufacturer's instructions.

Example 9

Correlating Interaction Partner Binding with Outcome/Responsiveness of Xenograft Tumors According to the present invention, panels of useful interaction partners may be defined through analysis of human tumor cells grown in a non-human host. In particular, such analyses may define interaction partner panels whose binding correlates with prognosis and/or with responsiveness to therapy.

Cells derived from human tumors may be transplanted into a host animal (e.g., a mouse), preferably into an immunocompromised host animal. In preferred embodiments of the invention, cells (e.g., cell lines, tumor samples obtained from human patients, etc.) from a variety of different human tumors (e.g., at least 10, 20, 30, 40, 50, 60 or more different tumors) are transplanted into host animals. The animals are then treated with different (e.g., increasing) concentrations of a chemical compound known or thought to be selectively toxic to tumors with a predetermined common characteristic (e.g., class or subclass). Relative growth or regression of the tumors may then be assessed using standard techniques.

In certain embodiments of the invention, a dataset of sensitivity of the transplanted cells to a given compound or set of compounds may optionally be created. For example, a dataset might consist of the concentration of compound administered to the host animal that inhibited tumor growth 50% at 96 hr (i.e., the $LD_{50}$) for each of the cell samples or cell lines tested. Such a dataset, for example across at least 10, 20, 30, 40, 50, 60 or more cell lines, could then be correlated with the relative staining of the binding partners across the same cell lines. Those binding partners whose interaction (or lack thereof) with cells was highly correlated with either sensitivity to or resistance to a given compound would be useful members of a predictive panel.

Example 10

Correlating Interaction Partner Binding with Clinical Prognostic Data in Breast Cancer According to the present invention, panels of useful interaction partners may be defined through analysis of correlations between binding patterns and clinical prognostic data. In particular, such analyses may define interaction partner panels whose binding correlates with prognosis.

The following describes the identification of exemplary panels of antibodies whose binding has been shown to correlate with the prognosis of breast cancer patients. The data was obtained using samples from the Huntsville Hospital breast cohort (the "HH breast" cohort) that was referred to in Example 3.

The HH breast cohort was generated from 1082 breast cancer patients that were treated by the Comprehensive Cancer Institute (Huntsville, Ala.) between 1990 and 2000. This larger group was filtered to a study group of 550 patients by eliminating patients according to the following criteria: 249 that had no chart which could be found; 103 that had no clinical follow up; and 180 that did not have sufficient clinical material in the paraffin block to sample. For the remaining 550 patients, clinical data through Dec. 31, 2002 was available. Every patient in the cohort therefore had between 2 and 13 years of follow-up. The average time of follow-up among patients who did not recur was 5.6 years. Of the 550 patients, 140 had a recurrence of cancer within the study period; 353 patients were estrogen receptor positive (ER+); 154 were estrogen receptor negative (ER−); and 43 were undetermined. Some patients within these groups received adjuvant hormone therapy as shown in Table 1:

TABLE 1

|  | Total | Hormone | No hormone | Unknown |
|---|---|---|---|---|
| ER+ | 353 | 278 | 68 | 7 |
| ER− | 154 | 70 | 83 | 1 |
| Undetermined | 43 | 28 | 15 | 0 |

In addition, 263 patients received chemotherapy. Up to 16 different regimens were used, however, most were variants of cyclophosphamide, doxorubicin (with and without 5-fluorouracil and/or cyclophosphamide), methotrexate and 5-fluorouracil. Finally, 333 of the patients received radiation. Clinical information regarding age, stage, node status, tumor size, and grade was obtained.

The clinical information for the patients in the cohort is summarized in Table 2.

TABLE 2

|  | All (550) | ER+ (353) | ER− (154) |
|---|---|---|---|
| Stage = 1 | 236 | 162 | 49 |
| Stage = 2 | 269 | 167 | 87 |
| Stage = 3 | 44 | 23 | 18 |
| Undetermined | 1 | 0 | 0 |
| Mean Age @ Dx | 58 | 59 | 55 |
| Tumor status = 0 | 1 | 0 | 1 |
| Tumor status = 1 | 295 | 203 | 63 |
| Tumor status = 2 | 195 | 122 | 62 |
| Tumor status = 3 | 26 | 14 | 11 |
| Tumor status = 4 | 14 | 6 | 8 |
| Undetermined | 21 | 8 | 9 |
| Node status = 0 | 326 | 215 | 76 |
| Node status = 1 | 205 | 127 | 71 |
| Node status = 2 | 10 | 6 | 3 |
| Undetermined | 10 | 5 | 4 |
| Metastasis = 0 | 527 | 338 | 147 |
| Metastasis = 1 | 5 | 4 | 1 |
| Undetermined | 19 | 11 | 6 |

Where each category is defined in Table 3. These rules are not fixed and staging is typically done by an oncologist based on TNM status and other factors. These definitions for staging will not necessarily match with the stage that each patient was actually given. Node status is the primary tool for staging purposes.

TABLE 3

| | |
|---|---|
| Tumor status = 0 | No evidence of tumor |
| Tumor status = 1 | <2 cm |
| Tumor status = 2 | 2-5 cm |
| Tumor status = 3 | >5 cm |
| Tumor status = 4 | Any size but extends to chest wall |
| Node status = 0 | No regional LN metastasis |
| Node status = 1 | Ancillary LN metastasis but nodes still moveable |
| Node status = 2 | Ancillary LN metastasis with nodes fixed to each other OR internal mammary node metastasis |
| Metastasis = 0 | No distant metastasis |
| Metastasis = 1 | Distant metastasis |
| Stage = 1 | T1, N0, M0 |
| Stage = 2 | T0, N1, M0    T1, N1, M0    T2, N0, M0    T2, N1, M0    T3, N0, M0 |
| Stage = 3 | T(0-3), N2, M0    T3, N1, M0    T4, NX, M0 |
| Stage = 4 | TX, NX, M1 |

Samples from patients in the cohort were stained with antibodies from the breast cancer classification panel identified in Appendix A (as previously described in Examples 2 and 3). The stained samples were then scored in a semi-quantitative fashion, with 0=negative, 1=weak staining, and 2=strong staining. When appropriate, alternative scoring systems were used (i.e., 0=negative, 1=weak or strong; or 0=negative or weak and 1=strong staining). For each antibody, the scoring system used was selected to produce the most significant prognostication of the patients, as determined by a log-rank test (e.g., see Mantel and Haenszel, *Journal of the National Cancer Institute* 22:719-748, 1959). The results are presented in Appendix C and are grouped into four categories that have been clinically recognized to be of significance: all patients, ER+ patients, ER− patients, and ER+/node− patients. As shown, the antibodies were found to have differing significances for each of these categories of breast cancer patients.

It is to be understood that exclusion of a particular antibody from any prognostic panel based on these experiments is not determinative. Indeed, it is anticipated that additional data with other samples may lead to the identification of other antibodies (from Appendix A and beyond) that may have prognostic value for these and other classes of patients.

The expected relationship between the staining of patient samples with each antibody and the recurrence of tumors was measured using the Kaplan-Meier estimate of expected recurrence (e.g., see Kaplan and Meier, *J. Am. Stat. Assn.* 53:457-81, 1958). The log-rank test was used to determine the significance of different expected recurrences for each antibody (e.g., see Mantel and Haenszel, *Journal of the National Cancer Institute*, 22:719-748, 1959). This produces the p-value that is listed for each antibody in Appendix C. Preferred antibodies are those that produce a p-value of less than 0.10.

The degree to which these antibodies predicted recurrence was determined using a Cox univariate proportional hazard model (e.g., see Cox and Oakes, "Analysis of Survival Data", Chapman & Hall, 1984). The "hazard ratio" listed in Appendix C for each antibody reflects the predicted increase in risk of recurrence for each increase in the staining score. Scores greater than 1.0 indicate that staining predicts an increased risk of recurrence compared to an average individual, scores less than 1.0 indicate that staining predicts a decreased risk.

It will be appreciated that these antibodies can be used alone or in combinations to predict recurrence (e.g., in combinations of 2, 3, 4, 5, 6, 7, 8, 9, 10 or more antibodies). It will also be appreciated that while a given antibody may not predict recurrence when used alone the same antibody may predict recurrence when used in combination with others. It will also be understood that while a given antibody or combination of antibodies may not predict recurrence in a given set of patients (e.g., ER+ patients), the same antibody or combination of antibodies may predict recurrence in a different set of patients (e.g., ER− patients). Similarly, it is to be understood that while a given antibody or combination of antibodies may not predict recurrence in a given set of patients (e.g., ER+ patients), the same antibody or combination of antibodies may predict recurrence in a subset of these patients (e.g., ER+/node negative patients).

These prognostic panels could be constructed using any method. Without limitation these include simple empirically derived rules, Cox multivariate proportional hazard models (e.g., see Cox and Oakes, "Analysis of Survival Data", Chapman & Hall, 1984), regression trees (e.g., see Segal and Bloch, *Stat. Med.* 8:539-50, 1989), and/or neural networks (e.g., see Ravdin et al., *Breast Cancer Res. Treat.* 21:47-53, 1992). In certain embodiments a prognostic panel might include between 2-10 antibodies, for example 3-9 or 5-7 antibodies. It will be appreciated that these ranges are exemplary and non-limiting.

The prognostic value of exemplary panels of antibodies were also assessed by generating Kaplan-Meier recurrence curves for ER+ and ER+/node− patients and then comparing these with curves produced for these same patients with the standard Nottingham Prognostic Index (NPI).

Figure 4A:
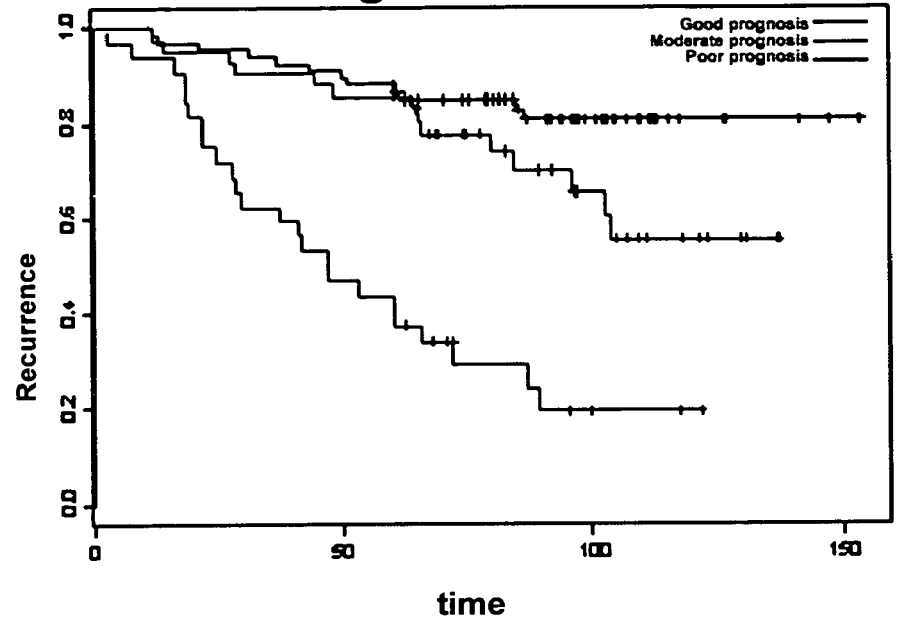
FIG. 4 shows Kaplan-Meier curves that were generated for ER+ patients after prognostic classification based on (A)

In order to generate Kaplan-Meier curves based on antibody panels, Cox univariate proportional hazard regression models were first run with all antibodies from Appendix C utilizing all three scoring procedures. The antibodies and scoring systems best able to predict recurrence were then used in a regression tree model and pruned to maintain predictive power while reducing complexity. Patients whom the panel predicted as being strongly likely to recur were placed in the "poor" prognosis group. Patients whom the panel predicted as being strongly unlikely to recur were given the prediction of "good". Patients whom the panel predicted as neither being strongly likely to recur or not recur were placed in the "moderate" prognosis group. Kaplan-Meier curves were then calculated based on recurrence data for patients within each group. FIG. 4A show the curves that were obtained for ER+ patients in each of these prognostic groups. FIG. 5A show the curves that were obtained for ER+/node− patients in each of these prognostic groups.

The antibodies from Appendix C that were used to predict recurrence for ER+ patients (FIG. 4A) were: s0296P1 (1:225 dilution, scoring method 3), s6006 (1:1 dilution, scoring method 2), s0545 (1:900 dilution, scoring method 2), s0063 (1:300 dilution, scoring method 2), s6002 (1:1 dilution, scoring method 3), s0081 (1:20 dilution, scoring method 2), s0255 (1:1000 dilution, scoring method 3), and s0039 (1:100 dilution, scoring method 2).

The antibodies from Appendix C that were used to predict recurrence for ER+/node– patients (FIG. 5A) were: s0143P3 (1:630 dilution, scoring method 1), s0137 (1:2500 dilution, scoring method 2), s0260 (1:5400 dilution, scoring method 2), s0702 (1:178200 dilution, scoring method 2), s0545 (1:900 dilution, scoring method 2), s6002 (1:1 dilution, scoring method 1), s6007 (1:1 dilution, scoring method 1).

Kaplan-Meier recurrence curves were then generated for the same patients based on their standard NPI scores. NPI scores were calculated for patients according to the standard formula NPI=(0.2× tumor diameter in cm)+lymph node stage+tumor grade. As is well known in the art, lymph node stage is either 1 (if there are no nodes affected), 2 (if 1-3 glands are affected) or 3 (if more than 3 glands are affected). The tumor grade was scored according to the Bloom-Richardson Grade system (Bloom and Richardson, *Br. J. Cancer* 11:359-377, 1957). According to this system, tumors were examined histologically and given a score for the frequency of cell mitosis (rate of cell division), tubule formation (percentage of cancer composed of tubular structures), and nuclear pleomorphism (change in cell size and uniformity). Each of these features was assigned a score ranging from 1 to 3 as shown in Table 4. The scores for each feature were then added together for a final sum that ranged between 3 to 9. A tumor with a final sum of 3, 4, or 5 was considered a Grade 1 tumor (less aggressive appearance); a sum of 6 or 7 a Grade 2 tumor (intermediate appearance); and a sum of 8 or 9 a Grade 3 tumor (more aggressive appearance).

TABLE 4

|  | Score |
|---|---|
| Tubule formation (% of carcinoma composed of tubular structures) | |
| >75% | 1 |
| 10-75% | 2 |
| <10% | 3 |
| Nuclear pleomorphism (Change in Cells) | |
| Small, uniform cells | 1 |
| Moderate increase in size and variation | 2 |
| Marked variation | 3 |
| Mitosis Count (Cell Division) | |
| Up to 7 | 1 |
| 8 to 14 | 2 |
| 15 or more | 3 |

Figure 4B:
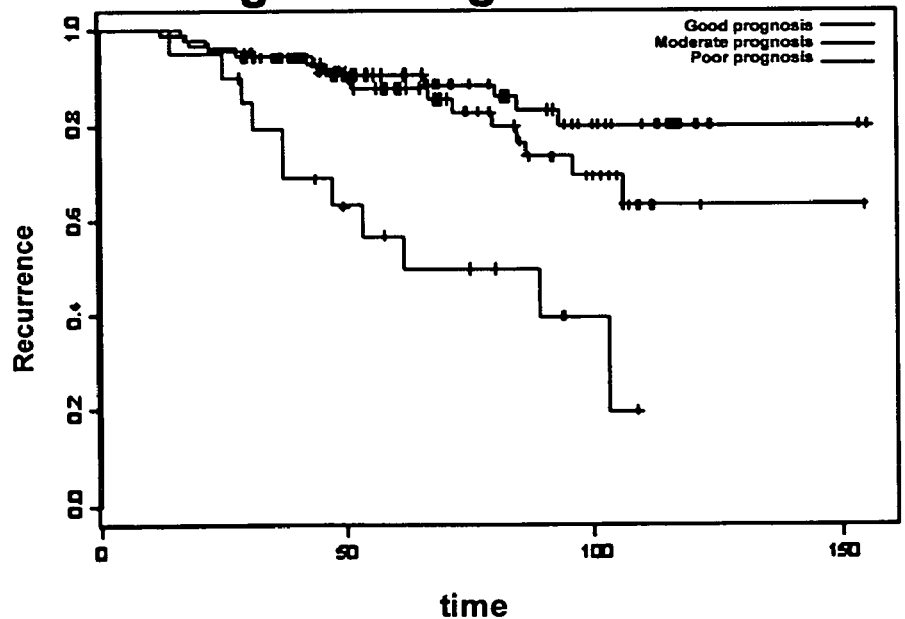

Patients with tumors having an overall NPI score of less than 3.4 were placed in the "good" prognosis group. Those with an NPI score of between 3.4 and 5.4 were placed in the "moderate" prognosis group and patients with an NPI score of more than 5.4 were placed in the "poor" prognosis group. Kaplan-Meier curves were then calculated based on recurrence data for patients within each group. FIG. 4B show the curves that were obtained for ER+ patients in each of these NPI prognostic groups. FIG. 5B show the curves that were obtained for ER+/node– patients in each of these NPI prognostic groups. By definition ER+/node– patients have an NPI score that is less than 5.4. This explains why there is no "poor" prognosis curve in FIG. 5B. Example 12 describes other exemplary prognostic panels for breast cancer patients.

Example 11

Correlating Interaction Partner Binding with Clinical Prognostic Data in Lung Cancer This Example describes the identification of exemplary panels of antibodies whose binding has been shown to correlate with the prognosis of lung cancer patients. The data was obtained using samples from the Huntsville Hospital lung cohort (the "HH lung" cohort) that was referred to in Example 5.

The HH lung cohort was generated from 544 lung cancer patients that were treated by the Comprehensive Cancer Institute (Huntsville, Ala.) between 1987 and 2002. This larger group was filtered to a study group of 379 patients by eliminating patients that had insufficient clinical follow up or that did not have sufficient clinical material in the paraffin block to sample. For the remaining patients, clinical data through Sep. 30, 2003 was available. This set of patients consisted of 232 males and 147 females. The average time of follow-up among patients who did not recur was 3.5 years. Of the 379 patients, 103 had a recurrence of cancer within the study period. All patients in this study were diagnosed at a pathological stage of 1 or 2, with 305 patients at stage 1, 1A, or 1B, and 74 patients at stage 2, 2A, or 2B.

Samples from patients in the cohort were stained with antibodies from the lung cancer classification panel identified in Appendix A (as previously described in Examples 4 and 5). The stained samples were then scored in a semi-quantitative fashion; scoring methods 1-3 use the following schemes: method 1 (0=negative; 1=weak; 2=strong); method 2 (0=negative; 1=weak or strong); and method 3 (0=negative or weak; 1=strong). For each antibody, the scoring system used was selected to produce the most significant prognostication of the patients, as determined by a log-rank test (e.g., see Mantel and Haenszel, *Journal of the National Cancer Institute* 22:719-748, 1959). The results are presented in Appendix D and are grouped into three categories that have been clinically recognized to be of significance: all patients, adenocarcinoma patients, and squamous cell carcinoma patients. As shown, the antibodies were found to have differing significances for each of these categories of lung cancer patients.

It is to be understood that exclusion of a particular antibody from any prognostic panel based on these experiments is not determinative. Indeed, it is anticipated that additional data with other samples may lead to the identification of other antibodies (from Appendix A and beyond) that may have prognostic value for these and other classes of patients.

As for the breast study of Example 10, the expected relationship between the staining of patient samples with each antibody and the recurrence of tumors was measured using the Kaplan-Meier estimate of expected recurrence and a log-rank test was used to determine the significance of different expected recurrences. This produces the p-value that is listed for each antibody in Appendix D. Preferred antibodies are those that produce a p-value of less than 0.10.

The degree to which these antibodies predicted recurrence was determined using a Cox univariate proportional hazard model. The "hazard ratio" listed in Appendix D for each antibody reflects the predicted increase in risk of recurrence for each increase in the staining score. Scores greater than 1.0 indicate that staining predicts an increased risk of recurrence compared to an average individual, scores less than 1.0 indicate that staining predicts a decreased risk.

As a number of patients had information regarding whether or not the cancer recurred but lacked information on time to recurrence, a chi-square test was also performed. This standard statistical test shows the degree of divergence between observed and expected frequencies and does not employ time to recurrence, as does the log-rank test. Preferred antibodies are those that produce a p-value of less than 0.10.

It will be appreciated that these prognostic antibodies can be used alone or in combinations to predict recurrence (e.g., in combinations of 2, 3, 4, 5, 6, 7, 8, 9, 10 or more antibodies). It will also be appreciated that while a given antibody may not predict recurrence when used alone, the same antibody may predict recurrence when used in combination with others. It will also be understood that while a given antibody or combination of antibodies may not predict recurrence in a given set of patients (e.g., adenocarcinoma patients), the same antibody or combination of antibodies may predict recurrence in a different set of patients (e.g., squamous cell carcinoma patients).

As for the breast study of Example 10, these prognostic panels could be constructed using any method. Without limitation these include simple empirically derived rules, Cox multivariate proportional hazard models, regression trees, and/or neural networks. In certain embodiments a prognostic panel might include between 2-10 antibodies, for example 3-9 or 5-7 antibodies. It will be appreciated that these ranges are exemplary and non-limiting. The construction of exemplary prognostic panels for lung cancer patients is described in Example 13.

Example 12

Prognostic Breast Cancer Panels

This Example builds on the results of Example 10 and describes the identification of additional exemplary panels of antibodies whose binding has been shown to correlate with the prognosis of breast cancer patients.

First, the individual prognostic ability of the antibodies of Appendix C was refined using samples from the HH breast cohort that was described in Example 2. In particular, certain antibodies were excluded based on subjective assessment of specificity and scoreability. The methodology paralleled that used in Example 10 and the updated antibody data is presented in Appendix E.

Second, prognostic panels in two currently identified clinically important subclasses of breast cancer patients were generated, namely ER+/node− patients and ER− patients. To minimize the chance of identifying spurious associations, only those antibodies from Appendix E that showed sufficient significance (p-value of less than 0.10) in either the ER+ or ER+/node− patient classes were used in creating prognostic panels for the ER+/node− patients, and only the similarly significant markers from the ER− patient set for creating a prognostic panel for the ER− patients. Using Cox proportional hazard analysis and regression tree analysis (as described in Example 10) candidate panels (and dendrograms for regression tree analysis) were derived for prediction of early recurrence. For both ER+/node− patients and ER− patients, panels and dendrograms were chosen that identified patients with significantly increased risks of recurrence.

Prognostic Panels Generated by Cox Analysis

Cox proportional hazard analysis treats the component antibodies of a panel as additive risk factors. The panels for the specified patient classes were created by initially using all applicable antibodies, and then iteratively removing antibodies from the panel. If the removal of an antibody increased or did not affect the significance and prognostic ability of the panel as a whole, it was excluded, otherwise it was retained.

In this manner preferred panels with minimal numbers of antibodies were created. The preferred panels for ER+/node− and ER− patients are presented in Tables 5 and 6, respectively. Antibodies within the preferred panels are ranked based on their relative contributions to the overall prediction function.

TABLE 5

| Panel | Analysis | P value[1] | Hazard ratio[2] |
|---|---|---|---|
| Breast ER+/node− | Cox | 8.17E−05 | 5.68 |
| AGI ID | Rank | P value[3] | Terms[4] |
| S0702/s0296P1 | 1 | 0.00015 | −0.213, 1.330 |
| s6006 | 2 | 0.00660 | −0.325, 0.799 |
| s0404 | 3 | 0.06200 | −0.099, 0.958 |
| s0545 | 4 | 0.10000 | −0.112, 0.604 |
| s0235 | 5 | 0.25000 | −0.114, 0.390 |

[1]P value of overall panel
[2]Hazard ratio of overall panel
[3]P value of the contribution of a given antibody to the overall panel
[4]Contribution of given antibody to overall panel prediction function depending on IHC score (e.g., scores of 0 or 1 for s6006 which uses scoring method 2 [see Appendix E] result in its term in the model equaling −0.325 or 0.799, respectively).

TABLE 6

| Panel | Analysis | P value[1] | Hazard ratio[2] |
|---|---|---|---|
| Breast ER− | Cox | 3.10E−03 | 2.25 |
| AGI ID | Rank | P value[3] | Terms[4] |
| s0691 | 1 | 0.04700 | −0.163, 0.436, 0.640 |
| s0545 | 2 | 0.08900 | −0.339, 0.259 |
| s0330x1 | 3 | 0.57000 | 0.510, −5.560 |

[1,2,3,4]See Table 5

The prognostic value of these exemplary panels were assessed by generating Kaplan-Meier recurrence curves for ER+/node− and ER− patients. Patients whom the panels predicted as being strongly likely to recur were placed in the "bad" prognosis group. Patients whom the panels predicted as being strongly unlikely to recur were given the prediction of "good". Patients whom the panels predicted as neither being strongly likely to recur or not recur were placed in the "moderate" prognosis group. Kaplan-Meier curves were then calculated based on recurrence data for patients within each group. FIG. 6 shows the curves that were obtained for ER+/node− patients in each of these prognostic groups. FIG. 7 shows the curves that were obtained for ER− patients in each of these prognostic groups.

When lymph node status was included as an additional variable for the ER− patient set the preferred panel was as shown in Table 7.

TABLE 7

| Panel | Type | P value[1] | Hazard ratio[2] |
|---|---|---|---|
| Breast ER− | Cox plus node | 3.70E−05 | 3.93 |
| AGI ID | Rank | P value[3] | Terms[4] |
| s6007 | 1 | 0.05000 | −0.460, 0.280 |
| s0545 | 2 | 0.06400 | −0.400, 0.290 |
| s0068 | 3 | 0.18000 | −0.350, 0.160 |
| s0330x1 | 4 | 0.62000 | −5.820, 0.450 |

[1,2,3,4]See Table 5

The prognostic value of this exemplary panel was also assessed by generating Kaplan-Meier recurrence curves for ER− patients. Patients whom the panel predicted as being strongly likely to recur were placed in the "bad" prognosis group. Patients whom the model predicted as being strongly unlikely to recur were given the prediction of "good". Patients whom the model predicted as neither being strongly likely to recur or not recur were placed in the "moderate" prognosis group. Kaplan-Meier curves were then calculated based on recurrence data for patients within each group. FIG. 8 shows the curves that were obtained for ER− patients in each of these prognostic groups.

While the preferred Cox panels of the invention for ER+/node− and ER− patients include each of the listed antibodies, it is to be understood that other related panels are encompassed by the present invention. In particular, it will be appreciated that the present invention is in no way limited to the specific antibodies listed. For example, other antibodies directed to the same biomarker(s) may be used (e.g., taking the Cox ER+/node− panel, it can be readily seen from Appendix A that antibodies s0702 or s0296P1 can be replaced with other antibodies directed to biomarker Hs.184601; antibody s6006 can be replaced with other antibodies directed to biomarker Hs.1846, etc.). As noted, addition of certain antibodies from Appendix E had no effect on the significance and prognostic ability of the panel as a whole. Thus, antibodies may be added to any given panel without necessarily diminishing the utility of a panel for patient prognosis. The inclusion of antibodies beyond those listed in Appendix E is also within the scope of the invention. In certain embodiments less than all of the listed antibodies may be used in a prognostic panel.

Generally, a Cox panel for ER+/node− patients will include at least two antibodies selected from the group consisting of antibodies directed to biomarkers Hs.184601, Hs.1846, Hs.75789, Hs.63609 and Hs.220529 (e.g., s0702 and/or s0296P1, s6006, s0404, s0545 and s0235, see Table 5 and Appendix A). Preferably, the panel will include an antibody directed to biomarker Hs.184601 and at least one antibody directed to a biomarker selected from the group consisting of Hs.1846, Hs.75789, Hs.63609 and Hs.220529. All permutations of these antibodies are encompassed. In one embodiment an antibody to biomarker Hs.184601 (e.g., s0702 and/or s0296P1) is used with an antibody to biomarker Hs.1846 (e.g., s6006). In another embodiment an antibody to biomarker Hs.184601 is used with antibodies to biomarkers Hs.1846 and Hs.75789 (e.g., s6006 and s0404). In other embodiments an antibody to biomarker Hs.184601 is used with antibodies to biomarkers Hs.1846, Hs.75789, Hs.63609 and optionally Hs.220529 (e.g., s6006, s0404, s0545 and optionally s0235). In preferred embodiments an antibody to Hs.184601 is used with antibodies to biomarkers Hs.1846, Hs.75789, Hs.63609 and Hs.220529.

Similarly, a Cox panel for ER− patients will include at least two antibodies selected from the group consisting of antibodies directed to biomarkers Hs.6682, Hs.63609 and Hs.306098 (e.g., s0691, s0545 and s0330x1, see Table 6 and Appendix A). Preferably, the panel will include an antibody directed to biomarker Hs.6682 and antibodies to one or both of biomarkers Hs.63609 and Hs.306098. In preferred embodiments an antibody to biomarker Hs.6682 is used with antibodies to biomarkers Hs.63609 and Hs.306098.

When lymph node status is used as an additional variable, an inventive prognostic Cox panel for ER− patients will include at least two antibodies selected from the group consisting of antibodies directed to biomarkers Hs.80976, Hs.63609, Hs.416854 and Hs.306098 (e.g., s6007, s0545, s0068 and s0330x1, see Table 7 and Appendix A). Preferably, the panel will include an antibody directed to biomarker Hs.80976 and antibodies to one or more of biomarkers Hs.63609, Hs.416854 and Hs.306098. All permutations of these antibodies are encompassed. In one embodiment an antibody to biomarker Hs.80976 is used with an antibody to biomarker Hs.63609. In another embodiment an antibody to biomarker Hs.80976 is used with antibodies to biomarkers Hs.63609 and Hs.416854 and optionally with a biomarker to Hs.306098. In preferred embodiments an antibody to biomarker Hs.80976 is used with antibodies to biomarkers Hs.63609, Hs.416854 and Hs.306098.

The present invention also encompasses methods of assessing the prognosis of a patient having a breast tumor using these exemplary panels. After obtaining a tumor sample from a patient with unknown prognosis the sample is contacted with two or more antibodies from the panels of Tables 5, 6 and/or 7. The patient's likely prognosis is then assessed based upon the pattern of positive and negative binding of the two or more antibodies to the tumor sample.

Prognostic Panels Generated by Regression Tree Analysis

Regression trees classify the patients into a number of subclasses each defined by their pattern of binding to a unique set of antibodies from within a panel. An exemplary tree (or "dendrogram") for ER+/node− patients is shown in FIG. 9 which is discussed below. Regression trees were initially created with all applicable antibodies, and then "pruned" to a minimal complexity (least number of terminal nodes without losing too much prognostic ability) using a cross validation procedure. This cross validation procedure involved building panels and dendrograms using a series of patient groups that were picked from the total patient set using a series of increasingly pruned trees. The results over the tested groups were summed and the minimally complex least error-prone panel and dendrogram were chosen. The resulting dendrogram was further simplified by placing nodes with a range of response values into the classes "good" or "poor" (or alternatively "good", "moderate" or "poor"). Table 8 lists the antibodies of an exemplary ER+/node− tree panel that was constructed as described above. The dendrograms for this panel is illustrated in FIG. 9.

TABLE 8

| Panel | Analysis | P value[1] | Hazard ratio[2] |
|---|---|---|---|
| Breast ER+/node− | Tree | 2.82E−05 | 6.06 |

| AGI ID | Rank |
|---|---|
| s0702/s0296P1 | 1 |
| s0081 | 2 |
| s6006 | 2 |
| s6007 | 3 |
| s0545 | 4 |
| s6002 | 4 |

[1]P value of overall panel
[2]Hazard ratio of overall panel

As illustrated in FIG. 9, if a patient is positive for staining at a given node his or her prognosis decision tree follows the branch marked with a "+". Conversely if a patient is negative for staining at a given node his or her prognosis decision tree follows the branch marked "−". This is done until a terminus is reached.

For example, if patient A is positive for staining with s0702 and negative for staining with s0081 then, based on the dendrogram, his or her prognosis is "bad". In contrast, if patient B is negative for staining with s0702, negative for staining with s6006, positive for staining with s6007 and negative for staining with s0545 then his or her prognosis is "good". It will be appreciated from the foregoing and FIG. 9 that the number of stains required in order to yield a prognosis will vary from patient to patient. However, from a practical standpoint (and without limitation), it may prove advantageous to complete all the stains for a given panel in one sitting rather than adopting an iterative approach with each individual antibody.

The prognostic value of the exemplary panel of Table 8 was also assessed by generating Kaplan-Meier recurrence curves for ER+/node− patients. Patients whom the panel predicted as being strongly likely to recur were placed in the "bad" prognosis group. Patients whom the panel predicted as being strongly unlikely to recur were given the prediction of "good". Patients whom the panel predicted as neither being strongly likely to recur or not recur were placed in the "moderate" prognosis group. Kaplan-Meier curves were then calculated based on recurrence data for patients within each group. FIG. 10 shows the curves that were obtained for ER+/node− patients in each of these prognostic groups.

Generally, a tree panel for ER+/node− patients will include an antibody to biomarker Hs.184601 (e.g., s0702 or s0296P1) with antibodies to one or both of biomarkers Hs.155956 and Hs.1846 (e.g., s0081 and s6006, see Table 8 and Appendix A). In certain embodiments an antibody to biomarker Hs.80976 (e.g., s6007) may be added, optionally with antibodies to one or both of biomarkers Hs.63609 and Hs.2905 (e.g., s0545 and s6002). In preferred embodiments, the tree panel includes an antibody to biomarker Hs.184601 and antibodies to biomarkers Hs.155956, Hs.1846, Hs.80976, Hs.63609 and Hs.2905.

Table 9 lists the antibodies of exemplary ER+ and ER− tree panels that were constructed as described above for the ER+/node− tree panel of Table 8. The dendrograms for theses panels are illustrated in FIG. 11.

TABLE 9

| Panel | Analysis | Panel | Analysis |
| --- | --- | --- | --- |
| Breast ER+ | Tree | Breast ER− | Tree |
| AGI ID | Rank | AGI ID | Rank |
| s0702/s0296P1 | 1 | s6007 | 1 |
| s0137 | 2 | s0303 | 2 |
| s6007 | 2 | s0398 | 2 |
| s5076 | 3 | s0063 | 3 |
| s0143 | 3 | s0545 | 4 |
| s6007 | 4 | s0702/s0296P1 | 4 |
| s0545 | 4 | s0068 | 5 |

The present invention also encompasses methods of assessing the prognosis of a patient having a breast tumor using an inventive tree panel. For example, after obtaining a tumor sample from a patient with unknown prognosis the sample is contacted with two or more antibodies from the panel of Table 8 (or one of the panels in Table 9). The patient's likely prognosis is then assessed based upon the positive or negative binding of the two or more antibodies to the tumor sample using the dendrogram of FIG. 9 (or FIG. 11). Taking the ER+/node− panel of Table 8 as an example, the method generally includes a step of contacting the tumor sample with an antibody to biomarker Hs.184601 (e.g., s0702 or s0296P1) and antibodies to one or both of biomarkers Hs.155956 and Hs.1846 (e.g., s0081 and/or s6006). In other embodiments the tumor sample is further contacted with an antibody to biomarker Hs.80976 (e.g., s6007) and optionally with antibodies to biomarkers Hs.63609 and/or Hs.2905 (e.g., s0545 and/or s6002). As mentioned above, the tumor sample may be contacted with these antibodies in a single sitting or sequentially based on the binding results of a previous stain. Obviously the tumor sample may be divided and different antibodies contacted with different fractions. Alternatively different original tumor samples may be contacted with different antibodies.

Whether created by Cox or regression tree analysis, the exemplary prognostic panels were determined to be independent of age, stage, and grade. To ensure that the panels were not identifying classes of patients unlikely to be found to be significant in an independent cohort, cross validation was used to estimate the error inherent in each panel. Ten-fold cross-validation was performed by sequentially "leaving-out" 10% of patients and building panels on the remaining patients ten times such that all patients were ultimately classified. This included re-determining the set of antibodies sufficiently significant to be employed in the panel building process (p-value <0.10). Cross validated p-values reflect the confidence calculated for the sum of the ten independent panels and confirmed the statistical significance of these panels. For the ER+/node− patient set, both the Cox (Table 5) and regression tree (Table 8) panels showed significance after cross-validation (p-value/hazard ratio of 1.12E-02/2.36 and 3.40E-03/2.91, respectively). For the ER− patient set, the Cox panels (Tables 6-7) were also shown to be able to retain significance (p-value/hazard ratios of 6.40E-02/1.37 and 1.80E-03/1.79 for the panels of Table 6 and 7, respectively).

It is to be understood that each of the exemplary Cox and tree panels described herein may be used alone, in combination with one another (e.g., the Cox panel of Table 5 and the tree panel of Table 8 for ER+/node− patients) or in conjunction with other panels and/or independent prognostic factors.

Example 13

Prognostic Lung Cancer Panels

This Example builds on the results of Example 11 and describes the identification of exemplary panels of antibodies whose binding has been shown to correlate with the prognosis of lung cancer patients.

Prognostic panels in two currently identified clinically important subclasses of lung cancer patients were generated, namely adenocarcinoma and squamous cell carcinoma patients. Consistent with the known clinical significance of diagnoses of these two subclasses of lung cancer patients it was found that the most robust models were derived when patients were first classified in this manner, and then the separate patient groups modeled independently. It will be appreciated that this approach is non-limiting and that models could be generated using all lung cancer patients or using other subclasses of patients. To minimize the chance of identifying spurious associations, only those antibodies from Appendix D that showed sufficient significance (p-value of less than 0.10) in the adenocarcinoma patient class were used in creating prognostic panels for the adenocarcinoma patients, and only the similarly significant markers from the squamous cell carcinoma patient class for creating a prognostic panel for the squamous cell carcinoma patients. Using Cox proportional hazard analysis (as described in Example 10) candidate panels were derived for prediction of early recurrence. For both adenocarcinoma and squamous cell carcinoma patients, panels were chosen that identified patients with significantly increased risks of recurrence.

As previously noted, Cox proportional hazard analysis treats the component antibodies of a panel as additive risk factors. The panels for the specified patient classes were created by initially using all applicable antibodies, and then iteratively removing antibodies from the panel. If the removal of an antibody increased or did not affect the significance and prognostic ability of the panel as a whole, it was excluded, otherwise it was retained. In this manner preferred panels with minimal numbers of antibodies were created. The preferred panels for squamous cell carcinoma and adenocarcinoma patients are presented in Tables 10 and 11, respectively. Antibodies within the preferred panels are ranked based on their relative contributions to the overall prediction function.

TABLE 10

| Panel | Analysis | P value[1] | Hazard ratio[2] |
|---|---|---|---|
| Lung squamous | Cox | 3.20E−05 | 6.88 |
| AGI ID | Rank | P value[3] | Terms[4] |
| s0022 | 1 | 0.00620 | 0.880, −1.240 |
| s0702/s0296P1 | 2 | 0.12000 | 0.980, −0.150 |
| s0330 | 3 | 0.13000 | 0.870, −0.034 |
| s0586 | 4 | 0.16000 | 0.680, −0.250 |

[1]P value of overall panel
[2]Hazard ratio of overall panel
[3]P value of the contribution of a given antibody to the overall panel
[4]Contribution of given antibody to overall panel prediction function depending on IHC score (e.g., scores of 0 or 1 for s0022 which uses scoring method 2 [see Appendix D] result in its term in the model equaling 0.880 or −1.240, respectively).

TABLE 11

| Panel | Analysis | P value[1] | Hazard ratio[2] |
|---|---|---|---|
| Lung adenocarcinoma | Cox | 1.30E−05 | 3.23 |
| AGI ID | Rank | P value[3] | Terms[4] |
| s6013 | 1 | 0.02000 | −0.430, 0.520 |
| s0545 | 2 | 0.03500 | −0.070, 1.150 |
| s0404 | 3 | 0.04000 | −0.270, 0.550 |
| s0702/s0296P1 | 4 | 0.08800 | −0.230, 0.450 |

[1,2,3,4]See Table 10

The prognostic value of these exemplary panels were assessed by generating Kaplan-Meier recurrence curves for the combined lung cancer patients of the HH lung cohort. Patients were initially classified as adenocarcinoma or squamous cell carcinoma patients. For each patient the pattern of antibody staining with the applicable panel (i.e., Table 10 or 11) was then assessed. Patients whom the panels predicted as being strongly likely to recur were placed in the "bad" prognosis group. Patients whom the panels predicted as being strongly unlikely to recur were given the prediction of "good". Patients whom the panels predicted as neither being strongly likely to recur or not recur were placed in the "moderate" prognosis group. Kaplan-Meier curves were then calculated based on five year recurrence data for patients within each group. FIG. 12 shows the curves that were obtained when the combined lung cancer patients were placed in "good", "moderate" or "bad" prognosis groups. FIG. 13 shows the curves that were obtained when patients in the "moderate" and "bad" groups were combined into a single "bad" prognostic group.

To ensure that the panels were not identifying classes of patients unlikely to be found to be significant in an independent cohort, cross validation was used to estimate the error inherent in each panel. Ten-fold cross-validation was performed by sequentially "leaving-out" 10% of patients and building panels on the remaining patients ten times such that all patients were ultimately classified. This included re-determining the set of antibodies sufficiently significant to be employed in the panel building process (p-value <0.10). Cross validated p-values reflect the confidence calculated for the sum of the ten independent panels and confirmed the statistical significance of these panels. The panels showed significance after cross-validation with the combined lung patients (p-value/hazard ratio of 2.20E−02/1.48 when a "good", "moderate" and "bad" scheme was used and 1.80E−02/2.07 when a "good" and "bad" scheme was used).

While preferred Cox panels of the invention for lung cancer patients include each of the listed antibodies, it is to be understood that other related panels are encompassed by the present invention. In particular, it will be appreciated that the present invention is in no way limited to the specific antibodies listed. For example, other antibodies directed to the same biomarker(s) may be used (e.g., taking the squamous cell carcinoma panel, it can be readily seen from Appendix A that antibody s0022 can be replaced with other antibodies directed to biomarker Hs.176588; s0702 or s0296P1 can be replaced with other antibodies directed to biomarker Hs.184601, etc.). Other antibodies from Appendix D may be added to any given panel without necessarily diminishing the utility of a panel for patient prognosis. The inclusion of antibodies beyond those listed in Appendix D is also within the scope of the invention. In certain embodiments less than all of the listed antibodies may be used in a prognostic panel.

Generally, a Cox panel for squamous cell carcinoma patients will include at least two antibodies selected from the group consisting of antibodies directed to biomarkers Hs.176588, Hs.184601, Hs.306098 and Hs.194720 (e.g., s0022, s0702 or s0296P1, s0330 and s0586, see Table 10 and Appendix A). Preferably, the panel will include an antibody directed to biomarker Hs.176588 and at least one antibody directed to a biomarker selected from the group consisting of Hs.184601, Hs.306098 and Hs.194720. All permutations of these antibodies are encompassed. In one embodiment an antibody to biomarker Hs.176588 (e.g., s0022) is used with an antibody to biomarker Hs.184601 (e.g., s0702 and/or s0296P1). In another embodiment an antibody to biomarker Hs.176588 is used with antibodies to biomarkers Hs.184601 and Hs.306098 (e.g., s0702 or s0296P1 and s0330). In preferred embodiments an antibody to biomarker Hs.176588 is used with antibodies to biomarkers Hs.184601, Hs.306098 and Hs.194720.

Similarly, a Cox panel for adenocarcinoma patients will include at least two antibodies selected from the group consisting of antibodies directed to biomarkers Hs.323910, Hs.63609, Hs.75789 and Hs.184601 (e.g., s6013, s0545, s0404 and s0702 or s0296P1, see Table 11 and Appendix A). Preferably, the panel will include an antibody directed to biomarker Hs.323910 and at least one antibody directed to a biomarker selected from the group consisting of Hs.63609, Hs.75789 and Hs.184601. All permutations of these antibodies are encompassed. In one embodiment an antibody to biomarker Hs.323910 (e.g., s6013) is used with an antibody to biomarker Hs.63609 (e.g., s0545). In another embodiment an antibody to biomarker Hs.323910 is used with antibodies to biomarkers Hs.63609 and Hs.75789 (e.g., s0545 and s0404). In preferred embodiments an antibody to biomarker Hs.323910 is used with antibodies to biomarkers Hs.63609, Hs.75789 and Hs.184601.

It is to be understood that these exemplary Cox panels may be used alone, in combination with one another or in conjunction with other panels and/or independent prognostic factors.

The present invention also encompasses methods of assessing the prognosis of a patient having a lung tumor using these exemplary panels. After obtaining a tumor sample from a patient with unknown prognosis the sample is contacted with two or more antibodies from the panels of Table 10 and/or 11. The patient's likely prognosis is then assessed based upon the positive or negative binding of the two or more antibodies to the tumor sample.

Example 14

Use of Prognostic Lung Cancer Panels with an Independent Cohort

This Example builds on the results of Example 13 by describing how the exemplary prognostic lung cancer panels were used to predict recurrence in an independent cohort of lung cancer patients.

A cohort of 119 lung cancer patients from the University of Alabama-Birmingham (UAB) was used for this purpose. Relatively limited clinical data was available for these patients, in most cases only survival time was available. The average time of follow-up among patients who did not die of disease was 28 months. Of the 119 patients, 54 were noted to have had a recurrence of cancer within the study period, and 74 died of disease. This cohort differed significantly from the HH lung cohort (see Example 11) in that it was not limited to early stage tumors, and therefore the cohort had a greater incidence of death due to disease. Since recurrence data for this cohort was limited, the prognostic panels of Example 13 (designed to predict recurrence) were used to predict survival in this independent cohort. Specifically, the prognostic value of the panels were assessed by generating Kaplan-Meier survival curves for the combined lung cancer patients of the UAB lung cohort. As in Example 13, patients were initially classified as adenocarcinoma or squamous cell carcinoma patients. For each patient the pattern of antibody staining with the applicable panel (i.e., Table 10 or 11) was then assessed. Patients were placed in "bad", "moderate" and "good" prognosis groups based on their binding patterns with these antibodies. Kaplan-Meier curves were then calculated based on survival data for patients within each group. FIG. 14 shows the curves that were obtained when the combined lung cancer patients were placed in "good", "moderate" or "bad" prognosis groups (p-value/hazard ratio of 5.20E-02/1.98). FIG. 15 shows the curves that were obtained when the patients in the "moderate" and "bad" groups were combined into a single "bad" prognostic group (p-value/hazard ratio of 2.50E-02/3.03). FIG. 16 shows the curves that were obtained when the subclass of adenocarcinoma patients were placed in "good", "moderate" or "bad" prognosis groups (no patients fell within the "bad" group hence there are only two curves, p-value/hazard ratio of 4.00E-02/2.19). FIG. 17 shows the curves that were obtained when the subclass of squamous cell carcinoma patients were placed in "good", "moderate" or "bad" prognosis groups (p-value/hazard ratio of 2.50E-02/3.03).

The prognostic significance of individual antibodies identified in the HH lung cohort (i.e., those listed in Appendix D) were also reassessed using the five year survival data from the UAB lung cohort. The methodology was as described in Example 11. The prognostic significance of these same antibodies was also recalculated using five year recurrence data from the HH lung cohort (instead of the complete follow-up period as in Example 11 where patients who did not die of disease were followed for a period of up to ten years). Based on these calculations, several antibodies from Appendix D were found to have a relatively significant individual prognostic value (p-value less than 0.2) in both the HH and UAB lung cohorts. These antibodies are presented in Appendix F.

Example 15

Use of a Lung Cancer Classification Panel with an Independent Cohort

The pattern of reactivity with the lung cancer classification panel of Example 5 (see Appendix A) was determined using samples from the HH lung cohort (data not shown). As in Example 4, patients were classified using k-means clustering. Seven sub-classes of lung cancer patients were chosen by their consensus pattern of staining.

The morphology of the lung cancers within each sub-class were determined and are shown graphically in FIG. 18. Interestingly, the sub-classes were found to comprise patients with lung cancers having similar morphological characteristics (i.e., sub-classes 1, 2, 3 and 7 were composed of a majority of patients with adenocarcinomas; sub-classes 4 and 5 were composed of a majority of patients with squamous cell carcinomas; and sub-class 6 was composed of a majority of patients with large cell carcinomas). These results suggest that the antibodies in the classification panel are recognizing biological and clinical diversity in lung cancers.

Out of interest, the prognostic value of these seven sub-classes was also assessed. (Note that these sub-classes were constructed based on sample staining patterns across the entire classification panel of Appendix A. This differs from the approach that was described in Example 14 where specific antibodies with predetermined prognostic value were combined into prognostic panels that were then used to classify patients). The average probability of recurrence for the overall HH cohort was first calculated and found to level out at about 38% after six years. Average probabilities within each of the seven HH sub-classes were then calculated and compared with the overall average. Sub-classes with an average probability of recurrence after six years that was greater than 48% (i.e., more than 10% worse than the overall population) were classified as having a "bad" prognosis. Sub-classes with an average probability of recurrence after six years that was less than 28% (i.e., more than 10% better than the overall population) were classified as having a "good" prognosis. Sub-classes with an average probability of recurrence after six years of 28 to 48% were classified as having a "moderate" prognosis. Based on this analysis, HH sub-classes 1, 6 and 7 were classified as "bad"; HH sub-classes 2 and 4 as "moderate"; and HH sub-classes 3 and 5 as "good". When the recurrence data for patients in the "bad", "moderate" and "good" classes were combined and plotted as Kaplan-Meier curves the different outcomes for the three prognostic groups were statistically significant (p-value <0.02, data not shown).

In order to assess whether the sub-classes of FIG. 18 would correlate across lung cancers in general, the k-means clustering criteria that were used in classifying the HH lung cohort were "forced" onto samples from an independent lung cohort (namely the UAB lung cohort that was described in Example 14). Note that while the HH lung cohort was composed of Stage I/II patients, the UAB lung cohort was composed of Stage III/IV patients. Thus, overall the prognosis of UAB patients was worse than the prognosis of HH patients. First, the mean values from the HH k-means analysis were calculated for each of the seven HH sub-classes of FIG. 18. Antibody staining results for each UAB sample were then compared with all seven means and samples were assigned to one of the seven "HH sub-classes" based on the closest match. The seven UAB clusters were then classified as having a "bad", "moderate" and "good" prognosis based simply on the prognoses that had been previously determined for the corresponding seven HH sub-classes (see above). When the recurrence data for patients in the "bad", "moderate" and "good" classes were combined and plotted as Kaplan-Meier curves the different outcomes for the three prognostic groups were again statistically significant (p-value <0.02, data not shown). Examination of the curves and subsequent analysis showed that "good" and "moderate" gave similar outcomes relative to each other while "bad" was clearly divergent from these two.

Example 16

Ovarian Cancer Classification Panel (Stanford Ovarian Cohort)

The present inventors prepared an exemplary panel of antibodies for use in classifying ovarian tumors. 17 of the 460 differentially staining antibodies of Example 1 exhibited a reproducibly robust staining pattern on tissues relevant for this application. These antibodies were therefore applied (at appropriate titers) to a tissue array comprised of approximately 382 independent ovarian tumor samples from a cohort of ovarian cancer patients (the Stanford ovarian cohort). Stained tissue samples were scored by a trained cytotechnologist or pathologist on a semi-quantitative scale in which 0=no stain on tumor cells; 1=no information; 2=weak staining of tumor cells; and 3=strong staining of tumor cells. Antibodies were included in a ovarian cancer classification panel if they stained greater than 10% and less than 90% of a defined "consensus panel" of the ovarian tumor tissue samples on at least two independent tissue arrays.

A given tissue sample was included in this "consensus panel" if at least 80% of the antibodies tested gave interpretable scores (i.e., a non-zero score) with that sample. Of the 382 ovarian tumor samples in the tissue array about 342 were included in the consensus panel. Also, in scoring antibody binding to the consensus panel, all scores represented a consensus score of replicate tissue arrays comprised of independent samples from the same sources. The consensus score was determined by computing the median (rounded down to an integer, where applicable) of all scores associated with a given antibody applied under identical conditions to the particular patient sample. In cases where the variance of the scores was greater than 2, the score was changed to 1 (i.e., no information). The data for each antibody was stored in an Oracle-based database that contained the semi-quantitative scores of tumor tissue staining and also contained links to both patient clinical information and stored images of the stained patient samples.

Through this analysis 16 of the 17 tested antibodies were selected for inclusion in an exemplary ovarian cancer classification panel (see Appendix A). It is to be understood that any sub-combination of these 16 antibodies may be used in constructing an inventive ovarian cancer classification panel. It will also be appreciated that additional antibodies may be added to or removed from an inventive ovarian cancer classification panel as more tumor markers are identified and/or more samples are tested (e.g., those identified in Examples 17 and 18 or others).

Example 17

Ovarian Cancer Classification Panel (UAB Ovarian Cohort)

The present inventors identified other exemplary antibodies for use in classifying ovarian tumors using a second tissue array comprised of approximately 160 independent ovarian tumor samples from a cohort of ovarian cancer patients (the UAB ovarian cohort). 75 of the 460 differentially staining antibodies of Example 1 exhibited a reproducibly robust staining pattern on tissues relevant for this application. Of the 160 ovarian tumor samples in the tissue array about 146 were included in the consensus panel. Using the method described in Example 16, 55 of the 75 tested antibodies were selected for inclusion in an exemplary ovarian cancer classification panel (see Appendix A). It is to be understood that any sub-combination of these 55 antibodies may be used in constructing an inventive ovarian cancer classification panel. It will also be appreciated that additional antibodies may be added to or removed from an inventive ovarian cancer classification panel as more tumor markers are identified and/or more samples are tested (e.g., those identified in Examples 16 and 18 or others).

Example 18

Ovarian Cancer Classification Panel (Russian Ovarian Cohort)

The present inventors identified yet other exemplary antibodies for use in classifying ovarian tumors using a third tissue array comprised of approximately 260 independent ovarian tumor samples from a cohort of ovarian cancer patients (the UAB ovarian cohort). 247 of the 460 differentially staining antibodies of Example 1 exhibited a reproducibly robust staining pattern on tissues relevant for this application. Of the 260 ovarian tumor samples in the tissue array about 226 were included in the consensus panel. Using the method described in Example 16, 47 of the 247 tested antibodies were selected for inclusion in an exemplary ovarian cancer classification panel (see Appendix A). It is to be understood that any sub-combination of these 47 antibodies may be used in constructing an inventive ovarian cancer classification panel. It will also be appreciated that additional antibodies may be added to or removed from an inventive ovarian cancer classification panel as more tumor markers are identified and/or more samples are tested (e.g., those identified in Examples 16 and 17 or others).

Example 19

Correlating Interaction Partner Binding with Clinical Prognostic Data in Ovarian Cancer This Example describes the identification of exemplary panels of antibodies whose binding has been shown to correlate with the prognosis of ovarian cancer patients.

Samples from patients were stained with antibodies from the ovarian cancer classification panel identified in Appendix A (as previously described in Examples 16-18). The stained samples were then scored in a semi-quantitative fashion; scoring methods 1-3 use the following schemes: method 1 (0=negative; 1=weak; 2=strong); method 2 (0=negative; 1=weak or strong); and method 3 (0=negative or weak; 1=strong). For each antibody, the scoring system used was selected to produce the most significant prognostication of the patients, as determined by a log-rank test (e.g., see Mantel and Haenszel, *Journal of the National Cancer Institute* 22:719-748, 1959). The results are presented in Appendix G. As shown, the antibodies were found to have differing significances for each of these categories of ovarian cancer patients.

It is to be understood that exclusion of a particular antibody from any prognostic panel based on these experiments is not determinative. Indeed, it is anticipated that additional data with other samples may lead to the identification of other antibodies (from Appendix A and beyond) that may have prognostic value for these and other classes of patients.

As for the breast study of Example 10 and the lung study of Example 11, the expected relationship between the staining of patient samples with each antibody and the recurrence of tumors was measured using the Kaplan-Meier estimate of expected recurrence and a log-rank test was used to determine the significance of different expected recurrences. This produces the p-value that is listed for each antibody in Appendix G. Preferred antibodies are those that produce a p-value of less than 0.10.

The degree to which these antibodies predicted recurrence was determined using a Cox univariate proportional hazard model. The "hazard ratio" listed in Appendix G for each antibody reflects the predicted increase in risk of recurrence for each increase in the staining score. Scores greater than 1.0 indicate that staining predicts an increased risk of recurrence compared to an average individual, scores less than 1.0 indicate that staining predicts a decreased risk.

It will be appreciated that these prognostic antibodies can be used alone or in combinations to predict recurrence (e.g., in combinations of 2, 3, 4, 5 or 6 antibodies). It will also be appreciated that while a given antibody may not predict recurrence when used alone, the same antibody may predict recurrence when used in combination with others. It will also be understood that while a given antibody or combination of antibodies may not predict recurrence in a subset of patients, the same antibody or combination of antibodies may predict recurrence in a different subset of patients.

As for the prognostic breast panels of Examples 10 and 12 and the prognostic lung panels of Example 13, these prognostic panels could be constructed using any method. Without limitation these include simple empirically derived rules, Cox multivariate proportional hazard models, regression trees, and/or neural networks. In certain embodiments a prognostic panel might include between 2-10 antibodies, for example 3-9 or 5-7 antibodies. It will be appreciated that these ranges are exemplary and non-limiting. Examples 20-23 describe some exemplary panels for ovarian cancer.

Example 20

Correlating Interaction Partner Binding with Prognosis and Response to Therapy in Ovarian Cancer This Example describes additional experiments identifying exemplary panels of antibodies whose binding has been shown to correlate with prognosis or response to therapy in ovarian cancer patients.

Antibody Selection

Targets for antibody production were selected on the basis of gene expression patterns in breast, ovarian cancer and other tumor types. 432 antibodies were screened by staining tissue arrays containing diverse normal and tumor tissue specimens. 21 of these antibodies were selected that separated tumors into divergent unsupervised groups; stained consistently using established protocols; and recognized proteins found to be differentially expressed in other tumor types (e.g., breast and lung). The 21 antibodies are set forth in Table 12 (see Appendix A for additional information).

TABLE 12

| AGI ID | Gene Name | Dilution |
| --- | --- | --- |
| s0015 | CPE-Receptor Claudin 4 | 200 |
| s0036 | Human GABA-A receptor pi subunit | 500 |
| s0059P2 | ataxia-telangiectasia group D-associated protein | 30 |
| s0063 | iroquois related homeobox 3 | 900 |
| s0090 | HUMAN MRNA FOR KIAA0275 GENE, COMPLETE CDS AA398230 | 200 |
| s0096 | ATPase, H+ transporting, lysosomal (vacuolar proton pump), beta polypeptide, 56/58 kD, isoform 1R7340 | 800 |
| s0124 | KIAA1252 (pterin-4a-carbinolamine dehydratase) | 990 |
| s0126 | Putative RHO-GAP containing protein AK002114 | 450 |
| s0143P3 | fasn | 300 |
| s0202 | PTK7 | 780 |
| s0244 | DACh dachshund (*drosophila*) homologue | 1350 |
| s0260 | KIAA0253 | 2400 |
| s0296P1 | Solute Carrier Family 7, member 5/LAT1 protein | 450 |
| s0330 | aldo-keto reductase family 1, member C1/C2 | 30000 |
| s0398 | FAT tumor suppressor (*Drosophila*) homolog (FAT) | 45 |
| s0447 | papillary renal cell carcinoma (translocation-associated) (prcc) | 4000 |
| s0545 | RNA methyltransferase (HpaII tiny fragments locus 9C) | 1200 |
| s0640 | PROC: protein C (inactivator of coagulation factors Va and VIIIa) | 1800 |
| s0691 | solute carrier family 7, (cationic amino acid transporter, y+ system) member 11 | 1500 |
| s0695 | integrin, beta 4 | 2700 |
| s0702 | Solute Carrier Family 7, member 5/LAT1 protein | 89100 |

Patient Selection

Patients were selected from the years 1995-2003 with initial surgery being performed at a single institution having a diagnosis of epithelial ovarian or primary peritoneal carcinoma. A summary of patient clinical data is provided in Table 13. Survival data calculated from completion of primary therapy is provided in Table 14. All patient tumor samples were from chemo-naïve patients undergoing initial debulking effort. All patient samples were treated with platinum containing regimens. Patients must have been followed for an adequate enough time to establish platinum sensitivity or resistance (>12 months for patients without recurrence or progression). Clinical data extracted included histology, tumor grade, stage, and debulking status (residual tumor).

TABLE 13

|  | Number | % |
|---|---|---|
| Stage |  |  |
| I | 9 | 6% |
| II | 23 | 14% |
| III/IV | 127 | 79% |
| Unknown | 2 | 1% |
| Grade |  |  |
| 1 | 8 | 5% |
| 2 | 37 | 23% |
| 3 | 72 | 45% |
| Unknown | 44 | 27% |
| Histology |  |  |
| Pap Serous | 62 | 39% |
| Endomet | 59 | 37% |
| Mucinous | 1 | 1% |
| Mixed | 17 | 11% |
| Undiff | 7 | 4% |
| Clear | 3 | 2% |
| Other/Unknown | 11 | 7% |
| Debulking |  |  |
| Optimal | 75 | 5% |
| Suboptimal | 72 | 45% |
| Unknown | 14 | 9% |
| Taxol/Platinum | 144 | 89% |

TABLE 14

|  | Months | 95% CI |
|---|---|---|
| Med PFS |  |  |
| Optimal | 25 | 15-36 |
| Suboptimal | 8.6 | 5.4-12 |
| Med OS |  |  |
| Optimal | 43 | 33-53 |
| Suboptimal | 35 | 28-42 |
| PFS by Stage |  |  |
| I | 42 | — |
| II | 43 | 16-70 |
| III/IV | 12 | 9-16 |

|  | Number | % |
|---|---|---|
| Chemosensitivity |  |  |
| Progressive Disease | 31 | 19 |
| <6 mo Platinum free | 24 | 15 |
| 6-12 mo Plat free | 24 | 15 |
| >12 mo Plat free | 79 | 49 |
| Unknown/not stated | 3 | 2 |
| Extreme Platinum Sensitivity |  |  |
| <6 mo/Progressive Disease | 55 | 34 |
| >12 mo Plat free | 79 | 49 |

Tissue Microarray Construction 0.6 mm cores were obtained from archival paraffin embedded tumor samples and arrayed into new paraffin blocks. These were then sectioned and stained with various antibodies using ENVISION immunohistochemistry established protocols. Each tissue array contained relevant positive and negative tissue controls from divergent tissue types. Each case was assigned a semi-quantitative score that reflected the presence or absence of tumor tissue and the relative strength of the stain (score: 0=tumor present-no stain, 1=no information, 2=tumor present-weak stain, 3=tumor present-strong stain).

Statistics

Univariate statistics were computed using Chi-Square for antibody prediction of debulking status, chemosensitivity (<12 months, >12 months platinum free interval to recurrence), and extreme chemosensitivity (<6 month vs. >12 month platinum free interval). Kaplan-Meier curves were generated for each antibody comparing binding (any staining vs. no staining) using log-rank test for disease free (DFS) and overall (OS) survival. An unsupervised two-step cluster analysis was performed to identify groups with similar IHC binding patterns. Kaplan-Meier curves were generated comparing cluster groups for DFS and OS. Cox regression was performed to assess for independence of cluster membership as a prognostic variable controlling for stage, grade, and debulking status. Logistic regression was performed to assess independence of antibody binding for debulking status and platinum sensitivity.

Results

Of the 21 antibodies analyzed by univariate analysis, three antibodies were determined to be significant for ability to achieve optimal debulking (s0063, s0090 and s0260), three for chemosensitivity (s0090, s0202 and s0260), and five for disease free survival (s0059P2, s0124, s0202, s0260 and s0296P1) (see Table 15, near-significant values are included for comparison only). All seven surpassed tumor grade and histology for their ability to predict dependent outcomes.

TABLE 15

| AGI ID | Debulking[1] | Platinum Sensitivity[1] | Extreme Plat Sensitivity[1] | DFS[2] | Direction of factor |
|---|---|---|---|---|---|
| s0015 | NS | NS | NS | NS |  |
| s0036 | NS | NS | NS | 0.090 |  |
| s0059P2 | NS | NS | NS | 0.040 | Negative |
| s0063 | 0.020 | NS | NS | NS | Negative |
| s0090 | 0.003 | 0.016 | 0.014 | NS | Negative |
| s0096 | NS | NS | NS | NS |  |
| s0124 | NS | NS | NS | 0.016 | Negative |
| s0126 | 0.090 | NS | NS | NS |  |
| s0143P3 | NS | NS | NS | 0.090 |  |
| s0202 | NS | 0.040 | NS | 0.007 | Negative |
| s0244 | NS | NS | NS | NS |  |
| s0260 | 0.030 | 0.004 | 0.010 | 0.007 | Negative |
| s0296P1 | NS | NS | NS | 0.050 | Positive |
| s0330 | NS | NS | NS | NS |  |
| s0398 | NS | NS | NS | NS |  |
| s0447 | 0.090 | NS | NS | NS |  |
| s0545 | NS | NS | NS | NS |  |
| s0640 | NS | NS | NS | NS |  |
| s0691 | NS | NS | NS | NS |  |
| s0695 | NS | NS | NS | 0.090 |  |
| s0702 | NS | NS | NS | NS |  |
| Stage | <0.001 | 0.001 | 0.013 | 0.004 |  |
| Grade | NS | 0.07 | NS | NS |  |
| Histology | NS | NS | NS | NS |  |
| Debulking | — | <0.001 | <0.001 | <0.001 |  |
| Cluster Membership | 0.007 | 0.008 | 0.026 | 0.001 |  |

[1]P value using Chi-Squared test
[2]P value using log rank test

It will be appreciated that these prognostic antibodies can be used alone or in combinations (e.g., in combinations of 2, 3, 4, 5, 6 or more antibodies). It will also be appreciated that while a given antibody may not be prognostic when used alone, the same antibody may add prognostic value when used in combination with others. It will also be understood that while a given antibody or combination of antibodies may not be prognostic in a subset of patients, the same antibody or combination of antibodies may be prognostic in a different subset of patients.

As for the prognostic breast panels of Examples 10 and 12 and the prognostic lung panels of Example 13, these prognostic panels could be constructed using any method. Without limitation these include simple empirically derived rules, Cox multivariate proportional hazard models, regression trees, and/or neural networks. In certain embodiments a prognostic panel might include between 2-10 antibodies, for example 3-9 or 5-7 antibodies. It will be appreciated that these ranges are exemplary and non-limiting.

Six antibodies were selected for inclusion into cluster analysis based on significant or near-significant univariate statistics as well as performance in similar analyses in other tumor arrays. Two-step cluster analysis distinguished three patient clusters (see Table 16) of which membership in cluster 1 (n=82, 50.9%) was associated with significantly longer DFS, optimal debulking and platinum sensitivity.

TABLE 16

| AGI ID | # Evaluated | Cluster 1 Pos (%) | Cluster 2 Pos (%) | Cluster 3 Pos (%) |
|---|---|---|---|---|
| s0059 | 151 | 4 (3%) | 47 (31%) | 0 (0%) |
| s0096 | 152 | 44 (29%) | 59 (39%) | 2 (1%) |
| s0124 | 152 | 31 (20%) | 35 (23%) | 4 (3%) |
| s0202 | 151 | 1 (1%) | 6 (4%) | 0 (0%) |
| s0260 | 153 | 0 (0%) | 35 (23%) | 1 (1%) |
| s0691 | 150 | 27 (18%) | 15 (10%) | 2 (1%) |

Cox regression analysis demonstrated that the association with DFS was independent of stage, grade, histology, and debulking status. Logistic regression was performed to assess independence of antibody binding for debulking status and platinum sensitivity. Table 17 summarizes the statistical results from the Cox and logistic regression analysis.

TABLE 17

| AGI ID | Debulking[1] | Platinum Sensitivity[1] | DFS[2] |
|---|---|---|---|
| s0059 | NS | NS | NS |
| s0063 | NS | NS | NS |
| s0090 | 0.043 | NS | NS |
| s0124 | NS | NS | 0.003 |
| s0202 | NS | NS | NS |
| s0260 | NS | NS | NS |
| s0296 | NS | NS | NS |
| s0691 | NS | NS | 0.028 |
| Stage | | | NS |
| Debulking | | | 0.002 |
| Cluster | | | 0.040 |

[1]Logistic regression
[2]Cox analysis

Discussion

Several correlations between antibody binding and prognosis or response to therapy have been identified in this Example. Binding with s0063, s0090 and/or s0260 correlates highly with inability to optimally debulk tumors. This correlation is particularly strong with s0090. Binding with s0090, s0202 and/or s0260 correlates highly with platinum resistance. This correlation is particularly strong with s0260 and to a slightly lesser extent s0090. Binding with s0059P2, s0124, s0202, s0260 and/or s0296P1 correlates highly with shorter disease free survival. This correlation is particularly strong with s0202 and s0260 and to a slightly lesser extent s0124.

Example 21

Prognostic Ovarian Cancer Panels (Cox Model)

This Example builds on the results of Example 19 and describes the identification of exemplary panels of antibodies whose binding has been shown to correlate with the prognosis of ovarian cancer patients. These exemplary panels were generated using Cox proportional hazard analysis (as described in Example 10). Candidate panels were derived for prediction of recurrence using samples from the UAB ovarian cohort (see Example 17). Panels were chosen that identified patients with significantly increased risks of recurrence.

As previously noted, Cox proportional hazard analysis treats the component antibodies of a panel as additive risk factors. The panels for the specified patient classes were created by initially using all applicable antibodies, and then iteratively removing antibodies from the panel. If the removal of an antibody increased or did not affect the significance and prognostic ability of the panel as a whole, it was excluded, otherwise it was retained. In this manner preferred panels with minimal numbers of antibodies were created. Exemplary panels for ovarian cancer patients are presented in Tables 18-21. Antibodies within the preferred panels are ranked based on their relative contributions to the overall prediction function.

TABLE 18

| Panel | Analysis | P value[1] | Hazard ratio[2] |
|---|---|---|---|
| Ovarian | Cox | 1.17E−03 | 1.35 |
| AGI ID | Rank | P value[3] | Terms[4] |
| s0691 | 1 | 0.010 | 0.110, −0.280 |
| s0059P2 | 2 | 0.031 | −0.130, 0.250 |
| s0124 | 3 | 0.170 | −0.130, 0.200 |
| s0202 | 4 | 0.370 | −0.030, 0.350 |
| s0096 | 5 | 0.490 | −0.150, 0.090 |

[1]P value of overall panel
[2]Hazard ratio of overall panel
[3]P value of the contribution of a given antibody to the overall panel
[4]Contribution of given antibody to overall panel prediction function depending on IHC score (e.g., scores of 0 or 1 for s0059P2 which uses scoring method 2 [see Appendix G] result in its term in the model equaling −0.130 or 0.250, respectively).

TABLE 19

| Panel | Analysis | P value[1] | Hazard ratio[2] |
|---|---|---|---|
| Ovarian | Cox | 4.6E−06 | 1.53 |
| AGI ID | Rank | P value[3] | Terms[4] |
| s0691 | 1 | 0.009 | 0.16, −0.59 |
| s0643 | 2 | 0.010 | 0.19, −0.41 |
| s0059P2 | 3 | 0.015 | −0.15, 0.35 |
| s0096 | 4 | 0.600 | −0.06, 0.04 |

[1,2,3,4]See Table 18

TABLE 20

| Panel | Analysis | P value[1] | Hazard ratio[2] |
|---|---|---|---|
| Ovarian | Cox | 4.5E−06 | 1.89 |

| AGI ID | Rank | P value[3] | Terms[4] |
|---|---|---|---|
| s0691 | 1 | 0.001 | 0.16, −0.57 |
| s0059P2 | 2 | 0.012 | −0.16, 0.39 |
| s0643 | 3 | 0.024 | 0.16, −0.36 |
| s6005 | 4 | 0.095 | −0.65, 0.09 |
| s0096 | 5 | 0.760 | −0.02, 0.02 |

[1,2,3,4]See Table 18

TABLE 21

| Panel | Analysis | P value[1] | Hazard ratio[2] |
|---|---|---|---|
| Ovarian | Cox | 5.5E−06 | 1.87 |

| AGI ID | Rank | P value[3] | Terms[4] |
|---|---|---|---|
| s0059P2 | 1 | 0.012 | −0.16, 0.38 |
| s0691 | 2 | 0.014 | 0.15, −0.52 |
| s0643 | 3 | 0.024 | 0.16, −0.36 |
| s6005 | 4 | 0.083 | −0.66, 0.09 |

[1,2,3,4]See Table 18

The prognostic value of these exemplary panels were assessed by generating Kaplan-Meier recurrence curves for the combined patients of the UAB ovarian cohort. For each patient the pattern of antibody staining with the applicable panel (i.e., Tables 18-21) was then assessed. Patients whom the panels predicted as being strongly unlikely to recur were given the prediction of "good". Patients whom the panels predicted as being strongly likely to recur or as neither being strongly likely to recur or not recur were grouped in a "poor" prognosis group. Kaplan-Meier curves were then calculated based on recurrence (and optionally survival) data for patients within each group. FIG. 19 shows the recurrence (and survival) curves that were obtained when the ovarian cancer patients were placed in "good" (upper curve) or "poor" (lower curve) prognosis groups using the panel of Table 18. FIGS. 20-22 show the recurrence curves that were obtained when the ovarian cancer patients were placed in "good" (upper curve) or "poor" (lower curve) prognosis groups using the panels of Tables 19-21, respectively.

While preferred Cox panels of the invention for ovarian cancer patients include each of the listed antibodies, it is to be understood that other related panels are encompassed by the present invention. In particular, it will be appreciated that the present invention is in no way limited to the specific antibodies listed. For example, other antibodies directed to the same biomarker(s) may be used (e.g., it can be readily seen from Appendix A that antibody s0059P2 can be replaced with other antibodies directed to biomarker Hs.504115; etc.). Other antibodies from Appendix G may be added to any given panel without necessarily diminishing the utility of a panel for patient prognosis. The inclusion of antibodies beyond those listed in Appendix G is also within the scope of the invention. In certain embodiments less than all of the listed antibodies may be used in a prognostic panel.

In one set of embodiments, a Cox panel for ovarian patients will include at least two antibodies selected from the group consisting of antibodies directed to the biomarkers with NCBI Entrez GeneIDs 23650, 525, 8879, 5754, 7090, 23657 and 3852 (e.g., s0059P2, s0096, s0124, s0202, s0643, s0691 and s6005, see Tables 18-21 and Appendix A). Preferably, the panel will include an antibody directed to the biomarker with NCBI Entrez GeneID 23650 (e.g., s0059P2) and/or an antibody directed to the biomarker with NCBI Entrez GeneID 23657 (e.g., s0691) and optionally at least one antibody directed to a biomarker selected from the group consisting of biomarkers with NCBI Entrez GeneIDs 525, 8879, 5754, 7090 and 3852 (e.g., s0096, s0124, s0202, s0643 and s6005). All permutations of these antibodies are encompassed. In some of these embodiment, a Cox panel for ovarian patients will include antibodies to the biomarker with NCBI Entrez GeneID 23650 (e.g., s0059P2) and the biomarker with NCBI Entrez GeneID 23657 (e.g., s0691).

As set forth in Table 18, in one set of preferred ovarian panels, antibodies to the biomarkers with NCBI Entrez GeneIDs 23650 (e.g., s0059P2) and 23657 (e.g., s0691) are used in conjunction with antibodies to one or more of the biomarkers with NCBI Entrez GeneIDs 525, 8879 and 5754 (e.g., s0096, s0124 and s0202). For example an ovarian panel may include antibodies to the biomarkers with NCBI Entrez GeneIDs 23650, 23657 and 8879 (e.g., s0059P2, s0691 and s0124). This ovarian panel may further include an antibody to the biomarker with NCBI Entrez GeneID 525 and/or 5754 (e.g., s0096 and/or s0202).

As set forth in Tables 19-21, in another set of preferred ovarian panels, antibodies to the biomarkers with NCBI Entrez GeneIDs 23650 (e.g., s0059P2) and 23657 (e.g., s0691) are used in conjunction with an antibody to the biomarker with NCBI Entrez GeneID 7090 (e.g., s0643). Optionally, an antibody to the biomarker with NCBI Entrez GeneID 525 (e.g., s0096) is also included. Alternatively (or additionally), an antibody to the biomarker with NCBI Entrez GeneID 3852 (e.g., s6005) is also included in an inventive ovarian panel.

It is to be understood that these exemplary Cox panels may be used alone, in combination with one another or in conjunction with other panels and/or independent prognostic factors. Each of the exemplary prognostic panels were determined to be independent stage.

The present invention also encompasses methods of assessing the prognosis of a patient having an ovarian tumor using these exemplary panels. After obtaining a tumor sample from a patient with unknown prognosis the sample is contacted with one of the aforementioned ovarian panels. The patient's likely prognosis is then assessed based upon the positive or negative binding of the antibodies in the panel to the tumor sample.

Example 22

Prognostic Ovarian Cancer Panels (Split Cox Model)

This Example builds on the results of Example 19 and 21 and describes the identification of exemplary panels of antibodies whose binding has been shown to correlate with the prognosis of ovarian cancer patients. These exemplary panels were generated using a "split" Cox model. Specifically, the patients in the UAB cohort were first divided based on whether they stained with an antibody to the biomarker with NCBI Entrez GeneID 55189 (e.g., s0126).

s0126 was chosen to split the ovarian data as it had been noted that it stained approximately half the patient samples and appeared to be a significant factor in driving the hierarchical clustering of the patient samples. Furthermore, it had a very significant interaction (p=0.008) with s0296, an antibody that has proven to be a strong prognosticator in breast, lung, and ovarian cancer. This interaction suggests that s0296 contributes differently to a prognostic model when s0126 is positive compared to when s0126 is negative. This is potentially similar to what we previously observed in lung cancer, wherein s0296 has very different associations with prognosis depending on whether the tumor was from an adenocatcinoma or a squamous cell lung cancer.

Two prognostic panels were then generated by independently using Cox proportional hazard analysis on the two patient sets (as described in Example 10). The panel generated from patients that were s0126 positive is shown in Table 22. The panel generated from patients that were s0126 negative is shown in Table 23.

TABLE 22

| Panel | Analysis | P value[1] | Hazard ratio[2] |
|---|---|---|---|
| Ovarian (s0126 +ve) | Cox | 2.1E−03 | 1.78 |

| AGI ID | Rank | P value[3] | Terms[4] |
|---|---|---|---|
| s0124 | 1 | 0.023 | −0.340, 0.420 |
| s0238 | 2 | 0.035 | −0.320, 0.410 |
| s0672 | 3 | 0.085 | −0.070, 0.440 |

[1,2,3,4]See Table 18

TABLE 23

| Panel | Analysis | P value[1] | Hazard ratio[2] |
|---|---|---|---|
| Ovarian (s0126 −ve) | Cox | 8.7E−05 | 4.36 |

| AGI ID | Rank | P value[3] | Terms[4] |
|---|---|---|---|
| s0059P2 | 1 | 0.005 | −0.450, 0.940 |
| s0140 | 2 | 0.011 | 0.440, −1.050 |
| s0296P1 | 3 | 0.230 | 0.190, −1.080 |

[1,2,3,4]See Table 18

The prognostic value of the exemplary panels of Tables 22 and 23 was also assessed by generating Kaplan-Meier recurrence curves for ovarian patients. Patients whom the panels predicted as being strongly unlikely to recur were given the prediction of "good". Patients whom the panels predicted as being strongly likely to recur were placed in the "bad" prognosis group. Patients whom the panels predicted as neither being strongly likely to recur or not recur were also placed in a third "moderate" prognosis group. Kaplan-Meier curves were then calculated based on recurrence data for patients within each group. FIG. 23 shows the recurrence and survival curves that were obtained for ovarian patients in the "good" (lower curve), "moderate" (middle curve) and "bad" (upper curve) prognostic groups.

While a preferred "split" Cox panels of the invention for ovarian cancer patients will include each of the antibodies of Tables 22-23, it is to be understood that other related panels are encompassed by the present invention. In particular, it will be appreciated that the present invention is in no way limited to the specific antibodies listed. For example, other antibodies directed to the same biomarker(s) may be used. Other antibodies from Appendix G may be added to any given panel without necessarily diminishing the utility of a panel for patient prognosis. The inclusion of antibodies beyond those listed in Appendix G is also within the scope of the invention. In certain embodiments less than all of the listed antibodies may be used in a prognostic panel.

In general, a "split" Cox panel for ovarian patients will include an antibody directed to the biomarker with NCBI Entrez GeneID 55789 (e.g., s0126).

The panel may then also include one or more of the antibodies selected from the group consisting of antibodies directed to the biomarkers with NCBI Entrez GeneIDs 8879, 9213, 605 (e.g., s0124, s0238 and s0672, see Table 22 and Appendix A). For example, the panel may include an antibody directed to the biomarker with NCBI Entrez GeneID 8879 (e.g., s0124). Optionally the panel may also include an antibody directed to the biomarkers with NCBI Entrez GeneIDs 9213 and/or 605 (e.g., s0238 and/or s0672).

Alternatively (or additionally), a "split" Cox panel may also include one or more of the antibodies selected from the group consisting of antibodies directed to the biomarkers with NCBI Entrez GeneIDs 23650, 667, 8140 (e.g., s0059P2, s0140 and s0296P1, see Table 23 and Appendix A). For example, the panel may include an antibody directed to the biomarker with NCBI Entrez GeneID 23650 (e.g., s0059P2). Optionally the panel may also include an antibody directed to the biomarkers with NCBI Entrez GeneIDs 667 and/or 8140 (e.g., s0140 and/or s0296P1).

It is to be understood that these exemplary "split" Cox panels may be used alone, in combination with one another or in conjunction with other panels and/or independent prognostic factors.

The present invention also encompasses methods of assessing the prognosis of a patient having an ovarian tumor using these exemplary panels. After obtaining a tumor sample from a patient with unknown prognosis the sample is contacted with one of the aforementioned panels. The patient's likely prognosis is then assessed based upon the positive or negative binding of the antibodies in the panel to the tumor sample.

Example 23

Prognostic Ovarian Cancer Panels (Regression Tree Model)

This Example builds on the results of Example 19 and describes the identification of exemplary panels of antibodies whose binding has been shown to correlate with the prognosis of ovarian cancer patients. These exemplary panels were generated using regression tree analysis (as described in Example 12).

As previously noted, regression trees classify the patients into a number of subclasses each defined by their pattern of binding to a unique set of antibodies from within a panel. An exemplary tree (or "dendrogram") for ovarian patients is shown in FIG. 24 which is discussed below. Regression trees were initially created with all applicable antibodies, and then "pruned" to a minimal complexity (least number of terminal nodes without losing too much prognostic ability) using a cross validation procedure. This cross validation procedure involved building panels and dendrograms using a series of patient groups that were picked from the total patient set using a series of increasingly pruned trees. The results over the tested groups were summed and the minimally complex least error-prone panel and dendrogram were chosen. The resulting dendrogram was further simplified by placing nodes with a range of response values into the classes "good" (G) or "poor" (P). Table 24 lists the antibodies of an exemplary ovarian tree panel that was constructed as described above. The dendrogram for this panel is illustrated in FIG. 24. This exemplary prognostic panel was determined to be independent of stage; however, stage was found to add prognostic information.

TABLE 24

| Panel | Analysis | P value[1] | Hazard ratio[2] |
|---|---|---|---|
| Ovarian | Tree | 8.9E−05 | 2.38 |
| AGI ID | | Rank | |
| s0059P2 | | 1 | |
| s0643 | | 2 | |
| s0691 | | 3 | |

[1]P value of overall panel
[2]Hazard ratio of overall panel

As illustrated in FIG. 24, if a patient is positive for staining at a given node his or her prognosis decision tree follows the branch marked with a "+". Conversely if a patient is negative for staining at a given node his or her prognosis decision tree follows the branch marked "−". This is done until a terminus is reached.

For example, if patient A is negative for staining with s0059P2 and positive for staining with s0643 then, based on the dendrogram, his or her prognosis is "G" or "good". In contrast, if patient B is negative for staining with s0059P2, negative for staining with s0643 and negative for staining with s0691 then his or her prognosis is "P" or "poor". Similarly, if patient C is positive for staining with s0059P2 then his or her prognosis is "P" or "poor". It will be appreciated from the foregoing and FIG. 24 that the number of stains required in order to yield a prognosis will vary from patient to patient. However, from a practical standpoint (and without limitation), it may prove advantageous to complete all the stains for a given panel in one sitting rather than adopting an iterative approach with each individual antibody.

The prognostic value of the exemplary panel of Table 24 was also assessed by generating Kaplan-Meier recurrence curves for ovarian patients. Patients whom the panels predicted as being strongly unlikely to recur were given the prediction of "good". Patients whom the panels predicted as being strongly likely to recur or as neither being strongly likely to recur or not recur were grouped in a "poor" prognosis group. Kaplan-Meier curves were then calculated based on recurrence data for patients within each group. FIG. 25 shows the recurrence and survival curves that were obtained for ovarian patients in the "good" (upper curve) and "poor" (lower curve) prognostic groups.

From Table 24 it will be seen that a tree panel for ovarian patients might include an antibody to the biomarker with NCBI Entrez GeneID 23650 (e.g., s0059P2). Preferably the panel will also include an antibody to the biomarker with NCBI Entrez GeneID 7090 (e.g., s0643) and optionally an antibody to the biomarker with NCBI Entrez GeneID 23657 (e.g., s0691). In preferred embodiments, the tree panel includes an antibody to the biomarkers with NCBI Entrez GeneIDs 23650, 7090 and 23657 (e.g., s0059P2, s0643 and s0691).

It is to be understood that these exemplary tree panels may be used alone, in combination with one another or in conjunction with other panels and/or independent prognostic factors.

The present invention also encompasses methods of assessing the prognosis of a patient having an ovarian tumor using an inventive tree panel. For example, after obtaining a tumor sample from a patient with unknown prognosis the sample is contacted with one or more antibodies from the panel of Table 24. The patient's likely prognosis is then assessed based upon the positive or negative binding of the one or more antibodies to the tumor sample using the dendrogram of FIG. 24. The method generally includes a step of contacting a tumor sample with an antibody with NCBI Entrez GeneID 23650 (e.g., s0059P2). Optionally, a tumor sample is further contacted with an antibody to the biomarker with NCBI Entrez GeneID 7090 (e.g., s0643) and optionally with an antibody to the biomarker with NCBI Entrez GeneID 23657 (e.g., s0691). As mentioned above, tumor samples may be contacted with these antibodies in a single sitting or sequentially based on the binding results of a previous stain. Obviously the tumor sample may be divided and different antibodies contacted in any order with different fractions. Alternatively different original tumor samples may be contacted with different antibodies in a specific sequence.

OTHER EMBODIMENTS

Other embodiments of the invention will be apparent to those skilled in the art from a consideration of the specification or practice of the invention disclosed herein. It is intended that the specification and examples be considered as exemplary only, with the true scope of the invention being indicated by the following claims.

APPENDIX A2

| | Antibodies & Genes | | Antibody Generation (SEQ ID NO.) | | | |
|---|---|---|---|---|---|---|
| AGI ID | GENE NAME | ALIASES | Peptide 1 | Peptide 2 | Peptide 3 | TITER |
| S0011 | vav 3 oncogene | VAV3; VAV3 ONCOGENE; ONCOGENE VAV3; vav 3 oncogene | TEESINDEDIYKG LPDLIDE (13) | EKRTINGLRRITPK QVD (12) | DYISKSKEDVKLK (11) | 1:90-1:300 |
| S0017 | WAP four-disulfide core domain 2 | WFDC2; WAP5; dJ461P17.6; major epididymis-specific protein E4; epididymal secretory protein E4; WAP four-disulfide core domain 2; WAP domain containing protein HE4-V4; epididymis-specific, whey-acidic protein type, four-disulfide core; WAP four-disulfide | EKTGVCPELQAD QNCTQE (338) | PNDKEGSCPQV NIN (339) | RDQCQVDTQCP GQMK (340) | 1:25-1:500 |
| S0018 | secretoglobin, family 2A, member 2 | UGB2; MGB1; SCGB2A2; mammaglobin 1; secretoglobin, family 2A, member 2 | SKTINPQVSKTE YKELLQE (14) | DDNATTNAIDEL KEC (15) | NQTDETLSNVEV FMQ (16) | 1:300-1:1000 |
| S0020 | PPAR binding protein | RB18A; TRIP2; PPARGBP; PBP; CRSP1; PPARBP; CRSP200; DRIP230; PPAR-BINDING PROTEIN; PPARG binding protein; PPAR binding protein; CRSP, 200-KD SUBUNIT; PEROXISOME PROLIFERATOR-ACTIVATED RECEPTOR-BINDING PROTEIN; THYROID HORMONE RECEPTOR INTERACTOR 2; RECOGN | SSDDGIRPLPEY STEKHKK (17) | DGKSKDKPPKR KKADTE (19) | NKTKKKKSSRLP PEK (18) | 1:100 |
| S0021 | hypothetical protein FLJ23834 | FLJ23834; hypothetical protein FLJ23834 | KNKEPLTKKGET KTAERD (20) | KLTCTDLDSSPR SFRYS (21) | EVDYENPSNLAA GNKYT (22) | 1:200-1:2500 |
| S0022 | cytochrome P450 4Z1 | CYP4Z1; cytochrome P450 4Z1; cytochrome P450, family 4, subfamily Z, polypeptide 1 | KTLQVFNPLRFS RENSEKIH (23) | QHFAIIECKVAVA LT (24) | RKFLAPDHSRPP QPVRQ (25) | 1:50-1:500 |
| S0024 | RAS-like, estrogen-regulated, growth-inhibitor | RERG; RAS-like, estrogen-regulated, growth-inhibitor | MAKSAEVKLAIF GRAGVGK (28) | VLPKNILDEIKK PKN (26) | YELCREVRRRR MVQGKT (27) | 1:900-1:2700 |
| S0032 | fatty acid binding protein 3, muscle and heart (mammary-derived growth inhibitor) | MDGI; O-FABP; FABP3; FABP11; H-FABP; FATTY ACID-BINDING PROTEIN, SKELETAL MUSCLE; Fatty acid-binding protein 3, muscle; fatty acid binding protein 11; FATTY ACID-BINDING PROTEIN, MUSCLE AND HEART; fatty acid binding protein 3, muscle and heart (mammary-de | TKPTTHFKNGDIL TLKTH (31) | KNTEISFKLGVEF DE (29) | HLQKWDGQETT LVRE (30) | 1:225 |
| S0036 | gamma-aminobutyric acid (GABA)A receptor, pi | GABRP; GAMMA-AMINOBUTYRIC ACID RECEPTOR, PI; GABA-A RECEPTOR, PI POLYPEPTIDE; gamma-aminobutyric acid (GABA) A receptor, pi | DGNDVEFTWLR GNDSVRGLEH (34) | LQQMAAKDRGT TKEVEEVS (32) | KRKISFASIEISS DNVDYSD (33) | 1:250-1:500 |
| S0037 | annexin A8 | ANX8; ANXA8; annexin VIII; annexin A8 | QRQQIAKSFKAQ FGKDLTE (35) | REIMKAYEEDYG SSLEEDIQ (36) | EEYEKIANKSIED SIKSE (37) | 1:30-1:40 |
| S0039 | CDNA FLJ25076 fis, clone CBL06117 | similar to 3110006E14Rik protein; CDNA FLJ25076 fis, clone CBL06117 | EGGSLVPAARQ QHCTQVRSRR (38) | RKAGKSKKSFSR KEAE (39) | KTHEKYGWVTP PVSDG (40) | 1:50-1:30000 |
| S0040 | ATP-binding cassette, sub-family B (MDR/TAP), member 1 | P-gp; PGY1; CLCS; ABCB1; ABC20; CD243; GP170; MDR1; doxorubicin resistance; colchicin sensitivity; P-GLYCOPROTEIN 1; multidrug resistance 1; P glycoprotein 1; ATP-binding cassette sub-family B member 1; ATP-BINDING CASSETTE, SUBFAMILY B, MEMBER 1; ATP-bin | MDLEGDRNGGA KKKN (41) | NLEDLMSNITNR SDINDTG (42) | RGSQAQDRKLS TKEA (43) | 1:200-1:400 |

APPENDIX A2-continued

| AGI ID | Antibodies & Genes | | Antibody Generation (SEQ ID NO.) | | | |
|---|---|---|---|---|---|---|
| | GENE NAME | ALIASES | Peptide 1 | Peptide 2 | Peptide 3 | TITER |
| S0041 | ATP-binding cassette, sub-family B (MDR/TAP), member 4 | MDR3; PGY3; PFIC-3; ABCB4; ABC21; MDR2/3; P-GLYCOPROTEIN 3; MULTIDRUG RESISTANCE 3; P-glycoprotein-3/multiple drug resistance-3; P glycoprotein 3/multiple drug resistance 3; ATP-binding cassette, sub-family B (MDR/TAP), member 4; ATP-binding cassette, sub | MDLEAAKNGTA WRPTSAE (44) | NFSFPVNFSLSL LNPGK (45) | KNSQMCQKSLD VETDG (46) | 1:60-1:300 |
| S0042 | ATP-binding cassette, sub-family C (CFTR/MRP), member 1 | ABCC1; MRP1; GS-X; ABC29; multidrug resistance protein; MULTIDRUG RESISTANCE-ASSOCIATED PROTEIN 1; multiple drug resistance-associated protein; multiple drug resistance protein 1; ATP-BINDING CASSETTE, SUBFAMILY C, MEMBER 1; ATP-binding cassette, sub-fami | MALRGFCSADG SD (47) | KNWKKECAKTR KQPVK (48) | DSIERRPVKDGG GTNS (49) | 1:40-1:500 |
| S0043 | ATP-binding cassette, sub-family C (CFTR/MRP), member 2 | MRP2; cMRP; CMOAT; ABCC2; ABC30; DJS; MULTIDRUG RESISTANCE-ASSOCIATED PROTEIN 2; canalicular multispecific organic anion transporter; MULTISPECIFIC ORGANIC ANION TRANSPORTER, CANALICULAR; ATP-BINDING CASSETTE, SUBFAMILY C, MEMBER 2; ATP-binding cassette, | MLEKFCNSTFW NSSFLDSPE (50) | SILCGTFQFQTLI RT (51) | ENNESSNNPSSI AS (52) | 1:50-1:333 |
| S0044 | ATP-binding cassette, sub-family C (CFTR/MRP), member 4 | MOAT-B; MRP4; MOATB, ABCC4; EST170205; MULTIDRUG RESISTANCE-ASSOCIATED PROTEIN 4; MULTISPECIFIC ORGANIC ANION TRANSPORTER B; ATP-binding cassette, sub-family C, member 4; ATP-BINDING CASSETTE, SUBFAMILY C, MEMBER 4; ATP-binding cassette, sub-family C (CFT | QEVKPNPLQDA NICSR (53) | DEISQRNRQLPS DGKK (54) | VQDFTAFWDKA SETPTLQ (55) | 1:20-1:100 |
| S0045 | ATP-binding cassette, sub-family C (CFTR/MRP), member 3 | MOAT-D; ABC31; MLP2; ABCC3; EST90757; cMOAT2; MULTIDRUG RESISTANCE-ASSOCIATED PROTEIN 3; canalicular multispecific organic anion transporter; CANALICULAR MULTISPECIFIC ORGANIC ANION TRANSPORTER 2; ATP-BINDING CASSETTE, SUBFAMILY C, MEMBER 3; ATP-binding cas | MDALCGSGELG SKFWDSN (56) | RKQEKQTARHK ASAA (57) | DPQSVERKTISPG (58) | 1:2000 |
| S0046 | ATP-binding cassette, sub-family C (CFTR/MRP), member 5 | MOAT-C; ABCC5; MRP5; EST277145; ABC33; SMRP; pABC11; MOATC; MULTIDRUG RESISTANCE-ASSOCIATED PROTEIN 5; canalicular multispecific organic anion transporter C; ATP-binding cassette, sub-family C, member 5; ATP-BINDING CASSETTE, SUBFAMILY C, MEMBER 5; ATP-bi | MKDIDIGKEYIIPS PGYRS (59) | RDREDSKFRRT RPLECQD (60) | SKHESSDVNCR RLER (61) | 1:100-1:450 |
| S0047 | ATP-binding cassette, sub-family C (CFTR/MRP), member 6 | MRP6; ARA; EST349056; ABCC6; MOATE; PXE; MLP1; ABC34; ANTHRACYCLINE RESISTANCE-ASSOCIATED PROTEIN; MULTIDRUG RESISTANCE-ASSOCIATED | MAAPAEPCAGQ GVWNQTEPE (62) | DPGVVDSSSSG SAAGKD (63) | HTLVAENAMNAEK (64) | 1:50 |

APPENDIX A2-continued

| | Antibodies & Genes | | Antibody Generation (SEQ ID NO.) | | | |
|---|---|---|---|---|---|---|
| AGI ID | GENE NAME | ALIASES | Peptide 1 | Peptide 2 | Peptide 3 | TITER |
| S0048 | ATP-binding cassette, sub-family B (MDR/TAP), member 11 | PROTEIN 6; ATP-binding cassette, sub-family C, member 6; ATP-BINDING CASSETTE, SUBFAMILY C, MEMBER 6; ATP-binding cassette, BSEP; AB0B11; PFIC-2; SPGP; PGY4; PFIC2; ABC16; SISTER OF P-GLYCOPROTEIN; bile salt export pump; progressive familial intrahepatic cholestasis 2; ABC member 16, MDR/TAP subfamily; ATP-BINDING CASSETTE, SUBFAMILY B, MEMBER 11; ATP-binding cassette, sub-fam | MSDSVILRSIKKF GEEND (67) | TNSSLNQNMTN GTR (67) | QEVLSKIQHGHT IIS (65) | 1:600 |
| S0049 | ATP-binding cassette, sub-family B (MDR/TAP), member 10 | MTABC2; EST20237; MABC2; M-ABC2; ABCB10; MITOCHONDRIAL ABC PROTEIN 2; ATP-BINDING CASSETTE, SUBFAMILY B, MEMBER 10; ATP-binding cassette, sub-family B, member 10; ATP-binding cassette, sub-family B (MDR/TAP), member 10 | GADDPSSVTAEE IQR (68) | NAVASPEPPRF NT (69) | KPNGIYRKLMNK QSFISA (70) | 1:10-1:25 |
| S0050 | transporter 1, ATP-binding cassette, sub-family B (MDR/TAP) | RING4; ABC17; D6S114E; ABCB2; TAP1; APT1; PEPTIDE TRANSPORTER PSF1; TRANSPORTER, ABC, MHC, 1; ABC transporter, MHC 1; antigen peptide transporter 1; peptide supply factor 1; ABC TRANSPORTER, MHC 1; ATP-BINDING CASSETTE, SUBFAMILY B, MEMBER 2; TRANSPORTER | MASSRCPAPRG CR (71) | QGGSGNPVRR (72) | EFVGDIYNNTM GHVHS (73) | 1:80 |
| S0052 | ATP-binding cassette, sub-family C (CFTR/MRP), member 8 | SUR1; MRP8; PHHI; ABC36; ABCC8; HRINS; sulfonylurea receptor (hyperinsulinemia); SULFONYLUREA RECEPTOR, BETA-CELL HIGH-AFFINITY; ATP-binding cassette, sub-family C, member 8; ATP-BINDING CASSETTE, SUBFAMILY C, MEMBER 8; ATP-binding cassette, sub-family C | MPLAFCGSENH SAAYR (74) | DHLGKENDVFQ PKTQFLG (75) | EIREEQCAPHEP TPQG (76) | 1:25-1:150 |
| S0053 | ATP-binding cassette, sub-family C (CFTR/MRP), member 9 | ABCC9; ABC37; sulfonylurea receptor 2A; ATP-BINDING CASSETTE, SUBFAMILY C, MEMBER 9; ATP-binding cassette, sub-family C (CFTR/MRP), member 9; ATP-binding cassette, sub-family C, member 9 isoform SUR2B; ATP-binding cassette, sub-family C, member 9 isoform | MSLSFCGNNISS (77) | QRVNETQNGTN NTTGiSE (78) | DEIGDDSWRTG ESSLPFES (79) | 1:25-1:50 |
| S0055 | integral membrane protein 2B | E25B; ABRI; E3-16; FBD; BRI2; BRICD2B; ITM2B; BRI GENE; BRICHOS domain containing 2B; integral membrane protein 2B | MVKVTFNSALAQ KEAKKDEPK (80) | QTIEENIKIFEEE EVE (81) | HDKETYKLQRRE TIKGIQKRE (82) | 1:450-1:500 |
| S0057 | ankyrin 3, node of Ranvier (ankyrin G) | ankyrin-G; ANK3; ankyrin-3, node of Ranvier; ankyrin 3 isoform 1; ankyrin 3 isoform 2; ankyrin 3, node of Ranvier (ankyrin G) | MAHAASQLKKN RDLEINAEE (85) | HKKETESDQDD EIEKTDRRQ (83) | EGFKVKTKKEIR HVEKKSHS (84) | 1:750 |
| S0058 | hypothetical protein FLJ21918 | FLJ21918; hypothetical protein FLJ21918 | ERALAAAQRCH KKVMKER (86) | TAGMKDLLSVFQ AYQ (87) | DPPRTVLQAPKE WVCL (88) | 1:20 |
| S0059 | tripartite motif-containing 29 | ATDC; TRIM29; tripartite motif-containing 29; | MEAADASRSNG | ELHLKPHLEGAA | EGEGLGQSLGN | 1:50-1:3000 |

APPENDIX A2-continued

| AGI ID | Antibodies & Genes | | Antibody Generation (SEQ ID NO.) | | | TITER |
|---|---|---|---|---|---|---|
| | GENE NAME | ALIASES | Peptide 1 | Peptide 2 | Peptide 3 | |
| | | ataxia-telangiectasia group D-associated protein; tripartite motif protein TRIM29 isoform alpha; tripartite motif protein TRIM29 isoform beta | SSPEARDAR (89) | FRDHQ (90) | FKDDLLN (91) | 1:30-1:90 |
| S0059P2 | tripartite motif-containing 29 | ATDC; TRIM29; tripartite motif-containing 29; ataxia-telangiectasia group D-associated protein; tripartite motif protein TRIM29 isoform alpha; tripartite motif protein TRIM29 isoform beta | ELHLKPHLEGAA FRDHQ (92) | N/A | N/A | |
| S0063 | iroquois homeobox protein 3 | IRX3; iroquois homeobox protein 3 | GSEERGAGRGS SGGREE (93) | KIWSLAETATSP DNPRRS (94) | KKLLKTAFQPVP RRPQNHLD (95) | 1:200-1:1200 |
| S0068 | RAS-like, estrogen-regulated, growth-inhibitor | RERG; RAS-like, estrogen-regulated, growth-inhibitor | RRSSTTHVKQAI NKMLTKISS (96) | N/A | N/A | 1:500-1:40000 |
| S0070 | G protein-coupled receptor 160 | GPCR150; GPR160; putative G protein-coupled receptor; G protein-coupled receptor 160 | MRRKNTCQNFM EYFCISLAF (97) | NETILYPFSSHS SYTVRSKK (98) | KVQIPAYIEMNIP LVILCQ (99) | 1:10-1:100 |
| S0072 | S100 calcium binding protein A8 (calgranulin A) | CP-10; L1Ag; CALPROTECTIN; 60B8AG; S100A8; MIF; CAGA; NIF; MRP8; MA387; CFAG; CGLA S100A8/S100A9 COMPLEX; cystic fibrosis antigen; S100 calcium-binding protein A8; S100 calcium binding protein A8 (calgranulin A) | MLTELEKALNSII DVYHK (100) | RDDLKKLLETEC PQYIRKKGAD (101) | KMGVAAHKKSH EESHKE (102) | 1:6500-1:10000 |
| S0073 | forkhead box A1 | HNF3A; MGC33105; TCF3A; FOXA1; HEPATOCYTE NUCLEAR FACTOR 3-ALPHA; hepatocyte nuclear factor 3, alpha | PESRKDPSGAS NPSADS (103) | HGLAPHESQLHL KGD (104) | EQQHKLDFKAYE QALQYS (105) | 1:100-1:2700 |
| S0073P2 | forkhead box A1 | HNF3A; MGC33105; TCF3A; FOXA1; HEPATOCYTE NUCLEAR FACTOR 3-ALPHA; hepatocyte nuclear factor 3, alpha | HGLAPHESQLHL KGD (106) | N/A | N/A | 1:50-1:450 |
| S0074 | trefoil factor 3 (intestinal) | TFF3; trefoil factor 3 (intestinal); trefoil factor 3; HITF, human intestinal trefoil factor | EEYVGLSANQC AVPAKDRVD (107) | RVDCGYPHVTP KECN (108) | VPWCFKPLQEA ECTF (109) | 1:2500-1:30000 |
| S0074P3 | trefoil factor 3 (intestinal) | TFF3; trefoil factor 3 (intestinal); trefoil factor 3, HITF, human intestinal trefoil factor | VPWCFKPLQEA ECTF (110) | N/A | N/A | 1:400-1:810 |
| S0076x1 | keratin 17 | PC2; PCHC1; KRT17; K17; CYTOKERATIN 17; keratin 17 | KKEPVTTRQVRT IVEE (111) | QDGKVISSREQV HQTTR (112) | SSSIKGSSGLGG GSS (113) | 1:200 |
| S0078 | kynureninase (L-kynurenine hydrolase) | 3.7.1.3; XANTHURENICACIDURIA; KYNU; HYDROXYKYNURENINURIA; KYNURENINASE DEFICIENCY; XANTHURENIC ACIDURIA; kynureninase (L-kynurenine hydrolase) | DEEDKLRHFREC FYIPKIQD (341) | KPRFGEETLRIE DILEVIEKE (342) | EERGCQLTITFS VPNKDVFQE (343) | 1:180-1:200 |
| S0079 | solute carrier family 39 (zinc transporter), member 6 | SLC39A6; LIV-1 protein, estrogen regulated; solute carrier family 39 (zinc transporter), member 6; solute carrier family 39 (metal ion transporter), member 6 | DHNHAASGKNK RKALCPDHD (114) | EEPAMEMKRGP LFSHLSSQNI (115) | QRYSREELKDA GVATL (116) | 1:200-1:800 |

APPENDIX A2-continued

| | Antibodies & Genes | | Antibody Generation (SEQ ID NO.) | | | |
|---|---|---|---|---|---|---|
| AGI ID | GENE NAME | ALIASES | Peptide 1 | Peptide 2 | Peptide 3 | TITER |
| S0081 | N-acetyltransferase 1 (arylamine N-acetyltransferase) | AAC1; 2.3.1.5; NAT1; arylamine N-acetyltransferase-1; ACETYL-CoA: ARYLAMINE N-ACETYLTRANSFERASE; ARYLAMINE N-ACETYLTRANSFERASE 1; N-acetyltransferase 1 (arylamine N-acetyltransferase); arylamide acetylase 1 (N-acetyltransferase 1) | MDIEAYLERIGYK KSRNKLDLE (117) | QMWQPLELISG KDQPQVPCVFR (118) | FNISLQRKLVPK HGDRFFTI (119) | 1:10-1:240 |
| S0086 | X-box binding protein 1 | XBP2; TREB5; XBP1; X-box-binding protein-1; X BOX-BINDING PROTEIN 1; X BOX-BINDING PROTEIN 2; X-box binding protein 1 | RQRLITHLSPEEK ALRRKLKNR (122) | EKTHGLVVENQE LRQRLGMD (121) | QPPFLCQWGRH QPSWKPLMN (120) | 1:180-1:400 |
| S0088 | claudin 10 | CPETRL3; OSP-L; CLDN10; claudin 10 isoform a; claudin 10 isoform b | NKITTEFFDPLFV EQK (344) | FSISDNNKTPRY TYNGAT (345) | EDFKTTNPSKQF DKNAYV (346) | 1:333-1:1000 |
| S0090 | sparc/osteonectin, cwcv and kazal-like domains proteoglycan (testican) 2 | KIAA0275; testican-2; SPOCK2; TESTICAN 2; SPARC/OSTEONECTIN, CWCV, AND KAZAL-LIKE DOMAINS PROTEOGLYCAN 2; sparc/osteonectin, cwcv and kazal-like domains proteoglycan (testican) 2 | EGDAKGLKEGE TPGNFMEDE (347) | EWCFCFWREKP PCLAELER (348) | EEEGEAGEADD GGYIW (349) | 1:100-1:800 |
| S0091 | lipocalin 2 (oncogene 24p3) | UTEROCALIN; NGAL; LCN2; NEUTROPHIL GELATINASE-ASSOCIATED LIPOCALIN; ONCOGENIC LIPOCALIN 24P3; lipocalin 2 (oncogene 24p3) | DKDPQKMYAITYE (350) | KKCDYWIRTFVP GCQ (351) | ENFIRFSKYLGLP EN (352) | 1:100 |
| S0092 | paired box gene 8 | PAX8; paired box gene 8; paired box gene 8 isoform PAX8C; paired box gene 8 isoform PAX8D; paired box gene 8 isoform PAX8E; paired box gene 8 isoform PAX8A; paired box gene 8 isoform PAX8B; PAIRED DOMAIN GENE 8 PAX8/PPARG FUSION GENE | DDSDQDSCRLSI DSQ (353) | RQHYPEAYASPS HTK (354) | NTPLGRNLSTHQ TYPVVAD (355) | 1:30-1:100 |
| S0093 | mesothelin | CAK1; SMR; MSLN; mesothelin; MEGAKARYOCYTE-POTENTIATING FACTOR; SOLUBLE MPF/MESOTHELIN-RELATED PROTEIN; mesothelin isoform 2 precursor; mesothelin isoform 1 precursor; megakaryocyte potentiating factor precursor; ANTIGEN RECOGNIZED BY MONOCLONAL ANTIBODY | RLVSCPGPLDQ DQQE (356) | KMSPEDIRKWN VTSLETLK (357) | SPEELSSVPPSSI WAVRPQD (358) | 1:500 |
| S0094 | kallikrein 6 (neurosin, zyme) | Bssp; PRSS18; KLK6; Klk7; SP59; PRSS9; MGC9355; protease M; kallikrein 6 preproprotein; protease, serine, 18; protease, serine, 9; kallikrein 6 (neurosin, zyme) | EEQNKLVHGGP CDKTSH (359) | ELIQPLPLERDC SANT (360) | GKTADGDFPDTI QC (361) | 1:150-1:300 |
| S0095 | Rap guanine nucleotide exchange factor (GEF) 3 | bcm910; MGC21410; 9330170P05Rik; EPAC; RAPGEF3; cAMP-GEFI; RAP guanine-nucleotide-exchange factor 3; EXCHANGE PROTEIN ACTIVATED BY cAMP; RAP guanine-nucleotide-exchange factor (GEF) 3; cAMP-REGULATED GUANINE NUCLEOTIDE EXCHANGE FACTOR I; RAP GUANINE NUCLE | REQWPERRRCH RLENGCGNA (362) | KVNSAGDAIGLQ PDAR (363) | QQLKVIDNQREL SRLSRELE (364) | 1:250-1:1000 |
| S0096 | ATPase, H+ transporting, lysosomal 56/58 kDa, V1 | Vma2; VPP3; ATP6V1B1; RTA1B; 3.6.3.14; VATB; ATP6B1; V-ATPase B1 subunit; H+ | REHMQAVTRNYI THPR (123) | KKSKAVLDYHDDN (124) | DEFYSREGRLQ DLAPDTAL (125) | 1:100-1:800 |

APPENDIX A2-continued

| | Antibodies & Genes | | Antibody Generation (SEQ ID NO.) | | | |
|---|---|---|---|---|---|---|
| AGI ID | GENE NAME | ALIASES | Peptide 1 | Peptide 2 | Peptide 3 | TITER |
| S0097 | subunit B, isoform 1 (Renal tubular acidosis with deafness) | ATPase beta 1 subunit; H(+)-transporting two-sector ATPase, 58 kD subunit; vacuolar proton pump, subunit 3; endomembrane proton pump 58 kDa subunit; ATPase, H+ transporting, lysos | KQQDGPTKTHK LEKLMIR (365) | ELRVLSKANAIVP GLSGGE (366) | RRGGEGGEENP SAAKGHLMG (367) | 1:100-1:500 |
| S0099 | frizzled homolog 8 (*Drosophila*) | FZ-8; hFZ8; FZD8; frizzled 8; frizzled homolog 8 (*Drosophila*); FRIZZLED, *DROSOPHILA*, HOMOLOG OF, 8 | MPEVSSKGATIS KK (368) | GFKKAWKTQK (369) | KEGKKRKRTRKE (370) | 1:333-1:500 |
| S0110 | histone 1, H2ba | HIST1H2BA; histone 1, H2ba | RYAFDFARDKD QRSLDID (126) | SVFYQYLEQSKY RVMNKDQ (127) | EDGAWPVLLDE FVEWQKVRQTS (128) | 1:500-1:2500 |
| S0117 | hypothetical protein MGC2714 | MGC2714; hypothetical protein MGC2714 | SFKSPQVYLKEE EEKNEKR (129) | RKKQQEAQGEK ASRYIE (130) | EDIGITVDTVLILE EKEQTN (131) | 1:200-1:375 |
| S0119 | reproduction 8 | D8S2298E; REP8; reproduction 8; Reproduction/chromosome 8 | KAFRGATDLKNL RLDKNQ (134) | DFRCEEGQEEG GCLPRPQ (132) | DGTSFAEEVEKP TKCGCALCA (133) | 1:900 |
| S0122 | slit homolog 1 (*Drosophila*) | SLIT3; MEGF4; SLIL1; Slit-1; SLIT1; slit homolog 1 (*Drosophila*); SLIT, *DROSOPHILA*, HOMOLOG OF, 1; MULTIPLE EPIDERMAL GROWTH FACTOR-LIKE DOMAINS 4 | QRIKEQASKISEA DKSKPKF (371) | HAKTKEKLEVTW EKMSKSKHN (372) | KSPQPQLLSNKE KAEARK (373) | 1:150 |
| S0123 | leucyl-tRNA synthetase 2, mitochondrial | 6.1.1.4; MGC2621; KIAA0028; LEURS; LARS2; leucine translase; leucine-tRNA ligase; LEUCYL-tRNA SYNTHETASE, MITOCHONDRIAL; leucyl-tRNA synthetase 2, mitochondrial; leucyl-tRNA synthetase 2, mitochondrial precursor | MLFEQGQQALE LPECT (374) | KDQKAKGILHSP ASQSPERS (375) | HSSQGRLPEAP KLITHL (376) | 1:100-1:500 |
| S0124 | homeo box D4 | HOX4B; HOXD4; HHO.C13; HOX-5.1; HOMEOBOX D4; HOMEOBOX 4B; HOMEOBOX X; homeo box D4; homeobox protein Hox-D4, mouse, homolog of homeo box X | KRGARRGGWK RKMPSTDL (377) | KIVRVPLTKMME VDVR (378) | QFLKDIRESVTQI MKNPKA (379) | 1:990-1:1500 |
| S0126 | sphingosine-1-phosphate lyase 1 | KIAA1252; SPL; SGPL1; sphingosine-1-phosphate lyase 1 | SKQGVVILDDKS KELPHW (380) | VQTFSRCIL.CSK DEVDLDEL (381) | LKKPFQPFQRTR SFRM (382) | 1:450-1:1600 |
| S0132 | HBxAg transactivated protein 1 | XTP1; HBxAg transactivated protein 1 | MNLLDPFMKMT DEQEKGLS (135) | NTFPKGEPDLKK ESEEDK (136) | KNGQAEAEEAT EQTHISPN (137) | 1:100-1:500 |
| S0137 | SRY (sex determining region Y)-box 9 (campomelic dysplasia, autosomal sex-reversal) | SRA1; CMD1; CMPD1; SOX9; SRY-BOX 9; transcription factor SOX9; SRY-RELATED HMG BOX GENE 9; SEX REVERSAL, AUTOSOMAL, 1; SRY (sex-determining region Y)-box 9 protein; SRY (sex-determining region Y)-box 9 (campomelic dysplasia, autosomal sex-reversal); SRY ( | QASSLRLEPGRA NDGDWH (138) | ElKGFAERLQRN ESGLDSGR (139) | RSGKSQPSYIPF LLREE (140) | 1:1800-1:5000 |
| | cadherin, EGF LAG seven-pass G-type receptor 2 (flamingo homolog, *Drosophila*) | Flamingo1; CELSR2; EGFL2; KIAA0279; MEGF3; CDHF10; EGF-like-domain, multiple 2; epidermal growth factor-like 2; multiple epidermal growth factor-like domains 3; cadherin EGF LAG seven-pass G-type receptor 2; cadherin, EGF LAG seven-pass G-type receptor | | | | |

APPENDIX A2-continued

| | Antibodies & Genes | | Antibody Generation (SEQ ID NO.) | | | |
|---|---|---|---|---|---|---|
| AGI ID | GENE NAME | ALIASES | Peptide 1 | Peptide 2 | Peptide 3 | TITER |
| S0139 | gamma-glutamyl hydrolase (conjugase, folylpolygammaglutamyl hydrolase) | 3.4.19.9; GGH; gamma-glutamyl hydrolase precursor; gamma-glutamyl hydrolase (conjugase, folylpolygammaglutamyl hydrolase) | RRSDYAKVAKIF YNLSIQSFDD (141) | KNFTMNEKLKKF FNVLTTN (142) | EFFVNEARKNNH HFKSESEE (143) | 1:2500-1:30000 |
| S0140 | bullous pemphigoid antigen 1, 230/240 kDa | BP240; FLJ13425; FLJ32235; FLJ21489; FLJ30627; CATX-15; KIAA0728; BPAG1; dystonin; hemidesmosomal plaque protein; bullous pemphigoid antigen 1, 230/240 kDa; bullous pemphigoid antigen 1 (230/240 kD); bullous pemphigoid antigen 1 isoform 1eA precursor; bullo | KNTQAAEALVKL YETKLCE (144) | QENQPENSKTLA TQLNQ (145) | KQMEKDLAFQK QVAEKQLK (146) | 1:250-1:20000 |
| S0143 | fatty acid synthase | 2.3.1.85; OA-519; FASN; MGC14367; MGC15706; fatty acid synthase | EFVEQLRKEGVF AKEVR (147) | DRIHPQALEAAQ AEIQQHD (148) | REVRQLTLRKLQ ELSSKADE (149) | 1:5000-1:30000 |
| S0143P3 | fatty acid synthase | 2.3.1.85; OA-519; FASN; MGC14367; MGC15706; fatty acid synthase | REVRQLTLRKLQ ELSSKADE (149) | N/A | N/A | 1:200-1:630 |
| S0144 | matrix metalloproteinase 14 (membrane-inserted) | MMP-X1; 3.4.24.—; MMP14; MTMMP1; MT1-MMP; membrane-type-1 matrix metalloproteinase; matrix metalloproteinase 14 preproprotein; MATRIX METALLOPROTEINASE 14, MEMBRANE-TYPE; matrix metalloproteinase 14 (membrane-inserted); membrane-type matrix metalloprotein | AYIREGHEKQAD IMIFFAE (150) | DEASLEPGYPKH IKELGR (151) | RGSFMGSDEVF TYFYK (152) | 1:500-1:20000 |
| S0147 | cystatin A (stefin A) | STFI; CSTA; STFA; cystatin AS; cystatin A (stefin A) | MIPGGLSEAKPA TPEIQEIV (383) | NETYGKLEAVQY KTQ (384) | DIVLTGYQVDKN KDDELTGF (385) | 1:100-1:5000 |
| S0149 | transient receptor potential cation channel, subfamily V, member 6 | TRPV6; ECAC2; CAT1; CATL; CALCIUM TRANSPORTER 1; CALCIUM TRANSPORTER-LIKE PROTEIN; EPITHELIAL CALCIUM CHANNEL 2; transient receptor potential cation channel, subfamily V, member 6 | RQEHCMSEHFK NRPACLGAR (153) | QGHKWGESPSQ GTQAGAGK (154) | RACGKRVSEGD RNGSGGGKWG (155) | 1:400-1:20000 |
| S0156 | fatty acid binding protein 7, brain | B-FABP; FABP7; FABPB; MRG, mammary-derived growth inhibitor-related; FATTY ACID-BINDING PROTEIN 7; FATTY ACID-BINDING PROTEIN, BRAIN; fatty acid binding protein 7, brain | MVEAFCATWKL TNSQN (156) | QVGNVTKPTVIIS QE (157) | KVVIRTLSTFKNTE (158) | 1:100-1:20000 |
| S0158 | cadherin 3, type 1, P-cadherin (placental) | CDHP; HJMD; PCAD; CDH3; placental cadherin; CADHERIN, PLACENTAL; cadherin 3, P-cadherin (placental); calcium-dependent adhesion protein, placental; cadherin 3, type 1 preproprotein; cadherin 3, type 1, P-cadherin (placental) | RAVFREAEVTLE AGGAEQE (159) | QEPALFSTDNDD FTVRN (160) | QKYEAHVPENA VGHE (161) | 1:150-1:2000 |
| S0165 | chemokine (C-X-C motif) ligand 1 (melanoma growth stimulating activity, alpha) | MGSA-α; NAP-3; CXCL1; SCYB1; GROα; GRO1, FORMERLY; GRO PROTEIN, ALPHA; GRO1 ONCOGENE, FORMERLY; MELANOMA GROWTH STIMULATORY ACTIVITY, ALPHA; GRO1 oncogene (melanoma growth-stimulating activity); CHEMOKINE, CXC MOTIF, LIGAND 1; GRO1 oncogene (melanoma grow | KKHEKMLNSDKSN (162) | N/A | N/A | 1:100-1:500 |

APPENDIX A2-continued

| AGI ID | Antibodies & Genes | | Antibody Generation (SEQ ID NO.) | | | TITER |
|---|---|---|---|---|---|---|
| | GENE NAME | ALIASES | Peptide 1 | Peptide 2 | Peptide 3 | |
| S0171 | baculoviral IAP repeat-containing 5 | BIRC5; baculoviral IAP repeat-containing 5 (survivin) | GKPGNQNSKNE PPKKRERER (163) | QAEAPLVPLSRQ NK (164) | NCFLTERKAQPDE (165) | 1:22500-1:30000 |
| S0193 | procollagen-lysine, 2-oxoglutarate 5-dioxygenase (lysine hydroxylase) 2 | PLOD2; LYSYL HYDROXYLASE 2; LYSINE HYDROXYLASE 2; PROCOLLAGEN-LYSINE, 2 OXOGLUTARATE 5-DIOXYGENASE 2; procollagen-lysine, 2-oxoglutarate 5-dioxygenase (lysine hydroxylase) 2; procollagen-lysine, 2-oxoglutarate 5-dioxygenase (lysine hydroxylase) 2 isoform | EFDTVDLSAVDV HPN (167) | NKEVYHEKDIKV FFDKAK (168) | KQVDLENVWLD FIRE (166) | 1:20000 |
| S0202 | PTK7 protein tyrosine kinase 7 | PTK7; CCK4; protein-tyrosine kinase PTK7; colon carcinoma kinase-4; PTK7 protein tyrosine kinase 7; PTK7 protein tyrosine kinase 7 isoform e precursor; PTK7 protein tyrosine kinase 7 isoform a precursor; PTK7 protein tyrosine kinase 7 isoform d precursor; | LKKPQDSQLEEG KPGYLD (386) | KAKRLQKQPEG EEPEME (387) | KDRPSFSEIASA LGDSTVDSKP (388) | 1:500-1:800 |
| S0211 | cytochrome P450, family 2, subfamily A, polypeptide 7 | CYP2A7; P450-IIA4; 1.14.14.1; CPAD; CYP2A7; CPAD; CYTOCHROME P450, SUBFAMILY IIA, POLYPEPTIDE 7; cytochrome P450, subfamily IIA (phenobarbital-inducible), polypeptide 7; cytochrome P450, family 2, subfamily A, polypeptide 7; cytochrome P450, family 2, su | KRGIEERIQEES GFLIE (169) | DRVIGKNRQPKF EDRTIK (170) | NPQHFLDDKGQ FKKSD (171) | 1:500-1:2500 |
| S0218 | solute carrier family 29 (nucleoside transporters), member 4 | SLC29A4; solute carrier family 29 (nucleoside transporters), member 4 | RHCILGEWLPILI MAVFN (172) | KQRELAGNTMT VSYMS (173) | RNAHGSCLHAS TANGSILAGL (174) | 1:20-1:50 |
| S0221 | solute carrier family 28 (sodium-coupled nucleoside transporter), member 2 | HCNT2; SLC28A2; HsT17153; SPNT1; CONCENTRATIVE NUCLEOSIDE TRANSPORTER 2; SODIUM-DEPENDENT PURINE NUCLEOSIDE TRANSPORTER 1; solute carrier family 28 (sodium-coupled nucleoside transporter), member 2 | ELMEKEVEPEGS KRTD (175) | KARSFCKTHARL FKK (176) | KNKRLSGMEEW IEGEK (177) | 1:500-1:1200 |
| S0223 | angiopoietin-like 4 | HFARP; FIAF; ANGPTL4; PGAR; angiopoietin-like 4; FASTING-INDUCED ADIPOSE FACTOR; PPARG ANGIOPOIETIN-RELATED PROTEIN; HEPATIC FIBRINOGEN/ANGIOPOIETIN-RELATED PROTEIN | EGSTDLPLAPES RVDPE (178) | KVAQQQRHLEK QHLR (179) | DHKHLDHEVAKP ARRKRLPE (180) | 1:30-1:10000 |
| S0235 | carcinoembryonic antigen-related cell adhesion molecule 5 | CEACAM5; CD66e; carcinoembryonic antigen-related cell adhesion molecule 5 | KLTIESTPFNVAE GKEC (181) | KSDLVNEEATGQ FRVYPELPK (182) | KPVEDKDAVAFT CEPEAQ (183) | 1:500-1:4500 |
| S0237 | podocalyxin-like | podocalyxin-like; Gp200; PCLP; PODXL; PODOCALYXIN-LIKE PROTEIN; podocalyxin-like precursor | DEKLISLICRAVK ATFNPAQDK (184) | KDKWDELKEAG VSDMKLGD (185) | DSWIVPLDNLTK DDLDEEDTHL (186) | 1:1000-1:2000 |
| S0238 | xenotropic and polytropic retrovirus receptor | X3; XPR1; X RECEPTOR; SYG1, YEAST, HOMOLOG OF; xenotropic and polytropic retrovirus receptor | EAVVTNELEDGD RQKAMKRLR (389) | RRYRDTKRAFP HLVNAGK (390) | KARDTKVLIEDT DDEANT (391) | 1:100-1:500 |

APPENDIX A2-continued

| | Antibodies & Genes | | Antibody Generation (SEQ ID NO.) | | | |
|---|---|---|---|---|---|---|
| AGI ID | GENE NAME | ALIASES | Peptide 1 | Peptide 2 | Peptide 3 | TITER |
| S0241 | glycyl-tRNA synthetase | GlyRS; GARS; CMT2D; 6.1.1.14; SMAD1; GLYCYL-tRNA SYNTHETASE; glycine tRNA ligase; Charcot-Marie-Tooth neuropathy, neuronal type, D | RKRVLEAKELAL QPKDDIVD (187) | RHGVSHKVDDS SGSIGRRYAR (188) | EARYPLFEGQET GKKETIEE (189) | 1:500-1:7500 |
| S0244 | dachshund homolog 1 (Drosophila) | DACH1; FLJ10138; dachshund homolog (Drosophila); DACHSHUND, DROSOPHILA, HOMOLOG OF; dachshund homolog 1 (Drosophila); dachshund homolog 1 isoform a; dachshund homolog 1 isoform b; dachshund homolog 1 isoform c | DLAGHDMGHES KRMHEKDE (407) | EKQVQLEKTELK MDFLRERE (408) | EADRSGGRTDA ERTIQDGR (409) | 1:100-1:3000 |
| S0251 | transcription factor CP2-like 2 | TFCP2L2; LBP-32; MGR; GRHL1; mammalian grainyhead; LBP protein 32; transcription factor CP2-like 2; leader-binding protein 32 isoform 2; leader-binding protein 32 isoform 1 | EALYPQRRSYTS EDEAWK (190) | DYYKVPRERRSS TAKPEVE (191) | DKYDVPHDKIGK IFKKCKK (192) | 1:5400 |
| S0253 | lysosomal associated protein transmembrane 4 beta | LAPTM4B; lysosomal associated protein transmembrane 4 beta | DPDQYNFSSSEL GGDFEFMDD (193) | EYIRQLPPNFPY RDD (194) | DTTVLLPPYDDA TVNGAAKE (195) | 1:500-1:2000 |
| S0255 | cyclin E2 | CYCE2; CCNE2; cyclin E2; G1/S-specific cyclin E2; cyclin E2 isoform 2; cyclin E2 isoform 3; cyclin E2 isoform 1 | RREEVTKKHQY EIR (196) | KESRYVHDKHFE VLHSDLE (197) | DFFDRFMLTQK DINK (198) | 1:1000-1:2000 |
| S0260 | nicastrin | KIAA0253; nicastrin; NCSTN; APH2; ANTERIOR PHARYNX DEFECTIVE 2, C. ELEGANS, HOMOLOG OF | ESKHFTRDLMEK LKGRTSR (199) | ETDRLPRCVRST ARLAR (200) | ESRWKDIRARIF LIASKELE (201) | 1:2400-1:5400 |
| S0265 | FXYD domain containing ion transport regulator 3 | MAT-8; MAT8; PLML; FXYD3; phospholemman-like protein; MAMMARY TUMOR, 8-KD; FXYD domain-containing ion transport regulator 3; FXYD domain containing ion transport regulator 3; FXYD domain containing ion transport regulator 3 isoform 2 precursor; FXYD domai | KVTLGLLVFLAG FPVLDANDLED (204) | SEWRSSGEQAGR (202) | KCKCKFGQKSG HHPGE (203) | 1:400-1:1200 |
| S0267 | immunoglobulin superfamily, member 3 | EWI-3; V8; IGSF3; immunoglobin superfamily, member 3; immunoglobulin superfamily, member 3 | KVAKESDSVFVL KIYHLRQED (205) | EREKTVTGEFID KESKRPK (206) | KRAEDTAGQTAL TVMRPD (207) | 1:200-1:250 |
| S0270 | signal transducing adaptor molecule (SH3 domain and ITAM motif) 2 | STAM2B; STAM2; DKFZp564C047; Hbp; STAM2A; SIGNAL-TRANSDUCING ADAPTOR MOLECULE 2; signal transducing adaptor molecule 2; STAM-like protein containing SH3 and ITAM domains 2; signal transducing adaptor molecule (SH3 domain and ITAM motif) 2 | KVARKVRALYDF EAVEDNE (208) | ETEVAAVDKLNV IDDDVE (209) | EIKKSEPEPVYID EDKMDR (210) | 1:1000-1:9000 |
| S0273 | dickkopf homolog 1 (Xenopus laevis) | DKK1; DKK-1; SK; dickkopf-1 like; dickkopf (Xenopus laevis) homolog 1; dickkopf homolog 1 (Xenopus laevis); DICKKOPF, XENOPUS, HOMOLOG OF, 1 | DEECGTDEYCA SPTRGGD (211) | RGEIEETTESFG NDHSTLD (212) | N/A | 1:400-1:500 |
| S0280 | solute carrier family 26, member 6 | SLC26A6; solute carrier family 26, member 6 | MDLRRRDYHME RPLLNQEHLEE (213) | DTDIYRDVAEYS EAKE (214) | EFYSDALKQRC GVDVDFLISQKKK (215) | 1:1800-1:2400 |
| S0286 | WNT inhibitory factor 1 | WIF1; WIF-1; WNT inhibitory factor 1; Wnt inhibitory factor-1 precursor | DAHQARVLIGFE EDILIVSE (216) | ERRICECPDGFH GPHCEK (217) | KRYEASLIHALR PAGAQLR (218) | 1:90 |

APPENDIX A2-continued

| | | | Antibody Generation (SEQ ID NO.) | | | |
|---|---|---|---|---|---|---|
| AGI ID | GENE NAME | ALIASES | Peptide 1 | Peptide 2 | Peptide 3 | TITER |
| S0288 | preferentially expressed antigen in melanoma | MAPE; PRAME; OPA-INTERACTING PROTEIN 4; Opa-interacting protein OIP4; preferentially expressed antigen in melanoma; melanoma antigen preferentially expressed in tumors | KRKVDGLSTEAE QPFIPVE (220) | KEGACDELFSYL IEKVKRKK (221) | DIKMILKMVQLD SIEDLE (219) | 1:1200 |
| S0295 | prostaglandin E synthase | PGES; TP53I12; MGST1L1; PP1294; PP102; PTGES; MGC10317; PIG12; MGST1-L1; MGST IV; MGST1-like 1; p53-INDUCED GENE 12; prostaglandin E synthase; p53-induced apoptosis protein 12; prostaglandin E synthase isoform 2; prostaglandin E synthase isoform 1; micros | RLRKKAFANPED ALR (222) | RSDPDVERCLR AHRND (223) | RVAHTVAYLGKL RAPIR(224) | 1:100-1:2400 |
| S0296 | solute carrier family 7 (cationic amino acid transporter, y+ system), member 5 | SLC7A5; MPE16; D16S469E; CD98; LAT1; 4F2 light chain; Membrane protein E16; L-TYPE AMINO ACID TRANSPORTER 1; Solute carrier family 7, member 5; solute carrier family 7 (cationic amino acid transporter, y+ system), member 5 | KRRALAAPAAEE KEEAR (225) | EAREKMLAAKSA DGSAPAGE (226) | MIWLRHRKPELE RPIK (227) | 1:300-1:5000 |
| S0296P1 | solute carrier family 7 (cationic amino acid transporter, y+ system), member 5 | SLC7A5; MPE16; D16S469E; CD98; LAT1; 4F2 light chain; Membrane protein E16; L-TYPE AMINO ACID TRANSPORTER 1; Solute carrier family 7, member 5; solute carrier family 7 (cationic amino acid transporter, y+ system), member 5 | KRRALAAPAAEE KEEAR (225) | N/A | N/A | 1:225-1:3150 |
| S0297 | v-maf musculoaponeurotic fibrosarcoma oncogene homolog K (avian) | FLJ32205; NFE2U; MAFK; NFE2, 18-KD SUBUNIT; nuclear factor erythroid-2, ubiquitous (p18); NUCLEAR FACTOR ERYTHROID 2, UBIQUITOUS SUBUNIT; v-maf musculoaponeurotic fibrosarcoma oncogene homolog K (avian); v-maf avian musculoaponeurotic fibrosarcoma oncogen | KPNKALKVKKEA GE (228) | KRVTQKEELERQ RVELQQEVEK (229) | RLELDALRSKYE (230) | 1:333-1:800 |
| S0301 | signal peptide, CUB domain, EGF-like 2 | SCUBE2; signal peptide, CUB domain, EGF-like 2 | KMHTDGRSCLE REDTVLEVTE (231) | KKGFKLLTDEKS CQDVDE (232) | KRTEKRLRKAIR TLRKAVHRE (233) | 1:3500-1:5400 |
| S0303 | gamma-aminobutyric acid (GABA) A receptor, epsilon | GABRE; GABA-A RECEPTOR, EPSILON POLYPEPTIDE; GAMMA-AMINOBUTYRIC ACID RECEPTOR, EPSILON; gamma-aminobutyric acid (GABA) A receptor, epsilon; gamma-aminobutyric acid (GABA) A receptor, epsilon isoform 2; gamma-aminobutyric acid (GABA) A receptor, epsilon is | RVEGPQTESKN EASSRD (234) | EETKSTETETGS RVGKLPE (235) | KWENFKLEINEK NSWKLFQFD (236) | 1:300-1:500 |
| S0305 | S100 calcium binding protein A10 (annexin II ligand, calpactin I, light polypeptide (p11)) | CAL1L; GP11; p10; 42C; S100A10; ANX2LG; CLP11; Cal1]; CALPACTIN I, p11 SUBUNIT; ANNEXIN II, LIGHT CHAIN; CALPACTIN I, LIGHT CHAIN; S100 calcium-binding protein A10 (annexin II ligand, calpactin I, light polypeptide (p11)); S100 calcium binding protein A10 | DKGYLTKEDLRV LMEKE (237) | KDPLAVDKIMKD LDQCRDGK (238) | N/A | 1:8332-1:24996 |

APPENDIX A2-continued

| AGI ID | Antibodies & Genes | | Antibody Generation (SEQ ID NO.) | | | |
|---|---|---|---|---|---|---|
| | GENE NAME | ALIASES | Peptide 1 | Peptide 2 | Peptide 3 | TITER |
| S0311 | v-myb myeloblastosis viral oncogene homolog (avian)-like 2 | MYBL2; MGC15600; MYB-RELATED GENE BMYB; MYB-related protein B; v-myb myeloblastosis viral oncogene homolog (avian)-like 2; V-MYB AVIAN MYELOBLASTOSIS VIRAL ONCOGENE HOMOLOG-LIKE 2 | MSRRTRCEDLD ELHYQDTDSD (240) | EEDLKEVLRSEA GIELIIEDDIR (239) | RRSPIKKVRKSL ALDIVDED (241) | 1:750-1:5000 |
| S0312 | nucleoside phosphorylase | NP; 2.4.2.1; nucleoside phosphorylase; PURINE NUCLEOSIDE:ORTHOPHOSPHATE RIBOSYLTRANSFERASE; purine nucleoside phosphorylase; PNP NUCLEOSIDE PHOSPHORYLASE DEFICIENCY; ATAXIA WITH DEFICIENT CELLULAR IMMUNITY | EDYKNTAEWLLS HTKHR (242) | DEREGDRFPAM SDAYDRTMRQR (243) | KVIMDYESLEKA NHEE (244) | 1:1000-1:3600 |
| S0314 | chaperonin containing TCP1, subunit 5 (epsilon) | KIAA0098; CCT5; chaperonin containing TCP1, subunit 5 (epsilon) | DQDRKSRLMGL EALKSHIMAAK (245) | KGVIVDKDFSHP QMPKKVED (246) | RMILKIDDIRKPG ESEE (247) | 1:6000-1:30000 |
| S0315 | non-metastatic cells 1, protein (NM23A) expressed in | GAAD; NME1; NDPKA; 2.7.4.6; NM23H1; AWD NM23H1B; GZMA-ACTIVATED DNase; NUCLEOSIDE DIPHOSPHATE KINASE-A; AWD, *DROSOPHILA*, HOMOLOG OF; METASTASIS INHIBITION FACTOR NM23; nucleoside-diphosphate kinase 1 isoform b; NONMETASTATIC PROTEIN 23, HOMOLOG 1; nucleo | RLQPEFKPKQLE GTMANCER (248) | KFMQASEDLLKE HYVDLKDR (249) | DSVESAEKEIGL WFHPEELVD (250) | 1:9000-1:18000 |
| S0316 | squalene epoxidase | SQLE; 1.14.99.7; squalene epoxidase; squalene monooxygenase | KSPPESENKEQL EARRRR (251) | RDGRKVTVIERD LKEPDR (252) | DHLKEPFLEATD NSHLR (253) | 1:1000-1:10000 |
| S0319 | pregnancy-induced growth inhibitor | OKL38; pregnancy-induced growth inhibitor; PREGNANCY-INDUCED GROWTH INHIBITOR OKL38 | DLEVKDWMQKK RRGLRNSR (254) | EYHKVHQMMRE QSILSPSPYEGYR (255) | RHQLLCFKEDC QAVFQDLEGVEK (256) | 1:900 |
| S0326 | mal, T-cell differentiation protein 2 | MAL2; mal, T-cell differentiation protein 2 | GPDILRTYSGAF VCLE (257) | CSLGLALRRWRP (258) | N/A | 1:120-1:1200 |
| S0330 | aldo-keto reductase family 1, member C1/2 (dihydrodiol dehydrogenase 1; 20-alpha (3-alpha)-hydroxysteroid dehydrogenase) | 1.1.1.213; 2-ALPHA-HSD; 1.3.1.20; 20-ALPHA-HSD; MGC8954; H-37; HAKRC; MBAB; C9; DDH1; AKR1C1; trans-1,2-dihydrobenzene-1,2-diol dehydrogenase; chlordecone reductase homolog; aldo-keto reductase C; 20 alpha-hydroxysteroid dehydrogenase; hepatic dihydrodiol | RYLTLDIFAGPP NYPFSDEY (259) | N/A | N/A | 1:2500-1:75000 |
| S0330-x1 | aldo-keto reductase family 1, member C1/2 (dihydrodiol dehydrogenase 1; 20-alpha (3-alpha)-hydroxysteroid dehydrogenase) | 1.1.1.213; 2-ALPHA-HSD; 1.3.1.20; 20-ALPHA-HSD, MGC8954; H-37; HAKRC; MBAB; C9; DDH1; AKR1C1; trans-1,2-dihydrobenzene-1,2-diol dehydrogenase; chlordecone reductase homolog; aldo-keto reductase C; 20 alpha-hydroxysteroid dehydrogenase; hepatic dihydrodiol | RYLTLDIFAGPP NYPFSDEY (259) | N/A | N/A | 1:600 |
| S0331 | aldo-keto reductase family 1, member C3 (3-alpha hydroxysteroid dehydrogenase, type II) | HA1753; 1.1.1.188; DD3; hluPGFS; HSD17B5; 1.3.1.20; 1.1.1.213; AKR1C3; KIAA0119; HAKRB; HAKRe; trans-1,2-dihydrobenzene-1,2-diol dehydrogenase; chlordecone reductase homolog; dihydrodiol dehydrogenase 3; | HYFNSDSFASHP NYPYSDEY (260) | N/A | N/A | 1:300-1:999 |

APPENDIX A2-continued

| AGI ID | GENE NAME | ALIASES | Peptide 1 | Peptide 2 | Peptide 3 | TITER |
|---|---|---|---|---|---|---|
| S0331-x1 | aldo-keto reductase family 1, member C3 (3-alpha hydroxysteroid dehydrogenase, type II) | prostaglandin F synthase; ALDO-KETO REDUCTASE B; 3-HA1753; 1.1.1.188, DD3; hluPGFS; HSD17B5; 1.3.1.20, 1.1.1.213; AKR1C3; KIAA0119; HAKRB, HAKRe, trans-1,2-dihydrobenzene-1,2-diol dehydrogenase; chlordecone reductase homolog; dihydrodiol dehydrogenase 3; prostaglandin F synthase; ALDO-KETO REDUCTASE B; 3- | HYFNSDSFASHP NYPYSDEY (260) | N/A | N/A | 1:150-1:300 |
| S0332 | aldo-keto reductase family 1, member C4 (dihydrodiol dehydrogenase 1; 20-alpha (3-alpha)-hydroxysteroid dehydrogenase) | 1.1.1.213; 2-ALPHA-HSD; 1.3.1.20; 20-ALPHA-HSD; MGC8954; H-37; HAKRC; MBAB; C9; DDH1; AKR1C1; trans-1,2-dihydrobenzene-1,2-diol dehydrogenase; chlordecone reductase homolog; aldo-keto reductase C; 20 alpha-hydroxysteroid dehydrogenase; hepatic dihydrodiol | RYVVMDFLMDH PDYPFSDEY (261) | N/A | N/A | 1:300-1:400 |
| S0332-x1 | aldo-keto reductase family 1, member C4 (dihydrodiol dehydrogenase 1; 20-alpha (3-alpha)-hydroxysteroid dehydrogenase) | 1.1.1.213; 2-ALPHA-HSD; 1.3.1.20; 20-ALPHA-HSD; MGC8954; H-37; HAKRC; MBAB; C9; DDH1; AKR1C1; trans-1,2-dihydrobenzene-1,2-diol dehydrogenase; chlordecone reductase homolog; aldo-keto reductase C; 20 alpha-hydroxysteroid dehydrogenase; hepatic dihydrodiol | RYVVMDFLMDH PDYPFSDEY (261) | N/A | N/A | 1:75-1:150 |
| S0336 | chromosome 20 open reading frame 139 | C20orf139; chromosome 20 open reading frame 139 | DPAKVQSLVDTI REDPD (262) | RETIPAKLVQSTL SDLR (263) | N/A | 1:1600-1:2400 |
| S0342 | solute carrier family 2 (facilitated glucose transporter), member 12 | SLC2A12; solute carrier family 2 (facilitated glucose transporter), member 12 | SDTTEELTVIKSS LKDE (264) | N/A | N/A | 1:400-1:1250 |
| S0343 | solute carrier family 2 (facilitated glucose transporter), member 12 | SLC2A12; solute carrier family 2 (facilitated glucose transporter), member 12 | HSRSSLMPLRN DVDKR (265) | N/A | N/A | 1:50-1:125 |
| S0357 | HTPAP protein | HTPAP; HTPAP protein | YRNPYVEAEYFP TKPMFVIA (392) | N/A | N/A | 1:100-1:300 |
| S0364 | KIAA0746 protein | KIAA0746; KIAA0746 protein | KKFPRFRNRELE ATRRQRMD (393) | N/A | N/A | 1:200-1:300 |
| S0367 | peroxisomal acyl-CoA thioesterase 2B | PTE2B; peroxisomal acyl-CoA thioesterase 2B | SGNTAINYKHSSIP (394) | N/A | N/A | 1:200-1:600 |
| S0374 | chloride intracellular channel 5 | CLIC5; chloride intracellular channel 5 | DANTCGEDKGS RRKFLDGDE (266) | N/A | N/A | 1:5000-1:9000 |
| S0380 | keratinocyte associated protein 3 | KRTCAP3; keratinocyte associated protein 3 | QLEEMTELESPK CKRQENEQ (267) | N/A | N/A | 1:2000-1:9000 |
| S0384 | FERM, RhoGEF (ARHGEF) and pleckstrin domain protein 1 (chondrocyte-derived) | p63RhoGEF; CDEP; FARP1; chondrocyte-derived ezrin-like protein; FERM, RhoGEF, and pleckstrin domain protein 1; FERM, ARHGEF, AND PLECKSTRIN DOMAIN-CONTAINING | QADGAASAPTE EEEVVKDR (268) | N/A | N/A | 1:100 |

APPENDIX A2-continued

| AGI ID | GENE NAME | Antibodies & Genes ALIASES | Peptide 1 | Peptide 2 | Peptide 3 | TITER |
|---|---|---|---|---|---|---|
| | | PROTEIN 1; FERM, RhoGEF (ARHGEF) and pleckstrin domain protein 1 (chondrocyte-derived) | | | | |
| S0388 | trichorhinophalangeal syndrome I | GC79; TRPS1; TRPS1 GENE; trichorhinophalangeal syndrome I; zinc finger transcription factor TRPS1 | SGDSLETKEDQK MSPKATEE (269) | N/A | N/A | 1:600 |
| S0396 | cytochrome P450, family 3, subfamily A, polypeptide 4 | 1.14.14.1; HLP; CYP3A3; CYP3A4; P450C3; NF 25; CP33; CP34; P450-III, STEROID-INDUCIBLE; nifedipine oxidase; glucocorticoid-inducible P450; CYTOCHROME P450PCN1; P450, FAMILY III; P450-III, steroid inducible; cytochrome P450, subfamily IIIA, polypeptide 4; | RKSVKRMKESR LEDTQKHRV (395) | N/A | N/A | 1:15 |
| S0398 | FAT tumor suppressor homolog 1 (Drosophila) | CDHF7; FAT; cadherin ME5; FAT tumor suppressor precursor; cadherin-related tumor suppressor homolog precursor; cadherin family member 7 precursor; homolog of Drosophila Fat protein precursor; FAT tumor suppressor homolog 1 (Drosophila); FAT TUMOR SUPPRESS | KIRLPEREKPDR ERNARREP (270) | N/A | N/A | 1:45-1:200 |
| S0401 | granulin | ACROGRANIN; PROEPITHELIN; PROGRANULIN; PEPI; PCDGF; granulin; GRN; EPITHELIN PRECURSOR | RGTKCLRREAP RWDAPLRDP (271) | N/A | N/A | 1:600-1:3000 |
| S0404 | N-myc downstream regulated gene 1 | HMSNL; TARG1; CMT4D; RTP; PROXY1; NDRG1; GC4; NMSL; TDD5; RIT42; NDR1; differentiation-related gene 1 protein; nickel-specific induction protein Cap43; protein regulated by oxygen-1; NMYC DOWNSTREAM-REGULATED GENE 1; reducing agents and tunicamycin-respon | GTRSRSHTSEG TRSRSHTSE (272) | N/A | N/A | 1:100-1:900 |
| S0411 | fatty acid binding protein 5 (psoriasis-associated) | PAFABP; EFABP; E-FABP; FABP5; PA-FABP; FATTY ACID-BINDING PROTEIN, EPIDERMAL; FATTY ACID-BINDING PROTEIN 5; FATTY ACID-BINDING PROTEIN, PSORIASIS-ASSOCIATED; fatty acid binding protein 5 (psoriasis-associated) | EETTADGRKTQT VCNFTD (273) | N/A | N/A | 1:1800 |
| S0413 | cyclin-dependent kinase inhibitor 1C (p57, Kip2) | WBS; p57(KIP2); BWCR; CDKN1C; BWS; Beckwith-Wiedemann syndrome; cyclin-dependent kinase inhibitor 1C (p57, Kip2) | AKRKRSAPEKSS GDVP (274) | N/A | N/A | 1:2700 |
| S0414 | alpha-methylacyl-CoA racemase | AMACR; 5.1.99.4; ALPHA-METHYLACYL-CoA RACEMASE; AMACR DEFICIENCY; AMACR ALPHA-METHYLACYL-CoA RACEMASE DEFICIENCY; alpha-methylacyl-CoA racemase isoform 1; alpha-methylacyl-CoA racemase isoform 2 | RVDRPGSRYDV SRLGRGKRS (275) | N/A | N/A | 1:100 |
| S0415 | gamma-aminobutyric acid (GABA) A receptor, beta 3 | MGC9051; GABRB3; GABA-A RECEPTOR, BETA-3 POLYPEPTIDE; GAMMA-AMINOBUTYRIC ACID RECEPTOR, BETA-3; gamma-aminobutyric acid (GABA) A receptor, | ETVDKLLKGYDI RLRPD (276) | N/A | N/A | 1:600-1:1800 |

APPENDIX A2-continued

| | Antibodies & Genes | | Antibody Generation (SEQ ID NO.) | | | |
|---|---|---|---|---|---|---|
| AGI ID | GENE NAME | ALIASES | Peptide 1 | Peptide 2 | Peptide 3 | TITER |
| S0417 | HSV-1 stimulation-related gene 1 | beta 3; gamma-aminobutyric acid (GABA) A receptor, beta 3 isoform 2 precursor; gamma-aminobutyric acid (GABA) A rece HSRG1; KIAA0872; HSV-1 stimulation-related 1; HSV-1 stimulation-related gene 1 | APGGAEDLEDT QFPSEEARE (277) | N/A | N/A | 1:9000 |
| S0425 | tumor necrosis factor receptor superfamily, member 21 | TNFRSF21; DR6; BM-018; TNFR-related death receptor 6; tumor necrosis factor receptor superfamily, member 21; tumor necrosis factor receptor superfamily, member 21 precursor | RKSSRTLKKGPR QDPSAIVE (278) | N/A | N/A | 1:9000 |
| S0429 | jumonji domain containing 1C | JMJD1C; TRIP8; jumonji domain containing 1C; THYROID HORMONE RECEPTOR INTERACTOR 8 | GSESGDSDESE SKSEQRTKR (279) | N/A | N/A | 1:1200 |
| S0432 | chromosome 9 open reading frame 140 | C9orf140; chromosome 9 open reading frame 140 | EADSGDARRLP RARGERRRH (280) | N/A | N/A | 1:90-1:300 |
| S0440 | cell division cycle 25B | 3.1.3.48; CDC25B; cell division cycle 25B; cell division cycle 25B isoform 4; cell division cycle 25B isoform 5; cell division cycle 25B isoform 1; cell division cycle 25B isoform 2; cell division cycle 25B isoform 3 | RLERPQDRDTP VQNKRRRS (281) | N/A | N/A | 1:350-1:3600 |
| S0445 | laminin, beta 1 | LAMB1; LAMININ, BETA-1; CUTIS LAXA-MARFANOID SYNDROME; laminin, beta 1; laminin, beta 1 precursor; LAMB1 NEONATAL CUTIS LAXA WITH MARFANOID PHENOTYPE | DRVEDVMMERE SQFKEKQE (282) | N/A | N/A | 1:600-1:1800 |
| S0447 | papillary renal cell carcinoma (translocation-associated) | TPRC; MGC17178; MGC4723; PRCC; proline-rich protein PRCC; RCCP1 PRCC/TFE3 FUSION GENE; papillary renal cell carcinoma (translocation-associated); RENAL CELL CARCINOMA, PAPILLARY, 1 GENE; papillary renal cell carcinoma translocation-associated gene product | DEAFKRLQGKR NRGREE (283) | N/A | N/A | 1:4000-1:6000 |
| S0455 | tumor necrosis factor (ligand) superfamily, member 10 | APO2L; TL2; Apo-2L; TNFSF10; Apo-2 ligand; APO2 LIGAND; TNF-RELATED APOPTOSIS-INDUCING LIGAND; TNF-related apoptosis inducing ligand TRAIL; tumor necrosis factor (ligand) superfamily, member 10; TUMOR NECROSIS FACTOR LIGAND SUPERFAMILY, MEMBER 10 | RFQEEIKENTKN DKQ (284) | N/A | N/A | 1:900 |
| S0459 | titin | connectin; TMD; titin; CMD1G; CMPD4; TTN; FLJ32040; CMH9, included; titin isoform N2-A; titin isoform N2-B; titin isoform novex-1; titin isoform novex-2; titin isoform novex-3 cardiomyopathy, dilated 1G (autosomal dominant); TTN CARDIOMYOPATHY, FAMILIAL | KRDKEGVRWTK CNKKTLTD (285) | N/A | N/A | 1:2700-1:8100 |
| S0469 | DNA fragmentation factor, 45 kDa, alpha polypeptide | DFF45; DFF1; DFFA; ICAD; DFF-45; INHIBITOR OF CASPASE-ACTIVATED DNase; | KEGSLLSKQEES KAAFGEE | N/A | N/A | 1:600 |

APPENDIX A2-continued

| AGI ID | Antibodies & Genes | | Antibody Generation (SEQ ID NO.) | | | |
|---|---|---|---|---|---|---|
| | GENE NAME | ALIASES | Peptide 1 | Peptide 2 | Peptide 3 | TITER |
| S0494 | caspase 2, apoptosis-related cysteine protease (neural precursor cell expressed, developmentally down-regulated 2) | DNA FRAGMENTATION FACTOR, 45-KD, ALPHA SUBUNIT; DNA fragmentation factor, 45 kDa, alpha polypeptide; DNA fragmentation factor, 45 kD, alpha subunit; DNA fragmentation factor, 45 kD, alp ICH-1L/1S; CASP2; ICH1; CASP-2; ICH-1 protease; caspase 2 isoform 3; caspase 2 isoform 4; NEDD2 apoptosis regulatory gene; caspase 2 isoform 2 precursor; caspase 2 isoform 1 preproprotein; NEURAL PRECURSOR CELL EXPRESSED, DEVELOPMENTALLY DOWNREGULATED 2; | (286) | N/A | N/A | 1:2000 |
| S0501 | G1 to S phase transition 1 | GSPT1; eRF3a; ETF3A; GST1; YEAST, HOMOLOG OF; PEPTIDE CHAIN RELEASE FACTOR 3A; G1-TO S-PHASE TRANSITION 1; G1 to S phase transition 1 | ESDAGKEKLPK MRLPTRSD (287) | N/A | N/A | 1:15000 |
| S0502 | GCN5 general control of amino-acid synthesis 5-like 2 (yeast) | hGCN5; GCN5L2; GCN5 (general control of amino-acid synthesis, yeast, homolog)-like 2; GCN5 general control of amino-acid synthesis 5-like 2 (yeast); General control of amino acid synthesis, yeast, homolog-like 2 | ERDKGKTVEVG RAYFETEK (288) | N/A | N/A | 1:9000 |
| S0503 | geminin, DNA replication inhibitor | GMNN; geminin, DNA replication inhibitor | EKFRVEKDKLVP EKR (289) | N/A | N/A | 1:333 |
| S0507 | ADP-ribosylation factor-like 6 interacting protein 2 | ARL6IP2; ADP-ribosylation factor-like 6 interacting protein 2 | EVAEKRRKALYE ALKENEK (396) | N/A | N/A | 1:8000-1:9000 |
| S0511 | DNA replication complex GINS protein PSF2 | Pfs2; DNA replication complex GINS protein PSF2 | ENYEDDDLVNS DEVMKKP (290) | N/A | N/A | 1:2000 |
| S0524 | ankyrin repeat domain 10 | ANKRD10; ankyrin repeat domain 10 | PKADEIRTLVKD MWDTR (291) | N/A | N/A | 1:4500 |
| S0527 | potassium channel tetramerisation domain containing 2 | KCTD2; potassium channel tetramerisation domain containing 2 | RKRCLEDSEDF GVKKARTE (292) | N/A | N/A | 1:900-1:1500 |
| S0528 | rabconnectin-3 | RC3; KIAA0856; rabconnectin-3 | EPKSFLCRLCCQ EDPELDS (293) | N/A | N/A | 1:350-1:1200 |
| S0538 | acidic (leucine-rich) nuclear phosphoprotein 32 family, member E | ANP32E; acidic (leucine-rich) nuclear phosphoprotein 32 family, member E | EEYDRESKSSD DVDYRGS (294) | N/A | N/A | 1:1200 |
| S0544 | chromosome 9 open reading frame 100 | C9orf100; chromosome 9 open reading frame 100 | CVNGEIFGLNDT FKELEF (397) | N/A | N/A | 1:40-1:240 |
| S0545 | HpaII tiny fragments locus 9C | D22S1733E; HTF9C; HpaII tiny fragments locus 9C; HpaII tiny fragments locus 9C isoform2; HpaII tiny fragments locus 9C isoform 1 | EQRARWERKRA CTARE (295) | N/A | N/A | 1:900-1:5400 |
| S0546 | cell division cycle associated 2 | CDCA2; cell division cycle associated 2 | ERKQLECEQVL QKLAKE (296) | N/A | N/A | 1:1200 |
| | | | RNSETKVRRST RLQKDLEN (297) | | | |

APPENDIX A2-continued

| AGI ID | GENE NAME | ALIASES | Peptide 1 | Peptide 2 | Peptide 3 | TITER |
|---|---|---|---|---|---|---|
| S0553 | mitotic phosphoprotein 44 | MP44; NUP35; LOC129401; NUCLEOPORIN, 35-KD; mitotic phosphoprotein 44 | SDYQVISDRQTP KKDE (298) | N/A | N/A | 1:3000-1:5400 |
| S0557 | SMC4 structural maintenance of chromosomes 4-like 1 (yeast) | SMC4L1; CAPC; hCAP-C; chromosome-associated polypeptide C; SMC4 (structural maintenance of chromosomes 4, yeast)-like 1; SMC4 structural maintenance of chromosomes 4-like 1 (yeast); structural maintenance of chromosomes (SMC) family member, chromosome-ass | DIEGKLPQTEQE LKE (299) | N/A | N/A | 1:200 |
| S0564 | phosphatidylserine synthase 1 | KIAA0024; PSSA; PTDSS1; phosphatidylserine synthase 1 | DDVNYKMHFRMI NEQQVED (300) | N/A | N/A | 1:1000-1:8000 |
| S0565 | polo-like kinase 1 (Drosophila) | 2.7.1.—; PLK1; STPK13; polo-like kinase (Drosophila); polo (Drosophila)-like kinase; SERINE/THREONINE PROTEIN KINASE 13; polo-like kinase 1 (Drosophila) | ENPLPERPREKE EPVVR (301) | N/A | N/A | 1:10-1:100 |
| S0567 | Pirin | Pirin; PIR | REQSEGVGARV RRSIGRPE (302) | N/A | N/A | 1:240 |
| S0578 | ATP-binding cassette, sub-family A (ABC1), member 3 | ABCA3; ABC3; LBM180; ABC-C; EST111653; ABC transporter 3; ATP-binding cassette 3; ATP BINDING CASSETTE TRANSPORTER 3; ATP-BINDING CASSETTE, SUBFAMILY A, MEMBER 3; ATP-binding cassette, sub-family A member 3; ATP-binding cassette, sub-family A (ABC1), memb | PRAVAGKEEED SDPEKALR (303) | N/A — | N/A | 1:1500 |
| S0579 | ATP-binding cassette, sub-family A (ABC1), member 7 | ABCX; ABCA7; ABCA-SSN; autoantigen SS-N; macrophage ABC transporter; SJOGREN SYNDROME ANTIGEN SS-N; ATP-BINDING CASSETTE, SUBFAMILY A, MEMBER 7; ATP-binding cassette, sub-family A (ABC1), member 7; ATP-binding cassette, sub-family A, member 7 isoform a; A | EKADTDMEGSV DTRQEK (304) | N/A | N/A | 1:300-1:400 |
| S0581 | ATP-binding cassette, sub-family B (MDR/TAP), member 7 | ABCB7; Atm1p; ASAT; ABC7; EST140535; ABC TRANSPORTER 7; ATP-binding cassette 7; ATP-BINDING CASSETTE TRANSPORTER 7; Anemia, sideroblastic, with spinocerebellar ataxia; ATP-BINDING CASSETTE, SUBFAMILY B, MEMBER 7; ATP-binding cassette, sub-family B, member | RVQNHDNPKWE AKKENISK (305) | N/A | N/A | 1:4000-1:10000 |
| S0585 | ATP-binding cassette, sub-family C (CFTR/MRP), member 12 | MRP9; ABCC12; MULTIDRUG RESISTANCE-ASSOCIATED PROTEIN 9; ATP-BINDING CASSETTE, SUBFAMILY C, MEMBER 12; ATP-binding cassette, sub-family C (CFTR/MRP), member 12 | RSPPAKGATGP EEQSDSLK (306) | N/A | N/A | 1:500 |
| S0586 | ATP-binding cassette, sub-family G (WHITE), member 2 | ABC15; MXR1; ABCP; EST157481; MRX; ABCG2; BCRP1; BMDP; MITOXANTRONE-RESISTANCE PROTEIN; mitoxantrone | REEDFKATEIIEP SKQDKP (307) | N/A | N/A | 1:333-1:400 |

APPENDIX A2-continued

| | Antibodies & Genes | | Antibody Generation (SEQ ID NO.) | | | |
|---|---|---|---|---|---|---|
| AGI ID | GENE NAME | ALIASES | Peptide 1 | Peptide 2 | Peptide 3 | TITER |
| S0593 | solute carrier organic anion transporter family, member 1B3 | resistance protein; placenta specific MDR protein; ATP-BINDING CASSETTE TRANSPORTER, PLACENTA-SPECIFIC; breast cancer resistance protein; ATP-BINDING CASS OATP1B3; SLC21A8; OATP8; SLCO1B3; ORGANIC ANION TRANSPORTER 8; solute carrier organic anion transporter family, member 1B3; SOLUTE CARRIER FAMILY 21, MEMBER 8 (ORGANIC ANION TRANSPORTER); solute carrier family 21 (organic anion transporter), member 8 | DKTCMKWSTNS CGAQ (308) | N/A | N/A | 1:500-1:2400 |
| S0597 | solute carrier family 22 (organic anion transporter), member 6 | ROAT1; MGC45260; HOAT1; PAHT; SLC22A6; PAH TRANSPORTER; para-aminohippurate transporter; renal organic anion transporter 1; solute carrier family 22 member 6 isoform b; solute carrier family 22 member 6 isoform c; solute carrier family 22 member 6 isoform | DANLSKNGGLEV WL (309) | N/A | N/A | 1:3000 |
| S0604 | solute carrier family 35 (UDP-galactose transporter), member A2 | UGT2; UGTL; UGAT; SLC35A2; UGT1; UDP-galactose translocator; UDP-GALACTOSE TRANSPORTER, ISOFORM 2; UGALT UDP-GALACTOSE TRANSPORTER, ISOFORM 1; solute carrier family 35 (UDP-galactose transporter), member A2; solute carrier family 35 (UDP-galactose transpo | EPFLPKLLTK (310) | N/A | N/A | 1:2400 |
| S0607 | cell division cycle 25B | 3.1.3.48; CDC25B; cell division cycle 25B; cell division cycle 25B isoform 4; cell division cycle 25B isoform 5; cell division cycle 25B isoform 1; cell division cycle 25B isoform 2; cell division cycle 25B isoform 3 | RKSEAGSGAAS SSGEDKEN (311) | N/A | N/A | 1:1800 |
| S0609 | stearoyl-CoA desaturase (delta-9-desaturase) | SCD; acyl-CoA desaturase; stearoyl-CoA desaturase (delta-9-desaturase); fatty acid desaturase | DDIYDPTYKDKE GPSPKVE (312) | N/A | N/A | 1:2000-1:5000 |
| S0611 | mitogen-activated protein kinase 12 | SAPK3; p38gamma; SAPK-3; p38-GAMMA; PRKM12; MAPK12; ERK3; ERK6; EXTRACELLULAR SIGNAL-REGULATED KINASE 6; mitogen-activated protein kinase 3; stress-activated protein kinase 3; mitogen-activated protein kinase 12 | QSDEAKNNMKG LPELEKKD (313) | N/A | N/A | 1:100 |
| S0612 | nuclear factor of kappa light polypeptide gene enhancer in B-cells 2 (p49/p100) | LYT-10; LYT10; NFKB2; ONCOGENE LYT 10; TRANSCRIPTION FACTOR NFKB2; NFKB, p52/p100 SUBUNIT; LYMPHOCYTE TRANSLOCATION CHROMOSOME 10; NUCLEAR FACTOR KAPPA-B, SUBUNIT 2; Nuclear factor of kappa light chain gene enhancer in B-cells 2; nuclear factor of kappa I | SRPQGLTEAEQ RELEQEAK (314) | N/A | N/A | 1:4500 |

APPENDIX A2-continued

| AGI ID | GENE NAME | ALIASES | Peptide 1 | Peptide 2 | Peptide 3 | TITER |
|---|---|---|---|---|---|---|
| | | | Antibody Generation (SEQ ID NO.) | | | |
| S0613 | tumor necrosis factor receptor superfamily, member 5 | Bp50; TNFRSF5; MGC9013; CDW40; CD40 antigen; CD40L receptor; B CELL-ASSOCIATED MOLECULE CD40; CD40 type II isoform; B cell surface antigen CD40; nerve growth factor receptor-related B-lymphocyte activation molecule; tumor necrosis factor receptor superfam | RVQQKGTSETD TIC (315) | N/A | N/A | 1:250-1:270 |
| S0614 | Epstein-Barr virus induced gene 3 | EBI3; IL27, EBI3 SUBUNIT; EPSTEIN-BARR VIRUS-INDUCED GENE 3; INTERLEUKIN 27, EBI3 SUBUNIT; Epstein-Barr virus induced gene 3; Epstein-Barr virus induced gene 3 precursor | VRLSPLAERQLQ VQWE (316) | N/A | N/A | 1:1200-1:3000 |
| S0616 | zinc finger protein 339 | ZNF339; zinc finger protein 339 | RRSLGVSVRSW DELPDEKR (317) | N/A | N/A | 1:2500 |
| S0617 | DAB2 interacting protein | DAB2IP; DAB2 interacting protein | DEGLGPDPHR DRLRSK (318) | N/A | N/A | 1:600 |
| S0618 | protein tyrosine phosphatase, receptor type, f polypeptide (PTPRF), interacting protein (liprin), alpha 1 | MGC26800; LIP1; PPFIA1; LIP.1; LAR-interacting protein 1; PTPRF interacting protein alpha 1 isoform a; PTPRF interacting protein alpha 1 isoform b; protein tyrosine phosphatase, receptor type, f polypeptide (PTPRF), interacting protein (liprin), alpha 1 | SGKRSSDGSLS HEEDLAK (319) | N/A | N/A | 1:150 |
| S0631 | RGM domain family, member A | RGMA; REPULSIVE GUIDANCE MOLECULE; RGM domain family, member A | SQERSDSPEICH YEKSFHK (320) | N/A | N/A | 1:600 |
| S0633 | hypothetical protein LOC144347 | LOC144347; hypothetical protein LOC144347 | KVNPEPTHEIRC NSEVK (321) | N/A | N/A | 1:100-1:200 |
| S0639 | tetratricopeptide repeat domain 7 | TTC7; tetratricopeptide repeat domain 7 | RELREVLRITVET KATQN (398) | N/A | N/A | 1:2000-1:3000 |
| S0640 | protein C (inactivator of coagulation factors Va and VIIIa) | PROC; 3.4.21.69; PROC DEFICIENCY PROTEIN C; THROMBOPHILIA, HEREDITARY, DUE TO PC DEFICIENCY; PROTEIN C DEFICIENCY, CONGENITAL THROMBOTIC DISEASE DUE TO; protein C (inactivator of coagulation factors Va and VIIIa) | RDTEDQEDQVD PRLIDGK (399) | N/A | N/A | 1:1000-1:1800 |
| S0643 | transducin-like enhancer of split 3 (E(sp1) homolog, Drosophila) | HsT18976; KIAA1547; ESG3; TLE3; transducin-like enhancer protein 3; enhancer of split groucho 3; transducin-like enhancer of split 3 (E(sp1) homolog, Drosophila) | KNHHELDHRER ESSAN (400) | N/A | N/A | 1:200-1:1440 |
| S0645 | frizzled homolog 7 (Drosophila) | FzE3; FZD7; frizzled 7; frizzled homolog 7 (Drosophila); Frizzled, drosophila, homolog of, 7 | SDGRGRPAFPF SCPRQ (322) | N/A | N/A | 1:900 |

APPENDIX A2-continued

| | Antibodies & Genes | | Antibody Generation (SEQ ID NO.) | | | |
|---|---|---|---|---|---|---|
| AGI ID | GENE NAME | ALIASES | Peptide 1 | Peptide 2 | Peptide 3 | TITER |
| S0646 | solute carrier family 3 (activators of dibasic and neutral amino acid transport), member 2 | MDU1; 4T2HC; SLC3A2; NACAE; 4F2HC; 4F2 HEAVY CHAIN; CD98 HEAVY CHAIN; CD98 MONOCLONAL ANTIBODY 44D7; ANTIGEN DEFINED BY MONOCLONAL ANTIBODY 4F2, HEAVY CHAIN; antigen identified by monoclonal antibodies 4F2, TRA1.10, TROP4, and T43; SOLUTE CARRIER FAMILY 3 | GSKEDFDSLLQS AKK (323) | N/A | N/A | 1:3600-1:5400 |
| S0648 | KIAA0738 gene product | KIAA0738; KIAA0738 gene product | EYRNQTNLPTEN VDK (401) | N/A | N/A | 1:200 |
| S0651 | phospholipase A2 receptor 1, 180 kDa | PLA2IR; PLA2-R; PLA2R1; PLA2G1R; PHOSPHOLIPASE A2 RECEPTOR, 180-KD; phospholipase A2 receptor 1, 180 kDa (324) | QKEEKTWHEAL RSCQADN (324) | N/A | N/A | 1:3600 |
| S0654 | KIAA0182 protein | KIAA0182; KIAA0182 protein | EKAEEGPRKRE PAPLDK (325) | N/A | N/A | 1:400 |
| S0659 | thymidine kinase 2, mitochondrial | TK2; THYMIDINE KINASE, MITOCHONDRIAL; thymidine kinase 2, mitochondrial | EQNRDRILTPEN RK (326) | N/A | N/A | 1:300 |
| S0663 | chromosome 14 open reading frame 135 | C14orf135; chromosome 14 open reading frame 135 | RDWYIGLVSDEK WK (327) | N/A | N/A | 1:900 |
| S0665 | KIAA1007 protein | KIAA1007; KIAA1007 protein; adrenal gland protein AD-005; KIAA1007 protein isoform a; KIAA1007 protein isoform b | DSYLKTRSPVTF LSDLR (328) | N/A | N/A | 1:1500-1:3000 |
| S0670 | DKFZP566O1646 protein | DC8; DKFZP566O1646 protein | KCRGETVAKEIS EAMKS (329) | N/A | N/A | 1:900 |
| S0672 | B-cell CLL/lymphoma 7A | BCL7A; B-cell CLL/lymphoma-7; B-cell CLL/lymphoma 7A | QRGSQIGREPIG LSGD (402) | N/A | N/A | 1:800 |
| S0673 | likely ortholog of mouse nin one binding protein | ART4; NOB1P; adenocarcinoma antigen recognized by T lymphocytes 4; likely ortholog of mouse nin one binding protein | KPPQETEKGHS ACEPEN (330) | N/A | N/A | 1:50 |
| S0676 | guanine nucleotide binding protein (G protein) alpha 12 | RMP; NNX3; GNA12; GUANINE NUCLEOTIDE-BINDING PROTEIN, ALPHA-12; guanine nucleotide binding protein (G protein) alpha 12 | ERRAGSGARDA ERE (331) | N/A | N/A | 1:1200-1:2400 |
| S0677 | GrpE-like 1, mitochondrial (E. coli) | HMGE; GRPEL1; HUMAN MITOCHONDRIAL GrpE PROTEIN; GrpE-like 1, mitochondrial (E. coli); GrpE, E. COLI, HOMOLOG OF, 1 | SEQKADPPATEK TLLE (332) | N/A | N/A | 1:500-1:1000 |
| S0684 | hypothetical protein FLJ34922 | FLJ34922; hypothetical protein FLJ34922 | EAEWSQGVQGT LRIKKYLT (333) | N/A | N/A | 1:8100 |
| S0687 | hypothetical protein FLJ20457 | FLJ20457; hypothetical protein FLJ20457 | EESKSITEGLLT QKQYE (334) | N/A | N/A | 1:600-1:1260 |
| S0691 | solute carrier family 7, (cationic amino acid transporter, y+ system) member 11 | CCBR1; SLC7A11; xCT; cystine/glutamate transporter; SYSTEM Xc(−) TRANSPORTER-RELATED PROTEIN; SOLUTE CARRIER FAMILY 7, MEMBER 11; solute carrier family 7, (cationic amino acid transporter, y+ system) member 11 | QNFKDAFSGRD SSITR (335) | N/A | N/A | 1:1000-1:1575 |
| S0692 | glutamate-cysteine ligase, catalytic subunit | GLCLC; GCLC; 6.3.2.2; GCS; GAMMA-GLUTAMYLCYSTEINE SYNTHETASE, | EKIHLDDANESD HFEN (403) | N/A | N/A | 1:100-1:400 |

APPENDIX A2-continued

| AGI ID | GENE NAME | Antibodies & Genes ALIASES | Peptide 1 | Peptide 2 | Antibody Generation (SEQ ID NO.) Peptide 3 | TITER |
|---|---|---|---|---|---|---|
| S0695 | integrin, beta 4 | CATALYTIC SUBUNIT; glutamate-cysteine ligase, catalytic subunit ITGB4; INTEGRIN, BETA-4; integrin, beta 4 | TEDVDEFRNKLQ GER (336) | N/A | N/A | 1:2700-1:4050 |
| S0702 | solute carrier family 7 (cationic amino acid transporter, y+ system), member 5 | SLC7A5; MPE16; D16S469E; CD98; LAT1; 4F2 light chain; Membrane protein E16; L-TYPE AMINO ACID TRANSPORTER 1; Solute carrier family 7, member 5; solute carrier family 7 (cationic amino acid transporter, y+ system), member 5 | KGDVSNLDPNFS FEGTKLDV (337) | N/A | N/A | 1:21160-1:178200 |
| S0705 | breast cancer metastasis suppressor 1 | DKFZp564A063; BRMS1; breast cancer metastasis-suppressor 1; breast cancer metastasis suppressor 1 | KARAAVSPQKR KSDGP (404) | N/A | N/A | 1:1000-1:2000 |
| S0706 | KiSS-1 metastasis-suppressor | MGC39258; KISS1; KiSS-1 metastasis-suppressor; KISS1 METASTIN; malignant melanoma metastasis-suppressor; KISS1 METASTASIS SUPPRESSOR | RQIPAPQGAVLV QREKD (405) | N/A | N/A | 1:180 |
| S0708 | cofactor required for Sp1 transcriptional activation, subunit 3, 130 kDa | DKFZp434H0117; CRSP133; SUR2; DRIP130; CRSP3; mediator; transcriptional co-activator CRSP130; CRSP; 130-KD SUBUNIT; CRSP 130-kD subunit; 133 kDa transcriptional co-activator; 130 kDa transcriptional co-activator; vitamin D3 receptor interacting protein; c | SVKEQVEKIICNL KPALK (406) | N/A | N/A | 1:2430 |
| S5002 | keratin 14 (epidermolysis bullosa simplex, Dowling-Meara, Koebner) | CK; KRT14; K14; EBS4; EBS3; cytokeratin 14; CK 14; KERATIN, TYPE I CYTOSKELETAL 14; keratin 14 (epidermolysis bullosa simplex, Dowling-Meara, Koebner) | Antibody obtained from Chemicon | | | 1:50 |
| S5003 | keratin 17 | PCHC1; PC; PC2; 39.1; KRT17; K17; CYTOKERATIN 17; VERSION 1; CK 17; KERATIN, TYPE I CYTOSKELETAL 17 | | | | 1:10-1:25 |
| S5004 | keratin 18 | K18; CYK18; KRT18; CYTOKERATIN 18; CK 18; KERATIN, TYPE I CYTOSKELETAL 18 | Antibody obtained from Dako | | | 1:200-1:400 |
| S5005 | keratin 18 | K18; CYK18; KRT18; CYTOKERATIN 18; CK 18; KERATIN, TYPE I CYTOSKELETAL 18 | Antibody obtained from Dako | | | 1:50-1:100 |
| S5012 | tumor-associated calcium signal transducer 1 | TROP1; LY74; Ep-CAM; GA733-2; EGP40; MK-1; CO17-1A; EPCAM; M4S1; KSA; TACSTD1; EGP; MK-1 antigen; EPITHELIAL CELLULAR ADHESION MOLECULE; GASTROINTESTINAL TUMOR-ASSOCIATED ANTIGEN 2, 35-KD GLYCOPROTEIN; tumor-associated calcium signal transducer 1 precurso | Antibody obtained from Becton Dickinson | | | 1:40 |
| S5014 | estrogen receptor 2 (ER beta) | ER-BETA; ESR-BETA; ESR2; Erb; ESRB; NR3A2; ESTROGEN RECEPTOR, BETA; estrogen receptor 2 (ER beta) | Antibody obtained from Oncogene Research Products (Calbiochem) | | | 1:2500 |
| S5038 | mucin 1, transmembrane | PEMT; MUC1; episialin; EMA; PUM; H23AG; CD227; PEM; CARCINOMA-ASSOCIATED MUCIN; H23 antigen; TUMOR-ASSOCIATED MUCIN; DF3 antigen; peanut-reactive urinary | Antibody obtained from Imperial Cancer Research Technology (ICRT) | | | 1:1 |

APPENDIX A2-continued

| AGI ID | Antibodies & Genes | | Antibody Generation (SEQ ID NO.) | | | |
|---|---|---|---|---|---|---|
| | GENE NAME | ALIASES | Peptide 1 | Peptide 2 | Peptide 3 | TITER |
| | | mucin; mucin 1, transmembrane; polymorphic epithelial mucin; MUCIN 1, URINARY; MUCIN, TUMOR-ASSOCIATE | | | | |
| S5044 | transferrin receptor (p90, CD71) | P90; TR; TRFC; TFR; CD71; T9; TRFR; ANTIGEN CD71; TRANSFERRIN RECEPTOR PROTEIN; transferrin receptor (p90, CD71) | | Antibody obtained from NeoMarkers | | 1:20 |
| S5045 | v-erb-b2 erythroblastic leukemia viral oncogene homolog 2, neuro/glioblastoma derived oncogene homolog (avian) | HER-2; ERBB2; NGL; P185ERBB2; HER2; C-ERBB-2; NEU; MLN 19; EC 2.7.1.112; TKR1 HERSTATIN; NEU PROTO-ONCOGENE; ONCOGENE ERBB2; RECEPTOR PROTEIN-TYROSINE KINASE ERBB-2 PRECURSOR; ONCOGENE NGL, NEUROBLASTOMA- OR GLIOBLASTOMA-DERIVED; TYROSINE KINASE-TYPE CELL | | Antibody obtained from NeoMarkers | | 1:600 |
| S5047 | major vault protein | MVP; LRP; VAULT1; LUNG RESISTANCE-RELATED PROTEIN; MAJOR VAULT PROTEIN, RAT, HOMOLOG OF | | Antibody obtained from NeoMarkers | | 1:300 |
| S5064 | tumor protein p73-like | LMS; TP73L; KET; SHFM4; p73H; EEC3; TP63; p51; TUMOR PROTEIN p63; TUMOR PROTEIN p73-LIKE; p53-RELATED PROTEIN p63; tumor protein 63 kDa with strong homology to p53 | | Antibody obtained from Dako | | 1:50 |
| S5065 | estrogen receptor 1 | ER; NR3A1; ESR1; Era; ESR; ER-ALPHA; ESRA; ESTRADIOL RECEPTOR; ESTROGEN RECEPTOR, ALPHA; estrogen receptor 1 (alpha) | | Antibody obtained from Dako | | 1:20 |
| S5066 | v-erb-b2 erythroblastic leukemia viral oncogene homolog 2, neuro/glioblastoma derived oncogene homolog (avian) | HER-2; ERBB2; NGL; P185ERBB2; HER2; C-ERBB-2; NEU; MLN 19; EC 2.7.1.112; TKR1 HERSTATIN; NEU PROTO-ONCOGENE; ONCOGENE ERBB2; RECEPTOR PROTEIN-TYROSINE KINASE ERBB-2 PRECURSOR; ONCOGENE NGL, NEUROBLASTOMA- OR GLIOBLASTOMA-DERIVED; TYROSINE KINASE-TYPE CELL | | Antibody obtained from Dako | | 1:300 |
| S5067 | cathepsin D (lysosomal aspartyl protease) | CTSD; MGC2311; CPSD; EC 3.4.23.5; cathepsin D preproprotein; Cathepsin D precursor; cathepsin D (lysosomal aspartyl protease); | | Antibody obtained from Dako | | 1:20-1:50 |
| S5069 | CA 125 | | | Antibody obtained from Dako | | 1:20 |
| S5070 | CA 15-3 | | | Antibody obtained from Dako | | 1:50 |
| S5071 | CA 19-9 | | | Antibody obtained from Dako | | 1:50 |
| S5072 | v-myc myelocytomatosis viral oncogene homolog (avian) | c-Myc; MYC; ONCOGENE MYC; Myc proto-oncogene protein; PROTOONCOGENE HOMOLOGOUS TO MYELOCYTOMATOSIS VIRUS; v-myc myelocytomatosis viral oncogene homolog (avian); v-myc avian myelocytomatosis viral oncogene homolog; Avian myelocytomatosis viral (v-myc) onco | | Antibody obtained from Dako | | 1:50 |

APPENDIX A2-continued

| AGI ID | Antibodies & Genes | | Antibody Generation (SEQ ID NO.) | | | TITER |
|---|---|---|---|---|---|---|
| | GENE NAME | ALIASES | Peptide 1 | Peptide 2 | Peptide 3 | |
| S5073 | cadherin 1, type 1, E-cadherin (epithelial) | CDH1; Cadherin-1; Arc-1; ECAD; CDHE; Uvomorulin; LCAM; Epithelial-cadherin precursor; cell-CAM 120/80; CADHERIN, EPITHELIAL; calcium-dependent adhesion protein, epithelial; cadherin 1, E-cadherin (epithelial); cadherin 1, type 1 preproprotein; cadherin 1, | | Antibody obtained from Dako | | 1:100-1:150 |
| S5074 | glutathione S-transferase pi | GSTP1; DFN7; GSTP1-1; GST3; GSTPP; GST class-pi; glutathione transferase; EC 2.5.1.18; glutathione S-transferase pi; GST, CLASS PI; deafness, X-linked 7; GLUTATHIONE S-TRANSFERASE 3; GLUTATHIONE S-TRANSFERASE, PI; FAEES3 GLUTATHIONE S-TRANSFERASE PI PSEUD | | Antibody obtained from Dako | | 1:50 |
| S5075 | tumor protein p53 (Li-Fraumeni syndrome) | p53; TP53; TRP53; PHOSPHOPROTEIN P53; TRANSFORMATION-RELATED PROTEIN 53; TUMOR SUPPRESSOR P53; CELLULAR TUMOR ANTIGEN P53; tumor protein p53 (Li-Fraumeni syndrome) | | Antibody obtained from Dako | | 1:50 |
| S5076 | progesterone receptor | NR3C3; PR; PGR; PROGESTERONE RESISTANCE; PSEUDOCORPUS LUTEUM INSUFFICIENCY PROGESTERONE RECEPTOR | | Antibody obtained from Dako | | 1:50 |
| S5077 | trefoil factor 1 (breast cancer, estrogen-inducible sequence expressed in) | | | Antibody obtained from Dako | | 1:50-1:100 |
| S5079 | enolase 2, (gamma, neuronal) | NSE; ENO2; 2-phospho-D-glycerate hydrolyase; ENOLASE, GAMMA; neurone-specific enolase; ENOLASE, NEURON-SPECIFIC; 2-phospho-D-glycerate hydrolyase; EC 4.2.1.11; Neural enolase; enolase-2, gamma, neuronal; neuron specific gamma enolase; enolase 2, (gamma, | | Antibody obtained from Dako | | 1:400 |
| S5080 | B-cell CLL/lymphoma 2 | BCL2; FOLLICULAR LYMPHOMA; APOPTOSIS REGULATOR BCL-2; B-cell CLL/lymphoma 2; B-cell lymphoma protein 2 alpha; B-cell lymphoma protein 2 beta; ONCOGENE B-CELL LEUKEMIA 2 LEUKEMIA, CHRONIC LYMPHATIC, TYPE 2 | | Antibody obtained from Dako | | 1:50 |
| S5081 | retinoblastoma 1 (including osteosarcoma) | p105-Rb; PP110; Retinoblastoma-1; RB; RB1; RETINOBLASTOMA-ASSOCIATED PROTEIN; RB OSTEOSARCOMA, RETINOBLASTOMA-RELATED; retinoblastoma 1 (including osteosarcoma) | | Antibody obtained from Dako | | 1:20 |
| S5082 | synaptophysin | SYP; Synaptophysin; Major synaptic vesicle protein P38 | | Antibody obtained from Dako | | 1:50 |

APPENDIX A2-continued

| AGI ID | Antibodies & Genes | | Antibody Generation (SEQ ID NO.) | | | |
|---|---|---|---|---|---|---|
| | GENE NAME | ALIASES | Peptide 1 | Peptide 2 | Peptide 3 | TITER |
| S5083 | BCL2-associated X protein | BAX; BCL2-associated X protein; APOPTOSIS REGULATOR BAX, MEMBRANE ISOFORM ALPHA | | Antibody obtained from Dako | | 1:500 |
| S5086 | estrogen receptor 2 (ER beta) | ER-BETA; ESR-BETA; ESR2; Erb; ESRB; NR3A2; ESTROGEN RECEPTOR, BETA; estrogen receptor 2 (ER beta) | | Antibody obtained from Abcam | | 1:200 |
| S5087 | mucin 1, transmembrane | PEMT; MUC1; episialin; EMA; PUM; H23AG; CD227; PEM; CARCINOMA-ASSOCIATED MUCIN; H23 antigen; TUMOR-ASSOCIATED MUCIN; DF3 antigen; peanut-reactive urinary mucin; mucin 1, transmembrane; polymorphic epithelial mucin; MUCIN 1, URINARY; MUCIN, TUMOR-ASSOCIATE | | Antibody obtained from Zymed | | 1:200-1:1600 |
| S6001 | estrogen receptor 1 | ER; NR3A1; ESR1; Era; ESR, ER-ALPHA; ESRA; ESTRADIOL RECEPTOR; ESTROGEN RECEPTOR, ALPHA; estrogen receptor 1 (alpha) | | Antibody obtained from US Labs | | 1:1 |
| S6002 | progesterone receptor | NR3C3; PR; PGR; PROGESTERONE RESISTANCE; PSEUDOCORPUS LUTEUM INSUFFICIENCY PROGESTERONE RECEPTOR | | Antibody obtained from US Labs | | 1:1 |
| S6003 | v-erb-b2 erythroblastic leukemia viral oncogene homolog 2, neuro/glioblastoma derived oncogene homolog (avian) | HER-2; ERBB2; NGL; P185ERBB2; HER2; C-ERBB-2; NEU; MLN 19; EC 2.7.1.112; TKR1 HERSTATIN; NEU PROTO-ONCOGENE; ONCOGENE ERBB2; RECEPTOR PROTEIN-TYROSINE KINASE ERBB-2 PRECURSOR; ONCOGENE NGL, NEUROBLASTOMA- OR GLIOBLASTOMA-DERIVED; TYROSINE KINASE-TYPE CELL | | Antibody obtained from US Labs | | 1:1 |
| S6004 | B-cell CLL/lymphoma 2 | BCL2; FOLLICULAR LYMPHOMA; APOPTOSIS REGULATOR BCL-2; B-cell CLL/lymphoma 2; B-cell lymphoma protein 2 alpha; B-cell lymphoma protein 2 beta; ONCOGENE B-CELL LEUKEMIA 2 LEUKEMIA, CHRONIC LYMPHATIC, TYPE 2 | | Antibody obtained from US Labs | | 1:1 |
| S6005 | keratin 5 (epidermolysis bullosa simplex, Dowling-Meara/Kobner/Weber-Cockayne types) | KRT5; EBS2; Keratin-5; K5; CYTOKERATIN 5; CK 5; 58 KDA CYTOKERATIN; KERATIN, TYPE II CYTOSKELETAL 5; keratin 5 (epidermolysis bullosa simplex, Dowling-Meara/Kobner/Weber-Cockayne types) | | Antibody obtained from US Labs | | 1:1 |
| S6006 | tumor protein p53 (Li-Fraumeni syndrome) | p53; TP53; TRP53; PHOSPHOPROTEIN P53; TRANSFORMATION-RELATED PROTEIN 53; TUMOR SUPPRESSOR P53; CELLULAR TUMOR ANTIGEN P53; tumor protein p53 (Li-Fraumeni syndrome) | | Antibody obtained from US Labs | | 1:1 |
| S6007 | KI67 | | | Antibody obtained from US Labs | | 1:1 |
| S6008 | epidermal growth factor receptor (erythroblastic | S7; EGFR; 2.7.1.112; ERBB; ONCOGENE ERBB; ERBB1 SPECIES ANTIGEN 7; V-ERB-B | | Antibody obtained from US Labs | | 1:1 |

APPENDIX A2-continued

| | Antibodies & Genes | | Antibody Generation (SEQ ID NO.) | | | |
|---|---|---|---|---|---|---|
| AGI ID | GENE NAME | ALIASES | Peptide 1 | Peptide 2 | Peptide 3 | TITER |
| | leukemia viral (v-erb-b) oncogene homolog, avian) | AVIAN ERYTHROBLASTIC LEUKEMIA VIRAL ONCOGENE HOMOLOG; epidermal growth factor receptor (avian erythroblastic leukemia viral (v-erb-b) oncogene homolog) | | | | |
| S6011 | enolase 2, (gamma, neuronal) | NSE; ENO2; 2-phospho-D-glycerate hydrolyase; ENOLASE, GAMMA; neurone-specific enolase; ENOLASE, NEURON-SPECIFIC; 2-phospho-D-glycerate hydrolyase; EC 4.2.1.11; Neural enolase; enolase-2, gamma, neuronal; neuron specific gamma enolase; enolase 2, (gamma, | | Antibody obtained from US Labs | | 1:1 |
| S6012 | thyroid transcription factor 1 | benign chorea; chorea, hereditary benign; NK-2 (*Drosophila*) homolog A (thyroid nuclear factor); Thyroid transcription factor 1 (NK-2, Drosophila, homolog of, A); BCH; BHC; TEBP; TTF1; NKX2A; TTF-1; NKX2.1 | | Antibody obtained from US Labs | | 1:1 |
| S6013 | v-erb-b2 erythroblastic leukemia viral oncogene homolog 2, neuro/glioblastoma derived oncogene homolog (avian) | HER-2; ERBB2; NGL; P185ERBB2; HER2; C-ERBB-2; NEU; MLN 19; EC 2.7.1.112; TKR1 HERSTATIN; NEU PROTO-ONCOGENE; ONCOGENE ERBB2; RECEPTOR PROTEIN-TYROSINE KINASE ERBB-2 PRECURSOR; ONCOGENE NGL, NEUROBLASTOMA- OR GLIOBLASTOMA-DERIVED; TYROSINE KINASE-TYPE CELL | | Antibody obtained from US Labs | | 1:1 |

APPENDIX A1

| AGI ID | GENE NAME | BREAST? Russ. | BREAST? HH | LUNG? Russ. | LUNG? HH | COLON? Russ. | OVARIAN? Stanf. | OVARIAN? UAB | OVARIAN? Russ. | LocusLink ID | UniGene ID |
|---|---|---|---|---|---|---|---|---|---|---|---|
| S0011 | vav 3 oncogene | | X | | | | | | | 10451 | Hs.267659 |
| S0017 | WAP four-disulfide core domain 2 | | | | | | X | X | X | 10406 | Hs.2719 |
| S0018 | secretoglobin, family 2A, member 2 | | X | | | | | | | 4250 | Hs.46452 |
| S0020 | PPAR binding protein | | X | | | | | | | 5469 | Hs.462956 |
| S0021 | hypothetical protein FLJ23834 | X | X | X | X | | | X | X | 222256 | Hs.202120 |
| S0022 | cytochrome P450 4Z1 | X | X | X | X | X | | X | X | 199974 | Hs.176588 |
| S0024 | RAS-like, estrogen-regulated, growth-inhibitor | | X | | | | | | | 85004 | Hs.199487 |
| S0032 | fatty acid binding protein 3, muscle and heart (mammary-derived growth inhibitor) | | X | | | | | | | 2170 | Hs.112669 |
| S0036 | gamma-aminobutyric acid (GABA) A receptor, pi | | | | | X | | X | | 2568 | Hs.26225 |
| S0037 | annexin A8 | | X | | | | | | | 244 | Hs.524293 |
| S0039 | CDNA FLJ25076 fis, clone CBL06117 | X | X | X | | X | | | X | 134111 | Hs.126856 |
| S0040 | ATP-binding cassette, sub-family B (MDR/TAP), member 1 | X | X | X | | X | | | | 5243 | Hs.489033 |
| S0041 | ATP-binding cassette, sub-family B (MDR/TAP), member 4 | X | | | | | | | X | 5244 | Hs.287827 |
| S0042 | ATP-binding cassette, sub-family C (CFTR/MRP), member 1 | X | X | X | | X | | | X | 4363 | Hs.391464 |
| S0043 | ATP-binding cassette, sub-family C (CFTR/MRP), member 2 | X | X | X | | X | | | X | 1244 | Hs.368243 |
| S0044 | ATP-binding cassette, sub-family C (CFTR/MRP), member 4 | X | X | X | | X | | | | 10257 | Hs.508423 |
| S0045 | ATP-binding cassette, sub-family C (CFTR/MRP), member 3 | X | | | | | | | | 8714 | Hs.463421 |
| S0046 | ATP-binding cassette, sub-family C (CFTR/MRP), member 5 | X | | X | X | X | | | | 10057 | Hs.368563 |
| S0047 | ATP-binding cassette, sub-family C (CFTR/MRP), member 6 | X | | X | | X | | | | 368 | Hs.274260 |
| S0048 | ATP-binding cassette, sub-family B (MDR/TAP), member 11 | X | | | | | | | | 8647 | Hs.158316 |
| S0049 | ATP-binding cassette, sub-family B (MDR/TAP), member 10 | X | X | | | | | | | 23456 | Hs.17614 |
| S0050 | transporter 1, ATP-binding cassette, sub-family B (MDR/TAP) | X | X | | | | | | | 6890 | Hs.352018 |
| S0052 | ATP-binding cassette, sub-family C (CFTR/MRP), member 8 | X | | X | | X | | | | 6833 | Hs.54470 |
| S0053 | ATP-binding cassette, sub-family C (CFTR/MRP), member 9 | X | X | | | | | | | 10060 | Hs.446050 |
| S0055 | integral membrane protein 2B | | X | | | | | | | 9445 | Hs.446450 |
| S0057 | ankyrin 3, node of Ranvier (ankyrin G) | | X | | | | | | | 288 | Hs.499725 |
| S0058 | hypothetical protein FLJ21918 | | | X | | | | | | 80004 | Hs.436585 |
| S0059 | tripartite motif-containing 29 | X | X | X | | X | | | | 23650 | Hs.504115 |
| S0059P2 | tripartite motif-containing 29 | | | | X | | | X | | 23650 | Hs.504115 |
| S0063 | iroquois homeobox protein 3 | | X | X | X | X | | X | | 79191 | Hs.499205 |
| S0068 | RAS-like, estrogen-regulated, growth-inhibitor | | X | | X | | | | | 85004 | Hs.199487 |
| S0070 | G protein-coupled receptor 160 | X | | | | | | | X | 26996 | Hs.231320 |
| S0072 | S100 calcium binding protein A8 (calgranulin A) | | X | | X | | | | | 6279 | Hs.416073 |
| S0073 | forkhead box A1 | | X | | | | | | | 3169 | Hs.163484 |
| S0073P2 | forkhead box A1 | | X | | X | | | | | 3169 | Hs.163484 |
| S0074 | trefoil factor 3 (intestinal) | X | X | X | | X | | | | 7033 | Hs.82961 |
| S0074P3 | trefoil factor 3 (intestinal) | | | | X | | | | | 7033 | Hs.82961 |
| S0076x1 | keratin 17 | | X | | | | | | | 3872 | Hs.2785 |
| S0078 | kynureninase (L-kynurenine hydrolase) | | | | | | | X | | 8942 | Hs.470126 |
| S0079 | solute carrier family 39 (zinc transporter), member 6 | | X | | X | | | | | 25800 | Hs.79136 |
| S0081 | N-acetyltransferase 1 (arylamine N-acetyltransferase) | X | X | | | | | | X | 9 | Hs.155956 |
| S0086 | X-box binding protein 1 | | X | | | | | | | 7494 | Hs.437638 |
| S0088 | claudin 10 | | | | | | | X | | 9071 | Hs.534377 |
| S0090 | sparc/osteonectin, cwcv and kazal-like domains proteoglycan (testican) 2 | | X | | X | | X | X | X | 9806 | Hs.523009 |
| S0091 | lipocalin 2 (oncogene 24p3) | | | | | | X | X | | 3934 | Hs.204238 |
| S0092 | paired box gene 8 | | | | | | X | X | X | 7849 | Hs.469728 |
| S0093 | mesothelin | | | | | | X | X | | 10232 | Hs.408488 |
| S0094 | kallikrein 6 (neurosin, zyme) | | | | | | X | X | | 5653 | Hs.79361 |
| S0095 | Rap guanine nucleotide exchange factor (GEF) 3 | | | | | | X | X | | 10411 | Hs.8578 |
| S0096 | ATPase, H+ transporting, lysosomal 56/58 kDa, V1 subunit B, isoform 1 (Renal tubular acidosis with deafness) | | X | | X | | | X | X | 525 | Hs.64173 |

APPENDIX A1-continued

| | Panels | BREAST? | | LUNG? | | COLON? | OVARIAN? | | | NCBI | |
|---|---|---|---|---|---|---|---|---|---|---|---|
| AGI ID | GENE NAME | Russ. | HH | Russ. | HH | Russ. | Stanf. | UAB | Russ. | LocusLink ID | UniGene ID |
| S0097 | frizzled homolog 8 (*Drosophila*) | | | | | | X | X | | 8325 | Hs.302634 |
| S0099 | histone 1, H2ba | | | | | | X | X | | 255626 | Hs.371887 |
| S0110 | hypothetical protein MGC2714 | X | | X | | X | | | | 84259 | Hs.503716 |
| S0117 | reproduction 8 | | | | | X | | X | | 7993 | Hs.153678 |
| S0119 | slit homolog 1 (*Drosophila*) | | | | | X | | | | 6585 | Hs.500712 |
| S0122 | leucyl-tRNA synthetase 2, mitochondrial | | | | | | | | X | 23395 | Hs.526975 |
| S0123 | homeo box D4 | | | | | | X | X | X | 3233 | Hs.386365 |
| S0124 | sphingosine-1-phosphate lyase 1 | | | | | | X | X | | 8879 | Hs.499984 |
| S0126 | HBxAg transactivated protein 1 | | | | | X | | X | | 55789 | Hs.482233 |
| S0132 | SRY (sex determining region Y)-box 9 (campomelic dysplasia, autosomal sex-reversal) | X | | X | | X | | | X | 6662 | Hs.2316 |
| S0137 | cadherin, EGF LAG seven-pass G-type receptor 2 (flamingo homolog, *Drosophila*) | X | X | X | X | X | | | | 1952 | Hs.57652 |
| S0139 | gamma-glutamyl hydrolase (conjugase, folylpolygammaglutamyl hydrolase) | X | X | | | | X | X | | 8836 | Hs.78619 |
| S0140 | bullous pemphigoid antigen 1, 230/240 kDa | X | X | X | X | X | | X | X | 667 | Hs.485616 |
| S0143 | fatty acid synthase | X | X | X | | | | | | 2194 | Hs.83190 |
| S0143P3 | fatty acid synthase | | X | | X | | | X | | 2194 | Hs.83190 |
| S0144 | matrix metalloproteinase 14 (membrane-inserted) | X | | X | | | X | X | X | 4323 | Hs.2399 |
| S0147 | cystatin A (stefin A) | | X | | X | | | | | 1475 | Hs.518198 |
| S0149 | transient receptor potential cation channel, subfamily V, member 6 | X | | | | | | | | 55503 | Hs.302740 |
| S0156 | fatty acid binding protein 7, brain | X | | X | | X | | | X | 2173 | Hs.26770 |
| S0158 | cadherin 3, type 1, P-cadherin (placental) | X | X | X | X | X | | | X | 1001 | Hs.191842 |
| S0165 | chemokine (C—X—C motif) ligand 1 (melanoma growth stimulating activity, alpha) | X | X | | | | | | | 2919 | Hs.789 |
| S0171 | baculoviral IAP repeat-containing 5 (survivin) | X | | | | | | | | null | Hs.514527 |
| S0193 | procollagen-lysine, 2-oxoglutarate 5-dioxygenase (lysine hydroxylase) 2 | | X | | | | | | | 5352 | Hs.477866 |
| S0202 | PTK7 protein tyrosine kinase 7 | | | | | X | | | | 5754 | Hs.90572 |
| S0211 | cytochrome P450, family 2, subfamily A, polypeptide 7 | X | | X | | | | | | 1549 | Hs.439056 |
| S0218 | solute carrier family 29 (nucleoside transporters), member 4 | X | | | | | | | X | 222962 | Hs.4302 |
| S0221 | solute carrier family 28 (sodium-coupled nucleoside transporter), member 2 | X | X | | | | | | | 9153 | Hs.367833 |
| S0223 | angiopoietin-like 4 | X | | X | | X | | X | X | 51129 | Hs.9613 |
| S0235 | carcinoembryonic antigen-related cell adhesion molecule 5 | | X | | | | | X | | 1048 | Hs.220529 |
| S0237 | podocalyxin-like | | X | | | | | | | 5420 | Hs.16426 |
| S0238 | xenotropic and polytropic retrovirus receptor | | | | | | | X | | 9213 | Hs.227656 |
| S0241 | glycyl-tRNA synthetase | X | | X | | X | | X | X | 2617 | Hs.404321 |
| S0244 | dachshund homolog 1 (*Drosophila*) | | | X | | | | X | | 1602 | Hs.129452 |
| S0251 | transcription factor CP2-like 2 | | | | | X | | | | 29841 | Hs.546382 |
| S0253 | lysosomal associated protein transmembrane 4 beta | X | X | | | | | | | 55353 | Hs.492314 |
| S0255 | cyclin E2 | | X | X | X | X | | | | 9134 | Hs.521693 |
| S0260 | nicastrin | | | X | X | | | X | | 23385 | Hs.517249 |
| S0265 | FXYD domain containing ion transport regulator 3 | | | X | | X | | | | 5349 | Hs.301350 |
| S0267 | immunoglobulin superfamily, member 3 | | | X | | | | | X | 3321 | Hs.171057 |
| S0270 | signal transducing adaptor molecule (SH3 domain and ITAM motif) 2 | | | X | | | | | X | 10254 | Hs.17200 |
| S0273 | dickkopf homolog 1 (*Xenopus laevis*) | | | X | | | | | | 22943 | Hs.40499 |
| S0280 | solute carrier family 26, member 6 | X | | | | | | | | 65010 | Hs.436194 |
| S0286 | WNT inhibitory factor 1 | | X | | | | | | | 11197 | Hs.284122 |
| S0288 | preferentially expressed antigen in melanoma | | | X | | | | | | 23532 | Hs.30743 |
| S0295 | prostaglandin E synthase | | | X | | | | | X | 9536 | Hs.146688 |
| S0296 | solute carrier family 7 (cationic amino acid transporter, y+ system), member 5 | X | X | X | | X | | | X | 8140 | Hs.513797 |
| S0296P1 | solute carrier family 7 (cationic amino acid transporter, y+ system), member 5 | | | X | | X | | X | | 8140 | Hs.513797 |
| S0297 | v-maf musculoaponeurotic fibrosarcoma oncogene homolog K (avian) | | | X | | | | | X | 7975 | Hs.520614 |
| S0301 | signal peptide, CUB domain, EGF-like 2 | X | | | | | | | | 57758 | Hs.523468 |
| S0303 | gamma-aminobutyric acid (GABA) A receptor, epsilon | | X | X | X | X | | | | 2564 | Hs.22785 |

APPENDIX A1-continued

| AGI ID | GENE NAME | BREAST? Russ. | BREAST? HH | LUNG? Russ. | LUNG? HH | COLON? Russ. | OVARIAN? Stanf. | OVARIAN? UAB | OVARIAN? Russ. | NCBI LocusLink ID | UniGene ID |
|---|---|---|---|---|---|---|---|---|---|---|---|
| S0305 | S100 calcium binding protein A10 (annexin II ligand, calpactin I, light polypeptide (p11)) | | X | X | | X | | | | 6281 | Hs.143873 |
| S0311 | v-myb myeloblastosis viral oncogene homolog (avian)-like 2 | X | | X | | X | | | X | 4605 | Hs.179718 |
| S0312 | nucleoside phosphorylase | X | | | | | | X | X | 4860 | Hs.75514 |
| S0314 | chaperonin containing TCP1, subunit 5 (epsilon) | | | X | | X | | | | 22948 | Hs.1600 |
| S0315 | non-metastatic cells 1, protein (NM23A) expressed in | X | X | X | | X | | | | 4830 | Hs.118638 |
| S0316 | squalene epoxidase | X | X | X | | | | | X | 6713 | Hs.71465 |
| S0319 | pregnancy-induced growth inhibitor | | | X | | | | | | 29948 | Hs.528383 |
| S0326 | mal, T-cell differentiation protein 2 | X | | X | | X | | | X | 114569 | Hs.201083 |
| S0330 | aldo-keto reductase family 1, member C1/2 (dihydrodiol dehydrogenase 1; 20-alpha (3-alpha)-hydroxysteroid dehydrogenase) | | | X | X | X | X | X | | 1645 | Hs.460260 |
| S0330-x1 | aldo-keto reductase family 1, member C1/2 (dihydrodiol dehydrogenase 1; 20-alpha (3-alpha)-hydroxysteroid dehydrogenase) | | | X | X | | | | | 1645 | Hs.460260 |
| S0331 | aldo-keto reductase family 1, member C3 (3-alpha hydroxysteroid dehydrogenase, type II) | | | X | X | | X | X | | 8644 | Hs.78183 |
| S0331-x1 | aldo-keto reductase family 1, member C3 (3-alpha hydroxysteroid dehydrogenase, type II) | | | X | X | | | | | 8644 | Hs.78183 |
| S0332 | aldo-keto reductase family 1, member C4 (dihydrodiol dehydrogenase 1; 20-alpha (3-alpha)-hydroxysteroid dehydrogenase) | | | X | X | | | | | 1645 | Hs.460260 |
| S0332-x1 | aldo-keto reductase family 1, member C4 (dihydrodiol dehydrogenase 1; 20-alpha (3-alpha)-hydroxysteroid dehydrogenase) | | | X | X | | | | | 1645 | Hs.460260 |
| S0336 | chromosome 20 open reading frame 139 | | | X | X | | | | | 140809 | Hs.516830 |
| S0342 | solute carrier family 2 (facilitated glucose transporter), member 12 | X | X | X | | X | | | X | 154091 | Hs.486508 |
| S0343 | solute carrier family 2 (facilitated glucose transporter), member 12 | X | X | X | | | | | | 154091 | Hs.486508 |
| S0357 | HTPAP protein | | | | | | | | X | 84513 | Hs.437179 |
| S0364 | KIAA0746 protein | | | | | | | | X | 23231 | Hs.479384 |
| S0367 | peroxisomal acyl-CoA thioesterase 2B | | | | | | | | X | 122970 | Hs.49433 |
| S0374 | chloride intracellular channel 5 | X | | X | | X | | | X | 53405 | Hs.485489 |
| S0380 | keratinocyte associated protein 3 | | | X | | | | X | X | 200634 | Hs.59509 |
| S0384 | FERM, RhoGEF (ARHGEF) and pleckstrin domain protein 1 (chondrocyte-derived) | | | | | X | | | | 10160 | Hs.403917 |
| S0388 | trichorhinophalangeal syndrome I | X | | | | | | | | 7227 | Hs.253594 |
| S0396 | cytochrome P450, family 3, subfamily A, polypeptide 4 | | | | | | | | X | 1576 | Hs.442527 |
| S0398 | FAT tumor suppressor homolog 1 (Drosophila) | | X | X | X | | | | | 2195 | Hs.481371 |
| S0401 | granulin | | | X | | X | | X | | 2896 | Hs.514220 |
| S0404 | N-myc downstream regulated gene 1 | X | X | X | X | X | X | X | X | 10397 | Hs.372914 |
| S0411 | fatty acid binding protein 5 (psoriasis-associated) | | | X | | | | | | 2171 | Hs.408061 |
| S0413 | cyclin-dependent kinase inhibitor 1C (p57, Kip2) | | | X | | | | | | 1028 | Hs.106070 |
| S0414 | alpha-methylacyl-CoA racemase | | | | | X | | | | 23600 | Hs.508343 |
| S0415 | gamma-aminobutyric acid (GABA) A receptor, beta 3 | | X | X | | | | | | 2562 | Hs.302352 |
| S0417 | HSV-1 stimulation-related gene 1 | X | X | | | | | | | 22879 | Hs.436089 |
| S0425 | tumor necrosis factor receptor superfamily, member 21 | | | | | X | | | | 27242 | Hs.443577 |
| S0429 | jumonji domain containing 1C | | | | | X | | | | 221037 | Hs.413416 |
| S0432 | chromosome 9 open reading frame 140 | X | X | X | X | X | | | | null | Hs.19322 |
| S0440 | cell division cycle 25B | X | X | | | | | | X | 994 | Hs.153752 |
| S0445 | laminin, beta 1 | | | X | | | | | | 3912 | Hs.489646 |
| S0447 | papillary renal cell carcinoma (translocation-associated) | X | | | | | | X | | 5546 | Hs.516948 |
| S0455 | tumor necrosis factor (ligand) superfamily, member 10 | | | | | X | | | | 8743 | Hs.478275 |
| S0459 | titin | X | X | | | | | | | 7273 | Hs.134602 |
| S0469 | DNA fragmentation factor, 45 kDa, alpha polypeptide | | | X | | | | | | 1676 | Hs.484782 |
| S0494 | caspase 2, apoptosis-related cysteine protease (neural precursor cell expressed, developmentally down-regulated 2) | X | | | | | | | | 835 | Hs.368982 |
| S0501 | G1 to S phase transition 1 | X | | X | | X | | | | 2935 | Hs.528780 |

APPENDIX A1-continued

| AGI ID | GENE NAME | BREAST? Russ. | BREAST? HH | LUNG? Russ. | LUNG? HH | COLON? Russ. | OVARIAN? Stanf. | OVARIAN? UAB | OVARIAN? Russ. | LocusLink ID | UniGene ID |
|---|---|---|---|---|---|---|---|---|---|---|---|
| S0502 | GCN5 general control of amino-acid synthesis 5-like 2 (yeast) | X | | X | | X | | | | 2648 | Hs.463045 |
| S0503 | geminin, DNA replication inhibitor | | | | | | | | X | 51053 | Hs.234896 |
| S0507 | ADP-ribosylation factor-like 6 interacting protein 2 | | | X | | | | | | 64225 | Hs.190440 |
| S0511 | DNA replication complex GINS protein PSF2 | X | | | | | | | | 51659 | Hs.433180 |
| S0524 | ankyrin repeat domain 10 | X | | | | | | | | 55608 | Hs.525163 |
| S0527 | potassium channel tetramerisation domain containing 2 | | | | | X | | | | null | Hs.514468 |
| S0528 | rabconnectin-3 | X | | X | | | | | X | 23312 | Hs.511386 |
| S0538 | acidic (leucine-rich) nuclear phosphoprotein 32 family, member E | | | | | X | | | | 81611 | Hs.385913 |
| S0544 | chromosome 9 open reading frame 100 | X | | | | | | X | | 84904 | Hs.277026 |
| S0545 | HpaII tiny fragments locus 9C | X | X | | X | | | X | | 27037 | Hs.528643 |
| S0546 | cell division cycle associated 2 | X | | | | | | | | 157313 | Hs.33366 |
| S0553 | mitotic phosphoprotein 44 | | | X | | X | | | | 129401 | Hs.180591 |
| S0557 | SMC4 structural maintenance of chromosomes 4-like 1 (yeast) | | | | | X | | | | 10051 | Hs.58992 |
| S0564 | phosphatidylserine synthase 1 | X | X | X | | X | | | | 9791 | Hs.292579 |
| S0565 | polo-like kinase 1 (Drosophila) | X | X | | | | | | X | 5347 | Hs.329989 |
| S0567 | Pirin | X | | | | X | | | | 8544 | Hs.495728 |
| S0578 | ATP-binding cassette, sub-family A (ABC1), member 3 | | | X | | | | | | 21 | Hs.26630 |
| S0579 | ATP-binding cassette, sub-family A (ABC1), member 7 | | | X | X | | | | | 10347 | Hs.134514 |
| S0581 | ATP-binding cassette, sub-family B (MDR/TAP), member 7 | | X | X | | X | | | | 22 | Hs.370480 |
| S0585 | ATP-binding cassette, sub-family C (CFTR/MRP), member 12 | | | X | | X | | | | 94160 | Hs.410111 |
| S0586 | ATP-binding cassette, sub-family G (WHITE), member 2 | | | X | X | | | | X | 9429 | Hs.480218 |
| S0593 | solute carrier organic anion transporter family, member 1B3 | X | X | X | | X | | | | 28234 | Hs.504966 |
| S0597 | solute carrier family 22 (organic anion transporter), member 6 | X | | | | | | | | 9356 | Hs.369252 |
| S0604 | solute carrier family 35 (UDP-galactose transporter), member A2 | X | | | | X | | | | 7355 | Hs.21899 |
| S0607 | cell division cycle 25B | | | | | X | | | | 994 | Hs.153752 |
| S0609 | stearoyl-CoA desaturase (delta-9-desaturase) | | | X | | | | | X | 6319 | Hs.368641 |
| S0611 | mitogen-activated protein kinase 12 | | | X | | X | | | | 6300 | Hs.432642 |
| S0612 | nuclear factor of kappa light polypeptide gene enhancer in B-cells 2 (p49/p100) | | | X | | X | | | | 4791 | Hs.73090 |
| S0613 | tumor necrosis factor receptor superfamily, member 5 | | | X | | X | | | | 958 | Hs.472860 |
| S0614 | Epstein-Barr virus induced gene 3 | | | X | X | X | | X | | 10148 | Hs.501452 |
| S0616 | zinc finger protein 339 | | | X | | | | | | 58495 | Hs.546418 |
| S0617 | DAB2 interacting protein | | X | | | | | | | 153090 | Hs.522378 |
| S0618 | protein tyrosine phosphatase, receptor type, f polypeptide (PTPRF), interacting protein (liprin), alpha 1 | | | | | X | | | | 8500 | Hs.530749 |
| S0631 | RGM domain family, member A | | | | | X | | | | 56963 | Hs.271277 |
| S0633 | hypothetical protein LOC144347 | | X | | | X | | X | | 144347 | Hs.432901 |
| S0639 | tetratricopeptide repeat domain 7 | | | | | X | | X | | 57217 | Hs.370603 |
| S0640 | protein C (inactivator of coagulation factors Va and VIIIa) | | | | | X | | X | | 5624 | Hs.224698 |
| S0643 | transducin-like enhancer of split 3 (E(sp1) homolog, Drosophila) | | X | | X | | | X | | 7090 | Hs.287362 |
| S0645 | frizzled homolog 7 (Drosophila) | | | X | | | | | | 8324 | Hs.173859 |
| S0646 | solute carrier family 3 (activators of dibasic and neutral amino acid transport), member 2 | X | | X | | | | | | 6520 | Hs.502769 |
| S0648 | KIAA0738 gene product | | | | | X | | | | 9747 | Hs.406492 |
| S0651 | phospholipase A2 receptor 1, 180 kDa | | | | | X | | | | 22925 | Hs.410477 |
| S0654 | KIAA0182 protein | | X | | | | | | | 23199 | Hs.461647 |
| S0659 | thymidine kinase 2, mitochondrial | | X | | | | | | | 7084 | Hs.512619 |
| S0663 | chromosome 14 open reading frame 135 | | X | X | | X | | | | 64430 | Hs.509499 |
| S0665 | KIAA1007 protein | | X | X | | X | | | | 23019 | Hs.460923 |
| S0670 | DKFZP566O1646 protein | | X | | | | | | | 25936 | Hs.497692 |
| S0672 | B-cell CLL/lymphoma 7A | | | | | | | X | | 605 | Hs.530970 |
| S0673 | likely ortholog of mouse nin one binding protein | | | X | | | | | | 28987 | Hs.271695 |
| S0676 | guanine nucleotide binding protein (G protein) alpha 12 | | | X | | | | | | 2768 | Hs.487341 |
| S0677 | GrpE-like 1, mitochondrial (E. coli) | | | X | | | | | | 80273 | Hs.443723 |

APPENDIX A1-continued

| | | BREAST? | | LUNG? | | COLON? | OVARIAN? | | | NCBI | |
|---|---|---|---|---|---|---|---|---|---|---|---|
| AGI ID | GENE NAME | Russ. | HH | Russ. | HH | Russ. | Stanf. | UAB | Russ. | LocusLink ID | UniGene ID |
| S0684 | hypothetical protein FLJ34922 | | X | | | | | | | 91607 | Hs.462829 |
| S0687 | hypothetical protein FLJ20457 | | X | | | | | | | 54942 | Hs.29276 |
| S0691 | solute carrier family 7, (cationic amino acid transporter, y+ system) member 11 | | | X | | | | X | | 23657 | Hs.6682 |
| S0692 | glutamate-cysteine ligase, catalytic subunit | | | | | | | | X | 2729 | Hs.271264 |
| S0695 | integrin, beta 4 | | X | | X | | | X | | 3691 | Hs.370255 |
| S0702 | solute carrier family 7 (cationic amino acid transporter, y+ system), member 5 | | X | | X | | | X | | 8140 | Hs.513797 |
| S0705 | breast cancer metastasis suppressor 1 | | | | | | | X | | 25855 | Hs.100426 |
| S0706 | KiSS-1 metastasis-suppressor | | | | | | | X | | 3814 | Hs.95008 |
| S0708 | cofactor required for Sp1 transcriptional activation, subunit 3, 130 kDa | | | | | | | X | | 9439 | Hs.29679 |
| S5002 | keratin 14 (epidermolysis bullosa simplex, Dowling-Meara, Koebner) | X | | X | | X | | X | | 3861 | Hs.355214 |
| S5003 | keratin 17 | X | | | | | | | | 3872 | Hs.2785 |
| S5004 | keratin 18 | X | | | | | | | | 3875 | Hs.406013 |
| S5005 | keratin 18 | X | | X | | X | | | | 3875 | Hs.406013 |
| S5012 | tumor-associated calcium signal transducer 1 | X | | X | | X | | | | 4072 | Hs.692 |
| S5014 | estrogen receptor 2 (ER beta) | X | | | | | | | | 2100 | Hs.443150 |
| S5038 | mucin 1, transmembrane | X | | X | | X | | | | 4582 | Hs.89603 |
| S5044 | transferrin receptor (p90, CD71) | X | | X | | X | | | | 7037 | Hs.529618 |
| S5045 | v-erb-b2 erythroblastic leukemia viral oncogene homolog 2, neuro/glioblastoma derived oncogene homolog (avian) | X | | | | X | | | | 2064 | Hs.446352 |
| S5047 | major vault protein | X | | X | | X | | | | 9961 | Hs.513488 |
| S5064 | tumor protein p73-like | | | X | | | | | | 8626 | Hs.137569 |
| S5065 | estrogen receptor 1 | X | | | | | | | | 2099 | Hs.208124 |
| S5066 | v-erb-b2 erythroblastic leukemia viral oncogene homolog 2, neuro/glioblastoma derived oncogene homolog (avian) | X | | | | X | | | | 2064 | Hs.446352 |
| S5067 | cathepsin D (lysosomal aspartyl protease) | X | | X | | X | | | | 1509 | Hs.546248 |
| S5069 | CA 125 | | | X | | | | | | n/a | null |
| S5070 | CA 15-3 | X | | X | | X | | | | n/a | null |
| S5071 | CA 19-9 | X | | X | | X | | | | n/a | null |
| S5072 | v-myc myelocytomatosis viral oncogene homolog (avian) | | | X | | X | | | | 4609 | Hs.202453 |
| S5073 | cadherin 1, type 1, E-cadherin (epithelial) | X | | X | | X | X | | | 999 | Hs.461086 |
| S5074 | glutathione S-transferase pi | | | X | | X | | | | 2950 | Hs.523836 |
| S5075 | tumor protein p53 (Li-Fraumeni syndrome) | | | X | | X | | | | 7157 | Hs.408312 |
| S5076 | progesterone receptor | X | | | | X | | | | 5241 | Hs.368072 |
| S5077 | trefoil factor 1 (breast cancer, estrogen-inducible sequence expressed in) | X | X | | | | | | | 7031 | Hs.162807 |
| S5079 | enolase 2, (gamma, neuronal) | X | | X | | X | | | | 2026 | Hs.511915 |
| S5080 | B-cell CLL/lymphoma 2 | | | X | | | | | | 596 | Hs.150749 |
| S5081 | retinoblastoma 1 (including osteosarcoma) | | | X | | X | | | | 5925 | Hs.408528 |
| S5082 | synaptophysin | | | X | | X | | | | 6855 | Hs.75667 |
| S5083 | BCL2-associated X protein | | | | | X | | | | 581 | Hs.159428 |
| S5086 | estrogen receptor 2 (ER beta) | | | | X | | | | | 2100 | Hs.443150 |
| S5087 | mucin 1, transmembrane | | | | X | | | | | 4582 | Hs.89603 |
| S6001 | estrogen receptor 1 | | X | | | | | | | 2099 | Hs.208124 |
| S6002 | progesterone receptor | | X | | | | | | | 5241 | Hs.368072 |
| S6003 | v-erb-b2 erythroblastic leukemia viral oncogene homolog 2, neuro/glioblastoma derived oncogene homolog (avian) | | X | | | | | | | 2064 | Hs.446352 |
| S6004 | B-cell CLL/lymphoma 2 | | | | X | | | | | 596 | Hs.150749 |
| S6005 | keratin 5 (epidermolysis bullosa simplex, Dowling-Meara/Kobner/Weber-Cockayne types) | X | | | X | | | X | | 3852 | Hs.433845 |
| S6006 | tumor protein p53 (Li-Fraumeni syndrome) | | | X | X | | | | | 7157 | Hs.408312 |
| S6007 | KI67 | | | X | X | | | | | n/a | null |
| S6008 | epidermal growth factor receptor (erythroblastic leukemia viral (v-erb-b) oncogene homolog, avian) | | | | X | | | | | 1956 | Hs.488293 |
| S6011 | enolase 2, (gamma, neuronal) | | | | X | | | | | 2026 | Hs.511915 |
| S6012 | thyroid transcription factor 1 | | | | X | | | | | 7080 | Hs.94367 |
| S6013 | v-erb-b2 erythroblastic leukemia viral oncogene homolog 2, neuro/glioblastoma derived oncogene homolog (avian) | | | | X | | | | | 2064 | Hs.446352 |

APPENDIX C

| BREAST PROGNOSIS (HH COHORT) | | | All Log rank | | ER Pos Log rank | | ER Pos/Node Neg Log rank | | ER neg Log rank | |
|---|---|---|---|---|---|---|---|---|---|---|
| AGI ID | Dilution (1:X) | Scoring method | P value | Hazard ratio | P value | Hazard ratio | P value | Hazard ratio | P value | Hazard ratio |
| s0021 | 500 | 3 | 0.0001 | 2.8378 | 0.0014 | 3.6147 | 0.0003 | 4.9455 | 0.0588 | 2.0089 |
| s0022 | 100 | 2 | >0.10 | 0.9363 | >0.10 | 0.6376 | >0.10 | 0.8219 | >0.10 | 1.4664 |
| s0039 | 100 | 1 | >0.10 | 1.1066 | 0.0625 | 1.1982 | 0.0551 | 1.2810 | >0.10 | 1.0798 |
| s0040 | 200 | 3 | 0.0389 | 1.7357 | >0.10 | 1.2649 | 0.0983 | 2.2353 | 0.0449 | 2.0825 |
| s0059 | 300 | 3 | 0.0469 | 1.9686 | 0.0468 | 3.7769 | 0.0099 | 5.4146 | >0.10 | 1.3547 |
| s0063 | 300 | 2 | 0.0037 | 1.7351 | 0.0418 | 1.6450 | >0.10 | 1.5656 | >0.10 | 1.5060 |
| s0068 | 700 | 2 | 0.0218 | 0.6445 | >0.10 | 0.8501 | >0.10 | 0.7793 | 0.0982 | 0.5632 |
| s0072 | 6500 | 2 | 0.0627 | 1.4824 | 0.0069 | 2.2083 | >0.10 | 1.0843 | >0.10 | 0.7685 |
| s0073P2 | 450 | 2 | 0.0023 | 0.5703 | >0.10 | 0.7329 | >0.10 | 0.6297 | 0.0987 | 0.4909 |
| s0076x1 | 200 | 2 | 0.0807 | 1.2392 | >0.10 | 0.6988 | >0.10 | 0.9070 | >0.10 | 1.1187 |
| s00791 | 400 | 2 | 0.0007 | 1.9503 | 0.0002 | 2.5357 | >0.10 | 1.3644 | >0.10 | 1.1705 |
| s0081 | 60 | 2 | 0.0026 | 0.5093 | 0.0384 | 0.5774 | >0.10 | 0.8913 | >0.10 | 0.5235 |
| s0137 | 2500 | 2 | 0.0322 | 1.4856 | 0.0745 | 1.5241 | 0.0872 | 1.8527 | >0.10 | 1.2568 |
| s0143P3 | 630 | 1 | 0.0932 | 1.0806 | 0.0342 | 1.1450 | >0.10 | 1.1183 | >0.10 | 1.0291 |
| s0143P3 | 630 | 3 | 0.0294 | 1.7362 | 0.0103 | 2.1681 | >0.10 | 1.7919 | >0.10 | 1.2595 |
| s0235 | 4500 | 2 | 0.0174 | 1.6960 | 0.0284 | 1.8866 | >0.10 | 1.4827 | >0.10 | 1.4227 |
| s0237 | 1000 | 3 | >0.10 | 1.3805 | >0.10 | 1.9314 | 0.0431 | 3.2504 | >0.10 | 0.9726 |
| s0255n | 1000 | 2 | >0.10 | 0.7361 | 0.0933 | 0.6593 | >0.10 | 0.6550 | >0.10 | 0.9813 |
| s0260 | 5400 | 2 | >0.10 | 1.0896 | 0.0695 | 0.2945 | >0.10 | 0.6016 | >0.10 | 1.2113 |
| s0296P1 | 225 | 2 | 0.0038 | 1.7491 | 0.0002 | 2.5560 | 0.0466 | 2.3419 | >0.10 | 0.8519 |
| s0303 | 300 | 2 | 0.0860 | 1.4072 | >0.10 | 1.1960 | >0.10 | 1.5662 | >0.10 | 1.3788 |
| s0305 | 8332 | 2 | 0.0809 | 1.2267 | >0.10 | 1.1590 | >0.10 | 0.9719 | >0.10 | 1.2343 |
| s0330x1 | 600 | 2 | >0.10 | 0.9730 | 0.0134 | 3.3569 | 0.0632 | 5.4988 | 0.0555 | 0.0021 |
| s0343 | 125 | 2 | >0.10 | 0.7487 | 0.0795 | 0.6256 | >0.10 | 0.5594 | >0.10 | 1.1414 |
| s0398 | 200 | 2 | 0.0125 | 0.4725 | >0.10 | 0.6070 | >0.10 | 0.8846 | 0.0725 | 0.1956 |
| s0398 | 200 | 3 | 0.0551 | 0.3428 | 0.0790 | 0.3049 | >0.10 | 0.4646 | >0.10 | 0.6364 |
| s0404 | 150 | 1 | 0.0321 | 1.1427 | >0.10 | 1.1160 | >0.10 | 1.1811 | >0.10 | 1.0783 |
| s0404 | 150 | 3 | 0.0087 | 1.8696 | >0.10 | 1.7755 | 0.0727 | 2.3524 | >0.10 | 1.4714 |
| s0459 | 2700 | 2 | >0.10 | 1.3287 | >0.10 | 1.4538 | >0.10 | 1.2304 | >0.10 | 0.9768 |
| s0545 | 900 | 2 | 0.0000 | 2.2547 | 0.0048 | 2.1037 | >0.10 | 1.7913 | 0.0300 | 2.0266 |
| s0654 | 400 | 3 | 0.0050 | 2.8738 | >0.10 | 1.5890 | >0.10 | 1.2356 | 0.0119 | 3.1822 |
| s0670 | 900 | 2 | >0.10 | 0.7709 | 0.0715 | 0.5411 | 0.0652 | 0.2800 | >0.10 | 0.9506 |
| s0676 | 1200 | 1 | 0.0088 | 1.1968 | >0.10 | 1.0888 | >0.10 | 1.2110 | 0.0130 | 1.2678 |
| s0677 | 500 | 2 | 0.0041 | 1.7183 | 0.0289 | 1.7290 | >0.10 | 1.1095 | >0.10 | 1.3276 |
| s0691NM | 1575 | 2 | 0.0280 | 1.8399 | >0.10 | 1.0211 | >0.10 | 1.6936 | 0.0761 | 1.8725 |
| s0702 | 178200 | 2 | 0.0005 | 1.9066 | 0.0000 | 2.8624 | 0.0120 | 2.6656 | >0.10 | 0.9739 |
| s6001 | na | 1 | 0.0292 | 0.8715 | na | na | na | na | na | na |
| s6002 | na | 1 | 0.0027 | 0.8341 | 0.0214 | 0.8319 | >0.10 | 0.8850 | >0.10 | 0.9325 |
| s6003 | na | 3 | 0.0176 | 1.9477 | 0.0051 | 3.1766 | >0.10 | 1.3355 | >0.10 | 1.2017 |
| s6006 | na | 2 | 0.0194 | 1.5374 | 0.0958 | 1.5021 | 0.0135 | 2.3697 | >0.10 | 1.2597 |
| s6007 | na | 1 | 0.0756 | 1.1144 | 0.0107 | 1.2055 | >0.10 | 1.0747 | 0.0342 | 0.9164 |

APPENDIX D

| LUNG PROGNOSIS (HH COHORT) | | | All Log rank | | | Adenocarcinoma Log rank | | | Squamous cell Log rank | | |
|---|---|---|---|---|---|---|---|---|---|---|---|
| AGI ID | Dilution (1:X) | Scoring method | P value | Hazard ratio | Chi square P value | P value | Hazard ratio | Chi square P value | P value | Hazard ratio | Chi square P value |
| s0021 | 1500 | 3 | 0.1288 | 1.8320 | 0.0240 | 0.2188 | 1.6167 | 0.0860 | 0.0005 | 0.0657 | 0.0100 |
| s0022 | 250 | 2 | 0.0116 | 0.3747 | 0.1000 | >0.10 | nd | >0.10 | >0.10 | nd | >0.10 |
| s0039 | 400 | 2 | 0.3532 | 1.5469 | 0.0080 | >0.10 | nd | >0.10 | >0.10 | nd | >0.10 |
| s0046 | 300 | 2 | 0.0145 | 0.5165 | 0.0270 | >0.10 | nd | >0.10 | 0.0529 | 0.3302 | 0.0850 |
| s0063 | 1200 | 2 | >0.10 | nd | >0.10 | 0.0831 | 1.8631 | 0.0550 | >0.10 | nd | >0.10 |
| s0072 | 6500 | 2 | 0.2633 | 1.3570 | 0.0680 | >0.10 | nd | >0.10 | >0.10 | nd | >0.10 |
| s0073P2 | 50 | 2 | 0.0935 | 0.4640 | 0.0430 | >0.10 | nd | >0.10 | >0.10 | nd | >0.10 |
| s0074P3 | 810 | 3 | 0.0723 | 0.0022 | 0.0530 | >0.10 | nd | >0.10 | >0.10 | nd | >0.10 |
| s0137 | 5000 | 2 | 0.0610 | 1.6429 | 0.1010 | 0.2271 | 1.5312 | 0.0660 | >0.10 | nd | >0.10 |
| s0143P3 | 300 | 3 | >0.10 | nd | >0.10 | 0.0008 | 4.5211 | 0.0270 | >0.10 | nd | >0.10 |
| s0296P1 | 1350 | 2 | 0.0783 | 1.6148 | 0.0460 | 0.0237 | 2.1849 | 0.0180 | 0.1042 | 0.3968 | 0.0840 |
| s0303 | 300 | 2 | >0.10 | nd | >0.10 | 0.0469 | 2.0494 | 0.5360 | >0.10 | nd | >0.10 |
| s0330 | 15000 | 3 | >0.10 | nd | >0.10 | >0.10 | nd | >0.10 | 0.0124 | 0.2278 | 0.0460 |
| s0330 | 45000 | 3 | 0.0880 | 0.5248 | 0.0440 | 0.0440 | nd | >0.10 | 0.0188 | 0.1270 | 0.0130 |
| s0330x1 | 600 | 3 | >0.10 | nd | >0.10 | >0.10 | nd | >0.10 | 0.0455 | 0.1631 | 0.0080 |
| s0331 | 300 | 3 | 0.2157 | 0.6603 | 0.0850 | >0.10 | nd | >0.10 | 0.0404 | 0.2350 | 0.0050 |
| s0331x1 | 300 | 3 | >0.10 | nd | >0.10 | >0.10 | nd | >0.10 | 0.0705 | 0.2744 | 0.0360 |
| s0332 | 400 | 3 | 0.1496 | 0.5639 | 0.0680 | >0.10 | nd | >0.10 | 0.0621 | 0.1785 | 0.0160 |
| s0332x1 | 150 | 2 | >0.10 | nd | >0.10 | >0.10 | nd | >0.10 | 0.0321 | 0.1466 | 0.1290 |

APPENDIX D-continued

| LUNG PROGNOSIS (HH COHORT) | | | All Log rank | | | Adenocarcinoma Log rank | | | Squamous cell Log rank | | |
|---|---|---|---|---|---|---|---|---|---|---|---|
| AGI ID | Dilution (1:X) | Scoring method | P value | Hazard ratio | Chi square P value | P value | Hazard ratio | Chi square P value | P value | Hazard ratio | Chi square P value |
| s0398 | 200 | 2 | 0.1253 | 0.5775 | 0.0870 | >0.10 | nd | >0.10 | 0.3348 | 0.6094 | 0.0640 |
| s0404 | 900 | 3 | 0.1273 | 1.7817 | 0.0420 | >0.10 | nd | >0.10 | >0.10 | nd | >0.10 |
| s0545 | 2700 | 2 | 0.1246 | 1.8432 | 0.0150 | 0.0191 | 3.2839 | 0.0180 | >0.10 | nd | >0.10 |
| s0586 | 400 | 2 | 0.0204 | 0.4659 | 0.4380 | 0.1322 | 0.2457 | 0.0960 | >0.10 | nd | >0.10 |
| s0691 | 1575 | 3 | >0.10 | nd | >0.10 | >0.10 | nd | >0.10 | 0.0608 | 3.1820 | 0.0420 |
| s0702 | 178200 | 1 | >0.10 | nd | >0.10 | >0.10 | nd | >0.10 | 0.0463 | 0.6944 | 0.5360 |
| s6006 | 1 | 2 | >0.10 | nd | >0.10 | 0.1259 | 1.7720 | 0.0550 | >0.10 | nd | >0.10 |
| s6007 | 1 | 2 | >0.10 | nd | >0.10 | 0.0316 | 3.4266 | 0.0110 | >0.10 | nd | >0.10 |
| s6008 | 1 | 2 | >0.10 | nd | >0.10 | >0.10 | nd | >0.10 | 0.2388 | 1312.0118 | 0.0230 |
| s6013 | 1 | 2 | >0.10 | nd | >0.10 | 0.0154 | 2.5755 | 0.0540 | >0.10 | nd | >0.10 |
| s0614 | 3000 | 2 | 0.0930 | 1.5785 | 0.0860 | >0.10 | nd | >0.10 | >0.10 | nd | >0.10 |

APPENDIX E

| BREAST PROGNOSIS (HH COHORT) | | | All Log rank | | ER Pos Log rank | | ER Pos/Node Neg Log rank | | ER neg Log rank | |
|---|---|---|---|---|---|---|---|---|---|---|
| AGI ID | Dilution (1:X) | Scoring method | P value | Hazard ratio | P value | Hazard ratio | P value | Hazard ratio | P value | Hazard ratio |
| s0022 | 100 | 2 | >0.10 | 0.8660 | 0.0633 | 0.5679 | >0.10 | 0.8810 | >0.10 | 1.3696 |
| s0053 | 30 | 2 | 0.0496 | 0.6276 | >0.10 | 0.7265 | >0.10 | 1.0372 | >0.10 | 0.5002 |
| s0059P2 | 90 | 2 | 0.0088 | 1.9934 | >0.10 | 1.7964 | >0.10 | 1.8087 | >0.10 | 1.4654 |
| s0063 | 300 | 2 | 0.0031 | 1.7208 | 0.0955 | 1.5202 | >0.10 | 1.5656 | >0.10 | 1.7249 |
| s0063 | 600 | 2 | 0.0006 | 1.9517 | 0.0154 | 2.0148 | 0.0660 | 2.4507 | >0.10 | 1.4408 |
| s0068 | 700 | 2 | 0.0312 | 0.6537 | >0.10 | 0.8644 | >0.10 | 0.7793 | 0.0936 | 0.5597 |
| s0072 | 6500 | 2 | >0.10 | 1.4087 | 0.0307 | 2.0193 | >0.10 | 1.3344 | >0.10 | 0.7426 |
| s0073p2 | 450 | 2 | 0.0060 | 0.6051 | >0.10 | 0.8755 | >0.10 | 1.0495 | >0.10 | 0.4614 |
| s0076x1 | 200 | 2 | 0.0471 | 1.6431 | >0.10 | 0.5060 | >0.10 | 0.8227 | >0.10 | 1.3384 |
| s0079 | 400 | 2 | 0.0006 | 1.8382 | 0.0050 | 2.0469 | >0.10 | 1.0820 | >0.10 | 1.2420 |
| s0081 | 60 | 2 | 0.0006 | 0.5518 | 0.0621 | 0.6335 | >0.10 | 0.7897 | >0.10 | 0.4758 |
| s0140 | 500 | 2 | 0.0146 | 1.7628 | >0.10 | 1.7553 | >0.10 | 0.6881 | >0.10 | 1.3817 |
| s0235 | 4500 | 2 | 0.0002 | 1.9769 | 0.0017 | 2.1999 | >0.10 | 1.5655 | >0.10 | 1.5469 |
| s0253 | 2000 | 2 | 0.0579 | 1.5740 | >0.10 | 1.5128 | 0.0784 | 2.1386 | >0.10 | 1.4763 |
| s0253 | 500 | 2 | >0.10 | 1.1127 | >0.10 | 0.7030 | >0.10 | 0.8017 | 0.0377 | 2.1389 |
| s0255 | 1000 | 2 | 0.0610 | 0.6995 | 0.0603 | 0.6193 | >0.10 | 0.6550 | >0.10 | 0.8992 |
| s0296P1 | 225 | 1 | 0.0028 | 1.1896 | 0.0001 | 1.3344 | 0.0008 | 1.3554 | >0.10 | 0.9879 |
| s0296P1 | 225 | 2 | 0.0052 | 1.7183 | 0.0014 | 2.3378 | 0.0466 | 2.3419 | >0.10 | 0.8994 |
| s0305 | 8332 | 2 | 0.0945 | 1.5035 | >0.10 | 1.2945 | >0.10 | 0.9447 | >0.10 | 1.4199 |
| s0330x1 | 600 | 2 | >0.10 | 0.7456 | 0.0945 | 2.6186 | 0.0632 | 5.4988 | 0.0525 | 0.0021 |
| s0404 | 150 | 2 | 0.0265 | 1.6475 | >0.10 | 1.3534 | >0.10 | 1.8109 | >0.10 | 1.4264 |
| s0404 | 150 | 3 | 0.0027 | 2.0719 | 0.0706 | 1.8942 | 0.0623 | 2.4347 | >0.10 | 1.6912 |
| s0440 | 1200 | 2 | 0.0581 | 0.6270 | >0.10 | 0.8110 | >0.10 | 0.6788 | >0.10 | 0.2904 |
| s0545 | 2700 | 2 | 0.0000 | 2.4278 | >0.10 | 1.7002 | >0.10 | 0.7788 | 0.0024 | 2.4284 |
| s0545 | 900 | 2 | 0.0000 | 2.2447 | 0.0055 | 2.1160 | >0.10 | 1.7913 | 0.0412 | 1.9465 |
| s0654 | 400 | 2 | >0.10 | 0.8150 | 0.0676 | 0.4627 | >0.10 | 0.6037 | >0.10 | 1.7718 |
| s0670 | 900 | 2 | >0.10 | 0.7040 | 0.0258 | 0.4379 | 0.0652 | 0.2800 | >0.10 | 0.8549 |
| s0676 | 1200 | 1 | 0.0113 | 1.1614 | >0.10 | 1.0623 | >0.10 | 1.2110 | 0.0212 | 1.2442 |
| s0676 | 1200 | 2 | 0.0392 | 1.5231 | >0.10 | 1.2602 | >0.10 | 1.9314 | 0.0875 | 1.8335 |
| s0677 | 1000 | 1 | 0.0017 | 1.1649 | 0.0076 | 1.2173 | >0.10 | 1.0408 | >0.10 | 1.0892 |
| s0677 | 1000 | 2 | 0.0123 | 1.5683 | 0.0148 | 1.8170 | >0.10 | 1.0567 | >0.10 | 1.2487 |
| s0687 | 1260 | 2 | 0.0830 | 0.6973 | 0.0519 | 0.5427 | >0.10 | 1.1017 | >0.10 | 0.8919 |
| s0691 | 1575 | 1 | 0.0001 | 1.2824 | >0.10 | 1.0463 | >0.10 | 1.1225 | 0.0058 | 1.2902 |
| s0691 | 1575 | 2 | 0.0020 | 2.1106 | >0.10 | 1.1418 | >0.10 | 1.6936 | 0.0217 | 2.1925 |
| s0695 | 2700 | 2 | 0.0459 | 1.4465 | >0.10 | 1.0295 | >0.10 | 0.9663 | >0.10 | 1.2102 |
| s0702 | 178200 | 2 | 0.0001 | 2.0291 | 0.0000 | 3.1207 | 0.0010 | 3.3919 | >0.10 | 1.0431 |
| s6001 | na | 2 | 0.0009 | 0.5721 | >0.10 | 1.0000 | >0.10 | 1.0000 | >0.10 | 1.0000 |
| s6002 | na | 2 | 0.0004 | 0.5236 | 0.0083 | 0.5255 | >0.10 | 0.6236 | >0.10 | 0.9192 |
| s6006 | na | 1 | 0.0413 | 1.1246 | 0.0591 | 1.1129 | 0.0334 | 1.3081 | >0.10 | 1.0566 |
| s6006 | na | 2 | 0.0399 | 1.4388 | >0.10 | 1.3185 | 0.0095 | 2.4996 | >0.10 | 1.2815 |
| s6007 | na | 1 | >0.10 | 1.1140 | 0.0086 | 1.1848 | >0.10 | 1.0585 | 0.0284 | 0.9403 |
| s6007 | na | 2 | 0.0358 | 1.4803 | 0.0537 | 1.6016 | >0.10 | 1.0875 | >0.10 | 0.9724 |
| s6007 | na | 3 | >0.10 | 1.1979 | 0.0032 | 2.4860 | >0.10 | 2.1836 | 0.0232 | 0.4636 |

APPENDIX F

| LUNG PROGNOSIS (HH & UAB COHORTS) | | | HH 5 yr recurrence | | UAB 5 yr survival | | |
|---|---|---|---|---|---|---|---|
| AGI ID | Dilution (1:X) | Scoring method | P value | Hazard ratio | P value | Hazard ratio | |
| s0073P2 | 50 | 2 | 0.129 | 0.497 | 0.192 | 0.660 | All |
| s0074P3 | 810 | 3 | 0.091 | 0.002 | 0.096 | 0.002 | |
| s0586 | 400 | 2 | 0.007 | 0.385 | 0.148 | 0.619 | |
| s6007 | 1 | 2 | 0.081 | 2.420 | 0.112 | 2.099 | |
| s0074P3 | 810 | 3 | 0.166 | 0.002 | 0.076 | 0.002 | Adenocarcinoma |
| s0143P3 | 300 | 3 | 0.001 | 4.521 | 0.023 | 4.450 | |
| s0296P1 | 1350 | 2 | 0.024 | 2.185 | 0.021 | 2.214 | |
| s0303 | 300 | 2 | 0.047 | 2.049 | 0.007 | 3.358 | |
| s6006 | 1 | 2 | 0.126 | 1.772 | 0.164 | 1.650 | |
| s6007 | 1 | 2 | 0.032 | 3.427 | 0.033 | 2.734 | |

APPENDIX G

| OVARIAN PROGNOSIS | | | Disease Free Survival Log rank | | Survival Log rank | |
|---|---|---|---|---|---|---|
| AGI ID | Dilution (1:X) | Scoring method | P value | Hazard ratio | P value | Hazard ratio |
| S0059P2 | 30 | 2 | 0.017 | 1.613 | >0.10 | 1.487 |
| S0124 | 990 | 2 | 0.023 | 1.554 | 0.015 | 2.076 |
| S0202 | 780 | 2 | 0.048 | 2.270 | 0.001 | 5.084 |
| S0260 | 240 | 2 | 0.002 | 1.942 | 0.015 | 2.121 |
| S0296P1 | 450 | 3 | 0.047 | 0.521 | >0.10 | 0.387 |
| S0695 | 2700 | 3 | 0.034 | 0.445 | 0.045 | 0.168 |

We claim:

1. A method of assessing the likelihood that a patient having an ovarian tumor will die from ovarian cancer or have a recurrence, the method comprising steps of:
    contacting a tumor sample from a patient with an ovarian tumor with a panel of one or more antibodies, wherein the panel comprises an antibody to a biomarker with SEQ ID NO. 1; and
    assessing the likelihood that the patient will die from ovarian cancer or have a recurrence based upon detection of binding of the panel to the tumor sample, wherein across a population of patients with ovarian tumors, a higher level of binding of the antibody to a biomarker with SEQ ID NO. 1 is indicative of a higher likelihood that the patient will die from ovarian cancer or have a recurrence.

2. The method of claim 1, wherein the step of assessing comprises assessing the likelihood that the patient will die from ovarian cancer.

3. The method of claim 1, wherein the step of assessing comprises assessing the likelihood that the patient will have a recurrence.

4. A method of assessing the likelihood that a patient having an ovarian tumor will die from ovarian cancer or have a recurrence, the method comprising steps of:
    contacting a tumor sample from a patient with an ovarian tumor with a panel of one or more antibodies, wherein the panel comprises an antibody to a biomarker with SEQ ID NO. 2; and
    assessing the likelihood that the patient will die from ovarian cancer or have a recurrence based upon detection of binding of the panel to the tumor sample, wherein across a population of patients with ovarian tumors, a higher level of binding of the antibody to a biomarker with SEQ ID NO. 2 is indicative of a higher likelihood that the patient will die from ovarian cancer or have a recurrence.

5. The method of claim 4, wherein the step of assessing comprises assessing the likelihood that the patient will die from ovarian cancer.

6. The method of claim 4, wherein the step of assessing comprises assessing the likelihood that the patient will have a recurrence.

7. A method of assessing the likelihood that a patient having an ovarian tumor will die from ovarian cancer or have a recurrence, the method comprising steps of:
    contacting a tumor sample from a patient with an ovarian tumor with a panel of one or more antibodies, wherein the panel comprises an antibody to a biomarker with SEQ ID NO. 3; and
    assessing the likelihood that the patient will die from ovarian cancer or have a recurrence based upon detection of binding of the panel to the tumor sample, wherein across a population of patients with ovarian tumors, a higher level of binding of the antibody to a biomarker with SEQ ID NO. 3 is indicative of a lower likelihood that the patient will die from ovarian cancer or have a recurrence.

8. The method of claim 7, wherein the step of assessing comprises assessing the likelihood that the patient will die from ovarian cancer.

9. The method of claim 7, wherein the step of assessing comprises assessing the likelihood that the patient will have a recurrence.

* * * * *